(12) United States Patent
McBrine et al.

(10) Patent No.: US 10,900,025 B2
(45) Date of Patent: Jan. 26, 2021

(54) RECOMBINANT B11 BACTERIOPHAGES AND USES THEREOF

(71) Applicant: Charles Stark Draper Laboratory, Inc., Cambridge, MA (US)

(72) Inventors: Connor McBrine, Somerville, MA (US); Georgiana Kourepenos, Acton, MA (US); Parker Dow, Boston, MA (US); Jason Holder, Swampscott, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 36 days.

(21) Appl. No.: 16/447,209

(22) Filed: Jun. 20, 2019

(65) Prior Publication Data

US 2019/0309265 A1    Oct. 10, 2019

Related U.S. Application Data

(62) Division of application No. 15/908,197, filed on Feb. 28, 2018, now Pat. No. 10,329,539.

(51) Int. Cl.

| | |
|---|---|
| *C12N 7/00* | (2006.01) |
| *C12N 15/74* | (2006.01) |
| *C12Q 1/02* | (2006.01) |
| *C12Q 1/04* | (2006.01) |
| *C07K 14/01* | (2006.01) |
| *C12Q 1/18* | (2006.01) |
| *C12Q 1/66* | (2006.01) |
| *C12N 15/10* | (2006.01) |
| *C12N 15/82* | (2006.01) |

(52) U.S. Cl.
CPC ............... *C12N 7/00* (2013.01); *C07K 14/01* (2013.01); *C12N 15/1086* (2013.01); *C12N 15/74* (2013.01); *C12Q 1/025* (2013.01); *C12Q 1/04* (2013.01); *C12Q 1/18* (2013.01); *C12Q 1/66* (2013.01); *C12N 15/82* (2013.01); *C12N 2795/00021* (2013.01); *C12N 2795/00043* (2013.01)

(58) Field of Classification Search
CPC . C12N 7/00; C12N 9/00; C12N 15/11; C12N 15/1086
See application file for complete search history.

(56) References Cited

U.S. PATENT DOCUMENTS 6,461,608 B1    10/2002    Averback et al.

OTHER PUBLICATIONS

Non-Final Office Action on U.S. Appl. No. 15/908,197 dated Sep. 10, 2018.
Notice of Allowance on U.S. Appl. No. 15/908,197 dated Feb. 7, 2019.

*Primary Examiner* — Bao Q Li
(74) *Attorney, Agent, or Firm* — Foley & Lardner LLP

(57) ABSTRACT

The present disclosure provides compositions including recombinant B11 bacteriophages, methods for making the same, and uses thereof. The recombinant B11 bacteriophages disclosed herein are useful for the identification and/or antibiotic susceptibility profiling of specific bacterial strains/species present in a sample.

6 Claims, 32 Drawing Sheets
Specification includes a Sequence Listing.

Figure 1

B11 site 6 donor (SEQ ID NO: 2):

TTAATTGATGAACGTTATCCAGATATTGTAACGGATTAAAATACTTACAGCTATCTAGTATGTAACTAGGCGGATTG
CCATTTGTAAATTATCTATTTAATCGAACTGAGGAAATACTAATGAAACAATTCTTTCAACTACTTCTAAGCCTACT
TTTCAAACTACCGGTTCTATCATATTTTGCTGAGAAGAAACGATTAGAGAAAGAGAAAAAGGAAGAAGAAAAGCGTC
AGCAAGAACAACGTCAAAAAGAACTACTTGATGAACAACGTCGCGAACAAGAAGATCATTATCGAAAAACCGCTTAC
GATCGCCTAGCAAAACTTATTCATACTCGGTGGTATGATGAGTTTAATGCATACGAAAAGAAACTAGTTGATCTTGC
TGTATCGAGTGGTAAAGCAGTTAGTGTTAAGTATGGTAAAGTTACTAAGATGCAGCACCCTCATCAATTTAAACTAC
TTAATGATTGGCTGGATGATATTCCAGTAGAAGATTATTCTAAGTGAAGAGGAGATATACAATGGTCTTCACACTCG
AAGATTTCGTTGGGGACTGGCGACAGACAGCCGGCTACAACCTGGACCAAGTCCTTGAACAGGGAGGTGTGTCCAGT
TTGTTTCAGAATCTCGGGGTGTCCGTAACTCCGATCCAAAGGATTGTCCTGAGCGGTGAAAATGGGCTGAAGATCGA
CATCCATGTCATCATCCCGTATGAAGGTCTGAGCGGCGACCAAATGGGCCAGATCGAAAAAATTTTTAAGGTGGTGT
ACCCTGTGGATGATCATCACTTTAAGGTGATCCTGCACTATGGCACACTGGTAATCGACGGGGTTACGCCGAACATG
ATCGACTATTTCGGACGGCCGTATGAAGGCATCGCCGTGTTCGACGGCAAAAAGATCACTGTAACAGGGACCCTGTG
GAACGGCAACAAAATTATCGACGAGCGCCTGATCAACCCCGACGGCTCCCTGCTGTTCCGAGTAACCATCAACGGAG
TGACCGGCTGGCGGCTGTGCGAACGCATTCTGGCGTAAGTTTAAATAAAAGAAAATAAAGACGAAGTTTTTCTTTAC
ATGGAGAGGGGTTTATGCCGTAATTATACACTTACTTTGATAAGATTTTTAATATCAGTAAAATGGGTATATGTTGC
CTTTTTATCTTTGTGAACCAGTAAGCAACAGGTTCCTTCATTTACGGTATTGGTTTGTTTTAATGGGATATTTAAAG
CATATTCAAACAGATCATCCATCCAGTTAAATGCCATGAACTTATTGATAAGGACATGATCGAAATCAATTAATTCA
ATAAACGAATCGATCTCAGATTGATAATACTCTACAACCATTTTAGACCATTCTTTGTTTATCGC

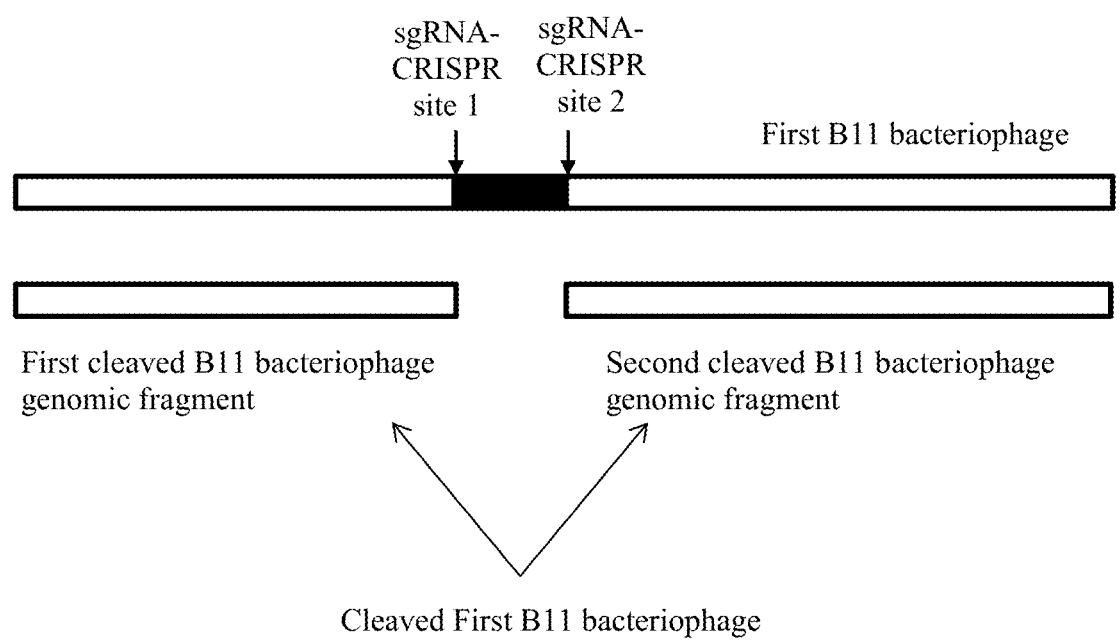

Figure 7(A)

```
>B11 contig 6, no Nanoluc insertion (SEQ ID NO: 1)
CGATTTGCTTAGTACATTCATTACATTTACTATTCATCCTTATTTACCTTTAATAAATTTGCTTATCAAAAGAGCAATTAATTGGGATAGTGATAAC
TTCATTAGTAACTACATGTTTGCCTGTCTTTTTAAAGAATTGGGCAAATTTTGAAGTAGCTGGAATTACAAAGGTATCATCCCGATCATTATTTGAC
ATATTGTANAAAGTAAANTTACCGTCTANNTNAAACCTAATNNNCCANTNAATATNNCGTANTTTGAAATCTATACCAAATCTTAANTGANCATCAA
TNAATTCAGAACCACCGTANTCATAAGCTCCGGTGAAATTCCAATTAATTTCTGCGAATTGGAAAGTTACAGGATGTTCGCCATGTTCATCTTGTAT
GTAGTAACCATCATGAGCTTTCCAATAGATNACTAAATCATGCATGCTACCAGCCTCAAAGAAATAATAGGGGAGTCTAGACTCCCCTATTAATTTA
TTTTGCTTTTAGCCANTCTTCTANTGGNGGTAAATANTTCTCATGNGCCCANTTAATNATTGTTTCTACAACAGGACCNTGTANNTCAAGGTTNCCT
GAGATTTCATGNGGTTCATCAATAGATAGAACCCACGTNTGTGGCGCAATGCGTTCAGTTGCTTTNGTTAGATACACATCAGGCATTAACGTAAGAT
TCAATTGATCGCCGTCAAAATCAGCCGTATTGTTCAGTATCAGTCGTTAATTGATACCCGCACCATTACGTGCAGCTCTAGCTTTCACTAGAAGACC
AGACTATATCTTCACCCTTCCTTTCGGAGTGGGGTGTCTCCCATTTCGAGTCACTTGACCCTACATCCTATTTCTAGGACCGGTGCACCTGATACCG
TGATAGTCGTTGAACCTTCTCCTATTCCTAAATGGAATGTTACGGAGCTTGGCTGCTGATTGACCCTACCTAATCTTTTTCAAACCTTGGCTTTGTC
TTTCGACTCGCAGTGGTAGATTAGTTTAACAGGATATCCCAGCAATTAGAGAGAACTCAACCCAACGATTACTCATTGGGGGAACTAGATTTGATTA
ACTTAATAAGGTATTTATCAAGCACCCCATTCTTTTCAAAGATTGCTTCGAACAGTATTCGGATGCTTAATACCGACATCTCTTGCAAAGTGTGG
AATACTCGGATACACTTTGGTAGTGTTCAAGATGGTGTCAGTTACTTCAATTGGAGTACCTTTTCCATTACTAGGTTTTCCAAATGAGGCTTCAATT
TCTTTTTGAGTGTATTTAGGGAAATCTTCAGGATTAGCGGTATATGAGAATACCAAACCATCCATGATTTCCTTACTACCTCTAACTAGATAGTAAT
AGGCTTTATTACGTTTAGTACCTAGTGCAAGTTCCATTTCTGCTAAGTTATGAAACACATGTAATGTCTTAGTCTTATAGTCTAAAACATAAACTGT
CTTGGTACTATCTCGATCAGCAATCTTAGTCTCACCGGTAATAAATTCAAATGTGAATCTATTTCTATACGGCTTAGTCTTATGATCACGTATAATA
ACCCAAACCGTATTTTATTAACTCCTAATGCCCGAGCAAGTTCATTCATCGAGTAATAAGTAGTCTTTTCACCAGTGGTAACGTCAGTTGCAATTA
CCCGTCTATTTTCTTTTCTTAATCCATTTTTGTAAGCATGCTCAATGTTTTCACCACGAGTCATCCACTCCAAATTAGATGGTAAGTTATTATGTTT
GTTGCCGTCTTTATGATTGACTTCATAATCTGGTCCAGGTGATGGACCATGGAAAGCTAAACAGATTAATATATGAACTCCCTTACTCTTAGATGTT
TTTTCATCATTTTTTGCACCAATATTGAGATATGTCCCAATCGATGTTTTAGTAAGGAAGAAATTACATATTCTATTTAACCGCTTATGACGAATTG
TTCCTAAGTTACTAGCTTCATATGCTGAGTATCCAGGAATATCCCGCCATTCAATTTTAAATGAAGCCGGATCAAAGACGGACACTACTCCGTTTTG
TTCCATTGTTTTTACCCTTATTTAGTTATTCAATTGTCCATTAGGCGCTTTAAGGCATAAAACTGACATGCTGATAGAATTATCATTAATGTCATCT
TTTACTTTAGTAATAAAGAACTGCTGCGTAGATCCACGTTGAAGCGTTGGCAATTCTTCAGATAGTTCGTTAGGCTATCCCGCACCATTACGTGCA
GCTCTAGTTCTCACTAGATGTTGAGACTATATCTTCACCTTTGGCTTTATCCAGTAAGGTGCTTCCCACTTCGATTTAAGGGATTCTATACCCACCC
ACTTGGGCCCTACTCTACTCCCTCTACCTTACGGCATGGTTTCGATAGTCGTTGAGGATTCCTCATACTCCTTTTAATTAAGAAGGTTAGAGGCTTT
CCTGCTGATTGACTCTATTCAATACTTTTCGAACTTTTCCGTATTAGCTTTCGCTATCCGTTTCAGTGTATTGACCTAGCGAGTTATCCCAGCATTT
CAAGAAGTTTTGTCGAGTATCATTTCTGATACAAGGAAACCATTATTAAGTTGATCCACTACACTAAGATTACTTAGGTGGTATGTAGCTTCTCTTT
ACGCGCTTTGTATCGGTTATATTCGTCAATGGATTTATTAACCATCTCTTGAGTTAATTTAGAAACGTATTCGAATAGCCGTTCCTTATCTTCAACT
CTACAGATGACATATCCATTAAATAATCTCAGTTCTGGTTTCTTCAAGATGTCTTGCACTGACCCCTTGATTAATCCAGTCCTAAGTTGCAATTGTG
TTAAGTTCTCATACCTGCCAAAGGTGTTAGTTTTGAAGTCTATGCAATAAACTTCAATAGCGTTCTTCCGCTTCTGTGGATGATAATCCCCAGTTAC
TTCAAACACGTACTTACCATTGTAAGGTTTAGTTAGATGCGCCATGACTACATGCAGCCCTTTACCATGACCTAGCTCTAAGAACTCTGCAACTTCT
TTCATCGAGATGAAGTTATACACCTCACCCGTGGTTACATCAGTGCATTTAACAGCTAATGCGTGTTTGTTTGCACCGGTTATAAATGCATGTTTTA
CATTACCACTGCGAGTTCCCACTCTAGGTTAAGGTAATGGTTATGATGCTTATTGGTGTCTTTATGGTTAACGTCCAAGGATACATAATTCTCAGG
TAATCCATGGAAAGCCATACATACGAAACGATGCACGTATCGATTCGTCATTCATCATTGTGGATATTAACCGTCAGGTAAGTACCCTTA
GATGTTTTGTTCTCATGTTGAGAAATCAACTCACCTTTAAGGTTCCTTACTTGACCATGGTCACTGACTTCATAGTTACTGAAACCAGGTATACTTC
GCCATCTTATTTCTTCATTCATATTTCCTCATTAGAGATTCTTGGTTACCACACCCAGAATCTGTAGCGCTACGACTTAATAAATTAATTTCGGTGA
AAAGTACAACCCATCCCTTTATAAGGGGCTGCTTCTGCAATTAGCTCTTTAAATAGATCTGCAATGATTTGGTTATATTGAAGTACATTCTCATATA
CAAATGAGAATGCTTCACGAGTTGTCATGTTAAACTTNGCTTTTAGNTTNTTNGTTAGATGATACTTTAATAATTGACAACCTACNCCCCANGGNAT
ATGTANTTCATCATAATCATGCGGGTCACTAATAGAAGTGATTACTGCACGTGCCGTAGCGTTGAGACGGACACCAAACATGTGACGCCGAGCAAGA
CCAGGCTTTTGAGCAATTCGTGATTTTGCGTAGATCTCGTAGAACTGGCCCATATAGTCTTAGTCCTCGCATAGTCCTATTCTGAGCTTTAATTGGAC
TAAGTGGTACAGATGATGCATCAATACTAGCGAAGGTTAAGGTAGCATCAATTGCTGCTTCAATTGGTTTATCTAAGTAAGTACCAGATGTGGTTGA
TTCTGCTACGAAACAGAGTTTAGAAGGAACTGGTAAATATTTAGGGAATAACTTATCTTATTCTGAGCAACGAATTGAGCGAATTCGGATTTATTA
TTAGANATAATATTTGCATCTAGTAGGAATTGGAAGATCTCATTGAAATTATCAATGAAGTGATTTAATCCTCTTTCAAATCCTCGATGCAGTAGCC
TATCTACTTTNCTGCGTGTTTCTTTAGAACCAATAGATTCNACATCGTATCGATAAGAAGTATCAGTTAGATATGCTAAGAAATCGAATTCTTTAGT
TACTAGATATCCGGTTAGCATAATGATTAAACGTGGGTTAATTAGNCTACGTACNTGTTTTGGTGTACGAACCCACATTGATGGTTCGATAGGACGG
CTAGAAGTATTGACAACTGGAGTATTACAAATATCACAGATTACTCCGAGTTTATGTGCGTCTTCGATTGCTCGACAATCACAGCTTACACTACTTT
CAATTGCTTCTGAATCTTGGAAATGAGAATAGAAATGCCTATCAAATTCTTCTTTCTCATCTGAGTTACTCGTATTGTAATCATTGGCATAAATTCG
TTTACCCGTAAATTGATCATGAACTTCATTATGATCAACAACTTTGGCATAAAGACCCATACCAAACTCCTATTTATCGATTAACAAAAAAGGAGAT
ATAAGCGGCCCCCGAAGGAGCCGCTATATCAGTTTTTACAATGGACCACCAACGGAGCCTGGCCCGATCCTAGCGTCATCTACAAAGCTTAACCTCC
GCTCTTCTCTGTAGCATACCGGCACTAGTATCATTTACCATCCATTGTAGTTTTTGATCACACGTCACCTTTTGATGTAACTCCTTTCGGTTAAGTGA
TCTATCATCCTCGTGTAGTGATAGGTCGACCTAGACTAAGTCCACTAGTCGATTACTTCACGGAACCTACTCCTAACCGTTATCACCGAAGTGAACC
AGGGTCGCAGTATTAGAATCGGGATGTTACTTATTTAACATCCCTATCTACCGAGGTATTTCCTATTAGTACCAGGTACCCGGTGCATTATAGGAAG
GAGCGCCGTAAGTTTGACCCATGCTGCCAGCCATNCCAACTTGTGCACTACCAGAAACAGCCATGTTACCCATACCGGTGTAACCAGCGAAGCGCTG
TTGACCGAAGTTGGTAATTAGGTTTTCCATGGTTACAGTTACACCAGCNGCTGCTGCTGCGGCATCCATTGCGGTGATGAATTTCGGGTTAAAGGTT
AGACGACGAGCACGACCAGTATAGGTAACGTTACCTAGGTACATCTTGTCGAAGCCTTTACTGTTATTCATACGACGCACAATGTGGTCATTACCTA
CCTGAGTAGCATACCAGGTCTTCCACTCTTGGTCATTACCTTCAGACATGTTCATGGCACCTAGAACGTCGAGATCACGGTCGCGTTAGTTCACC
ATGCTCATCAGTGTAGTGACCGAGGTCTACTTCATGATGGTTGTCAAAGATAATCGGACCAGCTTCAGCTAGATTATAGAACGTGACGGAAATCAGTG
CCGTATAGGTTAGTTAGAGCTTGGAAGATCAGACTAACTGCACGAGCTTGGTTTACGCCACCAGCTGCATCTAGGACGACTTGCTCAATAGCTGAGT
TGTCTCCCATTGGATCGACATCGATCTGGAATGCAGGGTTCTGGTTAACCATCTTGTTCATTAGCATTACGAAGTTGCTGTCGTCTGCCATGAATGC
TTCGGTGCGAGTTTCAATCGCTTTACCTAGCTCTGAGTAATAACCAAGTGCACCAATATCACGCATCTTACTAGTAGCGATCTTCGGCATTAGAGTA
CGAGCCCATGCCTGAGATGCAGTTGCACGATACGCGTTACCAAGCGCGAACAGCCACATTTCTAGAGTCCATGCTTGGATCCAGGACGCCTTACGAA
CGTCAGTAATAACGATGTAAGGAGTGAACTGCGGAGGTAGAACTGCACCAGGTAGAGTTACGCCAAACATGCCTTGTTGCTGGCCAGTGGTCGGAGT
CCAATGTAGATCTACGAATAGACTAACTTGGTTTAGCTGGCTATCGGTATCATAGAACTCGTTCTCAGGTACGTTGGTTTTCTTACCACGGCTAGTG
GAGATGACCAGGTCAGAACGGATCGGATTACCACAGCTATCTTTAACCGGAATACCATTGTAGTCTAGNTTGCAGGTAAGCTGTTCGTTTTCTGCTT
TGATGTGGGTCGCAATAGAGAACGGAGTCTCATTGTTACGACGNGCAATAGCATCTTCACAGATNTTAACNGATTCAACTAGTAGGTTCTTAACAGC
TAGTTCATCTTTGAAGTCGAAGTCAGCATACACTGCACGTGGACCGGCAGATAGTACTTCTAGACCAGGGATGTTGTAACGGTTCCGTAGGAACTCG
CCGATCTTGCTCCAGTATTGAGCAGTGAATACATCACGCGGTAGTACCTTCTCTTCAATGATGTCATCAGTTAGACCATTGTTGATTTTGTGGGTAC
```

Figure 7(B)

```
GGGGACGGATGCGAGTACCAGGTAGGTTATCGAGTACTAGAGTACGAACGAATGCCTTCATGGAACCATTGATATCTTTAGCTAGTTTAACAATGAG
TAGACCAGCCATACCNACTTGTTGNGCATCNCGATCGAAACGATGGATATCGAAGTCATCAGGTAGGTCCTGATGCGGATTGCTTCTTCTTTTACT
TTAGTGAATACTTGTAGGGCATCTGCTGAACGAGCATCAGAGCCATCTAGCCGACCAGAGCGACGCATTAGATGGTTAATGCCAGTAGTNGACCCAG
GNGCGCCAGNNGGACGTTGAGCTTGACGNTGTGCAGTGGGTTGCGGAGCNGGAGCNGTAGCTTGAGTTTGAACGGTGCCGATTTCGTTTTCGTTAAC
AGCCATTTTAAATACCTTTACGATTATGGTTTCTTGATCAAGAAGAACCTAAGTACTNAGTATACTAGATTCAATTTAGTAATATAAATCTCAAATT
TTTTTCATTACAACATAGACGCTATAATCTGCTATCAGCAGATCGTAACGAACACTATGTTCACTACATATTATTACAATCTGAGTATTATTTATTT
TTCATCTTACAATTTCCATATCTTCTTTTTTGAGTTTATGGGTATAAAGTTTGAATCCAGAAACTAATTTACGTCAGTCCTGTATTAAATAATAACT
ATCAGTATTTTTATAAAATGCAGTTATCATTTACTTCGCATATACTTACGAACTGTTCCAAAAAGAGAATGATACAGTTTGTATAGTTTACTAACTG
GATCAACTTTATTATTATCAGTTGTATCAAATTTAGCAATAAATGGTGAATGTGCCGAAGCAGATGTTTCATTTACTTTAACTACACTACCAAATCG
ATATGCGACTAATACCTTTATTAATTCCTCATGGAGTTTAGTAGCAGTTGCTAATGGATTGGGATCATTAGGATCTATCTTAATCCTACGCTCGACA
TTGAAAAAGTTTACTACAATTTCTTTGCTAGTCATGTATACAGTAAGATCTTTGTTATTACCTAAATATAGTGGCGGATCTTCAACATTATTTTTAG
CCATTGTATATTCCTATTTGTAATTACTACTGTTGTTACCAAACTATGATATAGATCTCAATTAATTTTTAATCGGATAATAACCATGTATAATTTA
TTTAAGAATGCTCCGTCACGTAAATTGGGGCAGGTGGTTGATCCTAACATCCATTATATCCGACGAATCTACGCTGAGCAAATTAGGGACGTTAAAA
GTTATTATAGACGGGCACCGAAGTATGTTGAATCTAAAAACATATTAGCACAAATGATTCGACATTTTAACGTAGAGTTACTAAGTGATGATGCTAC
TTTTATAAAGAACGTGGACGATCGTTCACGTGCTATTATTCGTTCATTTGGTATTACATCATCTTTAAATAAAAGGTAAGGTTCATGTAGGTGGTGTT
ACACTTGGTCCTCAAACTGAAGAAGTTCTAGTATCCACATCAGAGAGCTTTGATCTAAAAGATCTAAATAAAACATGGTATAAACTTTCCCCTGTTA
CGTATCTGTATCATACACGTACTGATACTAATTTACCTATCATGAACAATACCACACAGGGTAGAGGCTATGGTGTAACTCTAGTAAATATACCAAT
GCTTCTTGTGATGTACCGTTACTGGTATCGATGGCAAGTTGAGAAGAATCCTGATGAAGTAGAAGACACTTATAGGTTTATAGGATCATTTGTATTG
CCAAATATGGTTGACTCTTATTTAGATATTTCTTTCTTTAATAGGTTAGCAAGGAATGCTTTAGATATTAAAAATCCAACATTCCCTATACCGCATC
CATTTTACATCACTGATATGAATCCACGTATTGATAAACTATGTACAACTATCAATAGAGAATCCATATTAAAAGGTGTAGACATGGAAGGTTTATC
ATGGATAACACCAGCTATCGTACAATCTAATTTGTTCGATATGATGGGTCCCACGAGAACCTATTAACAGGAATAATGAATGGGCTTATGTATTG
GCTCGCACACCCTTCATTAAGTATCTTGTAGGGCAGCTTTTAAAGAATACTGGTTATGATCAATCTTCTGTTAACACTGTATTAATTGATCTTATG
AAGCATCTAATGATCAAGCATTTAAGCAACAAGCAAATAGTGAGTTTGTAAAAGCTCAACAGGCACAAGTTGATTGGATGATAGATGCACTTAAAAG
AAAAGAAATGTGACATAAACCCCCTCCTAAATTGGAGGGGGTTATATGCCGTTTTATTAGAAATTACCTTTCTTCATTTTAGAAAGTAATTTTCTAC
GTTCAGCTCGGTTAATTCCTGGGATAGCTGGTAATAGCATTTTATTACTAAACTTACCTGGCTTGCGGTCATGATTTAGTAATTGATCAACTACAGC
TTGGTCACTGCTTTTAACTCCATTATCCATTTCATCTAATGGGTCCATAATAGCTTTAGCAGTCAATCTTAGATGAGTAACTAGTTCATCAAATGAA
CTATCGGTATTAATAAGTTGTTTATCAACACCTTCTTTAAGAGCTTGTTTAATAGTTACGTCTTTTACCAGGATATTATCACATTCCCAAAGAGTTG
TATGATGGGTATTTAACATTAATTCAAGTGAGACATTATTGTAATCGTTGTCAGCACTTGAGTGCCAATTGAATTCATCAATATAGTCATTTAGACT
CATTAACTTTGGTGGTTCGTTACTAGAGGTAATTAAACCAATTGGTTGAACATCATCTAGTGAACTTTTATCACTAGTAATTGCAGTTGTTTCAGTA
GTAACATCAACTTCTTTTAATTCGTTGGTATAAGTTACATATACTAATTCTTCACTACCGTCATCCAAAAGAACATAGGCTGTTGCTTTGGTGGAAT
CATCAGGTGCTAATCCATGGATCCTAATACGATTATCATTTACTAATTTACTATAATCATTCCAGTGATTACACGAACTTCATTAGTCTTTTCCATT
ATCATCTACCTCTTTTAATTTATCTTTAATATATTTCGGATAAAGCTCGTTTTCTTCACGAGTTAANCCNGNTGGNNCGGTTGGTAATGTGATAGTN
CCNCTNTTAATTGCCTTCTTCATCCGATCTAAGTCAAAATTAAATTCGGTATGATTTNTCATTATATTGAACCATATTAAGTTAGTAATTGGCAATC
AGACTATATAAATCTTAATTATTTTTTAGTATATAAGCCTCCCACTAGGGGAGGCTATATTTCTTAATAGAAGTCAGAGATGAGTCGATCGTTATTT
TTATCAATAAGGAAAATACCTAGGGACTCTAAGGTTAGATAGAATACACCCATAGTNTTTCCAATGATAGTTCTAACGTCAGCAACACGCGTAATAA
CTTCTGGAATACGACCAGTTTCTACTACTGTACTCGGGATATGGAAATCACCAATACTGGTTTTATTTTCTTCAGTAACCCATGCTTGAATACGAGC
AGCTAATTTCTTATCTTCGATACCATCAATCCATTCTTTGATCGCAGTTTTATTAAGAGTAACTGAGATCTTTACATGTGAATAAGGTGGATCA
CCAGCGTCACCAAATGATGGAGCAAATACGGTCTTCCACACTAATCCCTTTTTATGGGTTGAGTTATCTTCAGATTTATAAGACTCAGGTCGTTTAG
TTTGACCACTTGTCAGATACTCAGCTTTACCACTTCTAACAGACTCAATAATTTCTCTTTCGATATCACCAACTTCTTTTAGAATTGAAGCCAAGTC
GATTTTCTCTTCAGTCTTTACAGTTTTAATGATATCTTCCATGAGTGTTTTAGCACGACTATTAATCTTCTTAGGTACTTTACTATCCCTTAGTCCN
ACNCCNTTNATCTCCATNCGNGANTCATTAAACATNACCCCTTCTTGGGCATCCTGTGATGCAAAGTAATGTTTAGAACGAGTAGTTAAGGCCAGTA
CTGCGAAATAANATTCGTTCTTCATTGCAAATAGACGAAGCTTATCTTTAGATACACCCATATTAGCGGATTGAATCGCNAAGATATGCATAACTAC
TTCAGANACTAGAAACACTAGTGCNAATACTAGTCGNTTAGCTTCATTGCTAAAAGTTACTTTACCAAAGAATTCCTCAACCCACCATTGTAATGTA
AACATAGTGGAGTCAGTATCTGAAATAACAGCAGCTCGTCTATACACAGTTGGAAAAGCATGAATGCTGATGGTACACATTTAGTCAAGAAGAAAG
CTTCAATCAATAGACGATATTCATTAAGAGTTTCAGCGATATTTCGACCAGTGCATAAACTTGGTTNANTGTATCTGGATCNGANTCTTTTAGTTT
AGCTTTAGATCGACCTTTAACAGTATCAAAGCAAATAAAGCTAGCCAANAGATCCATATCACCATCATAAGTTGAATATTCTTCTTCAGTGATGATT
TGTTCTTTTGTTCCAACCTGGCTTAATTTAATTAGAAAGCTCTTGATTAATTCTTTATTGTATTTATATAAGTGATATAGATCACCTACNTACATAA
CTGCTGCTCGTTCGACTGGTGTCATCCCAGTAGCTAGTTTTAAAATCTGNGCCGTGTANTACTTATTTTGCCAATAGTGTTTAGTTGAATAAAGAAC
CATATCAACTACTTCTTCTGGCGTTGGGCAATGTAGATTAAAATTAGTTACTGCTTTTTGAATTAACTCCATATCAGCTACATTAATANTNTTTACT
AAATTAGCTTTTGTGATTTCTGGAGTATAATAATGCCTATTACCCATAATGAATTTTTCATTATTTGAGTTAGCATAAGAGGTACCAGTTCTACAGG
TAGATGTTAAACTAGAGTGTGTGGACTTATAATAAAGAATAGTGGCAGCAGATACAGTACCGCCTGAATATGAGTTATTGTTAATTTTGAAGTTTTC
TTGNTCNCCCTTTACGTACTTGTGCAAGTTCTGTTTTAAATTTGTGAATTCTCTTTATCGCCGGCCTGTAGGAAAGCAGCTGCTTCACGTTCAGCCTGC
ATCTGNTCACCTTTAACACGCTTACGGTTTTTCACACCTTCNGCAATATAGATGGAGTGCGTNGACTGTCTAACAGACTCTGGTAAATATGCGGTCA
TTGATGGAGATAATAATAGATTCTGTTTCTTAACACGGTTAAGAAAAGCCATAAATGAAACCGTCTTTAATTCCCTATCACCAAACTTATTTTTATC
TAGAATAGTTGCTAATGGATTACGAAGTGCATATTCGCCATTTTGACGTAATTGTTCTTTAACAAATTCTTTACATTCTTCTAAACTAATATTTAAT
TCATCTTTTGTCATTAATTGAAGATATTTGGCATTATCATCAAGACATGCATTAATGATATCAATATCACGATGGTAATCATTGACATCTTTTAAAA
ACGGATTTGGTTGGGCAAATGCGGTCATTTCACATATCTCTCAGTATACTTATTTTTTAATTATAGTGAATGATTTCTCTCTNTTTAACTAAAAAAG
AAAAGGAAAGAATGGGTACCCTATACGGGNACCCTAAATTGAGAGGTAGCACATCAACTTACATTCACATTAGATGATGTAAGNAAGTAAAAATAAN
ACAACATAAAAGGAGCCATNATGGCTCCTTTATAGTTATTGTAATGTTAATGATAAGTGGTGGTGCATTATTTTGNCGCACTGCCAATAGAATGCGAT
CATACATTTTATTATCGACATCATCCCATACTAATGTCANACGNTTACCATCTACACGTTCTAATGTATTCGCAACAATCCAAGGNATNCCAATAAA
CATCACACTTTCATTATTGGCCATTCGTACACGAATNTAATTGTATTGTGTTGGATCAACTGGAGCTGANCCTGCTGGTAAACTTGGATATACTTGC
TGCCCNGCAGCAGCTACATCAAAACCCATTGCAGATGCTACAGACGCAGTAACAATACCTTCGACTGTAACGTTCTTAAAATTAGTACCTAGGATAG
CATATGGATAGACCTCGAATGAGATCCTATCACCTGCTTGAATGTCTCGAATATTAACAGCCATGGTAATACCCTAAAATAGTTGGTTACATAGGGT
ATTACTCATCTAGTAATACNACTACACCAAACAGACCTTTCGTATCCATTGGNACTGTAATGANTACATGTCCATNTGGATANTTTTCTTTAAAGCT
ATTGATAAAGTCGGTNCAATATTCAATAACATATCCTTTAGTAGAATAATTCTCTAACTCAATATCTTCNTCAGGATCATCAAATGAGTCATGTCCA
TACATCAGCATATGGATNTATATGTCATTATTAAGCGTATCCATATAACTTAACTTACGTGATTCTTCAAATAAATCAAGTGGTGTTGGACAATCTG
GATATATCATTCGTTTTGTATATTCACGAAGCAAATGTTGCGAATATACTTCTGACTCTTTAGATTTAAATACGATAAATACTCGTTTTTCCATATC
GGTTCCTAGTAGGAAGCCTATGTGAACCGATAGGCTTTCCTATTTGCGTCAATTGTTAATATGTGTCACTTAATCCCACATCATTGTAACAGTCCATA
CCAAAGTCTTCACCTTCTAGAATATAACCCTGATTATGTTGATCAACTGCTATTGATTGGATTCTTCTACACCTATATCCATTCTGATAGAGATGTG
CTATTTCAGATTGTAGTTTGCTAGCCAATGTTTTACACACGGTCGCAAACCACATATTAAGAATACTCAATGCATATTTATCTTGCATAATCACAGG
TGCTACCGATGGAAAGTATTCTTGTAAATAATAGTCAACCCCTATAATTGGTTGAGTAGGCTGTTGCGCTAGAAATTCAATATATGAATTAATTGCC
```

Figure 7(C)

```
TGATACCATAATTGTTCTATAGACTGGTGTTCAGTATATGGGTAAGGGTATTGTAAGACTTATTGACAACTACATCAGCCATTTTATTAACAATGGG
CCAGATATCACTGATGTTAATAACTACGAAACTCGTCATTCCTTGTTGACCTGGAGTTATGTTATTAGCATCATTTATCCGCTGCATTTCTTGTTGT
CTATAAAGAAGTGGATGCATCATGTTTGAGACCTCATAACTAATTTAGTTACCATCTTATATTTATCTACTTCTATACATTTAAGACTAGTAATAAG
ATTACCTGCTTGAATAACTTGTTTTTGGATTATCTCTAGGAAATCAGTTCCAAATAAATCCAATACCCTTTCGATAATCTCAGCAGATCTTAAGTGC
CAATTGATGGTATTAGGATTTCCCTGATGATCAAATACCATCATACTCGTCGGTCTATCCGGTTCTATATAGGTATCGCTTAAGTAATCTTCTAACC
ATTGCTCTAAAAGGTAGGCCAATCTAATCTCTGCCAGTGGTTAAAATATTCACATATGCTGCTAGAAGTCTATTGATACACCACAGTACAAAGTCA
GTCGGTTCATCTACACCTAGCTCTTCCGTAAAAGAACGCGGTTTCAAAATTAGCAACAATTGCATATTGACTCCACTCTTTACCAGTGACTATAGTT
AATAGAACAACTTTGTTATCTATTACACTAATGAACTTATAGTCTATTAAATTCTTCGGTGTTCTATGTAGTAATTGGATTCCAGTTGTATAGAACA
AATTAATGAACTCATCCCAATCTGGACCATTTCCTAGTTGTATTGATATATCCACAAAAGGAATAACCGTATTATCCTGTTGTAATTTAGACATCAT
CTTAACAACCCATTGAGTTAATAAGACGATGACTGTAGCTTCATCTTTATTTGTTAGGTAAGTAAATTTCTTTATCAATGTGATTAATTGTGGGAAT
ACCACTTCGATTGGCAATACATATACCAGACGTTGTACTTCCTCCGATGTACAATCCATCTCGTGCTTCTGTTTCATACCACAGTTCCTTAGTATTT
GTTGGAATGAGGTGCATGATCTGCTCAGCACCCTCATCGAGAAGTTCTATTAGTTTATGCATGAAATGAATGTCTTTAGCATATTCATAGAACATTT
CTTCTTTAACGACCATTTGCATAAGCTTCTGTTCTGCCAATGCAACAAGCAAATGCATTGCTTCGATATAACTAATATCTAAAAAGTCCAATACAAA
TCTTAGATAGTTATCATCTTTAATAAGTTTACTTTTAGTCGCTCTTAGTAAAAAACGAGGTTGTNGTGTGGGTAATGGTGACGTATAGATCTTCTGG
TTTCTCAGTATCATAAATAACCCTATTTAACTGGATGTTACCAGCTGATGGTAGAACTACCCGGTTAGAACAATTATACAGATAAGTTGTTAAATCA
ATATCACAAATATCCCTATAACCCAGCATCTGATTAATTAGTTCTATGACATCATTAGATGTNCNACCNGATGCNCTCTCAGACGCTGCTGCCAATA
CAATTGTTAATGCATATTCTGCACCAATACTATTTTTTATAGATTTCCAAATATCAGAATGTTGNTCTTGTACAAAGATCTTACTTCCATTCTGAT
ACACATTGATGTGTCTTTATCATTAGATATGTTCATTATAAAAACCTTATAANCGNTATAAAGCCCNCCNTANGGAGGGCTTTATTTAGTATAGATT
ATTTTCTAAAATGTATCGCTCAGCTTGCGCTCGCTGATCATCAGGTANATAATCACCACGTTGATATTCAAATACTAATTTCTCAATAGGATAAGTT
GCATTCTTATTCTTGTATACAGAAATTACATAGCTATGATACTCTAGTTCTATCACATCATGCTCAATTCTGGTTGAAAAATAAGCCATGTTAA
TAGAACTAACTAGAGGGCTAATATATTTCTCTTCAAATAGTAATAAATTATCAAGTCCTAAACTTGCAAAGAAATCATGGTTAACCTTAGGTATTAG
GTAAGATACTTTAATATTACTATATTGTTTAACAATTACGCCAATAAGTAATGCAGTTAACTGTTCTTGAATATATTCTACTGCGATGTTGTATGCA
TGGTTAGTGGTGATGTGGTCTTTATTTAAAGTATAGCTACCGCCATTGGTAATAGATGGCTGAGTTTTACGTCTAGATTCGTAGATACTATAACCTA
GTGTTTGTAAATTAATTTTGTCAAAGCCATGGAAGAAAGTCCGTAGAAATTCACTAAATAAATAGTTTAATGGGTTCAGTAGGTTAAGTGATACCAC
TGCATGATCATCACCATTATCAATCCCATGGACACGATCATATTCTGCGATTCGACATCTTTACCACTGATTAAAGTTATAACTGAACCAGCTTTA
ACTACATCCCATTGGATCCATGTACCGCTATCGATATATTTTGCTACTTGCTTATAGATATCTAGATAGATAGTTTCTAGATAAGGTAGTTTCATTA
GATTTTCTACCCAAGCAACTTTATTACTATCTACGTCAGTTACAGCACAATTAAAAATAGCTGCGGCCATCTTAAGATTGGTGTACTGGTCTTTGGC
TGTTTTATATGAAACTAAACTCTCTACTATATTTTCAACCATTAGATGTAAAAACTGTTGAGCCACATCTTTACTCAATTTCACCCCAATCGCTTCA
TCAATTGAAGCTGAAGCTGTAAGCTGACCTAGTAAATCGTATATTGCTTTTTCTTGGTGGCGCGTATCAAGTACAATGAGCTTATTCGACATTATAT
TTCTCCAATTAATTTTTGGAATAGCGATCCAAACTGTGTTCTTTAACCGATAGAATATTACAAACTTACCTGCATTTACTCTAGGTATAATTTTTA
ATATATCCCAAAGATCAGATGCGGCCTCATGATTATCATGAAACCATTGGATTTCTTGAGGGGTGTTATTTATTGGATTATATCCAGTAGTATACAT
GAATTCAAAAGAGTCAATAGAGTATTTAAAGAAGTCATCAATTAAGCTGTCCTCTACTGATTTAAATATATGCTCTAATGTACCATAGTCATCTGGA
TGTATTCCAAAGCTTTGGCACCTAATCGCTAAACGCGTATTTATTAACTCTTTTGGCGATCTTGGTACTAACTTGGCTATCACCCTCGTTACATCTA
TTACATACAGGTCAGCCACTTGGGGAGTAGTCACAGTACAATCTCTCGTTAAATGTTCAGGAACATGATATAGATCTAAAAATATTTTTAGTCAAAT
CTGTTCGTGGTAAGCCGATGTATATTATACCTTAGTTGGGTATTATCTCCATCGAAAAAACGCGTACAGCGCATTATAGGACGTTTTTATGAATCCA
ATTACTAAGGCTTTACGTGATATTTCTTTTAAGATCCCAAAAACAGTTCTGTTTCNTATCTANCGAAATGTCAGGCTGTGGTGCAGCTA
TCTCACTAGAAACCAGGATACGCGAAGCTGTTATTGAACCACGTGTTATGTTAGATATTGATTTAGTCGGTGGTTCAAAAGTATTCATTCCACTAGA
TTTTCCAGTGCAAGCAGAATATGTTGACCCTTATACAGTGGTTTATTACATTCCAGACGAATACACTCAGCAACGCCCAATTATCCAATGTTACAGT
ATCCATTTTGGAGTATTAGGATTCCATACTGCTGGCTATGCTATGCACTATAATGAATCAAGTATGGGTGCATTAACACGACGTGTACTAGATTCAG
CTAGACAGTTACCAGTCGCCCAAACAGCATATATCAACTTAATTAACCCACACACTGTCATGGTCAGGTATATCAATATCCCTAACTACTCATCATT
CCTTGCCTGTCGCGTAGGTAATGATGANGAGCTAAATACCATACGACCTACAGCCATACCTGCATTTTCAAAACTCATTGAGTATGCTGTTAAGTCA
TACATCTACAATGAGTTATTTGTATCTATGGGTGANGCACAGTTATCAGGTGGTGCTGAGTTAGGTGTATTCCGTGATAAGGTTTATGAATATGCCG
ATGCTGAAGACTATATCAGGAACAATTAATGCGTTGGATGAAAATATCCAGGCAGTTCAATGATCCTGAAGGTAAGCGACATCATATTCGGACAAT
CACAGCCGCTCAATAAAAAATAAAAAAAAGACATATTGCCCTCCCATTGCGGGAGGGCTTATGCCATTAAGGTAATATCTAAATAACACNATATTT
AAAAACATACTGGTATAANNCATCATCAATTAACACTGTTGAGAATCTTTTTGATGAGATCACCAGGTGCGATACCAATGCCTGAACAATACCGTCT
AAAGTTATTACACGGTTGACATGCTTTCTTTTCAACGATATTTAATTCAAAGCAAATATTGCCACGTGAATCTAGAATGGATATAAATGCTTTGTTA
CCTGTTACGCGATATGTCTTACCGAATACAACAGTTGTTTTATATGCAAGGCTATTCATGATTATTCCTTTAACATGGATTATTATCATGTTTGTAA
TATAGCCTTTAAATGTATTTAAATATTTATTAAACNNATAGCGATGNGCTATATATGTTTTNAATACCTCATANGCCTTATCNGTTGCCATGGANC
TATTGACAAAATCAGAATGATCAATCTTAATAATCTTACCGAATGAATCATAATCGATAGTTGTAACNNCTATTCGATCACTATCACGGATCAATAG
TTTATTTTATTTAAAACAAAAATATTCCATTTCTCGCCATCGGCTAAAATAACATCCTCATCTTTAAGATTAAGACGAACAAACTGTTTTACATAAA
TACTTAACTGAGCAACTGTTGACATAATGATTTCTCGATATCTGTTAATGAACTAATCATATCTCGGACATTNATGGTAATAACATTTTTATAAGTT
AAATAAGTTGGATATGAACCCATAAATGTAATAGTCCCACAGATTGATTTTTATATCTAATATCAANACANCCGTCATATCTCCAGATAAAATCAA
ATGATCCTTTAGTGTGGTGNTCAAGTGNAAGAATAGAACCACTAACTAATTTAGGATATTGTTCAAATTCAGACATTACATAATCTGCCAGTTCCTT
AACCTCAGGATAATCAATCAATAATAGCATATACGTAAATCTCAATNAGTTAATATAACACCCCATCCAGGGTGGACTCTTTCGAAAAATGGTAATG
TATTATTTCCTATACTNTCTGCATCAATATTTGGAATGTGCATGGTACAACAGTGGGCGTTACTGTCAATCTTGAAATAGAAATTATCTTTTAAATC
TTCAACCTTGGATGTTTGNAATGGATATAAAATACCATTCCCCCAAACATACCAACGNCTATACAGCTTATCGTTTAACCGCTTCTCAATAACCGAA
TGCGATTTGAAACGAGGAACTCGCAAACGCATCCCGTTTACTTCAGCCCATTTGTCTACCCGNTCATAGCTAATAATTCCATCCTTAACCATTACAA
AGATAAATCCCTCAACTATGTTGGGGAGACGAACTACGTGTTTCAGAACCATAGTAAACGGAGATAACGTCAGATCAAGTTCAGCTGCCATTTGCTC
GTCGAGCTTTTTAGCAGTGTTCTTTGCCATCGGTTATCTCCTAATATACAGATTATTAATTATCGCTAGTTATTTAATATCTGCAAAATTCTGATTT
ACTTTACCCATAAAAATACCATCGGCTCTATCGTCATAATAAAGCTTCCCTGCTTTAGCATTACATANAACTCCATAAATGTGACCATTGTAACCAT
CAAAATTAAATAAAGATGGATTATGCGGTACATGAATGAATCCCATTTTATCGCACAGAAACTTAGCTACAGCAGCCGATCGGCTAATACCTGCCTC
ACAGTGTACGAATAGGTGTTGANCCTTACCAAGAGCTTCACAGAANGAAATAATACGTTGTGCATGNCGATGATCAAATAGATCATAAGAAGAATCA
ACATAATCCTCAATGTCATCAACATTGATACGTAAATAATTAAGATGTTTTGCTGAATAAAGTGGGACTCTACCTTTCTCCAGTAGACAGATCATAT
TTCTAGGGGAATAAAATGATTCAGCCACATGCAAAGGAATATAAGTAACTGTATTTACTGGCTTCATATTACACCTCGTTACAAAAAAATAAAAGGA
GCCCCGAAGGGCTCCAGTATANGTTAATCGAATACAAGACCACTACTAGTTGCTTGGTCATCCACATCTAGAGTAGACTGACGCTTACGCATATTAG
CTTTGGCTCGATTCATCATTTCACGACGTTCTTCTAATCGNTTACGAATATCTTCAANAGATAGNCNANTGATCACAAAATGCATTTGATCGAAATC
ATATTTCTCGGGATCAGCATAACCAGTGGTACGAGTTAAAACAGTGTTAATGGATACTTCGCGATCAGGGTCAGTGTATAGCGAAGCAATAGAAATT
GGGTCCAGAATAGCCTGGGCTTCTGCTGACATCAAAACACCGTGTAATTGGACAGTCTGTACAGGTACATCATGTGTTTATGGAAGTGTGCCCAGT
TAGTGATATCCATTAGATCAAGACTTTGGTGTTCTTGATTAAATAGAGTTACTAGTGCATNTAGTACTTCNAGAAGTGTTTTGGTTCACCATTGACTG
CGGTANACCTTCAACATTCTCATGATAGTTAATAATCATCGGAACTTTACTAACAGAGGAAACCCCTTCAAANGTCTTAAGGCTACCACTNCTATTN
CGAAGACTAATATCACTGTCGTAAGATCCAATGACCACACTTACAACTACTTCACCTTGTTGTTGTAGATGACTNACAAGNGAAGGACCAATNGTTG
```

Figure 7(D)

```
AACCAGAAGCACCACCCATTGANTANACNACNATGTTAGNATCCCCTGCTGGGAAATGATGGGCAATGGCAGGAATATGTGCAGAGATTAGTTCTGC
GGCTGCCTTACGATCTTTACCCATACCGATAGCACGTTTACGTGCNGTCTGGTCAGCTAGCTTAGTATCCGCTTCAATAATGATCGTATTATCGTCA
GTATTGTGTTTGTGTTTATTNTGTACACTGGTATCAATGTAGCAAACATCCTCATGATAACCATGGAATAGTTCACCAATACGGAAACCAGCACCAC
CACAAAAGTAAATTCGAGTTTTACTTTAGACATCATTACACCCTCATTGTGATTAATATAATTCATATACCAACTTGTAAATGGTATCAGTGCTTAAA
AGTAACGATCTCTTCATGAGTTCGTTCTTGATGAACATTAATTCATTAACCACTTTACCAGTATCAGATTTAAATTCGATTACCATCTTATCTCGAC
ACATGTATGTTTGCCAAGTACCACCAGACTTAACACAATCAATAATCATGTTAAGTACATTCTTAACTTCAATCTTACTAACTTTATAACGATAAAC
GTTTAGAAGTTCAGTAAGCCATTTCGTTTTTGGGATTTTGGCATTTTTACGTTCTTTTGAAATATCAAAAGGAATTAGTGCAATGATCTCACCATCT
TTGTTGGTGAATTCAAATACCATTCCTTTTGAGTTAGCTAAAGGACGAATGTTNTAATTNCCTTTANCACTNCATACTTCTTCAGATAACTTAACTA
ACCTATCTAGTTGAACATCAGATGCATGAATGTTATCTTCTTTAAATGCTTTCTTTAGTTCATCATGAGTTAGTGGAGTACGTACTAGAGTGTAATC
TTTCTGTTCAGTCATTTTTCATTTTTNCNATTTTCNANTTCAAATTAAACGGTATTGGCTTTTATAGCCAATCCCTTATTACTAAAAGTAATAGATT
CTCGAACTAAGGATGGTTATACCCCTTCTCTAATAATAAGGAATATTATATGGGACCCCCCAAAGGGTCCCCCCACATAATATACTATTTATATAAT
TTCTTTTAGAAGAAAAGAGATAAATAAGAGAAATACAGTCTATTAAAGTAATGAATTTCTCAAAAATTAAATAGTACACCGCNCNNNNNNTTNCGNCG
GANGGTCCTGCCGGACNANNGTCCGGATGTGCGNNANTAGNGGGTTTTTCAAAAATACNTGCATCGCGGTTGAATTGAGNGGTTGATTATAACGTNN
GATCTTAATNGTAAATAGAACTTCNTCAACATCTGNATGNCATCCTTCNAAACTAAAATATACTTCAGTCCGATCAATAAACTGATACATTTCTACA
GCTGGTTCAGCTGGATCTTTAAAGGCCANCTTATTAGCGAAATAATCAGTATNGGCTAGAATTAATTCTTTTACATTANTTGCATTCTTCTTATCAA
CAAGGAATTCAAACTCTTCAAGGTTATCTGTTTTGAAAATACCTTGATANGATGACGACTNGATTAGTTNATCACTGATATCATCAACATGAACNCC
TGGCATAAATTCAATGACTGGTAGAATAAGCTTGTTACCTCCTACGCCNTNAGCNATATGAATNCCAANCACATTACCATCACTAATGTATTCGTCA
TTACCGCAAATAACGGCACCAGCCGCTAGATATAAATTATCAACATATTTCAGATTATCGGCAATAATGCGAGATAGTACATATTCTCGCACCATGG
CATCATCTGGACTTGACTGCGGTTTAAAAGTATAGTGGGTGTTATGACTACTCATGGTCGCACATGTAACAAAAACTGAAATATCTACTGGATTAAA
TACCCAATGAACGGAGATATCCTCTAATTTATGTGGATGATGTAAACCATCTAGCTTAGATAGGGCTTGGAGTTGTTCTTCCCAGGTGATGTTAAAT
TGAGTCATTTTTCTAACCTCTTCATTTATTAAAAATAATACACTTATTTTACTTTAGCAGTTGATACTTCACATACATTAACTAATTGTTCAAATAA
CGGTTCATTATCTGGATCATTAACTAATTTGATGTATTAATAATAATACCAGAATACAGCATATCAGCTGCATCTCGATCACTTGTTTTAATTCTGG
TTACACCTTCCCACTTCCATCCATAGTAAATTAAATCAAATGATGAACCAATGTTAAAGGTTGATTGAATAAATTTGCATGTACCATTTTCTTTTAA
CCAATCAGGCCTATATGGTTCATTTTTATAAAATTCATGCATGAGTACTTTAAAATCAGTTTTAATGTTTTCATGAATAATGCAATCAATAGAATTA
AGAGCTTCATCAAGAGCTGATTTAGACTCAATAATGATTTCTAATACATTGGCAGATTTTAGTGTAATCATACCTAGTTCATCTGAGTGTGCTCTTC
CGATTTGAAATACATTGAGCTTACCAATTGGTAAGGTGCTTTTAATGGCAGATTAGTATAGTGAGATACATCGCTTTTATAACTGTCTTCATATGA
CTCAATTAAATTAAGCCATGCTCTTTCAATACGTGTATTCTCAAAATGNTGTTCTTCTTCTAGTAGTCTAGAAATTAGATGATTAATGTATTGAACA
TTATGGCCAGTACCNGTAATTNAATTATATTTCGTATTACCGGTAATTCCCCATTTATTATTTTCTTTATTTATCCAACCGTAGATTACACTGTTTT
TAGGATATTTATTTTTAAAATTATCGTATATTTCTTTTAGATGTGGATTAGGGGTAAAACTAAAAGTAGTTGATTCAGTCATTATAGATACCTATTT
GAATATTGTTTATTATTGCAAATTAGTAATATAGATCTTAAACTTTTTTAACTCAGCATAAAGCCTCCCCTAGGGGAGGCNATATGTTCATTTATCT
ATTTCAGCGTTTGGATCATACCAAGGTAATAAACTTAGTAGTGCCGGTTGTTGTTTCTTCATATCCTCTAAGATTGTTGCTTCACTTGCACCTTCTA
ACATAGTGGTGAAAGTAATCATGTTCTTAGAGTTATATATCGGACGTAGACCATTACCAAAGAATTTNACNTGTTGAACCATTATTTTGAAATCAGG
GTTATCGACTACATCTGGGATATAGATANCAGGTGGCGCACTGAAATAACGTTTAATTAACTCAATAGCCCAATACGTTGGTAAATCACCAAACTGT
GATTTCACTGTAGCTAGGTTTAATTGGAATGCTTTAGGTTCTTCAGGCGGCGGTTCCACCGGATCAATTGGATCAGTGGGTTCTTCAGGGCCAGTAG
GTTCAGTAGGCTCTTCAGGATCCTCTGGATCGCCTTCTGTTGGCTTTTCTTCAGATGTGCCACCATCAGGGTCACNTGAACCATCATCATCTTCAAC
GGGCTCCTCAGGCGTTTCTATAGGCTCCTTCGGATCTTCCTGATTCTCCGATAGATCGGGCTCTTCTGATTCCCCATCTCCATTTGCTTCAGTAGAA
GACGTGTCTTCTGATTCTTCATCTGTTGTCGAGTCAGTTGNGGCTGTGTTTTCTGAATCGGCAGTGGTATTTCATTGATTCAGTAGAAAC
AATTTCAGTAGGAGTGGTTTCAAGTTCATTGACACTATCCTCTGCATTAGTTACTTCATTAGGGATTTCACTAATTTCTGATAATGTTACTGGTGCA
CTTACTGCGCGAGCTTTTCGTTTAGCCATGGTTGTACCTTAGATAGAATAGTATTATGGTAAGTGACTAATTCAGGATCAGTTAAATTGATACTTTG
AATAGTCATATTCAGAATTACATAGGAGTCCATTGTTCTCCGGGTATATCCAGTTAATTCCATCTTGTTATATTTCTGTACATGATCTGGAACCCAA
TCACCAAAGATAACACCCAGTTTATGAAAACGATACACCAATCTGGATAATGCACGTTGGGTTTCAGTTGGGAATATATCGGGAACATTTTCGGGAA
CAGTACATTTATCACTAAATGGAGTAATAATAGGACCACGATGAATGGTGTAGCTAAGCTTAAAGATAACAGCACCAAGTTCGTCATTAATACGCCT
AAGTATACGATAACCATAATCGGTACGCTCAAGTTTATATACATTACTAGGATCAGCATCTGCTAACCTTCTAGCATGTCGTCTAGTGCACGTTTGA
TACCACGGTTATAGATGAGTTCACGTTCTATGTAATCTCTCTCAAAAGCGGCCTGAGGGCTTTCTTTCTCAAATTCCTTAGTTACTGACCAAGAAAT
TGTTTCACCAGTTAATTCATCAGTTAAAACATACAGATATGTCATAGAGTCAACGTATGAATACTGGATAGAGTANCGTGATAAATCACATGGCTTA
GCATTTAATCGTTCTTCTTTTAAATAGAAAAACATATCTTGTAAATGATTATAAGTTTGGCAGCCACCACCAAGATGATCAATATCAATAGACGTAT
CTGGCTTGACTGGAGCTTTGCAGCAACTCATTACACACCTCTACAATTATATTTGAGTTATTGTACTACAGATGATAAAGAGAAAATACATCATAAG
CCCTCTCCTTATGGAGAGGGNATTATATTTACATAGTGTTAAAACACGCATTAAATTTAGATAATGAGCAGCCAGTATAAATTAATGATTGCTCTAG
TTGTATGATGACATCGCCATTACTATCAAAATCAGCAGCAATAAAAGTAGATTCAGTTATCTTAAAAGTAGATGGCAGCATTTCTAAATAATTAAAT
ATTGCTTGATTATCGATGTCATGAGGATTTAAATCCATATGTTACCTATACATNGATAGTTATGGACCAAATATTAACAGGNCTGCATAAGACAATT
GTGATTAAATCTCCATGAGTTCTCTGATAATGGTTGAAACACATAACTTTGATTAACTTTAATTTTTTAGTTTCTTTATTTTGAATTTCTTGATAA
GTGATTCAATAAGATCAGTAGTAATAAGTGAATGACCATCAATAAATGGTTTTATACTTACTAGCGAATCTTTGTTAAATAGAATTGCATCATCATA
TTCACATGTAGATGCGGTCTTGTATATGGATGCAACTTTATTTATTAACTTTGTCATNAGTGACTATAGAAAATTAAATTCANTCTTAGTTTTACTNAAC
GATGTTTCAAATAATTTATATTTATCAATAATAGTTTTATTATCAATAAATGATTTCATTCCAATATTTAAATCTATGTCCAGGGTATAAGANTTAT
GTATTAATCCAACTGATAGTTGAGTTTCATTACCACTATTGTTAAACTTAATATTATTAACTGAACATATCTGATTATTAATAAACGATAATAATAG
TTTAGAAATAGTTTTAATAACATTAACTTCATAATCATTATTAGTACAAGCAAGTGCAGTTGTCATGTATCGACTAACTTGACNAACATCTAGTTTC
TGATAGNNACTANCACTATCTANCCATGGGTCAATANTTAAAAAAATCCTTAGACTAGCTAGAATATCNGAAGATGTTTCAGAATAAATGAAAAACA
CATTATTATTAAGATCATCTTTTAGCCAACCACTAAGTCTAAGATTTTCTAGATCTTTTTCATTAGATACCGATTTAAGTTTAAGTTCATCAAAAAAATG
AGGGTTAGCTAGGTTTAATAAACTCATTTTTATAAACCATTTTATTATCCTCTAATTTATGTAATTACATGGAATAAATAACATAAGTACTTTTA
TGACTTATGATTTGATTCTCCAGGAGGTTTTCCCAATGGCAACTATTAAAGAAGTCCTTGATAGAAATTTTAAGGATGTTCAATTTGATCGCGATTT
ATGTAAAAGAATTATTGACTTTACTATCAGTTTATGAATAGGAATGCTGATCACTCTGCTTTCTTTGGTGGTGTATTACTAGGTGTACAACAAGTT
AAATTCTTCGATACGGATCGTGAGATTTGGTATGATGATGTTTTACGAATTGATGAAGCGCTGTTAGTCCAAGATTTTAAGTCAGTTGAATTCATTG
ACCCCTAACCATCGTGTAATGTCAGATGTATTCAATCATCTTCCTGCCTATATTTGTTCTAGGCTTTTAAAAACAACTAATGTTCCTTTGAATATTAG
ACATGAAGCAATGGTTAGTTGTTCATGGTGTTCATTTTAAATATCTAACATCTTTACTTGTACCACGCTTTAAATATCCTGCACGTAAAGAAGTA
GCCGAAGCTGCATTCGCCGCACTCAATTATCGATTTGACATTAAGACAATTGGGTCATGGGAGAAACTATTTAGGCAACGGCGTGAAGGTATCATTG
CACCTGATTCTATTTATGCACCTTTCTTAACTGGTAAAACACAAGAACTGGATTATTGGTCGGTCGTGTGGTATCTGATACTCAAACACGTCTACG
TGAATTAATCAACAAGTACTATGATGTTTATATCAGAACACTGCAATCAGGTGGTAAATTAGTTATTTCATCGGATATGGCTGTTAATTCTGATGGT
GAGCAGATTCTACGCGATAAGTCTACTGGGTATCGCTCATATCTTACTTATATCCATCAAGTTGCGCAACAAGAACAAAATTTCATTAGACCTGAGT
TAGTCGGTATTATTGAAAAGATAATGCCCACAATGCCACCAGAAATGTTCATGGCGACACTTAGACACCCTTTCCCGTAACATCGGTCAACCTAGGGC
ACAAAAGCTTGAGAAACTCGTAGATGAGTGCTTATTGTATGCTTTCGATTATATGCAATCACTCCGTACAATGGTTGCTAGAAATAATGATCTACAA
ACATTGCTTGTAAAAATACGAGCAAAGATAATGGCATCTAAAACAGAAAATGCTCAAGTTATTTTCATGCGTGAAGAAGGTGAGAAGTTAGTTAGGG
```

Figure 7(E)

```
ATGCGACTAATTCTAGGGTACCTGCATATATCGCAGCAACTAGGACTGGGTTGATGTTGTATTTAATTCTACGTGCTATGACTAAGAATTACTATAC
AAAACAAAATAAACATAATGCCCTCCCGCAATGGGAGGGCTTATGCTGTTAAGTAACATTAGCTAGATTGATCATTACATAAATTTTTCAGAGCATC
GTAAATAGCCACATAAGTAAAATAGTTAAACTATCTTTAATTTCCTTACGTGGGGTGCCACTGAATCCACCCCATGACATTTGTATTACTAACNC
ATACAGTGCTAATAGCTGGCTCATGATAGCCATCTACTTTACGCTTTACGCTGTGCATAAACCTTAGCCGTAATTTCTCCACGTAACTTTTTGAAGAAAAC
TAGAGCACCCGGAACGACTATACGTTTATTACCAATCTTCGTAATAAATTCTTTACGATTAGTAAAGTGCTCTTTTAATAAATCATTAATAATTTTA
GTTAAACTATCAATTTCATTCTTCATCGACACGTTGTTAGTTCCTTACAAATAAACTTGATAACGTGATCACTTACAAATTTCAATGGACCAGAACA
ATTAGATTTCTCAATAGCGGTTTCAGTGTATGAAATTATTTGATTTCCACTTAAGGATAATGAATCAAATAATTCATAAGAGTTATTATTTTATTCT
TAAAGGATACTGCATATTGACTATTTCACTATTGATGCAAAATAGGTTAATAGCTGGGATAGATACAGAGTTATCTGAAGTATGGCTATTTTCCGTA
ATATTCCAATTACTGTATACAGTGAAAATATTTGCAGCTAGTAAAAGGTTGGCATTAACCGTTTCTAAACTAACATACTCCACAGAAGTACCTTTAT
GCCAATATAGTTCAATTGGATTAACCCAAGTATACCCAATGGTTTTATAGAAGGCATGCATTACATATTCTCGCCAACGTGTGGGTTCTTATTATC
AGTTAAAACACACGTAATATTGCCTGACGGATAAATGTGGTGGATGCTACATGCATTAATTTCATCTCTAACATTAGTTGTTTCAGTAATATTAGAA
TGATCCTGTTTGAATAGCCATTTTAAATGACTATTAGTTGTGTCATCACCTTCCCCATTTGCAATGTCATTTCTAACCACTTTTCAAATGTAGCTT
GTCTATCAGGTGTTGGCATTCCCCAATAGGTAGCTAAATGAAACGATAATAGTATCGAATAATATCATCATCGTTAAGAATATTTTATCCAGTTTCC
AGTGATGTTGATACTCGTATACTTCGCTTGGAATATTATTTACTTGATACCATGTATTAATTAATACTTGAATTGTTAATTGCCGAATACTCTCACT
TGTTAGAGTGTAATATTCCCTGCTATGCGGCTCTTCAATTGTCACTTCTTGATCAGTATAACCAATGTATTTAGGTTTACCATCGATGAGTGCAAAA
TTAACATTCCATGATGTATCATTACTAAAAGTGATATTAATAAAACCTTGTTCAAAGCTAGGCTTCACTACGAAACTGACATCATCCTTCTGATATG
TCATTTGCGTTAGAATACCAAAATTAATTTTAGATGTAAATTCTTTATCGAAGTTATGTTTATAAAGTAATCCTAGTAAACAATCAATTTTATTAAT
AGTGTGGTTTCTAATAATAAATCAGTATTTGTAAGTTCATTAATTTTCATTTTAACCTCTCTAAAATTTACAATCTAGTTTTACTTATTGAATAAG
CAAACATGTAATATATATCTTAATTATTTTTAGCATAGTTTTTAACAACATAAAGCCTCCCCGAAGGGAGGCGATATGCTTTAGCTTTTTGGTTAGT
ACCGACAGTCTGCTCATTCTTTTCAGTTTGACATTTCGCCGAAGTTGACTAACCAGACCATTGCCAGCCGCAACTACATCGGGAGAAAAGAATGCA
TTGATATCAAAGTTCTGATCTTGGTTGCGAGTCTTCCCAGGTGGGACCATCGGATATACTTTTGCCATTAGCTTAATCCTACACCGTCGTAAGTTAC
CCGATTACCAACTGCACGTTCAATCTGGTCTTGAATACCATTACGTGCACGTAGTACGTCAGCAGATAAACCACCCCAGTCTAATTTCTGGTTATTG
GGGTTCATACCGCGAATGTTTAGTTTACGGAACATTTGACGAGCGTATTCTTGTACACCTTCAGAAACATCAGTCAGTGCAGAGAACTCAACGTTTA
GATCAAGGTTCTGACCAATCTGTGATGCATCTTTACGGTTTTCCCAAGGACCAGTAGTTAATGGGAACATGTTGGTGCAAAGATAAGCNTTAACGCA
ATCCTGGAAGGTAGGATCNGGTTCTACGAATAGAACAGTCATACCGTAGAAGGTAGCGTCGTATTTCTCAACCGGTACAATGCCATCTGATACAATA
CGCGGTACTTTGGTATTCTCATCTGCAATACCATAGTTGATCCACCATTGTAAGAAACGTTGGATAGCGCGGTTTTGTAATTCCCAGCAACCAAAGT
TTGGGTTAGACCGGGCACGGGTTACGTTAGTAGCCGTTGGATAACTTCACCAGAACCACCCCAGGGTGCTTCAGCGTTATCTACAGTAAGCGTACG
TTGTAAACCATCGATGGTACGAGTATGCGTTTCAACGAAAGCCTTAAGACATGCAACTAACCAGTTAGTATTACTAGCATACTTAAAGAATCGTGGA
GCATCTAGTAGGAACGGCACTAAGTTACGTGCCACATATGGCGTGTTAGTAGCCAGGTTAGCTAAGTCAGGCCGAAATACGTTAGTACCAGCCTGAG
CAAGGTTTACAGTGTTACGGGCACCACCAGCACCATAACCAGTCTCGGGTGCCATCGGATCATTATAGCGAGCCATTTAACTTTTCCTCATTCTGAA
AGCCACCCACTCATTGCTGAGCAGGTGGGGTTTCAATACGAACAGTTTCCAGATTGAAGTTCAACGTGGTCCGCGGGTTATTAGCCTCAACAGTTAC
GTTGCAAGTCCAGCTGGTGCCGTTATTTGCGTCAATCGGAGTGATCTCTGTACGCGGGATAATGTTGACACGAGTACCGAACATATCACGTACTAGA
TCGAGAATATACTCGTCACAACGCTCAACTAATTGTTCAGGTGTTAGTGTAGCATTACCGCTAAATTGAGCGTGTACTTTATGGATCAGTCGGATTA
ATACACAGCAAATATTAACAGTAATCGGTGATAGAAGTACAGATGTATCATCTAGCATTACTGAACGTAGGCACGGATAATAGGAGCTACGATGGTC
ATATGACTGACTCCAAGTAGCACCATTCGCCCAAGCTTGTGCCCGTACACGATCATCAAAGAATTTAACATTTAGATCTTTAACAAAAGTAACACGG
TTATTAGGACTTACATCCATTTCCATACCTGGAACTAGATTACCAGTTCTGCCAGCACCTGCATAGCGTGCCCATGACATAGCTACGTCTAAAAGCTGCG
GTACATATTTACGATAGGTACCATCCATTAGTTTGCCAGATTGCATTACAATCATAGCGCGACAAACACCAGTTCCGTATAGATGGATTCTGGGAA
AGCTTTTAGGCGAGTGATAATCTGTTGAACACGACTTAGCTCAGTAGCTTCATCAGGTAGACGACTATCAGTTTCTACGAATGTAGTGAAGAAATAT
TGTAGATCACGCCGCGCACTTAGTACGCGCATTGCCCGATATTTTGATTCCATCGGAAGGCCAGTGTCATAAAGAACACCGAACTGATATTCTGCAA
TGTTATTATAGCGATCATTTAATTTGCCAAAGTTAATATTTTCAATATCAACTAATTTGGCATATTCTTCTAGATCAGTTGTACCGTCAGTACCACC
ACTAGCATAGATGTTACCATCTTTACCTAACGTAATGCCGCCATCTAGTGGACCGAGTACNTGAATACCCTGGTAAGGATCACCATCAACAGCTAAG
AAGGTTAGGAAGTCAATTTCAACAGGTGCAGTAGTATGCGCAGCAGCGGCTGGGTTAACTCGCATCTCAGTGTCATAAATCATCTGACGAACAAGAT
CAATGTTCTCATGATAGACGTAGAACTGAGAGAACGGTGAATAAAGTGGACTTAGGCCAGAGACTACACCATCATCTGAGTAAGAATCAACTAATAC
ATCACCAACATAAAGGTCAGCGTTATACATATCGCTGTAAACACCTTTATCAAATGTAATGTTTAGATAATCTTGCTGGTCAGCAGTTTTGACAATA
ACTGGACTAGTGCCTACTTCAGGCTTCTCAATTAACTGAATACGAATTGACGAGTTTTAAACTTCGCCATAGCTGCTTCATCGAACTCTTCGATAT
CAGCAGTTGTAGTACTCCATACACGCATACCGTTAGAATCACCTAATTTACCAAAGAAGGAAACCGGTGCTTCAAATAACGGATATACTAGTGATTG
AGATCCATCTTTATCTGATACTAAAGTACCTGGTAGTACACGTTGTGTACCTACTTCAGGAGTATTATCTTCAATAAGAATAATACGTGCCTTTAGA
CCATCAACTTTATCAGCAGTCGGGACTGGTGCATTACCAATGTCACGAACACTGTTTGGATAGTTGAAACCACTAAGACGACGAATCGTAAGTGGGA
TTTCATCTTCCACAATTTCAATAGCAACAATTAACCGAGATGGATTAGCTGCATCTTCAGGACGTAGACGTTTAACATAAAACCATTACCACGGCCA
AGAAGGTTAAGTGCTAATAGTGATTGTGTATTGAAAAACTTACTACGTGGATCAAGCGATGCTTGACCATAGATGGATGCAAAACCATCATCAGAAT
CACCGACATAAGTGGTTTCAGTCGGTCCTGTCTCAGTGAAGAGACGTAATAGCGGACAGTGTTGTGCGAACGTGATGTCCGGACGGATCAGGGGCCG
GCGGCTACGATCCCGGATACCATTAAACACAACCCTAGGGACAGCGTTGTAATATGCCATCTTTTTGATTCTCCCAAGTTGGAGCTTTGAACTCGAT
GTTATGAGTGTTAACTAACAGTCAATCATAGATATTAATCATAGTTGACCATACTAGTTATTTTTTACTATCCATTTAAGGAGTAGCGGTAATGTTT
TTGCTACCGTATGAAACTACAGTTTGTAAAACTCTATACAATCCCACCGGCGGTGGAAAATTATATCCTAAACAATATGTTGATCAAATTGAAAATG
CGATCAAGAAAGCCAATGTGTATCTACCCATTCCACCTGTTGATGCACGTAATGGTGAAACGCTAGAGCATAGTGGACAGATTACCCCAGTTGATGA
TTTTGAGGATATTAAGAAATTTACTCAAATTGTCAATATCGGTGATCGTGATAATCCTAAGCTAGTNGTTGATGCTCGTCTATATAAAAAGATTGAA
CAGCGTACTGGTATTCCTAGGATTATTCAGCAGAATGAGTGGCAATTCCAATATATTCGGATGGCACTTAATATCAAACTATTACGTGAAGGCCCGG
ACTTCCTCCATCGCTTAGGTGATATCCCAGTTAAAGTTTTCTATAATTGGATCTCAGGCATCCTAACACAAAAATACAGCCTACCACCTGAATCAAC
CCAAGCTATTTGGGTAATCTGTGCTGTTTATTACTTTGCTATGCAAGATGATGNTCAACAGAACCAGNTCAGGAACGNGATCGGTTAATACCAATT
ATTTCCCGTCTTACATATATTCCAGCTGGTTTATTCNGATGTTATTGATACATTAGGTCCACTTCATAATGCCGGTGATCTAGCTTATGAGATTT
CAACTAANGGNCGTTCGATCAGGATGGGTAAACTAAAATTCAGTGATCTACAATTATTAGTATCACCGAGTTGGTTTGGTACCGCTTCCCGTGAAAA
CGTAGGTGTGGCACTAGAACACATGCCAACTTACATCACACTGATCTACATGGCATTAGCTGATCGCTCATACCGTAAAACAGTTTTAAGTCAGAAA
GTTGAAATGATTTCACGTTCTGATGATGCAAGTCGTTTTATTAATCTAGTGAATGAAGCTGTAAGTAGCCAATTCGTTAAGTAAATATAGGGGTGAA
TCAATGAACGCATATCTATTGCGNCATGCGATTGATAACGTTTGGTGTAACCCAGCCCAGGACCGACAGTTTGTTTATGAACTGAAACAGCTNACCC
CACGCTACGGCGTGAGGGTAAACTGGGTGGTTGATTGATACATGACCCGGTATAAGCTACCAGTCCAAAGTACACGTGATTATTGGCATCTTTATCAAATTGG
TAAAATGATTCCTAAACACCTGGGCTTGCCTAAGGTTTACAATAAGTGGATGAGCCTAAATGAGTTGGCTCAAAACCATTTAAATTTAGCAGACGTT
TATGTAAATAGTGGTATTAATTATTCACGTAATGATACATACGTTTTAATAACCAGTTCGCAAAATCTTTTAATTGCTGTTAAGATAGATCCATTAT
TCCCTGATCTCGATGAAAATCAACCCTATCTTCATGTTTATAACAATGCTTACTTTCAATCAAATAGATCGGATGTAGCTGGACATAGATGGTTAGT
TTCTGAATCGTATCGAGTTAAAACAATATCTGAATTAACTCAGATTAAGATAATGGATACCATAGCATCTAAAGGTGGTTCCTAAATAC
TTTGTAAATGGTAGATATGTTAATGAGATATCTCCTGTTACAGCAACAGTCGGTGATGTTTGTGATTTCATTCTAGATCCATCCATTAAAAGGATGG
TAGATTTTGATCTACGTACATTACCTGTTTTTCATGTCAGAAATAGATAGTGAAAGAAATATATTTTACACTACACTGATAAGACTGTGCAAACAATT
```

Figure 7(F)

```
GAGTTCTTTGATGATGTTGAAGCATATATCTATCAGCCATTAGGTAATAATCGTTATACTGGTGTTAATTACCATCATAACGAGAGCCGTTGGATGC
GGATGCTTACACATAAAGATTATTCTATACCAACTGCACGAATTGATCAGTTTAAAGCACTTCATCCAGAAGATCCTCGACGTGGTGCTGATCCTAC
TCGTTGGCCAAGTCAAAACTGGAAAGCATTAGATAATCTAGTATTTAGAATCTACATACATCATTCTGGTTATGATCGCCCATTAGTTGCTGATTCA
CATCGTATTCAAATTCTGTATCGTTTAAAATCAGAAGATATCATAAGGGCTATGACTGGTGCAGATTCTGGTAATCCTTTATGGCGAGCTGAAAATC
TAGAGCAATCACCATATTGCTGGTTCATGTCAGCACCATCTAGTTTCGTATACCCATTAACATTCAATCTACCTGAAGAAACATCGCCTAGTAAGGT
AGAAGCGCAGAATATGGCTGGTGATGTTTTTGGTTATTATGAAGCAGCTAATATTCAAGGTTATAATCCAGCTTGGGTTTATAATGATGCTGGTCTA
AAGACCGCTGATTTACGATACAACTACTGGCTAGATGCAACTGTATTTGAGTATGATGAGAAAGGTATCTTATTAGGTTATAATTATCATACAGCAG
GTCGCAAATATTTCCCTAAAGATAGTCGTTGTGCATATGTTGAATGCATTAATGGTAAAGGAAGTGTAGATCTACATGAAGCATATGGGAATGATCC
CGTGCCTTTACGTGATGGTGACAACTGGCGAGTTTATGTTAGTCCTGTTTGGGCTGGCGTACCAACTGGCGAATGGCAAGATATAACAGACCATCCA
GATCGAAACAACTGGGGTTTTTATGATGATACCACTGATGATAAACGTTGGGTTTGGATAGCTAAGTCAAATGAGTGGTATGGCCTAGTAAGAACCG
ATGAGTACTTCTATCTAAAAGAATTAAAGTTTAATAAAACTGATGGTATCATTAAATGGAGTATACGTAATACTGAAACTCATAATGGTGTAAAAGT
CGATAAATTGATGGAGATACCATTTGGTCAGTATGATGTGTTTGTAAATGGTCGGCCTATCATTGAAGGTCTTGATTACACGCGTGAATGGCCTCAA
ACTGTATTATGTAATCTGGAATATTTAAATGCAGATCCAAATGCAGTTAATACGATTCTTCTACGTGGAACAGGTTTCCCAACACCAGATTTAAAAC
CATACGAACCTGGCGAGATTGGTTTCATTGAGTATGGCGTATTGTCTAATGATGGTATTTATAAAGTACATTCAAATAAACAATCACGCATAATCAT
TGATGGTCATTATCGTGACCCTGCTGATCTTGAATTCCAAGAAGATCAAGGCACTACTGTTATCACTGATGAACGCAATGGTGCACCATTCCAAATA
CAAACACCACAGGCNCGCTTCCGNGATGTTTATAATGATGATTACCAAGCTAGGATTAAGGATGATGCACGGGATAAACAAGTCACTGATTTTATGA
CTGAATATTTCCCAATGAAACCTCAACCTAATCCGGACAAGATCGATTATAGATACCAGGTGCTTTCAGCGTTTTCATGTAAGATCATTCATGATAT
CGTAAAGAATATATCAAACCNCCATATCAAATGGACGGTATAGTGACGATGATATTGTTAAGCAGCTAAAAGATTACGAGTGGTTAGCAGCTTAT
GACATTATCAATAAAGGCTACAACAAAAATAAAGTTGTAGTTTATCCACATTGGTATACTGAACCTGTAGAACTAGATATTTCCAATGGGAATATTT
AAATCGTATTCTATCGATATATCTACGTGAAGTACCGCCACTATCCTTGTTCGTTAAGATTAAAAGGAATCAACCATGACAACGTCATATGAAAGTA
GCCAGTACCAACCACCACAGCATAAAAACCATTTCTGGTTTAGAGGTGATATTGTCTCATATGCTGGTGANACTGGNAAAGCAATCCCTGCTAAAGG
AGATTTAGTATTTGACGCAGCACAAGGTTGGTTTATTGTTCGTGAAGTTGATGAAACAACTGGGGTATCTATCTTAGATCCATGGTACATGCCCCAA
AAACCAGGCAATGAAAATGAACAAAACCTACTAGTTGCTGTAGGTCCAGGATATAGCTCAGAATCTTATCGGTTATTCCTAGATCAGTCTGTAACAC
CATTTAATATTTGCCCAGACCGGCGATTACATTTTTATGGATCAATGGTGCATGGCTATAAAGTTTTCCTAGGTTCAGATATATCAGAAATACATGG
TAAAGTGATTTCCCTGTTCTATGATAATGCTGGTAATTATCTAGGGCCAACTATACCAGTTGAATCAGTACCCGATCCATTGACTCAACAGAATGTT
GTTAAAGCGTTAATGAATGGTAGGACTGCTGAGAAAATGCAAAATGGTGAACGTGTAACTCTAGTAGCTTATGATGACGTGGGTGGGCCTGTTTCGA
TTGCTCAACTCGTTGTAATGAATACTGAAGTTATAGCNCAAGAGGATACCTCNAAGAAAATATGTAGGTGGTATCACTATTGAATCACCATTCATCTC
NCCAGCTGATCCNAAAGTTATTGAGTTCCCATTAAACGTACCAGTTGAATCATTACCGATGATGGGTGCTGTTCATTACCGTGATGGTAAGAAGCAT
GTGATGAATATTGATGGTACGGCAATGGCAATTTATGGTTTACGTAACTATATTGCCACTGAGGAAGGACAAGAGTTTAAATTAACTCTATCTTACC
AATTAGCACAAGATGAGTTATCATACTTATCGACTCCTTCGGCTAACCGTCGTATTCAGGAGACATATACAGCGCGTACCACGCCTGTACAGGGTGC
TTACAGTTGTCGTATGTTTGTTTATCCNGCTTGGGTTAATGAGGCAGTNGGTTACAGATTAGAATTCTGGTTAGCCAATATTGATCGTCAACAAATT
TGGAATATTACCCCATATGTTGAATTAGGTGCAAACTCAGCACCCTTTAACCCACGTGGTTATGGTACTATCCAAACACTAACATATGCGGTTAACC
TAAACCAAGTTGATGGACGATTCCTACCAGTTCGATTTGCATCTACTTTCCAAGTAGCACTATTGAGCGCTGGTAATAATCGGAATGCTAACTGGGA
NATCTATTCACGCCCTGANCAAGGTGAAGCATATGGTCGTGATCTTAAAGCCGATATNGAATTTATCAATGGTAATCTTTGGGATCTCCGGTTAGCT
AATGGNGCACAGTCACAAGCTGCCTGGCTTAAGAAAATGTACTTTGCTGCTGAGCCATTAACTGGTCAATGGAAGCTACTCCNCCNACACCTACGC
ATTTCCGGGTGCGTACAGTGCATAACGAGTATGAGTATACGGTAAGTCAATGGAATACTGCNTTNCGNATTAATGCTCAAGATATGGCCGATGGTGC
TTTACTACAANTCACCTGGATTCGTCGTGAGTATGATACNGACCTACAGTTAGCCATTACCGCATTACCTTGTTTACAACGTTAAATATANNGCCCC
CTAGGNNNNNCCTAGGGGGCTTTATAACGTCTTTTAACACATTATCCATATGAGACTATACTTTACAATTGCCGTTCAATACGGCTTTATTATGGCA
CATTAAAATAAGTACCTTAAAGGGCAGTGTATGGACGTTATACTTTTCAATAGTGATTGGGATAAATACTACAGCGCTAGTGTTGATCTTACTACTA
AAAATAAATCNTTTATAAAGTTAGCNTTNACTTATAAAAGATGGGTATTAAAAATTACAAATTTATACTAGCTATATTGGACCAAGGTTTAATTGG
GGTGGATCCATATGACCCTAATCTTAGCGAAGAAATGAAGTTNCGTATTAACATGGAATGCAAATATAATCCTTGGTATTTTTTAGGGAAGTGGCA
AGAATCCCCCCTAACTCGGGTAATAANCCAATTCCATTCCAAGCTAACCGTGGTAATATTGCTTTATTCTGGTGTTATTTCAATCACGTAGATTTTG
GTTTATTACAGCCTCGTCAGACAGGTAAGTCCGTATCAACTGACGTGCTCAATACAGGCATGATGTATATCTGGGNGAGAACCATAAGATTAANCT
TATTACTAAAGATAACAAACTACGNAATGCTAACATCGAGCGTCTAAAAGTAATGCGTGATTTGTTACCAGAGTATATCCACTATACNGATCCATTA
GATGCGGATAACTCCGAATTGATGACATGTATTAGATTAGGTAATAGGTATNTAACAGCTGTTGGTCGAAATGATGTTAACGCAGCTGATAAATTAG
GTCGTGGTCTTACTGTACCAAATATGCACTTTGACGAACTTGCCTATATTAACTTAATTGGTGTTTCACTACCTGTTGCACTTGCNTCAGGTTCAGC
AGCTCGTGATGAAGCTCGCCGTGAGAACCAGCCTTATGGTAACATCTATACAACTACAGCTGGTAACATCACTACCCGTGATGGTGAATTTGCATAT
CACTTCTTAACAGGTGGNTGCCCATGGTCAGAGGAATTCTTTGATCTACCAGATCAGAAAACTCTACATCGTGTTGTAGAAAAAGGCACTACTGGAA
AGAAACCTCTAGTTTATGGTGCATTTAACCACCGTCAATTAGGACGTACCGATGAGTGGTTATATAACACACTTCGTGAATCAGGTTCATTCGGTGA
AATTGCCGATAGGGACTTCTTCAATATCTGGACAGTTGGTGGTGAAGGTTCACCCTTATCATCAGATGAGAAAGATAAACTTAAAAACAATATGCGT
GAGCCAAGCTGGACAGAAATCACNGATGATGGTTANACACTTCGTTGGTATATACCAAAAGANGAAGTAGCCTCACGGATGATGAAGGGTAGGTTCG
TTATGGGTACCGACCCATCTGAACTTCTTGGTGAAGATAATGACGCCACTGGCACAGTTGTAGTTGACGTAGAAACACATGAGGTTATGTGTGTTGG
NAGATACAATGAATCATCAGTNCCATCAATGGGTAAATTTCTTTGCAACAATGCTATTNANATATCCTAATATTCTTTGGATACCAGAACGTAAATCA
ATAGGTATATCGTTAATTGACCATGTTTATCTTGATTCTNCATACTAAAGGANTAGATCCATTCCGGCGTATCTTTAACAGAATTGTCAATGAATCAT
CAGAAAGAGAAAATGATTTCAGAGACATTCAAACTCCGNTATCAGCAAGACAACCATCGTTNTATGATAGGTTTAAACGTTATTTGGCTATGCAAC
GTCAGGTACTGGCGAGTATTCTCGTGATAATCTATTTAAGGTGGCATTACCATCAGCAATGCATTATGGGGTAAGGACCATCTATGATAAACCACTT
AGCACGGAGTTATTAGCACTTACTATCCGTAATGGTAGAATTGACCATGCTAAGGGGAACCATGANGACTTAGTGGTATCATTATTATTAGCCCANT
GGTTATTAATACAAGGTAAGAATTTATCTTATTATGGTATCAATGTTCCCATCTTAGGTAAATCAAAATTACGTGATAAAGAACCAAGNCAACTTGA
AAAATATCATGAAGAGAAAGAACCAGCAAGGTCGNAAAGAATTGAAGAGGATTATTGANCAGCTTCGCGGTGAAAAGAACCCGATGATTGCAGCTAAA
TTAGAAATGCGNTTGAAACAATTGTCTAAACGTGTTAATATTGATGATANCAGTGGTGTAGGTATTGATGCCATGTTAAATCAAGCTCGTGCAGAGC
GTACACGTAGAGTGCGTATTAACAGATATTCTAGAAATAGTTGGTATTAAACAAAAAAAATAATAATACGTTACCCTCTTCGCAATGAAGAGGGTAT
TTGAAGTTAAGNAACTCTAGCGAACAAAAGATTACTGGAGTTAGAATTAATATGATAGTTAGACGATCCGTCAATCCATTTAGCATCGGAAATCTTG
TTTACAAGCTGACCATTGCCAATGTAACCTAGGAAAGTTTTATTATCATATACAGCAATTTTGATTAGCTCATTTCGTCCGTAGACTAGTGGCTTAC
CATTGAATGCTGTTACTTCTAAACCAGACATGTATCCATAAATTGGATCAGGTCTGGAACTTGTTTCAAAGACTTTCATTCGAAGTCTCATCTGCAA
GAAAGCCCATTTTGGGCAAAAAATGTCAAGCTTGACGACATATAGCCCTCCTGGTGCGACAGGAGGGCTAATCTTTTCAGAACGTACGGTG
TTGTTATAACTGCTACGCAAAATACCCATGATAGGTAGGTAGCTAATCCGCAGTTCTCTTGGATGATACCTACTGACAGTGTAGTTGCAAATGTG
CTGTTTGGAACCCCACTGGTTTAGCGGCCAGTGGGAATTCCTTTATGCCGCTTTTCTTTCTTTACTGGATATTTCTTATATTTACAAACCCACGT
TCTTACGCTGGTAGGTATCTTCCTTCTTATTATATTCGTAGTTCTCGATGAGGCACTTGTTGCTGAACTCGACCATCGAACACATCTTGTCCATGAT
GACTTCAGATATTTACCATGTTCATAAATTCGGCGTAGTTGTAGCCGGTATTCATGTCGAGATAGTCTTGTTCGACCATATCGTCATTCAGGTACTT
GACGTAAGCCTCGGCGTGAGCAGTGGCTACCGACTTGGTGAAGAAGTAACGAGCGTGCTGACGGTTCTGTTCGAACTGACGCAGATTAGTAGTGGCC
TGACCGCCGAAACCATTGACCTCCATTACCCCGTAAACAGTACGATCATCCAGAGTAGTGATCTGTGCAATCACTACACGAGAAGCATTTTCCGAAT
```

Figure 7(G)

```
GGTCGATGAACGTCATACTGTAAATCTCGATTTCTTTGAAGTCTTCCATTAGAATTTCCTGTTAAAAAAATGAATAGACAACCCCTACCTTCGGGTA
GGGGCTTTATGCCGTCAACCGACAATAAGGTCCCGAATCGTTACGATCTAGGTATCAGATGCAGGTTTAGTCAAACGAGTTACACGAATATAAACCA
TGTAGTCACTCAGAGATAGAACTTTTTCACTTATACATCTTCCAGCGTCATGATTACGACATGATAAGGACTATCAGCATTGTGACCCATGCACGTC
TCGCATTTGAAGATCCGCCACATGCCATACGAAGGCAGCTCGCGGTTTTTCACATAAACGTAGTCGTGCGCTGCCACGAGGTATTTTTGTTGAATCG
AGAATTCACAAGTGATGTAACCTTTTTCACGGATGAATTCTTGAGTCATCTGATCAAAAGTCTGTTTGAGTTCATCAGTAAGAGCGACTTGGGTTTC
GAACATTGAAATATTCCTTTTGATATATTAAATAGTTTTGATTATTTCGGAGTTATTGAATATTTAGGTTACCATCTGCTCTATATAGACTCGGCTG
ATTTCATTTAAGTAAGCGAGTGCCAATAGAATACCAGCCCAAATAACAATTTTTCGAGTAGTCTGTTTTTCTATTACACCTGGGTGTGATTCACGAA
TACTACGGTGACAAAATACATAAAACAGACACAGACTCATTGTAACAAAGATAATGGTAAACCATCCTAGATAGATCATTTTCTTCACCTATTTTTA
TAAATAGAGTTTATAGTTTAGTCAGGCGGATGATTTCTTCTAAAGCTGCATCAACTTGATAATACGGCCATGAATCAACACGAGGTTCGTTATCAAA
GTATGTCCAAAGTTGAATACCTTGGAGTTTATTGTAGAATACATTGATTCTGATTCCTTCATGGCCAACAAGACCTTCAATGTAAGCTGCACCATGC
ACATACGTAACATGTAGTGCGTACTCGCTATCTTCACCAGCGTATTGCATAGGTCTGGAGTAGATGAAGGAATAAGGATTAAATGGATCAGCCTGAG
TGATATGTTCGAAGAATTCTTTCAAACTAGATTTTTTCATATTGGACATTATATTTTCCTCATGATTTATTAAGTCTATCTTCAGGAGGTAGACTT
AATACTATTCGATGTTATTTTAAGACGCCTGCCTTGTAACCTTTAACAACAGTTCTAGCTTCTAATGCACTGATTTCGCCAATGTGTTTACGCAGTG
CTTTAATAGCGTTGATGGTAGGTTCATTATCCGCGATATGTCGCCAGTTTCCCTTACCCTTAATGAGTTCAACATCCTGGACATATAGACCATCTTT
AACTAGATCCATTGTTTCTACCAACTTTTCGACTTCTTTAGTTAGATGCGTATGAAGACTGGCGAGGGACATGTCAGTCATTTGATGCACATCATAG
AGAAATCCCTATTATCAGAAGACGATAAAATTTCTTTGGTGAGTTTATTTACAGTGTCAATGTTTGCTGCAATTGAAACTAGCAGTGCAGCATATTT
CTCTGCATTATAATTCATTAATACGTATTCCTATTTAAAATTGGATTTAGTGTAATGCGGTAATACTGCGAATATCTAATTCATGTAAATCATATTT
CTTTAGGAACTCATTCACCGCTTGCTGAATGGTGTACCCACTCGGAGATTCCCACTGAGTACCATTAAAAGCAATAATACGATAACCTACCATTTTT
TATTCCTCTAATCACAAAATAAATACCCTCCCGAAGGAGGGTATTTATATCGTTACCAATTGATTACAGCGACAAACTCAAATACCCGACACAATTC
TTTATCACGATGGGCATGATGAAAAGATTTACCTTCAATACCGCAATGACGATAAAACAATTTTCGGTGTTCCGTGTCGCCGAACCAGAAGGTGGTG
TTATTGGAATCAACCACACCATGGATAGCCACATCACGAATGTACTGAAATACATGAACTGCCTTATCGATGATCGAAGTTCTACACCGTGTT
CCTTCATCATAGCCAGGATGTCTTCCTTGGTGTAATCTGCTTGTTCAGCATTGGTCATGATCTTGTGAGTCAGAGAACGCTTTTCCTTGTCACCGAA
ACAGATACAGACCAATTGCACCAACTGACCTTCTACCTTGAGACCACTGGTCGGTTTTAGTAGAACGAACTCATCATATTTGTAATCATTGGTGACA
ATCAGTGCCGACTTATTGCGAGTGACAATGCCTAGGTTATACGACATAATTAATCTTCCTCATTTTAGAATATGTTGAACCTTGTGGATGTCTTCCA
GGCTATGACCAAGACCAGTGGCTTTGTAAGAATGTTCCTGATCAACACGCTTGTGATATGCAAGCAGTGCATCTACTGGATGTTCAGCGAAGAAGTA
TTCAGTGTTGTTGCAGTCCCAAGCGAACTCCCATTCACCATCACGAATCTCTATTTTGTTGACACTGAGGTAAGTGATATTGATGGTATTTACAGTG
GCATTACCACCAATGAGGTAGTACGATCCTTCATTGCTACGAACATCGATCCTGCCGCCATCGATAGTATCCTGATAGTAGAAACCACGGTCGAAGA
ATAACTTCAGCATCGAAGTGAAGTAGCTGTTCAATACAGCTTGAGCATCTTTCTCTTCGACCACCCATTTTCCATCAACGATGTTATTCAGGTAATT
ACGATCATGATTGATCCCGACATTATCCACGATGTCAGCGTAGTTCTTATGGAACTTAGCAATCTCGTACAAACGTTCCAGAGCAGCAAAACGGAAA
GGGCTGGTGGGATGCAGAGCCAGAATGATCCGACCTACGCTCCACAAACCGGTCCCGTTGACCTCGTAACTTTCTTCGAGGTAACCTTTGATACCAC
AGTTAACTTCAAGTTCATCTGCTGGGAAACCGGTGCGGAGCCGCCTACGGATACCCAATAGTACCGATTCGGATTCTTCCGGATCGAACAGGTCTAT
GCCGAAAGTAATCCAGCTACCACGTACTTTGTGCTGGTATGCCAGGCGTACAGTATCACCGAATGGAGAAATGAACCAGCGTTCGTCTTCCGATACG
ACCAAATGGCAACCACATTGCCACAGGGTACTTAGAGGATCGTTAGAGGCGAGAATGCGCTTGGTGTCGTTCATATCCGACGAAGTAGCATCTGGAC
TGCCATGTAGGTGTGTCAGAATAAACAGAAGCGATGATTCTGTAGTTTGAGCACTCAACATTGCGCGAGTGATGGTTGCATTGATGATCATGAGATA
TCTTCCTTTTTACAGTTTATGAATATATTGCTAAATAAAAAAATATTACGATGTAGAAAATAAAAGGGAGTCCGAAGACTCCCATTATTGCGTGTAA
TCTATTTGATGATAACCGCTTTAGAAAGAGTTTCCATACTTCCATAACTAATTTGGATTTCTCTTCTTCAGGGTTCNCCATTGCTTCACGCAGGAG
TTCACCAATAGTTTTGGGTTGAACATCATCACTGATTTCACGCGAGCATGCCGAGTCGTCGTACATATCAAACACATTCAGATCATCATCATCCAGG
GGCGTGCTGTCATTCCATGAATAGCTTGATTCATCCGAGGTATCATCAGACTCACCATACTGTTCACTGAGGTCACGGTCCAGTTCAGCCTCATACA
TCTCGCTAATTGCTTTATCGTCTTCTTCTTGCGCCTTACGACGAGAAGTCTTGTAGAACGGAAGCAGGCGTTGCAGGACTTTATGGAACTTCTTCTT
GCTGATCAACCAGCTAACAGAGTAGCGAGACAGCTTTACTTCAGCTGCTTTGATAGTCGGATCGGAGTACAGCGCCATGACTAGCTTGTCCAGTTTG
TGCAGATGATCTTTAAACGAGTTTGCATAAGCAGGATGTTCCCGAAGAGTGAACATCACAAAGGAACGCATGTCAGTGATATAGTACTGACTGTGAT
GTTTGTTGATTTCGATGTATACCGGATCTACTGCGCGGTTATAATCGAATTCCTCTGCCCAGGTAAGGCTACGTACTTTAGTAGGACGAGAACCTTC
TGCCCAACGAACAGTCGGATGTTTCTCACGGATGTTCCAACCATGATTGCGATCATACTCGGTTGACTCTTCTTTGAACCAGGTGAAATTACCTTCA
CCGCGCGATACAATACCACGGCACCAACTGACGTTGATTGCCTTGTTACGGCTTTCAGTAAGATCACAGGGCATGTCCAGAATAGCGACATAACTGT
TATGACCATTGGCCACAACGCCGAGAACAGTAGCTTCGAATGTCTCGTAGCGCTGTCCAGGATACACACGTTCATTCTCATCCAGGTAACGAAGGGA
GCAGGATTCGAAGATAGCACGAGTACCGGCAGGGAAATGGGCACGACCGAAAGGTTGTTCGGCCTTTCTTTCTTTACGACGGCTGATAACCCATTCC
AGTTTTCTTGGTCAGACGGGTTACGGGTTCACGATACTGTTTCATGGTAATTTCCTTTTTACGATTGATTGGGTTGAGTACATCTCAATGCATCC
TTTTCAAGACGCATTGAGATGGGGTCTTCCGAAGAGACCCATCTATTATTCTTGGGTCAGTTCCCCAAGACGACCTTCGGCTTTCATGCGACGGATTT
CCGAGATGGATTTACCGTACATTTTGGCCAGTTCTTTCACAGTACCTTCAGGCACAGGTTTGTTCATGTCGCGGAAGTTCTGCTTAGCGATATTGTA
ACGCTGATGTTGAAGAGTCTTCAGTTCCGAACGTACCAGAGCGTTACCGGCACATTGGGAGATGAATGTAACCATGAAGGTCTTCAGCTTGCCACGG
TAGACGTTGACCCAAGCACAGGACTCATCCACGTGGATGTTCTTGTACTCGGAAACCTTGGCGTATTCCAGCAGGCCGACGGCATCGGGACCGTTGT
CCTGATAAACCATCTTGTTGAACAGGCCCAGGGCGATATCGGAGGAACGCTCACCTTTTATGAAGGCGATGGCGTCTTCGATGATCTTGGTTTCCAG
GTCTTTGTACTTGACCGGGTCGTTCTTGATCAACAGTAGCATGGCGTCGACCTTGACAGTCAAACCCATGTCGGCACCGCGTCGATCGATCAACTCG
TTGTGCTGTTTCTGCGGTGAACACGGGATCTATGTTCTTGAAAGCTTTCAGGAGACGCTGTTCCATTTACTTGTCCTCTTTGAGTTGAATGCATACA
TGGTACATTTCGGCTTAGCCGGGTGTTGGCACCACTCTTTAGATACCTTGCCCTCAGGTTTAGTGAGATCGTAATAGAACTCACCACCTGCGGCAGC
GATACCCATCAGTACTGCAATGAATCCCATTCCGATCTTTACTTTCATTTGGCAATGATCCGTTGTACGAAGTGTTGAAGGTTGGCTACCAGGCGTT
CGAATTCTTCTTCGGTTACCTGGTCACGATGCGATTCCAGAAGTACTTCTACTTCCGGCAGGACGTTCATGGCGATATCCAACTGGATACGGCTGAT
GAACTCTTCCGTTGTGATATTTCGATCACGACGAATACGACTTACCGGTGTTGTTCGCTGTTGCGGTAGGTNGAGATCTTATCGATAAGA
ATATCAGAGATACTGCTTTCGATCTGTTCGGCTACAGCCTGACCGTCTTCCTTTACGGTAGCTTTGACCGCGAGGATGGCAGCAACGGCTGTTGCGC
CAACTGCCAGTGCAATAAGACCAAGTGCGTTTTCTTTGATGAAGTTCATATTGATTATCCTTTCAAAGTTGCATCATCATTGAAGTATCAGGACCC
ACCGAGAGACTTCCCAGAAGATCCGGAGCAATGTAAACAGAGTTGAGGGTTTCGTATACACCGGTAACAGCATCTACGTTAACCAGGCTAGAACTGC
GCATGGGTACCCATTCACCGTTACGGAAGGCTTCACCGACCAGTACACGAACATCATCTACGTCAGTGCGGTTCGGCCATAGATCCTTACCTTCTAC
TATTTTTACATTACGAGCATGGTAGACCAGTTTACCATTCATGCGAGCAACGATATTCGGACGGCACATGTTGTCGATTACTTTAACTGCTACGGAC
TTTTCCATTTTTATTTCTCTATTTAGTTACGAGCATTTCTTGACCATTGGGACCGATACGATGACCGAGGATAACAGTTTCATTAGAAATAGTTTGC
TCTTCAAACTTAGCGTTTACAAACAGTCCACCAAAAGTCAAACCAATAACCACTAGTGCGAATGCTTTCATTTTTAAAGTCCCTTTTTACATTAATT
GAAGGTTAAATATCAAGTTAGTAATATACTGTTTAAATATGGTTTGAATAAGGGAGTAGTAGTTATTACATATCGTCAGGTAGGTCTCATCAATGA
TGGCACGGGCTAGCTCAATGAGACTATCTTCATCAACAACAATGTTACCATCTTTCCAGGTAGCGCTATGGGATAACCAGTTACGGTAATCCTTACC
TCGTACAGGATTGATGCATACCTGACGAGTAGCTGCATCACGGTCACCACGGAAACCCATGATAGCACGTGCACGACGGATTGCTTCTTTCTCCAAG
TCTTCGTCAGATTTAAAAGTCAGGAAAGTTGTCATAGTTTGATTCCTTTTTACTGATTTAATAGGTTTAATTACACTGTTGTGATATACTGGTTAAA
ATGGTTTGAATGTATTATTTCATTTCCACAGACACAATAGTCATCTACATGTCGAGTGATTTCTGCAACAGCCCTGAGTCGCCGGCGGCCAGTTAA
TTTAGAGCAGTGTTTATTAACTAATGTATCAACAGTTTTACGTAACCTAACACAGCGTTCTTCATTAGGTATATCTTGTTCGATAAACAGGCTAGTT
```

Figure 7(H)

```
AATTTATGGATTTCCATATGGATTTTCTTACATACATCGTTAGCCGATTTTCTTCATTTAATTTGTTGTATGATTCGACTAACTTAACAATAGTTGT
AGCAACAGTAGTTGCGGCAACAAAAATTTGAATACCATTGATAAAATTTTTATTAAACATTTTTAAACTCCAACTAATGTATTAAAAAAATATGTCT
ATATTGAAAATAAAGCCCTCCCCGAAGGGAGGGTGTATGTCGCCAATAAGTGTTACTAATTTATTTAGTTAGTTTGACCATACGTTCTTTCAAAGTT
GTTTACATCATAACCTGAGTGGTGTGTTGCAGAACCACCTGAAGTAGTATCTATAATCTTAACTACCACTTCATCATTTTCAATGTAAACCGACAGT
TTATCTCGCATAAAATCCACGTGGTCATTTCGATAACGTAGATATTTCATTACAGCTTCGCCACTGATTTTACTGTTAGCCATTATTATTTCCTCGA
TTGATTCCAGTTAAAATTATCTTTTGCATTTTTAGTGAAGAACCCGTTACCCCAACCAAATGAGTATCTAAAGTCCTTGATTACACCAACATCCGAA
TCGATAACCTTATATTCAATGACTTTATCACTATTCTCCAGAATGACTAAGATCGCGATAAGATCTTTAGGATCACCTACAGTCAATTCATGTCTTT
CAGACTCGTCTCTGTGGATAACGATGTACATGGTACTTTATCCTCTAATTATACCCATTTAGTTACTGGGAGTTCGAAGGTTTCACACAAGTCGAGT
ACTTTACGATGTTCCAAGTTATTTTCTGGATAGAAGGTAATGGGTGTAGTCGGACTACCCCAATTAACACGACATCCAGTTTCTTTATGGATTTCGC
CAAGTACAGTATATGCACCTGCCCCATCTGCATAACCCATTTGATTAGGGTTAACGCAGATTTGAGTAAAACGCTCCGTCAATACTCGATTAATAGT
GATGGTCAAGAGACGAACGAACTCACGAGTCTTCTCGATGTCGTCTACCCAGAATTCCAGAAGGATCCATTTCCCATGAGGGTTATCATGCCCACCT
TGGAAGAATACACAGAAACCTTCTTTTGCCTTATAAAACTCGTGATTGGTAATGTTACATTCAACCATTTGTTTCACTGCATGCCATACACGCTCGG
TGACATAATCACCATAAAGTTCGATGCAGTGACCACGGCCAGGGAATTGTTCTTTTTTAGAAAATTTAATTTCGAACATGGTATAGATTCCTTTTTA
CATTAATTGAAGGTTAAATATCAAGTTAGTAATATACTGTTTAAAATGGTTTGAATGTATTATCGGTAGGGAGGGTTACCCTTTTAACTTTTTAAT
ACTATTGGATAAGTACATGACACTACGGAAAATTTTGAATCTTGAAAAGTATTCACGTACTTCTTTTTTAGTCAATACAAGTCTTCCATCTTTGTTT
ACATTATCACCAAAGACAATTTCCTGAGTATTCTTCCATAAAGATCTATAAAGATAACAGCCATGTGGTGCATCACACCAATCATAGATCTTAAGTT
CAAATTCAACTTTGTCGACAATATCATCATCAAATAAAATAGTATTTCCTTTACTATTTAATTCCATTAACTCATTTGCACAATTTATTGCAAACTC
AACCGCTGCCCAGGTTCTACCACCGCTGAACATATCTTTACTTAATTTATTTAGATCGATAGCATTATAAGTTGTTTCTTAGTGTTTTTCATGGAC
TGCACCCCTCAATAATAAATAGAATAATCTGTATTTAATTCACCTTTGTAATATACTTTAAATACATTTGAATACATGACATAAAGCCTTCCCCTGG
GGAAGGCTATTATTATGTTTTAATCCAATGGGTATATGTACATAGGTCAGTTTCTTTAATAATGGTTGATTTCCATTTATCCCATTTAATGATTTCT
TTAGGGAAATAAACACAACTACTATTATTCNATTTCCATCTTGACAGTAGTAATGTACATTTCGTCTAAAATATCCTTTTCAATGACTTCTTTATAAA
GTTGAGAACCGCCAATGATCCATACATCCTTTCCAGTTTCTTTATTGAAATGAGTGGCATAAACAATAGCTGCACTTAGATTAGGGGAGTACACCTAA
TTTATTATCATAGGCTACTGGATAATTACCGTTACGATATAAACTTGATGATACAACAATGTTATTACGATTAGGTAACGGTTTACTACCTAAGGAT
AAGAAAGTATTTTTACCCATGATAACACAGCAACCAGTTGTCATTTCTTTAAAGAAAGCTAAATCCTCAGGTATATGCCAAGGTAATAGATTATTAT
ATCCAATGACACCATTTAGGTCATGGGCAACGATTAATTTAATAGCCATTAATTTTCCTTAGGCCAGAATTTACAAGATACTTCATTATCTTTAAAT
TCAATAGCCCAACTACGACAAGTGAAATTAGTTTTAAACTTAAATGTAACGCTAATAGGTAATTAATTTGAGCCATTTGTAATAGCGTTAATTCAC
CATATACTTTCTCATCAATCAATACACCAGGTCTTTTATGTTTAATAACTAATTCATTCAACTTAATATCTTGTTCAATATAGAGGTATTCCACTTC
GCCTTTTTCTAGTATAGGCATGTCCCAAAGAATCAGACTAATCTGTTGTGTGAATTCCTCAATACTAGTTGTAATATCTAGTCCTTCATAACCTATC
AATAGATTTATAAGTACTTGTAGACTAATCAGATTAACAGGTAAGTCTTTTAAATCGTCTTCTTTAATAGTTGTTCTAAAATAAACAGTGCCATCTA
AGTTTTTAACTAATAATCTATTTAATAGATGATTGACTTCTGATTTAATCTGATAATCCAGTTTGATCATTAGCTAACTCCTTGAGTCTAGTCATGC
CATTACTAACTTCAATAATGTAACTAAAGTCAAAACTATATTTCATCATTTTGAATTCTTCTTTAAAGTTAGCGATATTTCCAGACAGAGCAATTTG
TTCAAATCGACTAAAATCAGTAATAGTTTCATCGAACATTAGTTCTCTTGCGGTAATATCTGGATCATAGTTAGGATGATCAACTACAGTACCTTCG
TGGTTTAAAGTACCTTGAAAATTCAAAGTCTTTTTAACATGGTCTACAGTTATTTTCCAACTAGTTGCAATATACCGAGCTTTAACTAAATTAGGAG
CATACCTGTAAATACACCATTGTAATGGAGTGCCAACAGTTTGCGTATCATGCGTGGCTTTTATAACTTTAATAAAATTCTCAAGTTGATCAAATGT
AACATTCCTAGTTACACCATCATTAGTGGTTATATTAAGAGATGGTCGAAGACCAGTACCAAGATCATTGGTGATGATTATATCCTCAACTAAAGCT
TCATATACTTTAGTCCTTCTTTTCTGGATCCAACATCATTACCCATTGTTTAGCTTCCTCTTTTGTTACCAGTTGATAAAGTTTATTAAATTCACG
TTGACGCATTAATTTGTAATCTAGTATACGCCCATTATTTTTACGAATTAAAATAATAAAATCACCCGGACAGACAATTTTATCTTTATCTGGGCCT
ACACGTAAAATACCATGACTAGATTCAGTTAGATTACATAATGGGCAAATCGCATTACTAAGAGTAGACTCTTTAGTAGGTATAGCATAACCAACAA
TAGCACCTTGGTTGATATTATTGATAACGCCATCACCAGGTATATCACCGTTCTTTTTCCATTCGATTGCTTCAATTGGATCGGTGTATTTCGGTAG
ATAAAAAGACATTCTTAATTAACTCCGATAAATAATAGTAGTATAGTAAAAAGCACTTAGGTATATTTCTATTTTAAGCTATATTGTTGATAAAATA
AAACCTAAGGGTACATAGTGGGTTATTATTTAAAGCTCTTAAATAGCATGGTAGAACGATATTGGACTATATAGCTGTAACCCTTAAGGCACTAAGG
CTACAGAGGTTTTTAAGATAAAGATATCCAATGTACCATAATATGCTTTTACAAGATCAACTAAATTCATTTAAAATGGGTCGTAAAAATACTTA
GTTGATCTAAAGATATGTTGAATACTTTTTCACATGAACTTACGACTCACAATTGGAAATTAACAATGTTAAAAACTATCATTAAACTAGACGGTAC
TGAAGAAGCATACTCACCTGCTAAGATTAATGGTTGGGGTGAATGGGCAGCCCAACATCTTGGCGATAAGGTGGATTGGAGTAGTGTTGTGATGGAT
GCTGTTCAAGCTCTTGGTGATAAAACTTCATCACAAGAACTACAATTACAACTTATTGAAGAATGTTTAAATCGTAAGACATGGTCTTATTATCTAA
TGGCTGGTAGACTATATGCGATTTATCTTCGTAAGAAGTTCTATGGTCTAAATGGCATCCCAACTGTTAAAGCGCTTCAAACCAGGATGCGTAAAGA
TGGTATCATTGTTAAATTAGATTATAGTAGTAAAGAATACGCTCAGATTGAAAAGATCATTGATCACGATCTTGACCTACTTTGTCCGCATTTTTCA
CTTCATCACATTCGTGGAAAGTATGCTCTACGTAATCGTAAAACTGTTCAAGAATATGAGACTGCCCAGTTTGTATATATGCGAATGGCAATGGCTC
TAGCTGAAAAAGAGCCAGCTGAAACTCGCATGACTCATGTGGAGAATTACTATAAACTACTTTCTAATAAAATTCTTAGTGCGCCAACACCTAACTA
CGTTAACCTAGGTACTAAGCTTCGTGGTTTTGCATCATGTTGCCTATTTGCTTCTGGTGATAATGGTGTATCACTGGCAATGGGCGATTATATTGCT
AACATCATGACCCAATCATCAGCAGGCATAGGTGTTAACTTAATGACTAGGTCAATTGGTGATCCTATCCGTAATGGCCTAATCATTCACCAAGGTA
AGAAACCATACATCGATGTAATTGTAAAGCAGTAAGGGCTAACCTACAAAATGGTCGAGGTGGTGCTGTTACGTGTTACTACAGTGCTTTCGATCC
TGAAGCAGATATGATTACTCAGCTACGTAATCCACGTTCTACTGAGGATAGGAGGAAGAACCGTGATCTTCACTATGCATTCCTAAGTAATAAGTTCTTT
GCTAAGAAAGCAGCTCAGAAAGATGGTATGATCTTTGTATTCAATCCATTTACTGCTCCAGATCTACATGATGCTTTCTATAGTGGTGATATTGATA
AGTTTATTAAGCTTTATGAAAAATATGAAGCGGATCCTAAATTTGAGAAAACTTATGTAAATGCTCGGGATCTTCTCAAATCAATGCTAGTTGAAGC
ATATGAGACTGGAACCATCTATTCAGCTCAAATTGATGAACTCAATCATCATACACCATTTAAAGAACCTATTTACAGTTCTAACCTATGCCTTGAA
ATCGCAGAACCCACTAAGCCTTACTATCGAATGGAAGATCTTTATTCTAGTGAGGATCACGGGCGCGGTGAGATTGCTACTTGTTCACTGGCTGCTA
TTGCAGTGGATAACGTTCCTGATAAGCAAACTTATGAAATGGCGGCTTACTACGCACTTAAGATGATTCATATTGTATCCTTAATGCAGAGTATGC
TTTCCCACACCTTGCACTAACCGCCTAAGAATCGAATGAGTGCTGGTGTTGGTCATCATGGGTCTAGCCACACATATGGCACGTGCTGGCCTTAAATAT
AGCAGCGATGCTGGTAAAGCTGAAATCCACTTCATTGCTGAACGGCATATGTACTTCCTTATCAAGGCGTCACTTAAGATTTCTAAAGAACGCGGGA
ATGCGCCTTGGATTCATAAGACTAAATGGCCAGAGGGATGGACTCCACGTAAGACTTATAATAAGTCAGTGGATACTATCATTGAAGGTGGCTTTGA
AGAACTTTATCCATGGGATGAGCTAGAGAAAGAAATTAAGGAGAATGGTGGTATTGCACACTCCGTACTAGCTGCATACATGCCTGGTGAGGCATCA
TCTAAAGCACTAGGGTCAACTAATGGTCCATATCCGGTACGTCGTCTAATTCTGAATAAGACTGATAATGGCGCACGTGTGTTATGGGCTGCTCCAT
ATGGAGATGATGATTCCTATGTGTATGAATCAGCTTATGATATCCCCACTAAAGATCTTATTGACTGCTATGCCATTATTCAAAAGTGGACTGATCA
AACAATCAGTGCAGACCTCTATCGACGCATTGTAGGTTCGGAAAAGATCTCTTCTAATGAAATGCTAAGTAATCACTTCTACATGGTGAAACGTGGA
ATGAAAACCGGTATTATGTAAATCTAGAAACAGCGGCAGGACTTGACATTAAATCACTTGAACGTGCGTTGAGGTAACTAATACTGAAGTTGGGT
GTGCAGGTGGTTCGTGCACTCTTTAAGTGTATACACCCTCCCTTAATTGGGAGGGTGTTATTCCCAATTTATACTAACCTCTATTATTTATTGTAAG
AAATATTTTTAAATTGTAAAGGAANTAACATGTCTACTAAATCTCAACTACCAAAGAAAATCTTCAATGTTGCTAAGAGTGATTATCATCTACCGGA
AATTATTCTTGGAGATGATCCAGGTCTACTAGATTCAATCACACTCATTATCTCTAAAATGTGGGAGCTATATAAGCGTCTAAAGATGCTTGATTGG
GATGAGCTAGAATTTGACTTTTCCACTTGTCTAGTAGAATTTGAAACGTGTGATAAATCAACTTATGACATGATGATTAAGCACTGGCCTGGCAAT
GGGAAGCTGACTCTGTAGCCAGTCGTTCCATTGTTAATATTCTATCACCTGTCATGACAGATTCACGAGTATGGGCGGGATATGTACGTATTAATGA
```

Figure 7(I)

```
TAATGAAGACGTACATGCTTTAACTTATTCTGAAATTGTACGTAATAGCTTTAAAGATCCTAAAGTTATTCTAGACGAAATTCTTAGGGTAGAAGAA
GCACAAGAACGAATGGTTGCAGTAGCCCGCACTATGGGTGAAGCACATGACGCAGTTCATGCGTATGCTCTTAATCAGGTACCCAATGATCAAGAAC
TTTACAATAAAGTATTCATGTTCTTCATCGCTCTATATTTCCTAGAACGTATCCAGTTCATGGCATCCTTTGCAGTAACCTTTGCTATTGGTCGTAC
TGGTGCATTCCAGCAAATTGCAACCGCTGTTAAGAAAATTGCCCAAGACGAATTCGAAATCCATGCACAATATGGACAAGAAGTTATTCGTGCACTA
CTGGCAACTGAACGCGGTAAACTCGCTTACAGTCAATGTAAAGATAAAATCATTGAACTACTATGGGAAATTGTAAAGACTGAAGTTACCTGGATTA
ATTATCTATTCTCTGAAGGTCGTGAACTAACTGGTGTTAATGCGACTAAACTTATTAACTGGGTACTTTTCAATGCTAATGCCGCAGCAACATTCCT
AAGTATTGAAATGATGTTGTAGAACAGTATCAAGTGGAGTTTAAAGAATCAGCTGGATTTGATTTTGTTTGGCCAGAGAAGAACCCACTTCTTTAT
ATGGAAGACTACCTAGATATTTCATCAACCCAAGCATCTCCTCAGGAAGAAGAGAAGCCTGATTACATGGTCAACGTTGTAAATGATGTTGGTGAAG
AAGAAGAATTTGAGGTTGACTTCTTATGATTAAGATTATCGCATTCGTAGTTTTAATGTGGTCCACTGTCCTATTTGCAGCAACTGAAGTAAAATCA
ACTACAGATGGTATTATTGCACATTCAGAATGTCAGCTAGTTGCTAAAGATAGTAGTGTTGTCGGCACTACTGTTGGAGGTGCGGTTGGAGCCACCG
CAGGCGCTGTATTAGGTCGAGCAATCTTTGGTAAATCTGGAGGTTGGGTAGGTGGTTTAATCGGTGGTGCCGCAGGCGGCGATCGGTAATAATGT
TAGTGCTACTGAAACATTTCAATGTAAACTGATTGTTAATACAGATGGCAAGCAGTACATGGTTCAAACAGTTACCAATGAAAACCAAAGGTTGGT
GATAAAGTCACTGTTGTTGAAATGAATGATGGTACACGAGATATAATGTAGACATAATGACCCTCCCTTAATTGGGAGGGTTTATGCTAACAATTCT
ATAGCACTCTTATTAACAGTCATCAACGAGAGAGTAGACATGAATAAAATGCTAAACTTCCTAAACCGTACGCTATATAGCGGTACTGAAAAAGTAT
CTTCAAAAGCTACACCAAGTCTAGAACACTTTAAAACAAATGTTGAACAAGTAGATAAAAAGATTCTACAACCCTTTAGTACTAAATTTAAAACCAT
TCTAAAAGAATGTTACAGTAATGAGGAGTGGGTTGAAGAACAATCATTTATTGAAGAACCTATTGATCTTGGTTCAGCTGCACGCGGTCTTACCGAG
CGCGGTATTATGCGTGGTGATTGGGGACGCTTAGCGCATTCCACTATTAAAGAAGCAGAAGGTATGATGCGTACTTATAGTGGTCGTCTAAATGAAG
ATATGGAGGCATCTGAAATTAATGAAGTAATTCAAGATATGCCTTATAACTTCACAGCTGGCTCAGCTAATACTAGCCGTTTAGAAGAAGATGACTC
TATTTTTGTTGAAGCAGATACAACTGTAGTTGAACCTCTGTCTAAGCAGACTCTGCCAAAAGTAGCAGAGCTTACTAATCAATTAGTGGAAGTCTAT
AACCGAATTACTGAAGAATTTACAGAAACTGGTATTGCTAAAGTTGAACAAGTTGAACAGCCAGCAGTTCTTGTAGCACTTGGTGAGATCATTAGTA
GTTTTAATAAACTAATTGATTTATCTTGCGGTGCTCTACCAGTGGAAGAAACTGTTATTGTAGAGGAGGATCCGTTACCTGCCATTGTTACTGGTCC
AACTACTGAACCCATTGATGGTGAAATTCTACCGGTTGATGCTATTAATAATTCTGCGGCATTAGAAGAATTCATTGAAGAAGTATTAAGTACTAAT
CCAGAATTCATTAAATATCAAAGTATGAATGATAGTAATATTGATTCATATCTAACTGGGGATGACTGGATTATACTGAAATTCAAAGATGGTTCTT
ATTATTTATACAATGCCCAAAGTGCCGGTGAAACGAATATAGAAATCATGAAAGATATGGCCGAAACTGGTAGTGGTCTTAATGGTTTTATAAATCG
GGTTATTCGTGGCGGGTATGTAGAGAAGTCCATCATTAATACTCCCGGTTTTATACAAGTCTCAAATGAAGGTCTTATCGATTCAATCAAAAAAGTT
CTTGGCATTTCTAATCGAGGTGATCAGAAACGTATCTGGCGTTCATCGTCTCCAGTGCAAGAGGATTTCTGGAACAACTAGAATCTACATTTGGCAATC
CACAATGGCTTAATAAGCAGGTATTCGTTACTGGCGATATCAATAGTAATGGTATAGCTAACGTACTGAGTATTAATGGTAAAGTCAGTATCGAGGA
TGCCATTCGTGCAGTAGAACCATTCTTCAAACTCGAAGAAAAGTCTAATCGCGAAATGGAGTCTTACAGGCAGAAGACTAAACCTGCATTGGATCTA
CTCATTAAGAATGCACATAACCTAGACGCTAACGTATACAAAGAAGCAAAGGCTATCGTAGACAAGGCACGTGCTGGATTCAAGACTAGTGTTAAAT
GGCCTGCCGGTACTATTACAGGTAAGGGTACCTATAATTCACCTCGCACCGTGGTCGCGAAATATCCATCTACTGATAGTAAACTCAAAGCTCTTAC
TGAAGAAGAAGCAGCTAAGGCCATGAACTTAATTATATCGGCATTGGAACGTCAGATAACTCTTAGCTTCAAGTTCCCTGATTTACCAGATCCACTG
GAAGGACTAATCTACGATATGTTGGATAACCCTAGTCCAATAGCTGGTATCGATTACTATGATTGGAATGATTTGTTATTCGCATGCTTTGGCCCTG
GGATTGATGATGATGTGATGGAAGTTAATAAAATGCGGCAATACCACTCATTCATTGATATCATGGAGGCCGCCGCAAAATGGGTAGATCGGTCTAT
AAAAGGTAGGTTAGCAATGGGTAATGAAAACTACCAGTAATGTATCTAATATTATGTAGAAATAATCCCTCCCCCTTGTTTCTACATTAGTCATAAT
AGATCGGAGCCAGTCCCCCTTCCAACTGGCTCCCAGAGAGTAAAACTCTTTGCTGGGCATTAATGACGATATATCGCCTCCCTTCGGGGAGGCTTTA
TATTTTGTTTTTACGTATGTATATTAAAATATGTATAAACAACATAGAGTAATTATAAAATGATCAAAAATGAACTTTTACCAGGGCTAATCTATGC
CCAAAAAGAATTTGATAAAATTGCAGCTAATGTAAAAGACTATGATAATATAAAAGACGCGAAGCTGGTAGGGCAAGTGCCGTTTTAAGAAGTCTA
GTGAGCAATATTGTAAATCAGAATAAACCATCCTCACTTGAACATGAAGGCAAAGTTAGTACTACTAATGAATATTTAGAAGAAGTTAATA
ATTACTTCTTTAACATTAATAATATTAAATTAATTTCTCCTAAACTCATAAAAGAGAAATTAACAATTGATCTAATGAATATTTATGTTAAATGGAA
TATGATTGGAGTGGCTGGCCGAAATGATGTTCCAATTATTGAACACAGAATTAATGATTGGTGCGAAGTGACCGATGTCTACATTAATGGTAATAAG
ATAACTTCTTTACAATGGCCACGTTGAATTTAAAATAAGTTGTAATAAAATACCTAGCATTACATGTTATGTATTGAAGCACAATGCCCGAATGGTG
AAATTGGTAAACACAGAAGACTTAAAATCTTCCGGCTACGGTCTTGTCGGTTCGAATCCGACTTCGGGGCACCAATTTAAATACGGAGTGTAGCCAG
TTGGTAGCGCGCCTGCTTTGGGAGCAGGATGTCGGGAGTTCGAGTCTCCCCACTCCGACCATTTTAATAATAGGTAAATAGGATGGATAATAAATGG
ATATCATGGGAACATCAAATTATAGGAACAGCTCTTTACGCTATTCTTAGTGACCCTGAATTAACTAATATTCAATTAGCTCAAGGCTTACACTATC
TAACAGAAGCAAAGTCTTCTGTATTACATGTTTGTAATAACCATATTACATTCACTGTAACCTATCCACATGGCACATTTAGAACCAATGTAATTAG
AGAGTGCCCTGCTAGTGATACAAATACATTCAAATGGTCAGGTGTATTAGTCCGTCAAAAAGATGGAACATTCTTACCAGAATAAATAAAAAGGGCC
TATAGCTCAGTTGGTTAGAGCAGGCGACTCATAATCGCTTGGTCGCAGGTTCAAGTCCTGCTGGGCCCACCATATACTAGCCTCCCACTTGGGGGAG
GTTTTATACTGTCTCATTGAGGAAAACATGAATACAGTAATAATGTTGGTATTATCTATCAAAGTTGGATTATTTGGTTTCATTTCGACTAATGAAA
GTAATATCCTATTTGAAAATAGGGAACAGTGTATTTCTCATCTGGATATTCTGAACATAAATACAAGTCTCTTGAAGTTATTCGAAATGAGAATAC
TCTAAAGATAACCGAAAGAGATAACCATTCTATTTATATTTTTAAATGTCTCTAGGAAAATACATGGAACATCAANAACAAAAAGAACTATTGAGAC
AACCATTACAAACACTTTATAATCTTACTTTTAGTCCCCGTTTACGTAATGGAGCGAAGGCTCCCGATTGGATTCACCTGACCGATGAAGTAACCCT
ATTCCCAAACGGATTAGATATTACAATCAACGCTGTTACACGTTGCATCAAATGGGAACTTATCGGCGAGGATGTAAGTAACATTACTTATGTTGAA
GCTATGTTCTTTAATAAAGGTCTTAAAGCAGTTAAAGCCTATCTCAAACATACGGAGTAAATATGGATCATCTAACCCAACGCAGAGCGCTGTATA
TTTCACATTTATTAGCCCCTGAGTTTATAAAGCTAACTCTTGTTGAATCTTTTGTAGCGATCCACAAGAAACATCCAGAAGTAAAGCATTGCGTTAAG
AAAAAGATTAGTGCTAATGAAACGCAGTTTATCTTTATCTTCAAAGATGGGACTGATAATTTAATCATTACACGTAAAACTGAACCTTGCCCTGAAC
TGGATAGCCCAGTAGGCGATAGTATTAAGTTGTCCGGCGAAGAACTTAAAAATATTCTTGCTAAGTACGATCGTCCCAAGGATGGTAACTATTTCAA
GCACTGGACTGATCGCCCGTAATAAAATATTACTGGTTATGTAATACTATGTAGGAAGTCATGTCCATACGTTTGCGCTCATAGTTCAGTTGGTTAG
AATACCCGCCTGTCACGCGGGTGGTCAGGGGTTCGAGTCCCCTTGGGCGCGCATTTAATTCCGTGATAGCTCAGTCGGTAGAGCAAGTGACTGTTA
ATCACTGGGTCCCTGGTTCGAGTCCAGGTCACGGAGCCATATTCTAAAGAGTAGCTTCGGCTACTCTTTTATGTTGCCATGGTTATCTTATGAATT
AAAATGATTTACTTGAGAGCACACTCATGTTTGAATTACTATTATCNCCAGATATAGGCGAAGAGTTACCCTTGGTTGGATTTAATGAAATTATTAA
ATTAGGTGATCTACCTGTAGCGTTAGCTGGTACAATGTCATATGTGGATGGAAATACACTGTATGTTGGATCGGTCATCATACTGAAGGACAAACA
GCTGCAACTGTGTTCAGACGTTTTACCATATCGCCATTTGCCGATATAGGTGCAACTGCTTCTGGAACATTCTTACCAGGGGTATCTTTAGGATTTG
GGACATTACATAAGAATAACTTTATTGTTTATGGCGGTATTACTGGATGGAACTCGGCTGGTAATGGTGGTACGGGAACATCTAACTTTATACAACA
TTTTGATATAGCTACAGGCAATAGGGTTGAGCGATATAGTGGTCCCGTACACCACTTTGGGGCACAGCCTCCCGCATCAGATGTAATGATCTTATTCTA
TGCGTTAACCCANTTGGGNTAANNGCAATGCGNTTAAAACCATCNNGTAAGNCNTGGCTTAGNGGNCAAGANTATTCAGGTGGTGCTCGTTCAGGTC
AACAGTTATTCTTTTATAATGGTTACTTTTACCATTTTGGTGGTTGGGATAATACAAAGAACATACCTAATCTTGAAGTTTATCGATATAATGCAAC
TACCTTAATGGGAGCAAACACCTTGGATGATTATACCTGCTGATAAAGGAACAATCTGGCAAGGTAANGGTTATGTAGATGGNGACTATTTTAAT
TACCTTAACGCTGTTGATGTCGGCGGTGTAACTAAAATGTTTGCACAACGTTTTAATATTAGGCGCCGGAAATGGGCTGAACCATTTGAACTAGGTA
TCGGATTCCTNAATATTTCATCTATAGCTAAAGGTCCGGATAATAGCATGATCATTGTAGGTGGATCTAAAATGCCAGTTGGTTGGTGGAGCANANAT
GTTGAAAAGCCAATTGTTATCAGGTNTCTATCAGGTAAAACTAGCACCATTAATCATTGATTAAAATAATAATATTTATAACTATTTAGATAATTAT
ACTGGCACGATGATATTATGTAAGAGTACTATANTAAAGTATTCTTAAATCTATCCACTAAACACACTCGGTGGTAGAACTTATTATAGAGTGTGTC
```

Figure 7(J)

```
TAAATGCCAGGGGTTTGCCACCCCTGGNTATATTCATTGTTACTATTATAAATTCATTTATAGATGAGAAAAGGTTTTATCACCTTTTCAAAATCGG
CATTTAATTCCAGTTAAAAAAACTGAATCTATGCTACATTGTAATAAAGGAGTCTATTATGACTAACTCTAATCCGTTTGTAAGAACTATTGTAAAG
TACCAAGATATCCTAGATGCTTTAATTCAAAAAACGAATGAGAACTGGGTTAATTATCGATCTAATTCTATTGGNCATATTGTTATTCGTGAATACA
GGACTGTTGCATTATTTGTAGGTCGGCAATGTGGTAGTACAACTGCATTGATTGCAGTTTGCTAATCGTCANCCTGCGAATGTCTAGCTGTATTTGT
AGAAGATAAAATTAAACAGGCTGTACTGGCTAAGTTCCAGAATGCTAAAGATAATATTGTTTCTTGTTTAATTACACACCAACTCCGNAAATATATT
CATCAACCTGAAGAATCATCTATTCAAAAAGATATTAAAGAAGAATTAATATCGTCTGTAAAATATATTCTTGTTGACAATGCCTCATTTAATCTGA
ACCTACGCGGTATCACTGATAAAGAATTTAACCAGTGGGTTGCAGATACTTTTGGTACAGAGGTAATGGTGGTTCGTTTTAGTTAGAATTAGTAACT
TTGATAGTTTCTAATAAGATTAACTACACGTTATTTACATAATGTCATAACAAGAAATAAATAATACTCAGATTGTAATAATATGTAGTTATTACAT
ATCTATATTAGGTTGTCAGTAACTCATCTCTAATATAAAATCGCCATAATTCTTCCGTGATAGCTCAGTCGGTAGAGCAAGTGACTGTTACGATTTC
ATTGGTAAGTACCCGAGTGGCAGCAGGGAGCGGACTGTTAATCCGTTGGCGAAAGCCCACCGTAGGTTCGAATCCTACCTTACCAGCCAAATTCTAA
AGAGTAGCCAGCTGGCTACTTTTATCTTGTTCTATAGATCGAACTAGCTATCTATTTTTAAACCCTAGGTTCGATATGAAAGAAAAAAATAATTAA
TGGTTATCGGGCTCTGTATTTACCTGAACATCGGCAGGCAAAAGCTAACCCCAAAATGTTTGGATGGGTATACGAACACCGTGTAGTCGGTGAAGAT
ACAATCGGAAGATCTCTTTACGATGACGAAGAGGTTCATCATTTGGATGAGAACAAACTCAATAACCATCCCGATAATCTTTTGATCCTCCCTCAAT
CACAGCATCTAAAACTACATGCATGGATGAAACGACTGGGCATTGATCCAAAGAACTATCCTACAAAACTTTGTGGTGCTTGTGGTAGGGTAATGAA
TCATAAATTGATTAAATTCTGTAACCCTGAGTGTTCTGCCAAAGGTCGACGTAAGGTTGATCGACCATCTAAAGAACAACTCGTCCTTGACGTTACA
TTGTTATCTCTTGTGAAAATAGGAGAAAAGTATGGGGTATCGGATAATGCAATTCGTAAATGGTGTCGGTCATACAAAATCAATATTCCAGCTAGGT
TTATTAGGGTCAGCACTAATGGGGGTATTAGCACCTTGGCCCCCACACAATAAAAATATACTCGATGTAGATTAATATACAAAAACATAATCACTGG
GTCCCTGGTTCNANNCCAGGTCACGGAGCCAATTCATAGTTTTAGATTTAGTTATATTTCACTACTATGTAAACTATAAAGGCAGCTAATGCTGCCT
TTATGTCGTCTTGTAAAAGTACCCAGTAGTTGAATCTTATAGCTGAATACAAATAGGGTAAAGACATGTCACTTAAAGCATTGCAAGATATAGTTAG
TAGTGTTCCTACAAATGAACAAAAGGAACAGATTAGTTAAAGTTCGGAAAACGATGGAAGAGCTAAATGAGTCTATTAAGAATCAGATTCGTAATAAA
CGACCTAGTCAAGCTCTTCTCGACAAAACGATAAACTGGGGTACCAAGTAGTTCGTGCAAAGCTGATTACTGAAGCTGGTCAA
TGGATGTCGTCTGACTGGGAATGTGGTTTCCGTGCATGTCGATTCGTGAAACTTGGTAATGATCATGTAAACATAAAAGACTTTGAGGCTATGATCA
CGGCATTCGAAGTTGGTGACATGTTAGTGATTTGGCCAAATGGGCTTAGAACTTCGTATAGTGTGGATAATTTCAATAAGTACTTTTCCCATATCAA
AGATGAATACCATGAGACTGATCTCCGTCCACTCTTTTACCCCAAGTAGTTGAGCTTATGATAACTATATTCGTGTATAAATACATTACATTCGTTA
TACCCTTTAATTGATTGAAATCAAGCTACATAAAAGTGATGAATACTTTAACCCAATGATGTATAAATTAAAAGTATGCACACTAAAAATACAGAT
GGTGTTTATTTGATATTTTTACCAACGCCTACTATCGATGATCAAATTAACACCATGCAAGGGTATATTTATCAATAAATCCGGTAATCTCATTAGGA
CTACTGTACAGTCATGGCGATTTGAGAAAATTGAATTCAAAGACTTAGCCAAACATGATAGACGTTGGTTATTTATTGAATATTACATTAATGTTAA
ACAAACGAAAATAATATAATCAAAGAGCAACAAGATGAATTAACTAAATTTATTTATTATAGTACTCTAAGTTAAAACAAATAAAAAAATAAATAT
AAGAGCTAGCCCCTAATGGGCTAGCTTTATGTTATCTTACTCTGCTACATCTTTTACATCAGGTTTATTATTCCAACGTACTGCTCTCGCAATACCA
TACGTAAGAATAAGAGCACCCACGGTGCCAATAGTGGTGCTAATAATAATGCCAAGAGTTTTTGGNTCNATATTCATATTTAGTNTCCTATTTACAA
TTAATAGAAAATATTACTTTTAGTAATATCANNTTNNTNATATACNNTTTAAATANGTTTGAATATAACTTTATTTATTATAATAAATTAAAATAAT
ACTTTCATATACACTATATGTAGAAGATTNCGCCGCTATAGCTCAGCTAGGTAGAGCAACGCACTTGTAATGCGTAGGTCCTCCGTTCGATTCGGAG
TGGCGGCACCAAATTTACTGAGGTTTAAACTATTCTTAAATATATTAGTTAGGATGGGATTGAACGNGAAAGACTCAGTAAATCATATTGCCCCTCC
ATATGGAGGGGCTTATGTTTGTCATTAATCAGGAAAATATAAAATGAGNCATCTATTATTTATCATCCAAGAATACATTACTAATAAATTTGAGATA
ACACGAATTGATATGAAGCCAGGTAATAGAATGTTACGTGTATGTTTATACGGTCAACATAAGGGAAAAGGTTTCGTCCGTATAGATTTATGGTCAG
TTGGTTATCGCATTACAAAGAAATAATACTCCAGATTATTTAATATGTATTAATCAAAGGAGTTTATAATGAGTAATGAAACTAACTATCTAGGTTA
TGAATGGAAAACAGATATAACTCTTAAATCTTAATAGAGTGGTTGATTTTATATACACTTGAATTAACATGGTTAAAAGAAGATTTTAATGATACT
CTTTTTATAAAGTCTTATAAAGTGCTAGAGGGTCTATTAGAGGAACCGTCTAGGGCAATCCATGATGATACAGTACCCATTCAAGATCAATTAGATG
AATTAAATACTGTTTTTAAATTAGTATTTGGAAAAGATAATAACGTAGAGTTATCAATTAATAATGATTCAATTATTGTGATCGGTGCTACAGATGC
AACTAAAGAAAAGTTAGAAGCAGAGGTGCGTGAGTTTGCATATAGAAAATCATTAATTGATGAACGTTATCCAGANATTGTAACGGATTAAAATACT
TACAGCTATCTAGTATGTAACTAGGCGGATTGCCATTTGTAAATTATCTATTTAATCGAACTGAGGAAATACTAATGAAACAATTCTTTCAACTACT
TCTAAGCCTACTTTTCAAACTACCGGTTCTATCATATTTTGCTGAGAAGAAACGATTAGAGAAAGAGAAAAAGGAAGAAAAGCGTCAGCAAGAA
CAACGTCAAAAAGAACTACTTGATGAACAACGTCGCGAACTAGAAGATCATTATCGAAAGACGGCTTACGATCGCCTAGCAAAACTTATTCATACTC
GGTGGTATGATGAGTTTAATGCATACGAAAAGAAACTAGTTGATCTTGCTGTATCGAGTGGTAAAGCAGTTAGTGTTAAGTATGGTAAAGTTACTAA
GATGCAGCACCCTCATCAATTTAAACTACTTAATGATTGGCTGGATGATATTCCAGTAGAAGATTATTCTAAGTGAGTTTAAATAAAAGAAAATAAA
GACATAGCCCCTCTCCANNTGGAGAGGGGGTTTATGCCGTAATTATACACTTACTTTGATAAGATTTTTAATATCAGTNAAATGGGTATATGTTGCCT
TTTTATCTTTGTGAACCAGTANGCAACAGGTNCCTTCATTTACNGTATTGGTTTGTTTAATGGGATATTTAAAGCATATTCAAANAGATCATCCAT
CCAGTTAAATNCCATGAACTTATTGATAAGGACATGATCGAAATCAATTAATNCAATAAACGAATCGATCTCANATTGATAATACTCTACAACCATT
TTAGACCATTCTTTGTTTATNGCCTCAATGACATTAGGATTATTTATTTTATTAAATAACTCANTNCGTTCCTNAGTAGGTAAACTGAGGTAATAAT
TAATATTACTCCTAACGATATCTGGATTAGTGATATCNATTTTTTCTGGTAAGTTATATTTACTATCTACATAATTCTTAGTTTCTGGTGTCATTCT
CCAGCAACCATAATCAGCAGTAGTACTTGATGGATCTATTTTAGTCTCCACTACTTTAGAAAATACATCTACATATAAATTAACAGATTCGTATACA
TCAGGTCTGATTGGATTAAAGTTTAAACTTTTAATAAGACCCCTAACTGGCCGAGTACCAATTAGACAATGCAATTCAAGCTTAACATTTTCCTCTT
TAGCCATCTTAAATANATCAGCAAAACTGAGCTTTTCTGCCATTTAGAATATTCACCTTTTATTAATTGGACAAATAGATTAGATACACATAGCAATAG
AATAAACCCATAAACCTAGTCTTTGTAATTTATCTATACGCTTAGCTTTTTGTTTCCTCTTTAATCTAACTAATAATGTATTTTTAATATCATTCATT
AAATTATCTCAGATTTTTAGACGGTGTATAAACCCTCAGTATTACATGTTGTTATGATATTGTAAAGACGATGCCAATAGCGATCATACGTATTTTT
ACGTTTGTAGCTATTGGTNCGGATGACTAGATTGGCGACCCAGTGATTCTGATCAATGGTCTCATGTAGATGCCCGAAATAAGCCCCCAGTTCAATT
TCGAATGGGATCTTACACTCACGCCCCTTACACATTGCTTCACGCAATAAACGCATTGCAGAATTCTCTGCATTGGTATCTTTAAATAAAAGACTAA
TGTATCCAGGGCTACCACCAGTTTCTTCATCAACATGGCCTGAACAGCAATAAATAGTTGCAACATTGATAAATTGATTAAACCATTTAATTAATGG
CCTACATGCTTCATCAATAAGATCTTCATATTCAGGTTTATACATTACTTTAACAGTATCATCTGCACGTTGTTTCACATGATGAAAATATTGCTCC
CAATTTACATTAGTGTAATATAGCATATCCATATTAGAATTACTCATACAAATCAACCCCATATGTTATTGGCATATTCGCGGTCATTGAAAATGCG
GGTAAGATCCATCCGCTTTTGAATGCGCGCTAGTATCCATTTTAGTTGTTTAGTTGATAGTTCTTGATTTTGCTTGTACTCACCTGTAGCATGGATG
TAATAATCAAATTTACGACTTACAGTAGTAGTATGTGCACATGCAATAGCAAATGCTTCAAGTGCAGTTAGTTTGGTTGATCCATTATCATTACAAT
TAGGGATAAACTCAAGTACACTATTAACTGCATCTACACCACTACCCAAATGAGCCCAATCTTTCTTGGTGATGTTGATACCCATGTCTTTAAGAAT
AACTGTATATATGTCACCATTCTCCATAGTGAACATCATAGAAGATTACCATTAAACAACCTGCGTTCTATGACTGGCAAGATATTTACTTCAACT
TTAAACCAATCAGCTAAATCAACACCTGCGGTAAGGGCATTCAATAGATCAATAACATTATCTATAGTTCCAGCAAAAGCCATAGTTTTAACACGTT
TACCTTGCCAAGTAACTGTCGGATGAAAAATTATCTTGTGGCAATCATTGTAATATACATCTACACCTTCAGCTTTAGCAGTTAGATCAATATAACC
GTTATCTAATACTGGAAGTCGCCCAATGCTATCAGTTGCATTATTCCGCTCAATTAATAGGCAGTCTGCAATCATGACTTTACCATCATTTACGATA
TATGTCATTTTCACTCCTTATAATAAAATAAATAGGCTTAAGCGAAATAAAGCCCTCCCCGAAGGGAGGGCATTATCAATAGGTGGGATCTCGGCGG
CACCTTCATTTGCGGACGGGAACGCTGAAGGGAGATATCCGGGAGATCCCGATTTGGGTATTCTTTACATATGGTATTACTGCAAGTATTTGTTCC
CCGCAGTATAATCACCATTGATCCAATTTTTGATTACAACACTGACCCCTTCATTTTCTTTAACGGTAACCCCCAACTCAAGATTCGATTGATTGATA
AGCTACAGCCGCCAGTGTTAACCGAAGATAAACGGATCCATCTTTTTCGATATCGTAGGATACTACGAACCCGTCTTGTAGATTTGTAGCTGGAATG
```

Figure 7(K)

```
TATTAGCATGTTGTGGATGGAGACGATCCATATTGTACTCGACGACATCTAGTAGATATTGCCGAGCATCAGCAGCATTATCAAATCCGAGANCGCA
CAGACCGATCGGATAGCGAGCTTGCGTGCATGTAACTTTCATAGATACTACACGATGTTGTTTGCACATTATATTTTCCTCTTAGATGTCAAAACCC
TCCCGATCAGGGGAGGGTATCTCATTGGTACTTCTTCAGCAAAACTGAAACTAAGATAAAAGAGCAATCGTAAAGGAACTACATAGAATAGTGTATT
TCTTTTACTATTTTTACACAACCTCTTTAGATGGGGGTTCTTTATGAATCCAGTCTAAAGTTGTTGGTAAACTATTATCTGATCTGAAGGTACACAC
CGTCCGGAACCGAGAGTGATCAACTACAGATAATTGCCCGTTAACTCGCAGCCTCATATTGCCTACACAACTTCACACACCTTTTCTCTAGATCAGTT
GGTTCGTAACCTTCTTCTCTTGGTTCAGTGTATGGTCCATCCCAAAAGAATATTAATCTAAGATCAATCCCAGATTTATACTCCGCTTGGTATGAAT
ATTGNTGAACATCAAATCATCTAATTCTTCAACTAGATGTGATGTTATTGTTCTAGGNTGTTCATGAGTTAATTCACTGTATATATGTTTATTTCT
AGGGTTTTGTAAATCAACTACGATAAGTTGACTAGTCATTTTAACTTTTATCCAGATGTCTATTACGAGTGCGTTCCACTGCTGTAGGTTCGACAGT
GGCTCGCGGTAGATAAGTAATCTCCGGGAAAGTCTTATTAAGAGCATCTTCAATTAGCTCTTTAGCAATCTCTGCATCGATGTAATGGTTTAGAATA
ATACCACGATGATACAGGAAGAAGCTGTATTCATCATAACCATGGCGAAGACTTACTTTACCCACGATACCCACCATAGGTTAGAGTATCTTCGTTAA
TTCATTCCGATAAATATCAAGTTGGATATTATTTTGAAGATGCATTTGAATGAAGTCATTACTATCACCGCCGAATAGGGTTGGTCGTTTCCGACCA
GTAACAACATCTTGGATGGAATCCATTAGTCGGTTAATGTCTGTTTCTAATCGTTGGATATCACATTGAGAATTCATTGCTTCATGGAAACGAGTTA
CAACTGCATTGAATTCTTCTTCAGTCCAACCACTGGTACGTTTTCATAATCAACAATGATAATACCGAACCAGGCATAACCGTTAGAATGTTTACTT
TAACACATAGATGAGGTACATTATCAGCACCTGACTGATGGTTAACAGTGTAATTATTATTACGGCTGATTACTAGTTTGATAAAAGGTAGACTAAT
GATTGACGCCATGGAAATATTCCTTTTGTATTTTTTAAATTAAAGTAGGAGTTATTATTGAGTTTCAACTCAATACATCAATAACTCCAGTATGTTT
TCAAAATTAAATACATGTATTTACAGTTACATTGTAACCAGTTAGTTTTGCCAACAATACAAATTAGCGAACCTGTTCGATTTTTTCAGAAACAATG
AAAATATGTGCAATACGATCCTCATCAANATACCGATATCGAAATGAGGTATAACTAGATGACACATCCGTATCGTTAAATAGGTGATATTAAAAT
CATCTACTTCCCTACCATTAGCAGCCGCAACGGTATTTAGAATGTTGAGTAGACTCATTTTACAGATTCCTTTTTAGTATATTAATATTTCAATAGA
CTATTGATAAAAGCATTAGGGTCATAACGGTTATTTGAAAAAGCCGCCATTACATCACACCCTGGCTGATCTTTAAATCTGATATCTTCAGGAATAT
CGAAGTCAGGGAACATTAGTTTAATATACTCCCTAACTTCTTGATCGTCGTAGATATGGAATCTCCACCATGTAATCAACGCGACCTTTCCTTAGAAG
TGCTTTATCAATATTCTCAGGATGGTTTGTAGTTAGAATGGTCATAGTCTCATCTAGTGGAACAATGCCATCTAGCCCATTTAATAGAGCTGACAAA
GTTAATCCGCTAGCTGGTTGTTCATACGTGATTCCATTCTTCATGCATTTCTTTAATTTCCACCATCGGCGAATTGTGGTAAATAATGGATCTTTTT
CATCGGCCCATTTGAAACACCCAGTTCAGCCATAGCATAAGCACTTATCCCAAAACCTTGATCATCGCTATTTTCATCAAAGATATAGATGGTGTCA
TTAACCCAACTACAGAGTATCCTTCATAGTCATCTTTAAGATCAACCCATGCAGACGGATATTTTCAATTAAATCAATAAAAGAATATTTCCTCTC
TAATTCCTTTATCTCTTTATCTAGTTTTACAGGATCATTTAAAACACGATCTTTAACTGCCGGGGTATCATCGAAATCTTCAATTAGAAGAATATTA
CCTTTAGGTAGTGTAGTAAATGCCCGCCTAAGACTATCATTGGTCATAGAGGCTAATGACAGTGCACTAACATTTTTATTAAAATGTGAGGCAATCG
CTTTACTGATTGAGGTTTACCAGTACCAGGAGGACCTGTTAGAACACAAGTGAATTTATAGGGTAGTCCACGATCATCGTACCATTTCCGATCAGAA
TAGAATTCTTCAATCTTATTAAGGAATTCTTCTTTGATCTCTTTACGCAAAATCACCGTGTTGATATCGCGTTTAGTAACTTCAATCTCATTGCCCC
AACGGTTACCATCCCAATGTGAAATAGTCAGACCCCTTTCATTTGGGCGCCAATGGTAAGCATCTACTAAATCAATAATTAGTTTACTACTCCTAGA
TAATCCACGGATAGTAATATCCATTTGATCTCGACTGGCATTTTGACTATCCCGGCGTGCTTTTACAAACCAGAATAACCTACCTTTAAACAGAAAG
AAATGTAAGCCAAAACCAACACCAATTTTCTGTTTAGTTGCACTATAACTTTGCTCATCAACATTAGTTGAAAAACGTCGATTAAATCCAGCTAATG
GCTGCTTAATATACCATTCCATGAAACAATCAAAGTTCTTCTCGTTCAGCCCATTACCCATGTTGGTAATATGTAGACTAACTGTAAACTGATTTAA
TGCGAACCTAGCTAGTTTACTTGGTAAGCCTCTTAGAGTGGTCCAGAATAAACCACCAATTGCCATTCCGATAGCTCCACCCATAACCATATTCTTC
TGAGAGATATCGATGAACATGGCGTAATATTGCAATAAGGTTTCTATAATCATACTAGCATCCCTCTGGATAGCTTAGGAAATATTGTCCACAGATC
ATGTATTCACGTTCTAGAAATCTAGAGTATGACTTTCAAATATTTCACCTACATCTTTACCATAGATTTCCGTATACCCATTTTTGAATACGGCCAT
TACATAAACATCAGACATAGTCATGCCGTAGTTATAAATTTGATTGTCTCTGTATTTTGGATGAAATAGGTCATATAAAAAACGAGTCATTGAACTA
TTGGCAACAGTTGTCACCCCTTTCTGCTTTAAGGCATAACGTACTTGTTTAACCACATAGTTAACTTTAGAGCGCTCGCCAAATACCGTCAGTTTAT
CTACATTGCAATTACGATATCCCATAACACCAGGATTAGCTATCACGGTGTGTTTTGGACACGTACATCAAAGATAATGCCATTAGGGGATAGAAT
AATCTTTTCATGGTTAAATAGAACATGAAATAAATGTCGTTCTGGTTTAGTGATTTTGATACTTAACCCAATCACCCCACTAATCTTTCTTTCTAGA
TCTTCTAGTGACTGCATCACCATGTGATATTGATTGAAGAAAGCATTGTTCTTATATTGATCTAATTCAAAGTATTTCCAACTTCCACGAAATGAAT
AGCATGGCTTTGGTATAACCTTTAGTTAATCGACACTTGAGTTTGTCAAACCAGCTTTCAAGATAACTCTCGACTGTAAACCAAGTGGGTTATTATA
TAAGTTTATTGGAATATGATAAGCTAAATCTGTACATAGTTCGACGATGCATTTATATTCCTGCCAAATAAAGAAAAATAAAGGGCTCCGAAGAGCC
CTTTATGTATTAGATTTTTTACAGACCAACTTTGCTCGAATTCCTGATATAGGAAATTGTCTGACGCATTATCCCAATTTTCTCGATCAGTTACACCA
TAATAATGGAATTCTAGTTCAGTAGGTCCACCAACAAAACCATTCTTAGCATAGCTATAAACTTGCCATTGGTTAGCTTAATCAGTGTATCCACATA
GAAACTATTACGGTTCCATATTTCATTGTGGATGTACTTAAATACCACACTGTNGATATACTTAAATTGCGCACTTGGTTTTCCGAGTACACTCCAA
TAGAATTTACGGATACCTATTTCGGTCTTGAAATTAAACTCTCCGTTGCGAATGTTGTTAGAAACAATACGTGCCAGTTTATTAACCCGATTTCTTC
ACCGATTAGATAGATCCCGGAAACACTACATCCATCTCCTATTGATCCATTATTAACTAGTGGATCAACACCATATTCATCAGTGAAAATGGTTTTG
ATAACCTCTTTACCTTCTCGACGCACTAACATATTCAGGTGACCATCTTCGATATATGACATATGGCTAGGCTGAATATATTCACTTGTATCGACGA
TAACATCATTCGCCATTACATTAAACTGTAGATGGTTTACCAGATCACTAATACCTTTAAAACGAATGGCTTGGTTCGCTGTATTTAGATCGACATA
CACCACGACATCAATAATGCCTTGTTTTAGTGATTTGTCATCTTTGTCAGTAGTTGTATCAATTTTACGTAATTTTGATATAGTTCACTAAAACAAG
ATATGATGTCATCATGTAGTTTAATTACATCAGATCCATTTCGTTCAAGCGCTTTAAGCGATACGTTAAACCAATACGAATTTTATTAGAACGACGT
GCCATGGTTATATCACCTATGTTAAATTAATGAATTATTTATTCAATTACCGTACTACATCTGTGATTAGAATAAGTTCACCATCACTATTGATAAC
ACTATAGCTTTTACAATTTCGATGCGCTTACTAATAATCTTATTCTTACGATCTACTTTTACGATATTAACACGAATTACCTTATTCGATTGATCAT
GCATTTCTTTAAAATGCATTCGATATTTTACCAATGACAGCTTTTAATTTTCAATGCTGTCAATGGATGAATATTTAAAACTATATGCTTCTGCCAG
GGTTTTGCATTACCCACAACCGTAGTTAGGGTACCCCAATAATCATAAACATACAACGCAGTATCACTATTGGGATTATCGATAATTTCAATTATAA
ATCCACTTGTATCACTCCTATTAGTTTATTGATAGTACACTTGTAATATAGATCTTAAATAAATTATGATCTAACCATTTAAAATAGATAAAGCCTC
TATATGCCAATGGTGTATTAGTTCTTCTTTACTAATAATATTATTGAAGTAGTTTAACCGATGTGATACCATTAATTTAGAATGCATATCGACTTCA
CTACTTACCTTAATCACCCCAGTCTCTAATAATTGCAGAGATCCAACATACGCAAATAAAGTTGGTTTTAAATACCAGTGTTCCCTATATTGTTTTT
GATCAGGTACATTTCCTATAATGTAGTCAGTAGAATTACTTCGGTATGCGTAAATAGTTGATTTAGAACCAAGTAAATTAAGATCGATATCATAACT
CCCGCTTTTAGCTGCAATACATTCAATAACTGATGGGGCCACACATATACGGTTGGTTACACTGTCTTCGCCATCAGCTCTATTACTTGGAATATAT
GGCCTTAATAAACATAATCCCCAAGGTATACTGTCGATATGTGATACATAATTAACCTATTTAATTAAAACAGATAACGCTCTGTTACTGAACGATA
TTGTGACATGATGTTTAATGGATCAACATCCACTGGTGCTTTAGTGACAGTTAAGCGAGCACCTTTTAAAAATCACCAATATCTAATTTCCTTACAG
TAACATCATGGATAGTGTTTTTCGTAATCCACTCAGTATCAATGCTATTGTGAGGATATTATTCTTAATCCATTTGTCAGAGTCCCTAAATGGAATG
GTATAAACATACACAACCATTTAAAATATCACTTTTATCGATATTATTTTGACAATAGATTGTAATATCCCTATCAACAGTAGCATATCTATCACTA
TCAAATAACTTTTCGATAGCGCTACCAATACCTAAATAAGATGCATCTTTTTCAGATGACGTTGCATATAGGTATTGGTTAGACTCAATACCATCCC
ACATAACAAGTTCACCAGATCTTTTAAATCCTGGCATTAATTCATCTTGTTTATAAAGAGAACCATGGTAAGTAATTCTGGTTTATTCATAATAAAA
TCCACTATGCTTTATAAGAGTTATGGTTATCAATTAACTTCAAGGTAGTAGTGTGGCAGTATTGAAGTGATTGGTTACTGCTTCGATCAGCATTTGC
TCGATGTTGATTTTGTAGTATTCTGGTTCTTCGTTCAATTCCCAATAATAGTCGCACGTAATAGTGCAGGTGCTATGAATCTAACTACCTTACCATG
TGTGTCAAACTCTACATGAACATTGCATATTGTTCAGTAGTATGATTTTATAGAAATGAATTACCAGCGTAACTGCGACCTCTATTTCACCATGAAT
ACTGGAGTAGGTTTCCTGGTGGAATCTTTACCTTTAAGGCGTGTATTCTCTTCAATGATATTACCAATTCTTTCAATTTGTCTTATCTAGTTGCAT
TTGTAGGTTCCTATTAATAAATGTATACGATGGATATCTTTTACGATTTCCGGTGCTTATCCATATCTAGTTTTATATCAGTATATATCTTGAATCT
```

Figure 7(L)

```
ATTAGATAGGCTATCCATATCTACGTGCAATGCCCGAATATGCATATCAGTATCTTTTGGTTTACCTTCAGACTCCCATACGGCCTTTGCGATATCA
AATGCTACATTGTTCAAATAGTATTCGACTTCATGTTCATCAAGCAAAAGAGCATCATGGAAACCAATACGTGATAGAATGGCGTAATCACGCTGAT
TAACATCTCTCCAATCTTTACGCACTAAGTAACTTTTACCAATTCCATCTTTTTTACAACTTTTACTAATAATTTCTATAATGAACTTATCATGCCA
TTTATAATCCATAATCATTACTCCTTTATTTAATCAGCTTCATTACTAGAGGAACAGATAGACTTATGCCATTAGCCATTTTAGCTAGAATATGATA
GACATCGTCTGCTTCTTGATTATTGTACAAGGTATAGAAATGGCATCACCATAGTAAGGACTGTAGTTAATACGGTCGCCATACACACCACTCACAA
AACTATAATCTAATCCATCCGTGGTAGTCATAATAACTACAACATGATCATCCCCAACTATACCGGATTCTAAATCCTCACATAGTTCTAGTTTTGT
TGCACACCTCGTTGACAGATCCATACTTCACGGTATTGATGATGAGGATATGGATTACATGCTACATCATTTTCACTAACGAAGTACATAGTCCCCC
AGTTGTAAGACTGGAATTGGGTTGTTGTTTGTGGGCTTCCCATACCTCTTCCATACAAAGGTATGTTGTTAACCCATAGACCATCGTTATTAAGACT
ATCAACGATCCATCACGGACACGTACTACACGGAGTGTTTTTGCCATTTTTAATTATCCTAAATACATAAAGGAATCACTTAGTAAACACCATTGAC
AATAGCATCGCGGAAACGAGACCATTCCGTTTGACCAACTACGAATACTCGTTCTTTAGGACGCCATAGATGATCACCGCAGTCAAGACCCAAGTAA
AGCATATTGGTTTTCCATGATTGCGATGAACACGTAGTTTAGCTGATACACTGAACTCACACATTACTTCATTTACATCAAGATGTGTAGTGTATCA
CTATCATACCTGACATACTGATACCAATTGATTTACGAACTCGGATTAGATCCTCAGTCATCACCCGCCAAGTTACCAGATGCTCGTAATACTCATC
TGGTGTCATGTTGTTTTTATAATTCAGTGCACCTGGAGTCATTGACATCAGTTAGTGAACTGGAAGTCATGTAATACATCCAATCACTATTATGACG
GAGTTCTTTAAGCTTCTCTGTATTACGATATTAGTAGTTGCTTTAGTCATCTACGTACCCTCATCAGATACATAAGTACGTTCAGGCTGAACACATA
TTTGATGTTATTAATTACAGCTGTGATATAAACCTGATATTCTTTTGAAATAGATTCCATCAGTTCAATAGATACGGAATTGAACTCTGAATAAGTT
ATTTACTTTCTTAGTTCATCAATTCTACCGACCGTAATTACACCAACATCTCTGAAACTGATAACTGGATAGTGTTTCCAATATAACAATTCAGTTT
ACCAAGATGAATTACTTGAATTGTTTCATCGCACCATTGTTTCTTTTCTATTGTAGTATTCAACACGACGTTCGATGAAGACGCGAGTACCAGAAAC
AGAGGTGTACGCATTCAGTCATAACCATACTTATGGTACGTTATTTGGATCTTGGCGCCATTTTGGATGAATGCTTTCATTTGTATTTTCCTTTTAC
GAAATAGAAGCCCTCCCGAAGGAGGGCAATTACCATTATTAAATTACGAGTCTATTACTTCTTTTAATTTTCACCAGGGGTAGCTAGATAATCTACA
TTATATTTAATAGCAATTACACCACAAGTTCTTTTTCATAGCTGTTCTACCTGATCGCATATTTATCAATAGCTCCCATCTTCTACATCCTCGTATAA
TGGATATTGACTATAATATTATCAGGTGTAAGTACAGACAGTTTCAATCCCATCTTTACCAATGACTGGGTGATATGTCTGTTTAAGACCTTTACAA
TGATAGTGATAGGTATGCGCTGTGTTTAGGTGGTCATGTAAAGATACCTCATAAACCGTTGGGTAGTCCGTCTTTAAGACAGTTAGTTGATTAACAT
CTTTCAATGATTATCTGCAATATTCTTAGCCAATAACAGTAGATCATTGGTGATATGTTTTAATGAGAACTTAAGCCTCTCCCTTTGTTTATATCGG
AACCTTATTATCACAGTAACTCCATCCGGTTATTTTTATAATTCAGTACAGTGATTGGTGTATTCGGTACAAAGACGGCTAGTTCGTCATCGAATAC
AATGTAAACCATCACTTTATAATTATTAACCGATTCTTGGAATTGTTGTGTGATTACATTATAGTCTTTTGTGCGATGGCTAAGAAACAGCTCACTA
TTAGCTCGGCAGAAACTATGTCGCGCTTTTTATCAGCACTCATAACAGCGATACCACGGATAATGAATTTATTATCTAAGGTATATTTCTTTGAGA
CATCGCATAGTCGACTACATCAACATCGCCGCCAAATAGCACGGCATTTTCACCGTATCCACAAATAAGAGCCATTTATAATTACCTGTTTAAAAAT
TATATTCAATAAATTGAGAGTGAATAGTTCACTACATTCCCATGTACGACTTGCTAATTTATATTTACCTTTAACAGGTAAGTCAAATAACGTAATG
CTTTTCTACTGAACCAGCCTCATGATTAACCAATAGAACATTCCTAGCCTTCAGAATATTTGAACAATTTACAAGTTCATAATCATCTCGCTTAGGT
GTCAATAGCTACATTAGTGCCTGGTTTCTAGCATACCAGAGCACCTCATGACCCTCTGGATTAATAATAGAGATATAGCTGACGTTCAGCGGGTAAC
CACAAGTTACGTGGATCATANTCTCCATTAACATCAAAGAATTTAAATATCATAGAGTTGGAACCGGTTTTGATGGATCAGCAATTANTGCAGATTC
NTCTACATAAACCATTGCNAAGTTTTCACCTTCTTTACGAATACCAGTAGAAGGTGTTTTCGATGGATCATAACGATAATTGGCACTGCTGTCCAGC
TGTTAAATAAGTTGGGCCAGTTAATGCATTGGGTTTTGGATGAGGAATATCAATTTTAGTAATACAATATTGACCAGTACGAAACTCACGCATTATA
TTAACCTCTTAATGAATAACTGTTGCAGAAGGACGACATTTCATAGTTTTAAAAATGTCAGTAGGATAGATATTACCAGCTTGTCCGAAAGGTTTAT
CGGCTAGAAGAAACTGCGGACAAACTGTTTGTAGATAACCACTATCAGTGGGTAGGAATCCTTCAATATCACTGATGAGAATTTGCCAGATGGGCAA
TTGGTTATAATAGTCATCCATATTGTAGTATGCGTGGAGTTTACCACCGAACCCATATACAAACTGATGAGTATCAATTAGACGAATACCAAATTTA
GGTTGTCGTCCCATCCTT
```

Figure 8(A)

```
>B11 contig 6, Nanoluc insertion (SEQ ID NO: 12)
CGATTTGCTTAGTACATTCATTACATTTACTATTCATCCTTATTTACCTTTAATAAATTTGCTTATCAAAAGAGCAATTAATTGGGATAGTGATAAC
TTCATTAGTAACTACATGTTTGCCTGTCTTTTTAAAGAATTGGGCAAATTTTGAAGTAGCTGGAATTACAAAGGTATCATCCCGATCATTATTTGAC
ATATTGTANAAAGTAAAANTTACCGTCTANNTNAAACCTAATNNNCCANTNAATATNNCGTANTTTGAAATCTATACCAAATCTTAANTGANCATCAA
TNAATTCAGAACCACCGTANTCATAAGCTCCGGTGAAATTCCAATTAATTTCTGCGAATTGGAAAGTTACAGGATGTTCGCCATGTTCATCTTGTAT
GTAGTAACCATCATGAGCTTTCCAATAGATNACTAAATCATGCATGCTACCAGCCTCAAAGAAATAATAGGGGAGTCTAGACTCCCCTATTAATTTA
TTTTGCTTTTAGCCANTCTTCTANTGGNGGTAAATANTTCTCATGNGCCCANTTAATNATTGTTTCTACAACAGGACCNTGTANNTCAAGGTTNCCT
GAGATTTCATGNGGTTCATCAATAGATAGAACCCACGTNTGTGGCGCAATGCGTTCAGTTGCTTTNGTTAGATACACATCAGGCATTAACGTAAGAT
TCAATTGATCGCCGTCAAAATCAGCCGTATTGTTCAGTATCAGTCGTTAATTGATACCCGCACCATTACGTGCAGCTCTAGCTTTCACTAGAAGACC
AGACTATATCTTCACCCTTCCTTTCGGAGTGGGGTGTCTCCCATTTCGAGTCACTTGACCCTACATCCTATTTCTAGGACCGGTGCACCTGATACCG
TGATAGTCGTTGAACCTTCTCCTATTCCTAAATGGAATGTTACGGAGCTTGGCTGCTGATTGACCCTACCTAATCTTTTTCAAACCTTGGCTTTGTC
TTTCGACTCGCAGTGGTAGATTAGTTTAACAGGATATCCCAGCAATTAGAGAGAACTCAACCCAACGATTACTCATTGGGGGAACTAGATTTGATTA
ACTTAATAAGGTATTTATCAAGCACCCCATTCTTTTCAAAGATTGCTCTTCGAACAGTATTCGGATGCTTAATACCGACATCTCTTGCAAAGTGTGG
AATACTCGGATACACTTTGGTAGTGTTCAAGATGGTGTCAGTTACTTCAATTGGAGTACCTTTTCCATTACTAGGTTTTCCAAATGAGGCTTCAATT
TCTTTTTGAGTGTATTTAGGGAAATCTTCAGGATTAGCGGTATATGAGAATACCAAACCATCCATGATTTCCTTACTACCTCTAACTAGATGGTAAT
AGGCTTTATTACGTTAGTACCTAGTGCAAGTTCCATTTCTGCTAAGTTATGAAACACATGTAATGTCTTAGTCTTATAGTCTAAAACATAAACTGT
CTTGGTACTATCTCGATCAGCAATCTTAGTCTCACCGGTAATAAATTCAAATGTGAATCTATTTCTATACGGCTTAGTCTTATGATCACGTATAATA
ACCCAAACCGTATTTTTATTAACTCCTAATGCCCGAGCAAGTTCATTCATCGAGTAATAAGTAGTCTTTTCACCAGTGGTAACGTCAGTTGCAATTA
CCCGTCTATTTCTTTTCTTAATCCATTTTTGTAAGCATGCTCAATGTTTTCACCACGAGTCATCCACTCCAAATTAGATGGTAAGTTATTATGTTT
GTTGCCGTCTTTATGATTGACTTCATAATCTGGTCCAGGTGATGGACCATGGAAAGCTAAACAGATTAATATATGAACTCCCTTACTCTTAGATGTT
TTTTCATCATTTTTTGCACCAATATTGAGATATGTCCCAATCGATGTTTTAGTAAGGAAGAAATTACATATTCTATTTAACCGCTTATGACGAATTG
TTCCTAAGTTACTAGCTTCATATGCTGAGTATCCAGGAATATCCCGCCATTCAATTTTAAATGAAGCCGGATCAAAGACGGACACTACTCCGTTTTG
TTCCATTGTTTTTACCCTTATTTAGTTATTCAATTGTCCATTAGGCGCTTTAAGGCATAAAACTGACATGCTGATAGAATTATCATTAATGTCATCT
TTTACTTTAGTAATAAAGAACTGCTGCGTAGATCCACGTTGAAGCGTTGGCAATATCTTCAGATAGTTCGTTAGGCTATCCCGCACCATTACGTGCA
GCTCTAGTTCTCACTAGATGTTGAGACTATATCTTCACCTTTGGCTTTATCCAGTAAGGTGCTTCCCACTTCGATTTAAGGGATTCTATACCCACCC
ACTTGGGCCCTACTCTACTCCCTCTACCTTACGGCATGGTTTCGATAGTCGTTGAGGATTCCTCATACTCCTTTTAATTAAGAAGGTTAGAGGCTTT
CCTGCTGATTGACTCTATTCAATACTTTTCGAACTTTTCCGTATTAGCTTTCGCTATCCGTTTCAGTGTATTGACCTAGCGAGTTATCCCAGCATTT
CAAGAAGTTTTGTCGAGTATCATTTCTGATACAAGGAAACCATTATTAAGTTGATCCACTACACTAAGATTACTTAGGTGGTATGTAGCTTCTCTTT
ACGCGCTTTGTATCGGTTATATTCGTCAATGGATTTATTAACCATCTTCTTGAGTTAATTTAGAAACGTATTCGAATAGCCGTTCCTTATCTTCAACT
CTACAGATGACATATCCATTAAATAATCTCAGTTCTGGTTTCTTCAAGATGTCTTGCACTGACCCCTTGATTAATCCAGTCCTAAGTTGCAATTGTG
TTAAGTTCTCATACCTGCCAAAGGTGTTAGTTTTGAAGTCTATGCAATAAACTTCAATAGCGTTCTTCCGCTTCGTGGATGATAATCCCCAGTTAC
TTCAAACACGTACTTACCATTGTAAGGTTTAGTTAGATGCGCCATGACTACATGCAGCCCTTTACCATGACCTAGCTCTAAGAACTCTGCAACTTCT
TTCATCGAGATGAAGTTATACACCTCACCCGTGGTTACATCAGTGCATTTAACAGCTAATGCGTGTTTGTTTGCACCGGTTATAAATGCATGTTTTA
CATTACCACTGCGAGTTTCCCACTCTAGGTTAAGGTAATGGTTATGATGCTTATTGGTGTCTTTATGGTTAACGTCCAAGGATACATAATTCTCAGG
TAATCCATGGAAAGCCATACATACGAAACGATGCACGATTCGTCGTATTTTGCGAACACCTTCATCATTGTGGATATTAACCGTCAGGTAAGTACCCTTA
GATGTTTTGTTCTCATGTTGAGAAATCAACTCACCCTTTAAGGTTCCTTACTTGACCATGGTCACTGACTTCATAGTTACTGAAACCAGGTATACTTC
GCCATCTTATTTCTTCATTCATATTTCCTCATTAGAGATTCTTGGTTACCACACCCAGAATCTGTAGCGCTACGACTTAATAAATTAATTTCGGTGA
AAAGTACAACCCATCCCTTTATAAGGGGCTGCTTCTGCAATTAGCTCTTTAAATAGATCTGCAATGATTTGGTTATATTGAAGTACATTCTCATATA
CAAATGAGAATGCTTCACGAGTTGTCATGTTAAACTTNGCTTTTAGNTTNTTNGTTAGATGATACTTTAATAATTGACAACCTACNCCCCANGGNAT
ATGTANTTCATCATAATCATGCGGGTCCACTAATAGAAGTGATTACTGCACGTGCCGTAGCGTTGAGACGGACACCAAACATGTGACGCCGAGCAAGA
CCAGGCTTTTGAGCAATTCGTGATTTTGCGTAGATCTCGTAGAACATGGCCATATAGTCTTAGTCCTCGCATAGTCCTATTCTGAGCTTTAATTGGAC
TAAGTGGTACAGATGATGCATCAATACTAGCGAAGGTTAAGGTAGCATCAATTGCTGCTTCAATTGGTTTATCTAAGTAAGTACCAGATGTGGTTGA
TTCTGCTACGAAACAGAGTTTAGAAGGAACTGGTAAATATTTAGGGAATAACTTATCTTATTCTGAGCAACGAATTGAGCGAATTCGGATTTATTA
TTAGANATAAATATTTGCATCTAGTAGGAATTGGAAGATCTCATTGAAATTATCAATGAAGTGATTTAATCCTCTTTCAAATCCTCGATGCAGTAGCC
TATCTACTTTNCTGCGTGTTTCTTTAGAACCAATAGATTCNACATCGTATCGATAAGAAGTATCAGTTAGATATGCTAAGAAATCGAATTCTTTAGT
TACTAGATATCCGGTTAGCATAATGATTAAACGTGGGTTAATTAGNCTACGTACNTGTTTTGGTGTACGAACCCACATTGATGGTTCGATAGGACGG
CTAGAAGTATTGACAACTGGAGTATTACAAATATCACAGATTACTCCGAGTTTATGTGCGTCTTCGATTGCTCGACAATCACAGCTTACACTACTTT
CAATTGCTTCTGAATCTTGGAAATGAGAATAGAAATGCCTATCAAATTCTTCTTTCTCATCTGAGTTACTCGTATTGTAATCATTGGCATAAATTCG
TTTACCCGTAAATTGATCATGAACTTCATTATGATCAACAACTTTGGCATAAAGACCCATACCAAACTCCTATTTATCGATTAACAAAAAAGGAGAT
ATAAGCGGCCCCCGAAGGAGCCGCTATATCAGTTTTTACAATGGACCACCAACGGAGCCTGGCCCGATCCTAGCGTCATCTACAAAGCTTAACCTCC
GCTCTTCTCTGTAGCATACCGGCACTAGTATCATTTACCATCCATTGTAGTTTTTGATCACACGTCACCTTTTGAGTAACTCCTTTCGGTTAAGTGA
TCTATCATCCTCGTGTAGTGATAGGTCGACCTAGACTAAGTCCACTAGTCGATTACTTCACGGAACCTACTCCTAACCGTTATCACCGAAGTGAACC
AGGGTCGCAGTATTAGAATCGGGATGTTACTTATTTAACATCCCTATCTACCGAGGTATTTCCTATTAGTACCAGGTACCCGGTGCATTATAGGAAG
GAGCGCCGTAAGTTTGACCCATGCTGCCAGCCATNCCAACTTGTGCACTACCAGAAACAGCCATGTTACCCATACCGGTGTAACCAGCGAAGCGCTG
TTGACCGAAGTTGGTAATTAGGTTTTCCATGGTTACAGTTACACCAGCNGCTGCTGCTGCGGCATCCATTGCGGTGATGAATTTCGGGTTAAAGGTT
AGACGACGAGCACGACCAGTATAGGTAACGTTACCTAGGTACATCTTGTCGAAGCCTTTACTGTTATTCATACGACGCACAATGTGGTCATTACCTA
CCTGAGTAGCATACCAGGTCTTCCACTCTTGGTCATTACCTTCAGACATGTTCATGGCACCTAGAACGTCGGAGATCACGACGGTCGCTTAGTTCACC
ATGCTCATCAGTGTATGCCGAGGTCTACTTCATGATGGTTGTCAAAGATAATCGGACCAGCTTCAGCTAGATTATAGAACGTGACGGAAATCAGTG
CCGTATAGGTTAGTTAGAGCTTGGAAGATCAGACTAACTGCACGAGCTTGGTTTACGCCACCAGCTGCATCTAGGACGACTTGCTCAATAGCTGAGT
TGTCTCCCATTGGATCGACATCGATCTGGAATGCAGGGTTCTGGTTAACCATCTTGTTCATTAGCATTACGAAGTTGCTGTCGTCTGCCATGAATGC
TTCGGTGCAGTTTCAATCGCTTTACCTAGCTCTGAGTAATAACCAAGTGCACCAATATCACGCATCTTACTAGTAGCGATCTTCGGCATTAGAGTA
CGAGCCCATGCCTGAGATGCAGTTGCACGATACGCGTTACCAAGCGCGAACAGCCACATTTCTAGAGTCCATGCTTGGATCCAGGACGCCTTACGAA
CGTCAGTAATAACGATGTAAGGAGTGAACTGCGGAGGTAGAACTGCACCAGGTAGAGTTACGCCAAACATGCCTTGTTGCTGGCCAGTGGTCGGAGT
CCAATGTAGATCTACGAATAGACTAACTTGGTTTAGCTGGCTATCGGTATCATAGAACTCGTTCTCAGGTACGTTGGTTTTCTTACCACGGCTAGTG
GAGATGACCAGGTCAGAACGGATCGGATTACCACAGCTATCTTTAACCGGAATACCATTGTAGTCTAGNTTGCAGGTAAGCTGTTCGTTTTCTGCTT
TGATGTGGGTCGCAATAGAGAACGGAGTCTCATTGTTACGACGNGCAATAGCATCTTCACAGATNTTAACNGATTCAACTAGTAGGTTCTTAACAGC
TAGTTCATCTTTGAAGTCGAAGTCAGCATACACTGCACGTGGACCGGCAGATAGTACTTCTAGACCAGGGATGTTGTAACGGTTCCGTAGGAACTCG
CCGATCTTGCTCCAGTATTGAGCAGTGAATACATCACGCGGTAGTACCTTCTCTTCAATGATGTCATCAGTTAGACCATTGTTGATTTTGTGGGTAC
```

Figure 8(B)

```
GGGGACGGATGCGAGTACCAGGTAGGTTATCGAGTACTAGAGTACGAACGAATGCCTTCATGGAACCATTGATATCTTTAGCTAGTTTAACAATGAG
TAGACCAGCCATACCNACTTGTTGNGCATCNCGATCGAAACGATGGATATCGAAGTCATCAGGTAGGTCCTGATGGCGGATTGCTTCTTCTTTTACT
TTAGTGAATACTTGTAGGGCATCTGCTGAACGAGCATCAGAGCCATCTAGCCGACCAGAGCGACGCATTAGATGGTTAATGCCAGTAGTNGACCCAG
GNGCGCCAGNNGGACGTTGAGCTTGACGNTGTGCAGTGGGTTGCGGAGCNGGAGCNGTAGCTTGAGTTTGAACGGTGCCGATTTCGTTTTCGTTAAC
AGCCATTTTAAATACCTTTACGATTATGGTTTCTTGATCAAGAAGAACCTAAGTACTNAGTATACTAGATTCAATTTAGTAATATAAATCTCAAATT
TTTTTCATTACAACATAGACGCTATAATCTGCTATCAGCAGATCGTAACGAACACTATGTTCACTACATATTATTACAATCTGAGTATTATTTATTT
TTCATCTTACAATTTCCATATCTTCTTTTTTGAGTTTATGGGTATAAAGTTTGAATCCAGAAACTAATTTACGTCAGTCCTGTATTAAATAATAACT
ATCAGTATTTTTATAAAATGCAGTTATCATTTACTTCGCATATACTTACGAACTGTTCCAAAAAGAGAATGATACAGTTTGTATAGTTTACTAACTG
GATCAACTTTATTATTATCAGTTGTATCAAATTTAGCAATAAATGGTGAATGTGCCGAAGCAGATGTTTCATTTACTTTAACTACACTACCAAATCG
ATATGCGACTAATACCTTTATTAATTCCTCATGGAGTTTAGTAGCAGTTGCTAATGGATTGGGATCATTAGGATCTATCTTAATCCTACGCTCGACA
TTGAAAAAGTTTACTACAATTTCTTTGCTAGTCATGTATACAGTAAGATCTTTGTTATTACCTAAATATAGTGGCGGATCTTCAACATTATTTTTAG
CCATTGTATATTCCTATTTGTAATTACTACTGTTGTTACCAAACTATGATATAGATCTCAATTAATTTTTAATCGGATAATAACCATGTATAATTTA
TTTAAGAATGCTCCGTCACGTAAATTGGGGCAGGTGGTTGATCCTAACATCCATTATATCCGACGAATCTACGCTGAGCAAATTAGGGACGTTAAAA
GTTATTATAGACGGGCACCGAAGTATGTTGAATCTAAAAACATATTAGCACAAATGATTCGACATTTTAACGTAGAGTTACTAAGTGATGATGCTAC
TTTTATAAAGAACGTGGACGATCGTTCACGTGCTATTATTCGTTCATTTGGTATTACATCATCTTTAAATAAAGGTAAGGTTCATGTAGGTGGTGTT
ACACTTGGTCCTCAAACTGAAGAAGTTCTAGTATCCACATCAGAGAGCTTTGATCTAAAAGATCTAAATAAAACATGGTATAAACTTTCCCCTGTTA
CGTATCTGTATCATACACGTACTGATACTAATTTACCTATCATGAACAATACCACACAGGGTAGAGGCTATGGTGTAACTCTAGTAAATATACCAAT
GCTTCTTGTGATGTACCGTTACTGGTATCGATGGCAAGTTGAGAAGAATCCTGATGAAGTAGAAGACACTTATAGGTTTATAGGATCATTTGTATTG
CCAAATATGGTTGACTCTTATTTAGATATTTCTTTCTTTAATAGGTTAGCAAGGAATGCTTTAGATATTAAAAATCCAACATTCCCTATACCGCATC
CATTTTACATCACTGATATGAATCCACGTATTGATAAACTATGTACAACTATCAATAGAGAATCCATATTAAAAGGTGTAGACATGGAAGGTTTATC
ATGGATAACACCAGCTATCGTACAATCTAATTTGTTCGATATGATGCGGCTCCCACGAGAACCTATTAACAGGAATAATGAATGGGCTTATGTATTG
GCTCGCACACCCTTCATTAAGTATCTTGTAGGGCAGCTTTTAAAGAATACTGGTTATGATCAATCTTCTGTTAACACTGTATTAATTGATCTTATAG
AAGCATCTAATGATCAAGCATTTAAGCAACAAGCAAATAGTGAGTTTGTAAAAGCTCAACAGGCACAAGTTGATTGGATGATAGATGCACTTAAAAG
AAAAGAAATGTGACATAAACCCCCTCCTAAATTGGAGGGGGTATATGCCGTTTTATTAGAAATTACCTTTCTTCATTTTAGAAAGTAATTTTCTAC
GTTCAGCTCGGTTAATTCCTGGGGATAGCTGGTAATAGCATTTTATTACTAAACTTACCTGGCTTGCGGTCATGATTTAGTAATTGATCAACTACAGC
TTGGTCACTGCTTTTAACTCCATTATCCATTTCATCTAATGGGTCCATAATAGCTTTAGCAGTCAATCTTAGATGAGTAACTAGTTCATCAAATGAA
CTATCGGTATTAATAAGTTGTTTATCAACACCTTCTTTAAGAGCTTGTTTAATAGTTACGTCTTTTACCAGGATATTATCACATTCCCAAAGAGTTG
TATGATGGGTATTTAACATTAATTCAAGTGAGACATTATTGTAATCGTTGTCAGCACTTGAGTGCCAATTGAATTCATCAATATAGTCATTTAGACT
CATTAACTTTGGTGGTTCGTTACTAGAGGTAATTAAACCAATTGGTTGAACATCATCTAGTGAACTTTTATCACTAGTAATTGCAGTTGTTTCAGTA
GTAACATCAACTTCTTTTAATTCGTTGGTATAAGTTACATATACTAATTCTTCACTACCGTCATCCAAAAGAACATAGGCTGTTGCTTTGGTGGAAT
CATCAGGTGCTAATCCATGGATCCTAATACGATTATCATTTACTAATTTACTATAATCATTCCAGTGATTACACGAACTTCATTAGTCTTTTCCATT
ATCATCTACCTCTTTTAATTTATCTTTAATATATTTCGGATAAAGCTCGTTTTCTTCACGAGTTAACCNGNTGGNNCGGTTGGTAATGTGATAGTN
CCNCTNTTAATTGCCTTCTTCATCCGATCTAAGTCAAAATTAAATTCGGTATGATTTNTCATTATATTGAACCATATTAAGTTAGTAATTGGCAATC
AGACTATATAAATCTTAATTATTTTTAGTATATAAGCCTCCCACTAGGGGAGGCTATATTTCTTAATAGAAGTCAGAGATGAGTCGATCGTTATTT
TTATCAATAAGGAAAATACCTAGGGACTCTAAGGTTAGATAGAATACACCCATAGTNTTTCCAATGATAGTTCTAACGTCAGCAACACGCGTAATAA
CTTCTGGAATACGACCAGTTTCTACTACTGTACTCGGGATATGGAAATCACAATACTGGTTTTATTTTCTCAGTAACCCATGCTTGAATACGAGC
AGCTAATTTCTTATCTTCGATACCACATCAATCCATTCTTTGATCGCAGTTTTATTATTAAGAGTAACTGAGTCTTTACATGTGAATAAGGTGGATCA
CCAGCGTCACCAAATGATGGAGCAAATACAGTCTTCCACACTAATCCCTTTTTATGGGTTGAGTTATCTTCAGATTTATAAGACTCAGGTCGTTTAG
TTTGACCACTTGTCAGATACTCAGCTTTACCACTTCTAACAGACTCAATAATTTCTCTTTCGATATCACCAACTTCTTTTAGAATTGAAGCCAAGTC
GATTTTCTCTTCAGTCTTTACAGTTTTAATGATATCTTCCATGAGTGTTTTAGCACGACTATTAATCTTCTTAGGTACTTTACTATCCCTTAGTCCN
ACNCCNTTNATCTCCATNCGNGANTCATTAAACATNACCCCTTCTTGGGCATCCTGTGATGCAAAGTAATGTTTAGAACGAGTAGTTAAGGCCAGTA
CTGCGAAATAANATTCGTTCTTCATTGCAAATAGACGAAGCTTATCTTTAGATACACCCATATTAGCGGATTGAATCGCNAAGATATGCATAACTAC
TTCAGANACTAGAAACACTAGTGCNAATACTAGTCGNTTAGCTTCATTGCTAAAAGTTACTTTACCAAAGAATTCCTCAACCCACCATTGTAATGTA
AACATAGTGGAGTCAGTATCTGAAATAACAGCAGCTCGTCTATACACAGTTGGAAAAGCATGAATGCTTGATGGTACACATTTAGTCAAGAAGAAAG
CTTCAATCAATAGACGATATTCATTAAGAGTTTCAGCGATATTTCGACCAGTGGCATAAACTTGGTTNANTGTATCTGGATCNGANTCTTTTAGTTT
AGCTTTAGATCGACCTTTAACAGTATCAAAGCAAATAAAGCTAGCCAANAGATCCATATCACCATCATAAGTTGAATATTCTTCTTCAGTGATGATT
TGTTCTTTTGTTCCAACCTGGCTTAATTTAATTAGAAAGCTCTTGATTAATTCTTTATTGTATTTATATAAGTGATATAGATCACCTACNTACATAA
CTGCTGCTCGTTCGACTGGTGTCATCCCAGTAGCTAGTTTTAAAATCTGNGCCGTGTANTACTTATTTTGCCAATAGTGTTTAGTTGAATAAAGAAC
CATATCAACTACTTCTTCTGGCGTTGGGCAATGTAGATTAAAATTAGTTACTGCTTTTTGAATTAACTCCATATCAGCTACATTAATANTNTTTACT
AAATTAGCTTTTGTGATTTCTGGAGTATAATAATGCCTATTACCCATAATGAATTTTTCATTATTTGAGTTAGCATAAGAGGTACCAGTTCTACAGG
TAGATGTTAAACTAGAGTGTGTGGACTTATAATAAAGAATAGTGGCAGCAGATACAGTACCGCCTGAATATGAGTTATTGTTAATTTTGAAGTTTTC
TTGNTCNCCTTTACGTACTTGTGCAAGTTCTGTTTTAATTTGTGAATTCTCTTTATCGCCGGCCTGTAGGAAAAGCAGCTGCTTCACGTTCAGCCTGC
ATCTGNTCACCTTTAACACGCTTACGGTTTTTCACACCTTCNGCAATATAGATGGAGTGCGTNGACTGTCTAACAGACTCTGGTAAATATGCGGTCA
TTGATGGAGATAATAATAGATTCTGTTTCTTAACACGGTTAAGAAAAGCCATAAATGAAACCGTCTTTAATTCCCTATCACCAAACTTATTTTTATC
TAGAATAGTTGCTAATGGATTACGAAGTGCATATTCGCCATTTTGACGTAATTGTTCTTTAACAAATTCTTTACATTCTTCTAAACTAATATTTAAT
TCATCTTTTGTCATTAATTGAAGATATTTGGCATTATCATCAAGACATGCATTAATGATATCAATATCACGATGGTAATCATTGACATCTTTTAAAA
ACGGATTTGGTTGGGCAAATGCGGTCATTTCACATATCTCTCAGTATACTTATTTTTAATTATAGTGAATGATTTCTCTCTNTTTAACTAAAAAAG
AAAAGGAAAGAATGGGTACCCTATACGGGNACCCTAAATTGAGAGGTAGCACATCAACTTACATTCACATTAGATGATGTAAGNAAGTAAAAATAAN
ACAACATAAAAGGAGCCATNATGGCTCCTTTATAGTTATTCATATGTCACTGAAGTTGGTGGTGCATTATTTTGNCGCACTGCCAATAGAATGCGAT
CATACATTTTATTATCGACATCATCCCACTAATAATGTCANACGNTTACCATCTACACGTTCTAATGTATTCGCAACAATCCAAGGNATNCCAATAAA
CATCACACTTTCATTATTGGCCATTCGTACACGAATNTAATTGTATTGTGTTGGATCAACTGGAGCTGANCCTGCTGGTAAACTTGGATATACTTGC
TGCCCNGCAGCAGCTACATCAAAACCCATTGCAGATGCTACAGACGCAGTAACAATACCTTCGACTGTAACGTTCTTAAAATTAGTACCTAGGATAG
CATATGGATAGACCTCGAATAGAGATCCTATCACCTGCTTGAATGTCTCGAATATTAAGCACGCATGGTAATACCCTAAAATAGTTGGTTACATAGGGT
ATTACTCATCTAGTAATACNACTACACCAAACAGACCTTTCGTATCCATTGGNACTGTAATGANTACATGTCCATNTGGATANTTTTCTTTAAAGCT
ATTGATAAAGTCGGTNCAATATTCAATAACATATCCTTTAGTAGAATAATTCTCTAACTCAATATCTTCNTCAGGATCATCAAATGAGTCATGTCCA
TACATCAGCATATGGATNTATATGTCATTATTAAGCGTATCCATATAACTTAACTTACGTGATTCTTCAAATAAATCAAGTGGTGTTGGACAATCTG
GATATATCATTCGTTTTGTATATTCACGAAGCAAATGTTGCGAATATACTTCTGACTCTTTAGATTTAAATACGATAAATACTCGTTTTTCCATATC
GGTTCCTAGTAGGAAGCCTATGTGAACCGATAGGCTTTCCTATTTGCGTCAATTGTTAATATGTGTCACTTAATCCACATCATTGTAACAGTCCATA
CCAAAGTCTTCACCTTCTAGAATATAACCCTGATTATGTTGATCAACTGCTATTGATTGGATTCTTTCTACACCATATCCATTCGATAGAGATGTG
CTATTTCAGATTGTAGTTTGCTAGCCAATGTTTTACACACGGTCGCAAACCATATTAAGAATACTCAATGCATATTTATCTTGCATAATCACAGG
TGCTACCGATGGAAAGTATTCTTGTAAATAATAGTCAACCCCTATAATTGGTTGAGTAGGCTGTTGCGCTAGAAATTCAATATATGAATTAATTGCC
```

Figure 8(C)

```
TGATACCATAATTGTTCTATAGACTGGTGTTCAGTATATGGGTAAGGGTATTGTAAGACTTATTGACAACTACATCAGCCATTTTATTAACAATGGG
CCAGATATCACTGATGTTAATAACTACGAAACTCGTCATTCCTTGTTGACCTGGAGTTATGTTATTAGCATCATTTATCCGCTGCATTTCTTGTTGT
CTATAAAGAAGTGGATGCATCATGTTTGAGACCTCATAACTAATTTAGTTACCATCTTATATTTATCTACTTCTATACATTTAAGACTAGTAATAAG
ATTACCTGCTTGAATAACTTGTTTTTGGATTATCTCTAGGAAATCAGTTCCAAATAAATCCAATACCCTTTCGATAATCTCAGCAGATCTTAAGTGC
CAATTGATGGTATTAGGATTTCCCTGATGATCAAATACCATCATACTCGTCGGTCTATCCGGTTCTATATAGGTATCGCTTAAGTAATCTTCTAACC
ATTGCTCTAAAAAGGTAGGCCAATCTAATCTCTGCCAGTGGTTAAAATATTCACATATGCTGCTAGAAGTCTATTGATACACCACAGTACAAAGTCA
GTCGGTTCATCTACACCTAGCTCTTCCGTAAAAGAACGCGGTTTCAAAATTAGCAACAATTGCATATTGACTCCACTCTTTACCAGTGACTATAGTT
AATAGAACAACTTTGTTATCTATTACACTAATGAACTTATAGTCTATTAAATTCTTCGGTGTTCTATGTAGTAATTGGATTCCAGTTGTATAGAACA
AATTAATGAACTCATCCCAATCTGGACCATTTCCTAGTTGTATTGATATATATCCACAAAAGGAATAACCGTATTATCCTGTTGTAATTTAGACATCAT
CTTAACAACCCATTGAGTTAATAAGACGATGACTGTAGCTTCATCTTTATTTGTTAGGTAAGTAAATTTCTTTATCAATGTGATTAATTGTGGGAAT
ACCACTTCGATTGGCAATACATATACCAGACGTTGTACTTCCTCCGATGTACAATCCATCCGTGCTTCTGTTTCATACCACAGTTCCTTAGTATTT
GTTGGAATGAGGTGCATGATCTGCTCAGCACCCTCATCGAGAAGTTCTATTAGTTTATGCATGAAATGAATGTCTTTAGCATATTCATAGAACATTT
CTTCTTTAACGACCATTTGCATAAGCTTCTGTTCTGCCAATGCAACAAGCAAATGCATTGCTTCGATATAACTAATATCTAAAAAGTCCAATACAAA
TCTTAGATAGTTATCATCTTTAATAAGTTTACTTTTAGTCGCTCTTAGTAAAAAACGAGGTTGTNGTGTGGGTAATGGTGACGTATAGATCTTCTGG
TTTCTCAGTATCATAAATAACCCTATTTAACTGGATGTTACCAGCTGATGGTAGAACTACCCGGTTAGAACAATTATACAGATAAGTTGTTAAATCA
ATATCACAAATATCCCTATAACCCAGCATCTGATTAATTAGTTCTATGACATCATTAGATGTNCACCNGATGCNCTCTCAGACGCTGCTGCCAATA
CAATTGTTAATGCATATTCTGCACCAATACTATTTTTTATAGATTTCCAAATATCAGAATGTTGNTCTTGTACAAAGATCTTACTTCCATTCTGAT
ACACATTGATGTGTCTTTATCATTAGATATGTTCATTATAAAAACCTTATAANCGNTATAAAGCCCNCCNTANGGAGGGCTTTATTTAGTATAGATT
ATTTTCTAAAATGTATCGCTCAGCTTGCGCTCGCTGATCATCAGGTANATAATCACCACGTTGATATTCAAATACTAATTTCTCAATAGGATAAGTT
GCATTCTTATTCTTGTATACAGAAATTACATAGCTATGATACTCTAGTTCATACTTAACATCATGCTCAATTCTGGTTGAAAAATAAGCCATGTTAA
TAGAACTAACTAGAGGGCTAATATATTTCTCTTCAAATAGTAATAAATTATCAAGTCCTAAACTTGCAAAGAAATCATGGTTAACCTTAGGTATTAG
GTAAGATACTTTAATATTACTATATTGTTTAACAATTACGCCAATAAGTAATGCAGTTAACTGTTCTTGAATATATTCTACTGCGATGTTGTATGCA
TGGTTAGTGGTGATGTGGTCTTTATTTAAAGTATAGCTACCGCCATTGGTAATAGATGGCTGAGTTTTACGTCTAGATTCGTAGATACTATAACCTA
GTGTTTGTAAATTAATTTTGTCAAAGCCATGGAAGAAAGTCCGTAGAAATTCACTAAATAAATAGTTTAATGGGTTCAGTAGGTTAAGTGATACCAC
TGCATGATCATCACCATTATCAATCCCATGGACACGATCATATTCTGCGATTCGATAATCTTTACCACTGATTAAAGTTATAACTGAACCAGCTTTA
ACTACATCCCATTGGATCCATGTACCGCTATCGATATATTTTGCTACTTGCTTATAGATATCTAGATAGATAGTTTCTAGATAAGGTAGTTTCATTA
GATTTTCTACCCAAGCAACTTTATTACTATCTACGTCAGTTACAGCACAATTAAAAATAGCTGCGGCCATCTTAAGATTGGTGTACTGGTCTTTGGC
TGTTTTATATGAAACTAAACTCTCTACTATATTTTCAACCATTAGATGTAAAAACTGTTGAGCCACATCTTTACTCAATTTCACCCCAATCGCTTCA
TCAATTGAAGCTGAAGCTGTAAGCTGACCTAGTAAATCGTATATTGCTTTTTCTTGGTGGCGCGTATCAAGTACAATGAGCTTATTCGACATTATAT
TTCTCCAATTAATTTTTTGGAATAGCGATCCAAACTGTGTTCTTTAACCGATAGAATATTACAAACTTACCTGCATTTACTCTAGGTATAATTTTTA
ATATATCCCAAAGATCAGATGCGGCCTCATGATTTATCATGAAACCATTGGATTTCTTGAGGGGTGTTATTTATTGGATTATATCCAGTAGTATACAT
GAATTCAAAAGAGTCAATAGAGTATTTAAAGAAGTCATCAATTAAGCTGTCCTCTACTGATTTAAATATATGCTCTAATGTACCATAGTCATCTGGA
TGTATTCCAAAGCTTTGGCACCTAATCGCTAAACGCGTATTTATTAACTCTTTTGGCGATCTTGGTACTAACTTGGCTATCACCCTCGTTACATCTA
TTACATACAGGTCAGCCACTTGGGGAGTAGTCACAGTACAATCTCTCGTTAAATGTTCAGGAACATGATATAGATCTAAAAATATTTTTAGTCAAAT
CTGTTCGTGGTAAGCCGATGTATATTATACCTTAGTTGGGTATTATCTCCATCGAAAAAACGCGTACAGCGCATTATAGGACGTTTTTATGAATCCA
ATTACTAAGGCTTTACGTGATATTTCTTTTAAGATCCCAAAACAGATATTAAATACTGTTTTCNTATCTANCGAAATGTCAGGCTGTGGTGCAGCTA
TCTCACTAGAAACCAGGATACGCGAAGCTGTTATTGAACCACGTGTTAGATATTGATTTAGTCGGTGGTTCAAAAGTATTCATTCCACTAGA
TTTTCCAGTGCAAGCAGAATATGTTGACCCTTATACAGTGGTTTATTACATTCCAGACGAATACACTCAGCAACGCCCAATTATCCAATGTTACAGT
ATCCATTTTGGAGTATTAGGATTCCATACTGCTGGCTATGCTATGCACTATAATGAATCAAGTATGGGTGCATTAACACGACGTGTACTAGATTCAG
CTAGACAGTTACCAGTCGCCCAAACAGCATATATCAACTTAATTAACCCACACACTGTCATGGTCAGGTATATCAATATCCCTAACTACTCATCATT
CCTTGCCTGTCGCGTAGGTAATGATGANGAGCTAAATACCATACGACCTACAGCCATACCTGCATTTTCAAAACTCATTGAGTATGCTGTTAAGTCA
TACATCTACAATGAGTTATTTGTATCTATGGGTGANGCACAGTTATCAGGTGGTGCTGAGTTAGGTGTATTCCGTGATAAGGTTTATGAATATGCCG
ATGCTGAAGAACTATATCAGGAACAATTAATGCGTTGGATGAAAATATCCAGCAGTTCAATGATCCTGAAGGTAAGCGACATCATATTCGGACAAT
CACAGCCGCTCAATAAAAAAATAAAAAAAAGACATATTGCCCTCCCATTGCGGGAGGGCTTATGCCATTAAGGTAATATCTAAATAACACNATATTT
AAAAACATACTGGTATAANNCATCATCAATTAACACTGTTGAGAATCTTTTTGATGAGATCACCAGGTGCGATACCAATGCCTGAACAATACCGTCT
AAAGTTATTACACGGTTGACATGCTTTCTTTTCAACGATATTTAATTCAAAGCAAATATTGCCACGTGAATCTAGAATGGATATAAATGCTTTGTTA
CCTGTTACGCGATATGTCTTACCGAATACAACAGTTGTTTTATATGCAAGGCTATTCATGATTATTCCTTTAACATGGATTATTATCATGTTTGTAA
TATAGCCTTTAAATGTATTTAAATATTTATTAAACNNATAGCGATGNGCTATATATGTTTTNAATACCTCATANGCCTTATCNGTTGCCATGGANC
TATTGACAAAATCAGAATGATCAATCTTAATAATCTTACCGAATGAATCATAATCGATAGTTGTAACNNCTATTCGATCACTATCACGGATCAATAG
TTTATTTTATTTAAAACAAAAATATTCCATTTCTCGCCATCGGCTAAAATAACATCCTCATCTTTAAGATTAAGACGAACAAACTGTTTTACATAAA
TACTTAACTGAGCAACTGTTGACATAATGATTTCTCGATATCTGTTAATGAACTAATCATATCTCGGACATTNATGGTAATAACATTTTTATAAGTT
AAATAAGTTGGATATGAACCCATAAATGTAATAGTCCCACAGATATGATTTTTATATCTAATATCAANACANCCGTCATATCTCCAGATAAAATCAA
ATGATCCTTTAGTGTGGTGNTCAAGTGNAAGAATAGAACCACTAACTAATTTAGGATATTGTTCAAATTCAGACATTACATAATCTGCCAGTTCCTT
AACCTCAGGATAATCAATCAATAATAGCATATACGTAAATCTCAATNAGTTAATATAACACCCCATCCAGGGTGGACTCTTTCGAAAAATGGTAATG
TATTATTTCGTATACTNTCTGCATCAATATTTGGAATGTGGATGGTACAACAGTGGGGTTACTGTCAATCTTGAAATAGAAATTATCTTTTAAATC
TTCAACCTTGGATGTTTGNAATGGATATAAAATACCATTCCCCAAACATACCAACGNCTATACAGCTTATCGTTAACCGCTTCTCAATAACCGAA
TGCGATTTGAAACGAGGAACTCGCAAACGCATCCCGTTTACTTCAGCCCATTTGTCTACCCGNTCATAGCTAATAATTCCATCCTTAACCATTACAA
AGATAAATCCCTCAACTATGTTGGGGAGACGAACTACGTGTTTCAGAACCATAGTAAACGGAGATAACGTCAGATCAAGTTCAGCTGCCATTTGCTC
GTCGAGCTTTTTAGCAGTGTTTCTTTGCCATCGGTTATCTCCTAATTATACGATTATTAATTATCGCTAGTTATTAATATCTGCAAAATTCTGATTT
ACTTTACCCATAAAAATACCATCGGCTCTATCGTCATAATAAAGCTTCCCTGCTTTAGCATTACATANAACTCCATAAATGTGACCATTGTAACCAT
CAAAATTAAATAAAGATGGATTATGCGGTACATGAATGAATCCCATTTTATCGCACAGAAACTTAGCTACAGCAGCCGATCGGCTAATACCTGCCTC
ACAGTGTACGAATAGGTGTTGANCCTTACCAAGAGCTTCACAGAANGAAATAATACGTTGTGCATGNCGATGATCAAATAGATCATAAGAAGAATCA
ACATAATCCTCAATGTCATCAACATTGATACGTAAATAATTAAGATGTTTTGCTGAATAAAGTGGGACTCTACCTTTCTCCAGTAGACAGATCATAT
TTCTAGGGGAATAAAATGATTCAGCCACATGCAAAGGAATAAGTAACTGTATTTACTGGCTTCATATTACACCTCGTTACAAAAAAATAAAGGGA
GCCCCGAAGGGCTCCAGTATANGTTAATCGAATACAAGACCACTACTAGTTGCTTGGTCATCCACATCTAGAGTAGACTGACGCTTACGCATATTAG
CTTTGGCTCGATTCATCATTTCACGACGTTCTTCTAATCGNTTACGAATATCTTCAANAGATAGNCNANTGATCACAAAATGCATTTGATCGAAATC
ATATTTCTCGGGATCAGCATAACCAGTGGTACGAGTTAAAACAGTGTTAATGGATACTTCGCGATCAGGGTCAGTGTATAGCGAAGCAATAGAAATT
GGGTCCAGAATAGCCTGGGCTTCTTGACGATCAAAACACACGTGTAATTGGACAGTCTGTACAGGTACATCATGGTGTTTATGGAAGTGTGCCCAGT
TAGTGATATCCATTAGATCAAGACTTTGGTGTTCTTGATTAAATAGAGTTACTAGTGCATNTAGTACTTCNAGAATGTTTTGGTTCACCATTGACTG
CGGTANACCTTCAACATTCTCATGATAGTTAATAATCATCGGAACTTTACTAACAGAGGAAACCCCTTCAAANGTCTTAAGGCTACCACTNCTATTN
CGAAGACTAATATCACTGTCCGTAAGATCCAATGACCCACACTTACAACTACTTCACCTTGTTGTTGTAGATGACTNACAAGNGAAGGACCAATNGTTG
```

Figure 8(D)

```
AACCAGAAGCACCACCCATTGANTANACNACNATGTTAGNATCCCCTGCTGGGAAATGATGGGCAATGGCAGGAATATGTGCAGAGATTAGTTCTGC
GGCTGCCTTACGATCTTTACCCATACCGATAGCACGTTTACGTGCNGTCTGGTCAGCTAGCTTAGTATCCGCTTCAATAATGATCGTATTATCGTCA
GTATTGTGTTTGTGTTTATTNTGTACACTGGTATCAATGTAGCAAACATCCTCATGATAACCATGGAATAGTTCACCAATACGGAAACCAGCACCAC
CACAAAAGTAAATTCGAGTTTTACTTTAGACATCATTACACCTCATTGTGATTAATTACATTCATATACCAACTTGTAAATGGTATCAGTGCTTAAA
AGTAACGATCTCTTCATGAGTTCGTTCTTGATGAACATTAATTCATTAACCACTTTACCAGTATCAGATTTAAATTCGATTACCATCTTATCTCGAC
ACATGTATGTTTGCCAAGTACCACCAGACTTAACACAATCAATAATCATGTTAAGTACATTCTTAACTTCAATCTTACTAACTTTATAACGATAAAC
GTTTAGAAGTTCAGTAAGCCATTTCGTTTTTGGGATTTTGGCATTTTTACGTTCTTTTGAAATATCAAAAGGAATTAGTGCAATGATCTCACCATCT
TTGTTGGTGAATTCAAATACCATTCCTTTTGAGTTAGCTAAAGGACGAATGTTNTAATTNCCTTTANCACTNCATACTTCTTCAGATAACTTAACTA
ACCTATCTAGTTGAACATCAGATGCATGAATGTTATCTTCTTTAAATGCTTTCTTTAGTTCATCATGAGTTAGTGGAGTACGTACTAGAGTGTAATC
TTTCTGTTCAGTCATTTTTCATTTTTNCNATTTTCNANTTCAAATTAAACGGTATTGGCTTTTATAGCCAATCCCTTATTACTAAAAGTAATAGATT
CTCGAACTAAGGATGGTTATACCCCTTCTCTAATAATAAGGAATATTATATGGGACCCCCCAAAGGGTCCCCCCACATAATATACTATTTATATAAT
TTCTTTTAGAAGAAAAGAGATAAATAAGAGAAATACAGTCTATTAAAGTAATGAATTTCTCAAAAATTAAATAGTACACCGCNCNNNNNTTNCGNCG
GANGGTCCTGCCGGACNANNGTCCGGATGTGCGNNANTAGNGGGTTTTTCAAAAATACNTGCATCGCGGTTGAATTGAGNGGTTGATTATAACGTNN
GATCTTAATNGTAAATAGAACTTCNTCAACATCTGNATGNCATCCTTCNAAACTAAAATATACTTCAGTCCGATCAATAAACTGATACATTTCTACA
GCTGGTTCAGCTGGATCTTTAAAGGCCANCTTATTAGCGAAATAATCAGTATNGGCTAGAATTAATTCTTTTACATTANTTGCATTCTTCTTATCAA
CAAGGAATTCAAACTCTTCAAGGTTATCTGTTTTGAAAATACCTTGATANGATGACGACTNGATTAGTTNATCACTGATATCATCAACATGAACNCC
TGGCATAAATTCAATGACTGGTAGAATAAGCTTGTTACCTCCTACGCCNTNAGCNATATGAATNCCAANCACATTACCATCACTAATGTATTCGTCA
TTACCGCAAATAACGGCACCAGCCGCTAGATATAAATTATCAACATATTTCAGATTATCGGCAATAATGCGAGATAGTACATATTCTCGCACCATGG
CATCATCTGGACTTGACTGCGGTTTAAAAGTATAGTGGGTGTTATGACTACTCATGGTCGCACATGTAACAAAAACTGAAATATCTACTGGATTAAA
TACCCAATGAACGGAGATATCCTCTAATTTATGTGGATGATGTAAACCATCTAGATAGGGCTTGGAGTTGTTCTTCCCAGGTGATGTTAAAT
TGAGTCATTTTTCTAACCTCTTCATTTATTAAAAATAATACACTTATTTTACTTTAGCAGTTGATACTTCACATACATTAACTAATTGTTCAAATAA
CGGTTCATTATCTGGATCATTAACTAATTTGATGTATTAATAATAATACCAGAATACAGCATATCAGCTGCATCTCGATCACTTGTTTTAATTCTGG
TTACACCTTCCCACTTCCATCCATAGTAAATTAAATCAAATGATGAACCAATGTTAAAGGTTGATTGAATAAATTTGCATGTACCATTTTCTTTTAA
CCAATCAGGCCTATATGGTTCATTTTTATAAAATTCATGCATGAGTACTTTAAAATCAGTTTTAATGTTTTCATGAATAATGCAATCAATAGAATTA
AGAGCTTCATCAAGAGCTGATTTAGACTCAATAATGATTTCTAATACATTGGCAGTTTTAGTGTAATCATACCTAGTTCATCTGAGTGTGCTCTTC
CGATTTGAAATACATTGAGCTTACCAATTGGTAAGGTGGCTTTTAATGGCAGATTAGTATAGTGAGATACATCGCTTTTATAACTGTCTTCATATGA
CTCAATTAAATTAAGCCATGCTCTTTCAATACGTGTATTCTCAAAATGNTGTTCTTCTTCTAGTAGTCTAGAAATTAGATGATTAATGTATTGAACA
TTATGGCCAGTACCNGTAATTNAATTATATTTCGTATTACCGGTAATTCCCCATTTATTATTTTCTTTATTTATCCAACCGTAGATTACACTGTTTT
TAGGATATTTATTTTTAAAATTATCGTATATTTCTTTTAGATGTGGATTAGGGGTAAAACTAAAAGTAGTTGATTCAGTCATTATAGATACCTATTT
GAATATTGTTTATTATTGCAAATTAGTAATATAGATCTTAAACTTTTTTAACTCAGCATAAAGCCTCCCCTAGGGGAGGCNATATGTTCATTTATCT
ATTTCAGCGTTTGGATCATACCAAGGTAATAAACTTAGTAGTGCCTGTTGTTTCTTCATATCCTCTAAGATTCTTGTGCTTCACTTGCACCTTCTA
ACATAGTGGTGAAAGTAATCATGTTCTTAGAGTTATATATCGGACGTAGACCATTACCAAAGAATTTNACNTGTTGAACCATTATTTTGAAATCAGG
GTTATCGACTACATCTGGGATATAGATANCAGGTGGCGCACTGAAATAACGTTTAATTAACTCAATAGCCCAATACGTTGGTAAATCACCAAACTGT
GATTTCACTGTAGCTAGGTTTAATTGGAATGCTTTAGGTTCTTCAGGCGGCGGTTCCACCGGATCAATTGGATCAGTGGGTTCTTCAGGGCCAGTAG
GTTCAGTAGGCTCTTCAGGATCCTCTGGATCGCCTTCTGTTGGCTTTTCTTCAGATGTGCCACCATCAGGGTCACNTGAACCATCATCATCTTCAAC
GGGCTCCTCAGGCGTTTCTATAGGCTCCTTCGGATCTTCCTGATTCTCCGATAGATCGGGCTCTTCTGATTCCCCATCTCCATTTGCTTCAGTAGAA
GACGTGTCTTCTGATTCTTCATCTGTTGTCGATCAGTTGNGGCTGTGTTTCTGAATCGGCAGTGGTATTTCATTTTCACTTGATTCAGTAGAAAC
AATTTCAGTAGGAGTGGTTTCAAGTTCATTGACACTATCCTCTGCATTAGTTACTTCATTAGGGATTTCACTAATTTCTGATAATGTTACTGGTGCA
CTTACTGCGCGAGCTTTTCGTTTAGCCATGGTTGTACCTTAGATAGAATAGTATTATGGTAAGTGACTAATTCAGGATCAGTTAAATTGATACTTTG
AATAGTCATATTCAGAATTACATAGGAGTCCATTGTTCTCCGGGTATATCCAGTTAATTCCATCTTGTTATATTTCTGTACATGATCTGGAACCCAA
TCACCAAAGATAACACCCAGTTTATGAAAACGATACACCAATCTGGATAATGCACGTTGGGTTTCAGTTGGGAATATATCGGGAACATTTTCGGGAA
CAGTACATTTATCACTAAATGGAATAATAGGACCACGATGAATGGTGTAGCTAAGCTTAAAGATAACAGCACCAAGTTCGTCATTAATACGCCT
AAGTATACGATAACCATAATCGGTACGCTCAAGTTTATATACATTACTAGGATGACTAGCAGCCATCTGCTAACCTTCTAGCATGTCGTCTAGTGCACGTTTGA
TACCACGGTTATAGATGAGTTCACGTTCTATGTAATCTCTCTCAAAAGCGGCCTGAGGGCTTTCTTTCTCAAATTCCTTAGTTACTGACCAAGAAAT
TGTTTCACCAGTTAATTCATCAGTTAAAACATACAGATATGTCATAGAGTCAACGTATGAATACTGGATAGAGTANCGTGATAAATCACATGGCTTA
GCATTTAATCGTTCTTCTTTTAAATAGAAAAACATATCTTGTAAATGATTATAAGTTTGGCAGCCACCACCAAGATGATCAATATCAATAGACGTAT
CTGGCTTGACTGGAGCTTTGCAGCAACTCATTACACACCTCTACAATTATATTTGAGTTATTGTACTACAGATGATAAAGAGAAAATACATCATAAG
CCCTCTCCTTATGGAGAGGGNATTATATTTACATAGTGTTAAAACACGCATTAAATTTAGATAATGAGCAGCCAGTATAAATTAATGATTGCTCTAG
TTGTATGATGACATCGCCATTACTATCAAAATCAGCAGCAATAAAAGTAGATTCAGTTATCTTAAAAGTAGATGGCAGCATTTCTAAATAATTAAAT
ATTGCTTGATTATCGATGTCATGAGGATTTAAATCCATATGTTACCTATACATNGATAGTTATGGACCAAATATTAACAGGNCTGCATAAGACAATT
GTGATTAAATCTCCATGAGTTCTCTGATAATGGTTGAAACACATAACTTTGATTAACTTTAATTTTTTAGTTTCTTTATTTTGAATTCTTTGATAA
GTGATTCAATAAGATCAGTAGTAATGTGATGAATGAACCATCAATAAATGGTTTTATACTTACTAGCGAATCTTTGTTAAATAGAATTGCATCATATA
TTCACATGTAGATGCGGTCTTGTATATGGATGCAACTTTATTAACTTTGTCATNAGTGACTATAGAAAAATTAAATTCANTCTTAGTTTTACTNAAC
GATGTTTCAAATAATTTATATTTATCAATAATAGTTTTATTATCAATAAATGATTTCATTCCAATATTTAAATCTATGTCCAGGGTATAAGANTTAT
GTATTAATCCAACTGATAGTTGAGTTTCATTACCACTATTGTTAAACTTAATATTATTAACTGAACATATCTGATTATTAATAAACGATAATAATAG
TTTAGAAATAGTTTTAATAACATTAACTTCATAATCATTATTAGTACAAGCAAGTGCAGTTGTCATGTATCGACTAACTTGACNAACATCTAGTTTC
TGATAGNNACTANCACTATCTANCCATGGGTCAATANTTAAAAAAATCCTTAGACTAGCTAGAATATCNGAAGATGTTTCAGAATAAATGAAAAACA
CATTATTATTAAGATCATCTTTTAGCCAACCACTAGCTCTAAGATTTTCTAGATCTTTTTCATTAGATACCGATTGCTTAATTGCTGAATTAAACT
AGGGTTAGCTAGGTTTAATAAACTAATCATTTTATAAACCATTTTATTATCCTCTAATTTATGTAATTACATGGAATAAATAACATAAGTACTTTTA
TGACTTATGATTTGATTCTCCAGGAGGTTTTCCCAATGGCAACTATTAAAGAAGTCCTTGATAGAAATTTTAAGGATGTTCAATTTGATCGCGATTT
ATGTAAAAGAATTATTGACTTTACTATCAGTTTATGAATAGGAATGCTGATCACTCTGCTTTCTTTGGTGGTGTATTACTAGGTGTACAACAAGTT
AAATTCTTCGATACGGATCGTGAGATTTGGTATGATGATGTTTTACGAATTGATGAAGCGCTGTTAGTCCAAGATTTTAAGTCAGTTGAATTCATTG
ACCCTAACCATCCGTGTAATGTCAGATGTATTCAATCATCCTTCCTGCCTATATTTGTTCTAGGCTTTAAAAACAACTAATGTTCCTTTGAATATTAG
ACATGACAGCAATGGTTAGTTGTTTCATGGTGTTGCATTTTAAATATCTAACATCTTTACTTGTACCACGCTTTAAATATCCTGCACGTAAAGAAGTA
GCCGAAGCTGCATTCGCCGCACTCAATTATCGATTTGACATTAAGCAATTGGGTCATGGGAGAAATATTTAGGCAACGGGCTGAAGGTATCATTG
CACCTGATTCTATTTATGCACCTTTCTTAACTGGTAAAACACAAGAACTGGATTATTGGTCTGGTCGTGTGGTATCTGATACTCAAACACGTCTACG
TGAATTAATCAACAAGTACTATGATGTTTATATCAGAACACTGCAATCAGGTGGTAAATTAGTTATTTCATCGGATATGGCTGTTAATTCTGATGGT
GAGCAGATTCTACGCGATAAGTCTACTGGGTATCGCTCATATCTTACTTATATCCATCAAGTTGCGCAACAAGAACAAAATTTCATTAGACCTGAGT
TAGTCGGTATTATTGAAAAGATAATGCCCACAATGCCACCAGAAATGTTCATGGCGACACTTAGACACCTTTCCCGTAACATCGGTCAACCTAGGGC
ACAAAAGCTTGAGAACATCGTGATGAGTGCTGCTTATTGTATGCTTTCGATTATATGCAATCACTCCGTACAATGGTTGCTAGAAATAATGATCTACAA
ACATTGCTTGTAAAAATACGAGCAAAGATAATGGCATCTAAAACAGAAAATGCTCAAGTTATTTTCATGCGTGAAGAAGGTGAGAAGTTAGTTAGGG
```

Figure 8(E)

```
ATGCGACTAATTCTAGGGTACCTGCATATATCGCAGCAACTAGGACTGGGTTGATGTTGTATTTAATTCTACGTGCTATGACTAAGAATTACTATAC
AAAACAAAATAAACATAATGCCCTCCCGCAATGGGAGGGCTTATGCTGTTAAGTAACATTAGCTAGATTGATCATTACATAAATTTTTCAGAGCATC
GTAAATAGCCACATAAGTAAAATAGTTAAACTATCTTTAATTTCCTTACGTGGGGTGCCACTGAATCCACCCCATGATACATTTGTATTACTAACNC
ATACAGTGCTAATAGCTGGCTCATGATAGCCACCATCTACTTTACGCTTGCATAAACCTTAGCCGTAATTTCTCCACGTAACTTTTTGAAGAAAAC
TAGAGCACCCGGAACGACTATACGTTTATTACCAATCTTCGTAATAAATTCTTTACGATTAGTAAAGTGCTCTTTTAATAAATCATTAATAATTTTA
GTTAAACTATCAATTTCATTCTTCATCGACACGTTGTTAGTTCCTTACAAATAAACTTGATAACGTGATCACTTACAAATTTCAATGGACCAGAACA
ATTAGATTTCTCAATAGCGGTTTCAGTGTATGAAATTATTTGATTTCCACTTAAGGATAATGAATCAAATAATTCATAAGAGTTATTATTTTATTCT
TAAAGGATACTGCATATTGACTATTTCACTATTGATGCAAAATAGGTTAATAGCTGGGATAGATACAGAGTTATCTGAAGTATGGCTATTTTCCGTA
ATATTCCAATTACTGTATACAGTGAAAATATTTGCAGCTAGTAAAAGGTTGGCATTAACCGTTTCTAAACTAACATACTCCACAGAAGTACCTTTAT
GCCAATATAGTTCAATTGGATTAACCCAAGTATACCCAATGGTTTTATAGAAGGCATGCATTACATATTCTCGCCAACGTGTGGGTTTCTTATTATC
AGTTAAAACACACGTAATATTGCCTGACGGATAAATGTGGTGGATGCTACATGCATTAATTTCATCTCTAACATTAGTTGTTTCAGTAATATTAGAA
TGATCCTGTTTGAATAGCCATTTTAAATGACTATTAGTTGTGTCATCACCTTCCCCATTTGCAATGTCATTTCTAACCACTTTTCAAATGTAGCTT
GTCTATCAGGTGTTGGCATTCCCCAATAGGTAGCTAAATGAAACGATAATAGTATCGAATAATATCATCATCGTTAAGAATATTTTATCCAGTTTCC
AGTGATGTTGATACTCGTATACTTCGCTTGGAATATTATTTACTTGATACCATGTATTAATTAATACTTGAATTGTTAATTGCCGAATACTCTCACT
TGTTAGAGTGTAATATTCCCTGCTATGCGGCTCTTCAATTGTCACTTCTTGATCAGTATAACCAATGTATTTAGGTTTACCATCGATGAGTGCAAA
TTAACATTCCATGATGTATCATTACTAAAAGTGATATTAATAAAACCTTGTTCAAAGCTAGGCTTCACTACGAAACTGACATCATCCTTCTGATATG
TCATTTGCGTTAGAATACCAAAATTAATTTTAGATGTAAATTCTTTATCGAAGTTATGTTTATAAAGTAATCCTAGTAAACAATCAATTTTATTAAT
AGTGTGGTTTTCTAATAATAAATCAGTATTTGTAAGTTCATTAATTTTCATTTTAACCTCTCTAAAATTTACAATCTAGTTTTACTTATTGAATAAG
CAAACATGTAATATATCTTAATTATTTTTAGCATAGTTTTTAACAACATAAAGCCTCCCCGAAGGGAGGCGATATGCTTTAGCTTTTTGGTTAGT
ACCGACAGTCTGCTCATTCTTTTCAGTTTGAGCATTTCGCCGAAGTTGACTAACCAGACCATTGCCAGCCGCAACTACATCGGGAGAAAAGAATGCA
TTGATATCAAAGTTCTGATCTTGGTTGCGAGTCTTCCCAGGTGGGACCATCGGATATACTTTTTGCCATTAGCTTAATCCTACTACACCGTCGTAAGTTAC
CCGATTACCAACTGCACGTTCAATCTGGTCTTGAATACCATTACGTGCACGTAGTACGTCAGCAGATAAACCACCCCAGTCTAATTCTGGTTATTG
GGGTTCATACCGCGAATGTTTAGTTTACGGAACATTTGACGAGCGTATTCTTGTACACCTTCAGAAACATCAGTCAGTGCAGAGAACTCAACGTTTA
GATCAAGGTTCTGACCAATCTGTGATGCATCTTTACGGTTTTCCCAAGGACCAGTAGTTAATGGGAACATGTTGGTGCAAAGATAAGCNTTAACGCA
ATCCTGGAAGGTAGGATCNGGTTCTACGAATAGAACAGTCATACCGTAGAAGGTAGCGTCGTATTTCTCAACCGGTACAATGCCATCTGATACAATA
CGCGGTACTTTGGTATTCTCATCTGCAATACCATAGTTGATCCACCATTGTAAGAAACGTTGGATAGCGCGGTTTTGTAATTCCCAGCAACCAAAGT
TTGGGTTAGACCGGGCACGGGTTACGTTAGTAGCCGTTTGGATAACTTCACCAGAACCACCCCAGGGGTGCTTCAGCGTTATCTACAGTAAGCGTACG
TTGTAAACCATCGATGGTACGAGTATGCGTTTCAACGAAAGCCTTAAGACATGCAACTAACCAGTTAGTATTACTAGCATACTTAAAGAATCGTGGA
GCATCTAGTAGGAACGGCACTAAGTTACGTGCCACATATGGCGTGTTAGTAGCCAGGTTAGCTAAGTCAGGCCGAAATACGTTAGTACCAGCCTGAG
CAAGGTTTACAGTGTTACGGGCACCACCAGCACCATAACCAGTCTCGGGTGCCATCGGATCATTATAGCGAGCCATTTAACTTTTCCTCATTCTGAA
AGCCACCCACTCATTGCTGAGCAGGTGGGGTTTCAATACGAACAGTTTCCAGATTGAAGTTCAACGTGGTCCGCGGGTTATTAGCCTCAACAGTTAC
GTTGCAAGTCCAGCTGGTGCCGTTATTTGCGTCAATCGGAGTGATCTCTGTACGCGGATAATGTTGACACGAGTACCGAACATATCACGTACTAGA
TCGAGAATATACTCGTCACAACGCTCAACTAATTGTTCAGGTGTTAGTGTAGCATTACCGCTAAATTGAGCGTGTACTTTATGGATCAGTCGGATTA
ATACACAGCAAATATTAACAGTAATCGGTGATAGAAGTACAGATGTATCATCTAGCATTACTGAACGTAGGCACGGATAATAGGAGCTACGATGGTC
ATATGACTGACTCCAAGTAGCACCATTCGCCCAAGCTTGTGCCCGTACACGATCATCAAAGAATTTAACATTTAGATCTTTAACAAAAGTAACACGG
TTATTAGGACTTACATCCATTTCCATACCTGGAACTAGATTACCAGTTCCAGCACCTGCATAGCGTGCCCATGACATAGCTACGTCTAAAAGCTGCG
GTACATATTTACGATAGGTACCATCCATTAGTTTGCCAGATTGCATTACAATCATAGCGCGACAAACACCAGTTCCGTATAGAGTGGATTCTGGGAA
AGCTTTTAGGCGAGTGATAATCTGTTGAACACGACTTAGCTCAGTAGCTTCATCAGGTAGACGACTATCAGTTTCTACGAATGTAGTGAAGAAATAT
TGTAGATCACGCCGCGCACTTAGTACGCGCATTGCCCGATATTTTGATTCCATCGGAAGGCCAGTGTCATAAAGAACACCGAACTGATATTCTGCAA
TGTTATTATAGCGATCATTTAATTTGCCAAAGTTAATATTTTCAATATCAACTAATTTGGCATATTCTTCTAGATCAGTTGTACCGTCAGTACCACC
ACTAGCATAGATGTTACCATCTTTACCTAACGTAATGCCGCCATCTAGTGGACCGAGTACNTGAATACCCTGGTAAGGATCACCATCAACAGCTAAG
AAGGTTAGGAAGTCAATTTCACCAGGTGCAGTAGTATGCGCAGCAGCGGCTGGGTTAACTCGCATCTCAGTGTCATAAATCATCTGACGAACAAGAT
CAATGTTCTCATGATAGACGTAGAACTGAGAGAACGGTGAATAAAGTGGACTTAGGCCAGAGACTACACCATCATCTGAGTAAGAATCAACTAATAC
ATCACCAACATAAAGGTCAGCGTTATACATATCGCTGTAAACACCTTTATCAAATGTAATGTTTAGATAATCTTGCTGGTCAGCAGTTTTGACAATA
ACTGGACTAGTGCCTACTTCAGGCTTCTCAATTAACTGAATACGGAATTGACGAGTTTTAAACTTCGCCATAGCTGCTTCATCGAACTCTTCGATAT
CAGCAGTTGTAGTACTCCATACACGCATACCGTTAGAATCACCTAATTTACCAAAGAAGGAAACCGGTGCTTCAAATAACGGATATACTAGTGATTG
AGATCCATCTTTATCTGATACTAAAGTACCTGGTAGTACACGTTGTGTACCTACTTCAGAGGTATTATCTTCAATAAGAATAATACGTGCCTTTAGA
CCATCAACTTTATCAGCAGTCGGGACTGGTGCATTACCAATGTCACGAACACTGTTTGGATAGTTGAAACCACTAAGACGACGAATCGTAAGTGGGA
TTTCATCTTCCACAATTTCAATAGCAACAATTAACCGAGATGGATTAGCTGCATCTTCAGGACGTAGACGTTTAACATAAAACCATTACCACGGCCA
AGAAGGTTAAGTGCTAATAGTGATTGTGTATTGAAAAACTTACTACGTGGATCAAGCGATGCTTGACCATAGATGGATGCAAAACCATCATCAGAAT
CACCGACATAAGTGGTTTCAGTCGGTCCTGTCTCAGTGAAGAGACGTAATAGCGGACAGTGTTGTGCGAACGTGATGTCCGACGGATCAGGGGCCG
GCGGCTACGATCCCGGATACCATTAAACACAACCCTAGGGACAGCGTTGTAATATGCCATCTTTTTGATTCTCCCAAGTTGGAGCTTTGAACTCGAT
GTTATGAGTGTTAACTAACAGTCAATCATAGATATTAATCATAGTTGACCATACTAGTTATTTTTTACTATCCATTTAAGGAGTAGCGGTAATGTTT
TTGCTACCGTATGAAACTACAGTTTGTAAAACTCTATACAATCCACCGGCGGTGGAAAATTATATCCTAAACAATATGTTGCAATTGAAAATG
CGATCAGAAAGCCAATGTGTATCTACCCATTCCACCTGTTGATGCACGTAATGGTGAAACGCTAGAGCATAGTGGACAGATTACCCCAGTTGATGA
TTTTGAGGATATTAAGAAATTTACTCAAATTGTCAATATCGGTGATCGTGATAATCCTAAGCTAGTNGTTGATGCTCGTCTATATAAAAGATTGAA
CAGCGTACTGGTATTCCTAGGATTATTCAGCAGAATGAGTGGCAATTCCAATATATTCGGATGGCACTTAATATCAAACTATTACGTGAAGGCCCGG
ACTTCCTCCATCGCTTAGGTGTATATCCCAGTTAAAGTTTTCTATAATTGGATCTCAGGCATCCTAACACAAAAATACAGCCTACCACCTGAATCAAC
CCAAGCTATTTGGGTAATCTGTGCTGTTTATTACTTTGCTATGCAAGATGATGNTCTAACAGAACCAGNTCAGGAACGNGATCGGTTAATACCAATT
ATTTCCCGTCTTACATATATTCCAGCTGGTTTTATTGCNGATGTTATTGATACATTAGGTCCACTTCATAATGCCGGTGATCTAGCTTATGAGATTT
CAACTAANGGNCGTTCGATCAGGATGGGTAAACTAAAATTCAGTGATCTACAATTATTAGTATCACCGAGTTGGTTTGGTACCGCTTCCCGTGAAAA
CGTAGGTGTGGCACTAGAACACATGCCAACTTACATCACACTGATCTACATGGCATTAGCTGATCGCTCATACCGTAAAACAGTTTTAAGTCAGAAA
GTTGAAATGATTTCACGTTCTGATGATGCAAGTCGTTTTATTAATCTAGTGAATGAAGCTGTAAGTAGCCAATTCGTTAAGTAAATATAGGGGTGAA
TCAATGAACGCATATCTATTCGGNCATGCGATTGATAACGTTTGGTGTAACCCAGCCCAGGACCGACAGTTTGTTTATGAACTGAAACAGCTNACCC
CACGCTACGGCGTGAGGGTAAACTGGGTGGTTGATTACACCCGGTATAAGCTACCAGTCCAAAGTACACGCTGATTATTGGCATCTTTATCAAATTGG
TAAAATGATTCTAAACACCTGGGCTTCCCTAAGGTTTACAATAAGTGGATGAGCCTCAAATGAGTTGGCTCAAAACCATTTAAATTTAGCAGACGTT
TATGTAAATAGTGGTATTAATTATTCACGTAATGATACATACGTTTTAATAACCAGTTCGCAAAATCTTTTAATTGCTGTTAAGATAGATCCATTAT
TCCCTGATCTCGATGAAAATCAACCCTATCTTCATGTTTATAACAATGCTTACTTTCAATCAAATAGATCGGATGTAGCTGGACATAGATGGTTAGT
TTCTGAATCGTATCGAGTTAAAACAATATCTGAATTAACTCAATTTCAGATTAAGATAATGGATACCATAGCATCTAAAGGTGGTGTTCCTAAATAC
TTTGTAAATGGTAGATATGTTAATGAGATATCTCCTGTTACAGCAACAGTCGGTGATGTTTGTGATTTCATTCTAGATCCATCCATTAAAAGGATGG
TAGATTTTGATCTACGTACATTACCTGTTTTCATGTCAGAAATAGATAGTGAAAGAAATATATTTTACACTACACTGATAAGACTGTGCAAACAATT
```

Figure 8(F)

```
GAGTTCTTTGATGATGTTGAAGCATATATCTATCAGCCATTAGGTAATAATCGTTATACTGGTGTTAATTACCATCATAACGAGAGCCGTTGGATGC
GGATGCTTACACATAAAGATTATTCTATACCAACTGCACGAATTGATCAGTTTAAAGCACTTCATCCAGAAGATCCTCGACGTGGTGCTGATCCTAC
TCGTTGGCCAAGTCAAAACTGGAAAGCATTAGATAATCTAGTATTTAGAATCTACATACATCATTCTGGTTATGATCGCCCATTAGTTGCTGATTCA
CATCGTATTCAAATTCTGTATCGTTTAAAATCAGAAGATATCATAAGGGCTATGACTGGTGCAGATTCTGGTAATCCTTTATGGCGAGCTGAAAATC
TAGAGCAATCACCCATATTGCTGGTTCATGTCAGCACCATCTAGTTTCGTATACCCATTAACATTCAATCTACCTGAAGAAACATCGCCTAGTAAGGT
AGAAGCGCAGAATATGGCTGGTGATGTTTTGGTTATTATGAAGCAGCTAATATTCAAGGTTATAATCCAGCTTGGGTTTATAATGATGCTGGTCTA
AAGACCGCTGATTTACGATACAACTACTGGCTAGATGCAACTGTATTTGAGTATGATGAGAAAGGTATCTTATTAGGTTATAATTATCATACAGCAG
GTCGCAAATATTTCCCTAAAGATAGTCGTTGTGCATATGTTGAATGCATTAATGGTAAAGGAAGTGTAGATCTACATGAAGCATATGGGAATGATCC
CGTGCCTTTACGTGATGGTGACAACTGGCGAGTTTATGTTAGTCCTGTTTGGGCTGGCGTACCAACTGGCGAATGGCAAGATATAACAGACCATCCA
GATCGAAACAACTGGGGTTTTTATGATGATACCACTGATGATAAACGTTGGGTTTGGATAGCTAAGTCAAATGAGTGGTATGCCTAGTAAGAACCG
ATGAGTACTTCTATCTAAAAGAATTAAAGTTTAATAAAACTGATGGTATCATTAAATGGAGTATACGTAATACTGAAACTCATAATGGTGTAAAAGT
CGATAAATTGATGGAGATACCATTTGGTCAGTATGATGTGTTTGTAAATGGTCGGCCTATCATTGAAGGTCTTGATTACACGCGTGAATGGCCTCAA
ACTGTATTATGTAATCTGGAATATTTAAATGCAGATCCAAATGCAGTTAATACGATTCTTCTACGTGGAACAGGTTTCCCAACACCAGATTTAAAAC
CATACGAACCTGGCGAGATTGGTTTCATTGAGTATGGCGTATTGTCTAATGATGGTATTTATAAAGTACATTCAAATAAACAATCACGCATAATCAT
TGATGGTCATTATCGTGACCCTGCTGATCTTGAATTCCAAGAAGATCAAGGCACTACTGTTATCACTGATGAACGCAATGGTGCACCATTCCAAATA
CAAACACCACAGGCNCGCTTCCGNGATGTTTATAATGATGATTACCAAGCTAGGATTAAGGATGATGCACGGATAAACAAGTCACTGATTTTATGA
CTGAATATTTCCCAATGAAACCTCAACCTAATCCGGACAAGATCGATTATAGATACCAGGTGCTTTCAGCGTTTTCATGTAAGATCATTCATGATAT
CGTAAAAGAATATATCAAACCNCCATATCAAATGGACGGTATAGTGACGATGATATTGTTAAGCAGCTAAAAGATTACGAGTGGTTAGCAGCTTAT
GACATTATCAATAAAGGCTACAACAAAAATAAAGTTGTAGTTTATCCACATTGGTATACTGAACCTGTAGAACTAGATATTTCCAATGGGAATATTT
AAATCGTATTCTATCGATATATCTACGTGAAGTACCGCCACTATCCTTGTTCGTTAAGATTAAAAGGAATCAACCATGACAACGTCATATGAAAGTA
GCCAGTACCAACCACCACAGCATAAAAACCATTTCTGGTTTAGAGGTGATATTGTCTCATATGCTGGTGANACTGGNAAAGCAATCCCTGCTAAAGG
AGATTTAGTATTTGACGCAGCACAAGGTTGGTTTATTGTTCGTGAAGTTGATGAAACAACTGGGGTATCTATCTTAGATCCATGGTACATGCCCCAA
AAACCAGGCAATGAAAATGAACAAAACCTACTAGTTGCTGTAGGTCCAGGATATAGCTCAGAATCTTATCGGTTATTCCTAGATCAGTCTGTAACAC
CATTTAATATTTGCCCAGACCGGCGATTACATTTTTATGGATCAATGGTGCATGGCTATAAAGTTTTCCTAGGTTCAGATATATCAGAAATACATGG
TAAAGTGATTTCCCTGTTCTATGATAATGCTGGTAATTATCTAGGGCCAACTATACCAGTTGAATCAGTACCCGATCCATTGACTCAACAGAATGTT
GTTAAAGCGTTAATGAATGGTAGGACTGCTGAGAAAATGCAAAATGGTGAACGTGTAACTCTAGTAGCTTATGATGACGTGGGTGGCCTGTTTCGA
TTGCTCAACTCGTTGTAATGAATACTGAAGTTATAGCNCAAGAGGATACCTCNAAGAAATATGAGGTGGTATCACTATTGAATCACCATTCATCTC
NCCAGCTGATCCNAAAGTTATTGAGTTCCCATTAAACGTACCAGTTGAATCATTACCGATGATGGGTGCTGTTCATTACCGTGATGGTAAGAAGCAT
GTGATGAATATTGATGGTACGGCAATGGCAATTTATGGTTTACGTAACTATATTGCCACTGAGGAAGGACAAGAGTTTAAATTAACTCTATCTTACC
TTACAGTTGTCGTATGTTTGTTTATCCNGCTTGGGTTAATGAGGCAGTNGGTTACAGATTAGAATTCTGGTTAGCCAATATTGATCGTCAACAAATT
TGGAATATTACCCCATATGTTGAATTAGGTGCAAACTCAGCACCCTTTAACCCACGTGGTTATGGTACTATCCAAACACTAACATATGCGGTTAACC
TAAACCAAGTTGATGGACGATTCCTACCAGTTCGATTTGCATCTACTTTCCAAGTAGCACTATTGAGCGCTGGTAATAATCGGAATGCTAACTGGGA
NATCTATTCACGCCCTGANCAAGGTGAAGCATATGGTCGTGATCTTAAAGCCGATATNGAATTTATCAATGGTAATCTTTGGGATCTCCGGTTAGCT
AATGGNGCACAGTCACAAGCTGCCTGGCTTAAGAAAATGTACTTTGCTGCTGAGCCATTAACTGGTCCAATGGAAGCTACTCCNCCNACACCTACGC
ATTTCCGGGTGCGTACAGTGCATAACGAGTATGAGTATGATACGGTAAGTCAATGGAATACTGCNTTNCGNATTAATGCTCAAGATATGGCCGATGGTGC
TTTACTACAANTCACCTGGATTCGTCGTGAGTATGATACNGACCTACAGTTAGCCATTACCGCATTACCTTGTTTACAACGTTAAATATANNGCCCC
CTAGGNNNNNCCTAGGGGGCTTTATAACGTCTTTTAACACATTATCCATATGAGACTATACTTTACAATTGCCGTTCAATACGGCTTTATTATGGCA
CATTAAAATAAGTACCTTAAAGGGCAGTGTATGGACGTTATACTTTTCAATAGTGATTGGGATAAATACTACAGCGCTAGTGTTGATCTTACTACTA
AAAATAAATCNTTTATAAAGTTAGCNTTNACTTATAAAAGATGGGTATTAAAAATTACAAATTTATACTAGCTATATTGGACCAAGGTTTAATTGG
GGTGGATCCATATGACCCTAATCTTAGCGAAGAAATGAAGTTNCGTATTAACATGGAATGCAAATATAATCCTTGGTATTTTTTAGGGAAGTGGCA
AGAATCCCCCCTAACTCGGGTAATAANCCAATTCCATTCCAAGCTAACCGTGGTAATATTGCTTTATTCTGGTGTTTATTTCAATCACGTAGATTTTG
GTTTATTACAGCCTCGTCAGACAGGTAAGTCCGTATCAACTGACGTGCTCAATACAGGCATGATGTATATCTGGGGNGAGAACACTAAGATTAANCT
TATTACTAAAGATAACAAACTACGNAATGCTAACATCGAGCGTCTAAAAGTAATGCGTGATTTGTTACCAGAGTATATCCACTATACNGATCCATTA
GATGCGGATAACTCCGAATTGATGACATGTATTAGATTAGGTAATAGGTATNTAACAGCTGTTGGTCGAAATGATGTTAACGCAGCTGATAAATTAG
GTCGTGGTCTTACTGTACCAAATATGCACTTTGACGAACTTGCCTATATTAACTTAATTGGTGTTTCACTACCTGTTGCACTTGCNTCAGGTTCAGC
AGCTCGTGATGAAGCTCGCCGTGAGAACCAGCCTTATGGTAACATCTATCCAACTACAGCTGGTAACATCACTACCCGTGATGGTGAATTTGCATAT
CACTTCTTAACAGGTGGNTGCCCATGGTCAGAGGAATTCTTTGATCTACCAGATCAGAAAACTCTACATCGTGTTGTAGAAAAAGGCACTACTGGAA
AGAAACCTCTAGTTTATGGTGCATTTAACCACCGTCAATTAGGACGTACCGATGAGTGGTTATATACACTTCGTGAATCAGGTTCATTCGGTGA
AATTGCCGATAGGGACTTCTTCAATATCTGGACAGTTGGTGGTGAAGGTTCACCCTTATCATCAGATGAGAAAGATAAACTTAAAAACAATATGCGT
GAGCCAAGCTGGACAGAAATCACNGATGATGGTTANACACTTCGTTGGTATATACCAAAAGANGAAGTAGCCTCACGGATGATGAAGGGTAGGTTCG
TTATGGGTACCGACCCATCTGAACTTCTTGGTGAAGATAATGACGCCACTGGCACAGTTGTAGTTGACGTAGAAACACATGAGGTTATGTGTGTTGG
NAGATACAATGAATCATCAGTNCCATCAATGGGTAATTTCTTTGCAACAATGCTATTNANATATCCTAATATTCTTTGGATACCAGAACGTAAATCA
ATAGGTATATCGTTAATTGACCATGTTATCTTGATTCTNCATACTAAAAGGANTAGATCCATTCCGGCGTATCTTTAACAGAATTGTCAATGAATCAT
CAGAAAGAGAAATGATTTCAGAGACATTCAAACTCCGNTATCAGCAAGACAACCATCGTNTATGATAGGTTTAAACGTTATTTGGCTATGCAAC
GTCAGGTACTGGCGAGTATTCTCGTGATAATCTATTTAAGGTGGCATTACCATCAGCAATGCATTATGGGTAAGGACCATCTATGATAAACCACTT
AGCACGGAGTTATTAGCACTTACTATCCGTAATGGTAGAATTGACCATGCTAAGGGGAACCATGANGACTTAGTGGTATCATTATTATTAGCCCANT
GGTTATTAATACAAGGTAAGAATTTATCTTATTATGGTATCAATGTTCCCATCTTAGGTAAATCAAAATTACGTGATAAAGAACCAAGNCAACTTGA
AAAATATCATGAAGAGAAAGAACAGCAAGGTCGNAAAGAATTTGAAGAGATAATTGANCAGCTTCGCGGTGAAAAGAACCCGATGATTGCAGCTAAA
TTAGAAATGCGNTTGAAACAATTGTCTAAACGTGTTAATATTGATGATANCAGTGGTGTAGGTATTGATGCCATGTTAAATCAAGCTCGTGCAGAGC
GTACACGTAGAGTGCGTATTAACAGATATTCTAGAAATAGTTGGTATTAAACAAAAAAAATAATAATACGTTACCCTCTTCGCAATGAAGAGGGTAT
TTGAAGTTAAGNAACTCTAGCGAACAAAAGATTACTGGAGTTAGAATTAATATGATAGTTAGACGATCCGTCAATCCATTTAGCATCGGAAATCTTG
TTTACAAGCTGACCATTGCCAATGTAACCTAGGAAAGTTTTATTATCATATACAGCAATTTTGATTAGCTCATTTCGTCCGTAGACTAGTGGCTTAC
CATTGAATGCTGTTACTTCTAAACCAGACATGTATCCATAAATTGGATCAGGTCTGGAACTTGTTTCAAAGACTTTCATTCGAAGTCTCATCTGCAA
GAAAGCCCATTTTGGGCAAAAAATGTCAAGCTTAAACTTTGACGACATATAGCCCTCCTGGTGCGACAGGAGGGCTAATCTTTTCAGAACGTACGGTG
TTGTTATAATACTGCTAGCGAAAATACCCATGATAGGTAAGTAGCTAATCCGCAGTTCTCTTGGATGATACCTACTGACAGTGTAGTTGCAAATGTG
CTGTTTGGAACCCCACTGGTTTAGCGGCCAGTGGGAATTCCTTTTATGCCGCTTTTTCTTTCTTTACTGGATATTTCTTATATTTACAAACCCACGT
TCTTACGCTGGTAGGTATCTTCCTTCTTATTATATTCGTAGTTCTCGATGAGGCACTTGTTGCTGAACTCGACCATCGAACACATCTTGTCCATGAT
GACTTCAGATATTTACCATGTTCATAAATTCGGCGTAGTTGTAGCCGGTATTCATGTCGAGATAGTCTTGTTCGACCATATCGTCATTCAGGTACTT
GACGTAAGCCTCGGCGTGAGCAGTGGCTACCGACTTGGTGAAGAAGTAACGAGCGTGCTGACGGTTCTGTTCGAACTGACGCAGATTAGTAGGCC
TGACCGCCGAAACCATTGACCTCCATTACCCCGTAAACAGTACGATCATCCAGAGTAGTGATCTGTGCAATCACTACACGAGAAGCATTTTCCGAAT
```

Figure 8(G)

```
GGTCGATGAACGTCATACTGTAAATCTCGATTTCTTTGAAGTCTTCCATTAGAATTTCCTGTTAAAAAAATGAATAGACAACCCCTACCTTCGGGTA
GGGGCTTTATGCCGTCAACCGACAATAAGGTCCCGAATCGTTACGATCTAGGTATCAGATGCAGGTTTAGTCAAACGAGTTACACGAATATAAACCA
TGTAGTCACTCAGAGATAGAACTTTTTCACTTATACATCTTCCAGCGTCATGATTACGACATGATAAGGACTATCAGCATTGTGACCCATGCACGTC
TCGCATTTGAAGATCCGCCAACATGCCATACGAAGGCAGCTCGCGGTTTTTCACATAAACGTAGTCGTGCGCTGCCACGAGGTATTTTTGTTGAATCG
AGAATTCACAAGTGATGTAAACCTTTTTCACGGATGAATTCTTGAGTCATCTGATCAAAAGTCTGTTTGAGTTCATCAGTAAGAGCGACTTGGCGTTTC
GAACATTGAAATATTCCTTTTGATATATTAAATAGTTTTGATTATTTCGGAGTTATTGAATATTTAGGTTACCATCTGCTCTATATAGACTCGGCTG
ATTTCATTTAAGTAAGCGAGTGCCAATAGAATACCAGCCCAAATAACAATTTTTCGAGTAGTCTGTTTTTCTATTACACCTGGGTGTGATTCACGAA
TACTACGGTGACAAAATACATAAAACAGACACAGACTCATTGTAACAAAGATAATGGTAAACCATCCTAGATAGATCATTTTCTTCACCTATTTTTA
TAAATAGAGTTTATAGTTTAGTCAGGCGGATGATTTCTTCTAAAGCTGCATCAACTTGATAATACGGCCATGAATCAACACGAGGTTCGTTATCAAA
GTATGTCCAAAGTTGAATACCTTGGAGTTTATTGTAGAATACATTGATTCTGATTCCTTCATGGCCAACAAGACCTTCAATGTAAGCTGCACCATGC
ACATACGTAACATGTAGTGCGTACTCGCTATCTTCACCAGCGTATTGCATAGGTCTGGAGTAGATGAAGGAATAAGGATTAAATGGATCAGCCTGAG
TGATATGTTCGAAGAATTCTTTCAAACTAGATTTTTTCATATTGGACATTATATTTTCCTCATGATTTATTAAGTCTATCTTCTAGGAGGTAGACTT
AATACTATTCGATGTTATTTTAAGACGCCTGCCTTGTAACCTTTAACAACAGTTCTAGCTTCTAATGCACTGATTTCGCCAATGTGTTTACGCAGTG
CTTTAATAGCGTTGATGGTAGGTTCATTATCCGCGATATGTCGCCAGTTTCCCTTACCCTTAATGAGTTCAACATCCTGGACATATAGACCATCTTT
AACTAGATCCATTGTTTCTACCAACTTTTCGACTTCTTTAGTTAGATGCGTATGAAGACTGGCGAGGGACATGTCAGTCATTTGATGCACATCATAG
AGAAATCCCTATTATCAGAAGACGATAAAATTTCTTTGGTGAGTTTATTTACAGTGTCAATGTTTGCTGCAATTGAAACTAGCAGTGCAGCATATTT
CTCTGCATTATAATTCATTAATACGTATTCCTATTTAAAATTGGATTTAGTGTAATGCGGTAATACTGCGAATATCTAATTCATGTAAATCATATTT
CTTTAGGAACTCATTCACCGCTTGCTGAATGGTGTACCCACTCGGAGATTCCCACTGAGTACCATTAAAAGCAATAATACGATAACCTACCATTTTT
TATTCCTCTAATCACAAAATAAATACCCTCCCGAAGGAGGGTATTTATATCGTTACCAATTGATTACAGCGACAAACTCAAATACCCGACACAATTC
TTTATCACGATGGGCATGATGAAAAGATTTACCTTCAATACCGCAATACGGATAAAACAATTTTCGGTGTTCCGTGTCGCCGAACCAGAAGGTGGTG
TTATTGGAATCAACCACACCATGGATAGCCACATCACGAATGTACTGAAATACATGAACTGCCTTATCAGTGATCACTCGAAGTTCTACACCGTGTT
CCTTCATCATAGCCAGGATGTCTTCCTTGGTGTAATCTGCTTGTTCAGCATTGGTCATGATCTTGTGAGTCAGAGAACGCTTTTCCTTGTCACCGAA
ACAGATACAGACCAATTGCACCAACTGACCTTCTACCTTGAGACCACTGGTCGGTTTTAGTAGAACGAACTCATCATATTTGTAATCATTGGTGACA
ATCAGTGCCGACTTATTGCGAGTGACAATGCCTAGGTTATACGACATAATTAATCTTCCTCATTTTAGAATATGTTGAACCTTGTGGATGTCTTCCA
GGCTATGACCAAGACCAGTGGCTTTGTAAGAATGTTCCTGATCAACACGCTTGTGATATGCAAGCAGTGCATCTACTGGATGTTCAGCGAAGAAGTA
TTCAGTGTTGTTGCAGTCCCAAGCGAACTCCCATTCACCATCACGAATCTCTATTTTGTTAGCACTGAGGTAAGTGATATTGATGGTATTTACAGTG
GCATTACCACCAATGAGGTAGTACGATCCTTCATTGCTACGAACATCGATCCTGCCGCCATCGATAGTATCCTGATAGTAGAAACCACGGTCGAAGA
ATAACTTCAGCATCGAAGTGAAGTAGCTGTTCAATACAGCTTGAGCATCTTTCTCTTCGACCACCCATTTTCCATCAACGATGTTATTCAGGTAATT
ACGATCATGATTGATCCCGACATTATCCACGATGTCAGCGTAGTTCTTATGGAACTTAGCAATCTCGTACAAACGTTCCAGAGCAGCAAAACGGAAA
GGGCTGGTGGGATGCAGAGCCAGAATGATCCGACCTACGCTCCACAAACCGGTCCCGTTGACCTCGTAACTTTCTTCGAGGTAACCTTTGATACCAC
AGTTAACTTCAAGTTCATCTGCTGGGAAACCGGTGCGGAGCGCGCTACGGATAGCCAATAGTACCGATTCGGATTCTTCCGGATCGAACAGGTCTAT
GCCGAAAGTAATCCAGCTACCACGTACTTTGTGCTGGTATGCCAGGCGTACAGTATCACCGAATGGAGAAATGAACCAGCGTTCGTCTTCCGATACG
ACCAAATGGCAACCACATTGCCACAGGGTACTTAGAGGATCGTTAGAGGCGAGAATGCGCTTGGTGTCGTTCATATCCGACGAAGTAGCATCTGGAC
TGCCATGTAGGTGTGTCAGAATAAACAGAAGCGATGATTCTGTAGTTTGAGCACTCAACATTGCGCGAGTGATGGTTGCATTGATGATCATGAGATA
TCTTCCTTTTTACAGTTTATGAATATATTGCTAAATAAAAAAATATTACGATGTAGAAAATAAAAGGGAGTCCGAAGACTCCCATTATTGCGTGTAA
TCTATTTGATGATAACCGCTTTAGAAAGAGTTTCCATACTTCCAATAACTAATTTGGATTTCTCTTCTTCAGGGTTCNCCATTGCTTCACGCAGGAG
TTCACCAATAGTTTTGGGTTGAACATCATCACTGATTTCACGCGAGCATGCCGAGTCGTCGTACATATCAAACACATTCAGATCATCATCATCCAGG
GGCGTGCTGTCATTCCATGAATAGCTTGATTCATCCGAGGTATCATCAGATCTCACCATACTCTGTTCACTGAGGTCACGGTCCAGTTCAGCCTCATACA
TCTCGCTAATTGCTTTATCGTCTTCTTCTTGCGCCTTACGACGAGAAGTCTTGTAGAACGGAAGCAGGCGTTGCAGGACTTTATGGAACTTCTTCTT
GCTGATCAACCAGCTAACAGAGTAGCGAGACAGCTTTACTTCAGCTGCTTTGATAGTCGGATCGGAGTACAGCGCCATGACTAGCTTGTCCAGTTTG
TGCAGATGATCTTTAAACGAGTTTGCATAAGCAGGATGTTCCCGAAGAGTGAACATCACAAACGAACGCATGTCAGTGATATAGTACTGACTGTGAT
GTTTGTTGATTTCGATGTATACCGGATCTACTGCGCGGTTATAATCGAATTCCTCTGCCCAGGTAAGGCTACGTACTTTTAGTAGGACGAGGACCTTC
TGCCCAACGAACAGTCGGATGTTTCTCACGGATGTTCCAACCATGATTGCGATCATACTCGGTTGACTCTTCTTTGAACCAGGTGAAATTACCTTCA
CCGCGCGATACAATACCACGGCACCAACTGACGTTGATTGCCTTGTTACGGCTTTCAGTAAGATCACAGGGCATGTCCAGAATAGCGACATAACTGT
TATGACCATTGGCCACAACGCCGAGAACAGTAGCTTCGAATGTCTCGTAGCGCTGTCCAGGATACACACGTTCATTCTCATCCAGGTAACGAAGGGA
GCAGGATTCGAAGATAGCACGAGTACCGGCAGGGAAATGGGCACGACCGAAAGGTTGTTCGGCCTTTCTTTCTTTACGACGGCTGATAACCCATTCC
AGTTTTTCTTTGGTCAGACGGGTTACGGGTTCACGATACTGTTTCATGGTAATTTCCTTTTTACGATTGATTGGGTTGAGTACATCTCAATGCATCC
TTTTCAAGACGCATTGAGATGGGGTCTCCGAAGAGACCCATCTATTATTCTTGGGTCAGTTCCCCAAGACGACCTTCGGCTTTCATGCGACGGATTT
CCGAGATGGATTTACCGTACATTTTGGCCAGTTCTTTCACAGTACCTTCAGGCACAGGTTTGTTCATGTCGCGGAAGTTCTGCTTAGCGATATTGTA
ACGCTGATGTTGAAGAGTCTTCAGTTCCGAACGTACCAGAGCGTTACCGGCACATTGGGAGATGAATGTAACCATGAAGGTCTTCAGCTTGCCACGG
TAGACGTTGACCCAAGCACAGGACTCATCCACGTGGATGTTCTTGTACTCGGAAACCTTGGCGTATTCCAGCAGGCCGACGGCATCGGGACCGTTGT
CCTGATAAACCATCTTGTTGAACAGGCCCAGGGCGATATCGGAGGAACGCTCACCTTTTATGAAGGCGATGGCGTCTTCGATGATCTTGGTTTCCAG
GTCTTTGTACTTGACCGGGTCGTTCTTGATCAACAGTAGCATGGTCGCGCACTTGACAGTCAAACCCATGTCGGCACCGCGTCGATCGATCAACTCG
TTGTGCTGTTTCTGCGTGAACACGGGATCTATGTTCTTGAAAGCTTTCAGGAGACGCTGTTCCATTTACTTGTCCTCTTTGACGTTGAATGCATACA
TGGTACATTTCGGCTTAGCCGGGTGTTGGCACCACTCTTTAGATACCTTGCCCTCAGGTTTAGTGAGATCGTAATAGAACTCACCACCTGCGGCAGC
GATACCCATCAGTACTGCAATGAATCCCATTCCGATCTTTACTTTCATTTGGCAATGATCCGTTGTACGAAGTGTTGAAGGTTGGCTACCAGGCGTT
CGAATTCTTCTTCGGTTACCTGGTCACGATGCGATTCCAGAAGTACTTCTACTTCCGGCAGGACGTTCATGGCGATATCCAACTGGATACGGCTGAT
GAACTCTTCCGTTGTGATATTTCGATCACGACGAATACGACTTACCAGCTTGCGATGTTGTTCGCTGTTGCGGTAGGTNGAGATCTTATCGATAAGA
ATATCAGAGATACTGCTTTCGATCTGTTCGGCTACAGCCTGACGCGTCTTCCTTTACGGTAGCTTTGACCGGAGGATGGCAACGGCTGTTGCGC
CAACTGCCAGTGCAATAAGACCAAGTGCGTTTTCTTTGATGAAGTTCATATTGATTATCCTTTCAAAGTTGCATCATCATTGAAGATATCAGGACCC
ACCGAGAGACTTCCCAGAAGATCCGGAGCAATGTAAACAGAGTTGAGGGTTTCGTATACACCGGTAACAGCATCTACGTTAACCAGGCTAGAACTGC
GCATGGGTACCCATTCACCGTTACGGAAGGCTTCACCGACCAGTACACGAACATCATCTACGTCAGTGCGGTTCGGCCATAGATCCTTACCTTCTAC
TATTTTTACATTACGAGCATGGTAGACCAGTTTACCATTCATGCGAGCAACGATATTCGGACGGCACATGTTGTCGATTACTTTAACTGCTACGGAC
TTTTCCATTTTTATTTCTCTATTTAGTTACGAGCATTTCTTGACCATTGGGACCGATACGATGACCGAGGATAACAGTTTCATTAGAAATAGTTTGC
TCTTCAAACTTAGCGTTTACAAACAGTCCACCAAAAGTCAAACCAATAACCACTAGTGCGAATGCTTTCATTTTTAAAGTCCCTTTTTACATTAATT
GAAGGTTAAATATCAAGTTAGTAATATACTGTTTAAATATGGTTTGAATAAGGGAGTAGTAGTTATTACATATCGTGCAGGTAGGTCTCATCAATGA
TGGCACGGCTAGCTCAATGAGACTATCTTCATCAACAACAATGTTACCATCTTTCCAGGTAGCGCTATGGGATAACCAGTTACGGTAATCCTTACC
TCGTACAGGATTGATGCATACCTGACGAGTAGCTGCATCACGGTCACCACGGAAACCCATGATAGCACGTGCACGACGGATTGCTTCTTTCTCCAAG
TCTTCCGTCAGATTTAAAAGTCAGGAAAGTTGTCATAGTTTGATTCCTTTTTACTGATTTAATAGGTTAATTACACTGTTGTGATATACTGGTTAAA
ATGGTTTGAATGTATTATTTCATTTCCACAGACGACAATAGTCATCTACATGTCGAGTGATTTCTGCAACAGCCCTGAGTCGCCGGCGGCCAGTTAA
TTTAGAGCAGTGTTTATTAACTAATGTATCAACAGTTTTACGTAACCTAACACAGCGTTCTTCATTAGGTATATCTTGTTCGATAAACAGGCTAGTT
```

Figure 8(H)

```
AATTTATGGATTTCCATATGGATTTTCTTACATACATCGTTAGCCGATTTTCTTCATTTAATTTGTTGTATGATTCGACTAACTTAACAATAGTTGT
AGCAACAGTAGTTGCGGCAACAAAAATTTGAATACCATTGATAAAATTTTTATTAAACATTTTTAAACTCCAACTAATGTATTAAAAAAATATGTCT
ATATTGAAAATAAAGCCCTCCCCGAAGGGAGGGTGTATGTCGCCAATAAGTGTTACTAATTTATTTAGTTAGTTTGACCATACGTTCTTTCAAAGTT
GTTTACATCATAACCTGAGTGGTGTGTTGCAGAACCACCTGAAGTAGTATCTATAATCTTAACTACCACTTCATCATTTTCAATGTAAACCGACAGT
TTATCTCGCATAAAATCCACGTGGTCATTTCGATAACGTAGATATTTCATTACAGCTTCGCCACTGATTTTACTGTTAGCCATTATTATTTCCTCGA
TTGATTCCAGTTAAAATTATCTTTTGCATTTTTAGTGAAGAACCCGTTACCCCAACCAAATGAGTATCTAAAGTCCTTGATTACACCAACATCCGAA
TCGATAACCTTATATTCAATGACTTTATCACTATTCTCCAGAATGACTAAGATCGCGATAAGATCTTTAGGATCACCTACAGTCAATTCATGTCTTT
CAGACTCGTCTCTGTGGATAACGATGTACATGGTACTTTATCCTCTAATTATACCCATTTAGTTACTGGGAGTTCGAAGGTTTCACACAAGTCGAGT
ACTTTACGATGTTCCAAGTTATTTTCTGGATAGAAGGTAATGGGTGTAGTCGGACTACCCCAATTAACACGACATCCAGTTTCTTTATGGATTTCGC
CAAGTACAGTATATGCACCTGCCCCATCTGCATAACCCATTTGATTAGGGTTAACGCAGATTTGAGTAAAACGCTCCGTCAATACTCGATTAATAGT
GATGGTCAAGAGACGAACGAACTCACGAGTCTTCTCGATGTCGTCTACCCAGAATTCCAGAAGGATCCATTTCCCATGAGGGTTATCATGCCCACCT
TGGAAGAATACACAGAAACCTTCTTTTGCCTTATAAAACTCGTGATTGGTAATGTTACATTCAACCATTTGTTTCACTGCATGCCATACACGCTCGG
TGACATAATCACCATAAAGTTCGATGCAGTGACCACGGCCAGGGAATTGTTCTTTTTTAGAAAATTTAATTTCGAACATGGTATAGATTCCTTTTTA
CATTAATTGAAGGTTAAATATCAAGTTAGTAATATACTGTTTAAAATGGTTTGAATGTATTATCGGTAGGGGAGGGTTACCCTTTTAACTTTTTAAT
ACTATTGGATAAGTACATGACACTACGGAAAATTTTGAATCTTGAAAAGTATTCACGTACTTCTTTTTTAGTCAATACAAGTCTTCCATCTTTGTTT
ACATTATCACCAAAGACAATTTCCTGAGTATTCTTCCATAAAGATCTATAAAGATAACAGCCATGTGGTGCATCACACCAATCATAGATCTTAAGTT
CAAATTCAACTTTGTCGACAATATCATCATCAAATAAAATAGTATTTCCTTTACTATTTAATTCCATTAACTCATTTGCACAATTTATTGCAAACTC
AACCGCTGCCCAGGTTCTACCACCGCTGAACATATCTTTACTTAATTTATTTAGATCGATAGCATTATAAGTTGTTTTCTTAGTGTTTTTCATGGAC
TGCACCCCTCAATAATAAATAGAATAATCTGTATTTAATTCACCTTTGTAATATACTTTAAATACATTTGAATACATGACATAAAGCCTTCCCCTGG
GGAAGGCTATTATTATGTTTTAATCCAATGGGTATATGTACATAGGTCAGTTTCTTTAATAATGGTTGATTTCCATTTATCCCATTTAATGATTTCT
TTAGGGAAATAAACACAACTACTATTATCNATTTCCATTCTTGACAGTAGTAATGTACATTTCGTCTAAAATATCCTTTTCAATGACTTCTTTATAAA
GTTGAGAACCGCCAATGATCCATACATCCTTTCCAGTTTCTTTATTGAAATGAGTGGCATAAACAATAGCTGCACTTAGATTAGGGAGTACACCTAA
TTTATTATCATAGGCTACTGGATAATTACCGTTACGATATAAACTTGATGATACAACAATGTTATTACGATTAGGTAACGGTTTACTACCTAAGGAT
AAGAAAGTATTTTTACCCATGATAACACAGCAACCAGTTGTCATTTCTTTAAAGAAAGCTAAATCCTCAGGTATATGCCAAGGTAATAGATTATTAT
ATCCAATGACACCATTTAGGTCATGGGCAACGATTAATTTAATAGCCATTAATTTTCCTTAGGCCAGAATTTACAAGATACTTCATTATCTTTAAAT
TCAATAGCCCAACTACGACAAGTGAAATTAGTTTTAAACTTAAATGTAGACGCTAATAGGTAATTAATTTGAGCCATTTGTAATAGCGTTAATTCAC
CATATACTTTCTCATCAATCAATACACCAGGTCTTTTATGTTTAATAACTAATTCATTCAACTTAATATCTTGTTCAATATAGAGGTATTCCACTTC
GCCTTTTTCTAGTATAGGCATGTCCCAAAGAATCAGACTAATCTGTTGTGTGAATTCCTCAATACTAGTTGTAATATCTAGTCCTTCATAACCTATC
AATAGATTTATAAGTACTTGTAGACTAATCAGATTAACAGGTAAGTCTTTTAAATCGTCTTCTTTAATAGTTGTTCTAAAATAAACAGTGCCATCTA
AGTTTTTAACTAATAATCTATTTAATAGATGATTGACTTCTGATTTAATCTGATAATCCAGTTTGATCATTAGCTAACTCCTTGAGTCTAGTCATGC
CATTACTAACTTCAATAATGTAACTAAAGTCAAAACTATATTTCATCATTTTGAATTCTTCTTTAAAGTTAGCGATATTTCCAGACAGAGCAATTTG
TTCAAATCGACTAAAATCAGTAATTAGTTTCATCGAACATTAGTTTCTTCGCGGTAATATCTGGATCATAGTTAGGATGATCAACTACAGTACCTTCG
TGGTTTAAAGTACCTTGAAAATTCAAAGTCTTTTTAACATGGTCTACAGTTATTTTCCAACTAGTTGCAATATACCGAGCTTTAACTAAATTAGGAG
CATACCTGTAAATACACCATTGTAATGGAGTGCCAACAGTTTGCGTATCATGCGTGGCTTTTATAACTTTAATAAAATTCTCAAGTTGATCAAATGT
AACATTCCTAGTTACACCATCATTAGTGGTTATATTAAGAGATGGTCGAAGACCAGTACCAAGATCATTGGTGATGATTATATCCTCAACTAAAGCT
TCATATAACTTTAGTCCTTCTTTTCTGGATCCAACATCATTACCCATTGTTTAGCTTCCTCTTTTGTTACCAGTTGATAAAGTTTATTAAATTCACG
TTGACGCATTAATTTGTAATCTAGTATACGCCCATTATTTTTACGAATTAAAATAATAAAATCACCCGGACAGACAATTTTATCTTTATCTGGGCCT
ACACGTAAAATACCATGACTAGATTCAGTTAGACTATAATAATGGGCAAATCGCATTACTAAGAGTAGACTCTTTAGTAGGTATAGCATAACCAACAA
TAGCACCTTGGTTGATATTATTGATAACGCCATCACCAGGTATATCACCGTTCTTTTTCCATTCGATTGCTTCAATTGGATCGGTGTATTTCGGTAG
ATAAAAAGACATTCTTAATTAACTCCGATAAATAATAGTAGTATAGTAAAAAGCACTTAGGTATATTTCTATTTTAAGCTATATTGTTGATAAAATA
AAACCTAAGGGTACATAGTGGGTTATTATTTAAAGCTCTTAAATAGCATGGTAGAACGATATTGGACTATATAGCTGTAACCCTTAAGGCACTAAGG
CTACAGAGGTTTTTAAGATAAAGATATCCAATGTACCATAATATGCTTTTACAATAGATCAACTAAATTCATTTAAAATGGGTCGTAAAATACTTA
GTTGATCTAAAGATATGTTGAATACTTTTTCACATGAACTTACGACTCACAATTACGACTCACAATGTTAAAAACTATCATTAAACTAGACAGGTAC
TGAAGAAGCATACTCACCTGCTAAGATTAATGGTTGGGGTGAATGGGCAGCCCAACATCTTGGCGATAAGGTGGATTGGAGTAGTGTTGTGATGGAT
GCTGTTCAAGCTCTTGGTGATAAAACTTCATCACAAGAACTACAATTACAACTTATTGAAGAATGTTAAATCGTAAGCATGGTCTTATTATCTAA
TGGCTGGTAGACTATATGCGATTTATCTTCGTAAGAAGTTCTATGGTCTAAATGGCATCCCAACTGTTAAAGCGCTTCAAACCAGGATGCGTAAAGA
TGGTATCATTGTTAAATTAGATTATAGTAGTAAAGAATACGCTCAGATTGAAAAGATCATTGATCACGATCTTGACCTACTTTGTCCGCATTTTTCA
CTTCATCACATTCGTGGAAAGTATGCTCTACGTAATCGTAAAACTGGTCAAGAATATGAGACTGCCCAGTTTGTATATATGCGAATGGCAATGGCTC
TAGCTGAAAAAGAGCCAGCTGAAACTCGCATGACTCATGTGGAGAATTACTATAAACTACTTTCTAATAAAATTCTTAGTGCGCCAACACCTAACTA
CGTTAACCTAGGTACTAAGCTTCGTGGTTTTGCATCATGTTGCCTATTTGCTTCTGGTGATAATGGTGTATCACTGGCAATGGGCGATTATATTGCT
AACATCATGACCCAATCATCAGCAGGCATAGGTGTTAACTTAATGACTAGGTCAATTGGTGATCCTATCCGTAATGGCCTAATCATTCACCAAGGTA
AGAAACCATACATCGATGTAATTGGTAAAGCAGTAAGGGCTAACCTACAAAATGGTCGAGGTGGTGCTGTTACGTGTTACTACAGTGCTTTCGATCC
TGAAGCAGATATGATTACTCAGCTACGTAATCCACGTTCTACTGAGGATAGGAGAACCGTGATCTTCACTATGCATTCCTAAGTAATAAGTTCTTT
GCTAAGAAAGCAGCTCAGAAAGATGGTATGATCTTTGTATTCAATCCATTTACTGCTCCAGATCTACATGATGCTTTCTATAGTGGTGATATTGATA
AGTTTATTAAGCTTTATGAAAAATATGAAGCGGATCCTAAATTTGAAAAACTTATGTAAATGCTCGGGATCTTCTCAAATCAATGCTAGTTGAAGC
ATATGAGACTGGAACCATCTATTCAGCTCAAATTGATGAACTCAATCATCATACACCATTTAAAGAACCTATTTACAGTTCTAACCTATGCCTTGAA
ATCGCAGAACCCACTAAGCCTTACTATCGAATGGAAGATCTTTATTCTAGTGAGGATCACGGGCGGTGAGATTGCTACTTGTTCACTGGCTGCTA
TTGCAGTGGATAACGTTCCTGATAAGCAAACTTATGAAATGGCGGCTTACTACGCACTTAAGATGATTGACTATTGTATCCTTAATGCAGAGTATGC
TTTCCCACACCTTGCACTAACCGCTAAGAATCGAATGAGTGCTGGTGTTGACTATCATGGGTCTAGCCACACATATGGCGCTGCTGGCCTTAAATAT
AGCAGCGATGCTGGTAAAGCTGAAATCCACTTCATTGCTGAACGGCATATGTACTTCCTTATCAAGGCGTCACTTAAGATTCTAAAGAACGCGGGA
ATGCGCCTTGGATTCATAAGACTAAATGGCCAGAGGGATGGACTCCACGTAAGACTTATAATAAGTCAGTGGATACTATCATTGAAGGTGGCTTTGA
AGAACTTTATCCATGGGATGAGCTAGAGAAAGAAATTAAGGAGAATGGTGGTATTGCACACTCCGTACTAGCTGCATACATGCCTGGTGAGGCATCA
TCTAAAGCACTAGGGTCAACTAATGGTCCATATCCGGTACGTCGTCTAATTCTGAATAAGACTGATAATGGCGCACGTGTGTTATGGGCTGCTCCAT
ATGGAGATGATGATTCCTATGTGTATGAATCAGCTTATGATATCCCACTAAAGATCTTATTGACTGCTATGCCATTATTCAAAAGTGGACTGATCA
AACAATCAGTGCAGACCTCTATCGACGCATTGTAGGTTCGGAAAAGATCTCTTCTAATGAAATGCTAAGTAATCACTTCTACATGGTGAAACGTGGA
ATGAAAACCGGTATTATGTAAATCTAGAAACAGCGGCAGGACTTGACATTAAATCACTTGAACGTGCTGTTGAGGTAACTAATACTGAAGTTGGGT
GTGCAGGTGGTTCGTGCACTCTTTAAGTGTATACACCCTCCCTTAATTGGGAGGGTGTTATTCCCAATTTATACTAACCTCTATTATTTATTGTAAG
AAATATTTTTAAATTGTAAAGGAANTAACATGTCTACTAAATCTCAACTACCAAAGAAAATCTTCAATGTTGCTAAGAGTGATTATCATCTACCGGA
AATTATTCTTGGAGATGATCCAGGTCTACTAGATTCAATCCACACTCATTATCCTAAAATGTGGGAGCTATATAAGCGTCTAAAGATGCTTGATTGG
GATGAGCTAGAATTTGACTTTTCCACTTGTCTAGTAGAATTTGAAACGTGTGATAAATCAACTTATGACATGATGATTAAGACACTGGCCTGGCAAT
GGGAAGCTGACTCTGTAGCCAGTCGTTCCATTGTTAATATTCTATCACCTGTCATGACAGATTCACGAGTATGGGCGGGATATGTACGTATTAATGA
```

Figure 8(I)

```
TAATGAAGACGTACATGCTTTAACTTATTCTGAAATTGTACGTAATAGCTTTAAAGATCCTAAAGTTATTCTAGACGAAATTCTTAGGGTAGAAGAA
GCACAAGAACGAATGGTTGCAGTAGCCCGCACTATGGGTGAAGCACATGACGCAGTTCATGCGTATGCTCTTAATCAGGTACCCAATGATCAAGAAC
TTTACAATAAAGTATTCATGTTCTTCATCGCTCTATATTTCCTAGAACGTATCCAGTTCATGGCATCCTTTGCAGTAACCTTTGCTATTGGTCGTAC
TGGTGCATTCCAGCAAATTGCAACCGCTGTTAAGAAAATTGCCCAAGACGAATTCGAAATCCATGCACAATATGGACAAGAAGTTATTCGTGCACTA
CTGGCAACTGAACGCGGTAAACTCGCTTACAGTCAATGTAAAGATAAAATCATTGAACTACTATGGGAAATTGTAAAGACTGAAGTTACCTGGATTA
ATTATCTATTCTCTGAAGGTCGTGAACTAACTGGTGTTAATGCGACTAAACTTATTAACTGGGTACTTTTCAATGCTAATGCCGCAGCAACATTCCT
AAGTATTGAAATGATGTTGTAGAACAGTATCAAGTGGAGTTTAAAGAATCAGCTGGATTTGATTTTGTTTGGCCAGAGAAGAACCCACTTCTTTAT
ATGGAAGACTACCTAGATATTTCATCAACCCAAGCATCTCCTCAGGAAGAAGAGAAGCCTGATTACATGGTCAACGTTGTAAATGATGTTGGTGAAG
AAGAAGAATTTGAGGTTGACTTCTTATGATTAAGATTATCGCATTCGTAGTTTTAATGTGGTCCACTGTCCTATTTGCAGCAACTGAAGTAAAATCA
ACTACAGATGGTATTATTGCACATTCAGAATGTCAGCTAGTTGCTAAAGATAGTAGTGTTGTCGGCACTACTGTTGGAGGTGCGGTTGGAGCCACCG
CAGGCGCTGTATTAGGTCGAGCAATCTTTGGTAAATCTGGAGGTTGGGTAGGTGGTTTAATCGGTGGTGCCGCAGGCGGCGATCGGTAATAATGT
TAGTGCTACTGAAACATTTCAATGTAAACTGATTGTTAATACAGATGGCAAGCAGTACATGGTTCAAACAGTTACCAATGAAAACCAAAGGTTGGT
GATAAAGTCACTGTTGTTGAAATGAATGATGGTACACGAGATATAATGTAGACATAATGACCCTCCCTTAATTGGGAGGGTTTATGCTAACAATTCT
ATAGCACTCTTATTAACAGTCATCAACGAGAGAGTAGACATGAATAAAATGCTAAACTTCCTAAACCGTACGCTATATAGCGGTACTGAAAAAGTAT
CTTCAAAAGCTACACCAAGTCTAGAACACTTTAAAACAAATGTTGAACAAGTAGATAAAAAGATTCTACAACCCTTTAGTACTAAATTTAAAACCAT
TCTAAAAGAATGTTACAGTAATGAGGAGTGGGTTGAAGAACAATCATTTATTGAAGAACCTATTGATCTTGGTTCAGCTGCCACGCGGTCTTACCGAG
CGCGGTATTATGCGTGGTGATTGGGGACGCTTAGCGCATTCCACTATTAAAGAAGCAGAAGGTATGATGCGTACTTATAGTGGTCGTCTAAATGAAG
ATATGGAGGCATCTGAAATTAATGAAGTAATTCAAGATATGCCTTATAACTTCACAGCTGGCTCAGCTAATACTAGCCGTTTAGAAGAAGATGACTC
TATTTTTGTTGAAGCAGATACAACTGTAGTTGAACCTCTGTCTAAGCAGACTCTGCCAAAAGTAGCAGAGCTTACTAATCAATTAGTGGAAGTCTAT
AACCGAATTACTGAAGAATTTACAGAAACTGGTATTGCTAAAGTTGAACAAGTTGAACAGCCAGCAGTTCTTGTAGCACTTGGTGAGATCATTAGTA
GTTTTAATAAACTAATTGATTTATCTTGCGGTGCTCTACCAGTGGAAGAAACTGTTATTGTAGAGGAGGATCCGTTACCTGCCATTGTTACTGGTCC
AACTACTGAACCCATTGATGGTGAAATTCTACCGGTTGATGCTATTAATAATTCTGCGGCATTAGAAGAATTCATTGAAGAAGTATTAAGTACTAAT
CCAGAATTCATTAAATATCAAAGTATGAATGATAGTAATATTGATTCATATCTAACTGGGGATGACTGGATTATACTGAAATTCAAAGATGGTTCTT
ATTATTTATACAATGCCCAAAGTGCCGGTGAAACGAATATAGAAATCATGAAAGATATGGCCGAAACTGGTAGTGGTCTTAATGGTTTTATAAATCG
GGTTATTCGTGGCGGGTATGTAGAGAAGTCCATCATTAATACTCCCGGTTTTATACAAGTCTCAAATGAAGGTCTTATCGATTCAATCAAAAAAGTT
CTTGGCATTTCTAATCGAGGTGATCAGAAACGTATCTGGCGTTCATCGTCCAGTGCAAGAGGATTTCTGGAACAACTAGAATCTACATTTGGCAATC
CACAATGGCTTAATAAGCAGGTATTCGTTACTGGCGATATCAATAGTAATGGTATAGCTAACGTACTGAGTATTAATGGTAAAGTCAGTATCGAGGA
TGCCATTCGTGCAGTAGAACCATTCTTCAAACTCGAAGAAAAGTCTAATCGCGAAATGGAGTCTTACAGGCAGAAGACTAAACCTGCATTGGATCTA
CTCATTAAGAATGCACATAACCTAGACGCTAACGTATACAAAGAAGCAAAGGCTATCGTAGACAAGGCACGTGCTGGATTCAAGACTAGTGTTAAAT
GGCCTGCCGGTACTATTACAGGTAAGGGTACCTATAATTCACCTCGCACCGTGGTCGCGAAATATCCATCTACTGATAGTAAACTCAAAGCTCTTAC
TGAAGAAGAAGCAGCTAAGGCCATGAACCTTAATTATATCGGCATTGGAACGTCAGATAAACTCTTAGCTTCAAGTTCCCTGATTTACCAGATCCACTG
GAAGGACTAATCTACGATATGTTGGATAACCCTAGTCCAATAGCTGGTATCGATTACTATGTTGGAATGATTTGTTATTCGCATGCTTTGGCCCTG
GGATTGATGATGATGTGATGGAAGTTAATAAAATGCGGCAATACCACTCATTCATTGATATCATGGAGGCCGCCGCAAAATGGGTAGATCGGTCTAT
AAAAGGTAGGTTAGCAATGGGTAATGAAAACTACCAGTAATGTATCTAATATTATGTAGAAATAATCCCTCCCCCTTGTTTCTACATTAGTCATAAT
AGATCGGAGCCAGTCCCCCTTCCAACTGGCTCCCAGAGAGTAAAACTCTTTGCTGGGCATTAATGACGATATATCGCCTCCCTTCGGGGAGGCTTTA
TATTTTGTTTTTACGTATGTATATTAAAATATGTATAAACAACATAGAGTAATTATAAAATGATCAAAAATGAACTTTTACCAGGGCTAATCTATGC
CCAAAAAGAATTTGATAAAATTGCAGCTAATGTAAAAGACTATGATAANTATAAAAGACGCGAAGCTGGTAGGGCAAGTGCCGTTTTAAGAAGTCTA
GTGAGCAATATTGTAAATCAGAATAAACCATCCTCACTTGAACATGAAGGCAAAGTTAGTACTACTAATACTAATGAATATTTAGAAGAAGTTAATA
ATTACTTCTTTAACATTAATAATATTAAATTAATTTCTCCTAAACTCATAAAAGAGAAATTAACAATTGATCTAATGAATATTTATGTTAAATGGAA
TATGATTGGAGTGGCTGGCCGAAATGATGTTCCAATTATTGAACACAGAATTAATGATTGGTGCGAAGTGACCGATGTCTACATTAATGGTAATAAG
ATAACTTCTTTACAATGGCCACGTTGAATTTAAAATAAGTTGTAATAAAATACCTAGCATTACATGTTATGTATTGAAGCACAATGCCCGAATGGTG
AAATTGGTAAACACAGAAGACTTAAAATCTTCCGGCTACGGTCTTGTCGGTTTCGAATCCGACTTCGGGCACCAATTTAAATACGGAGTGTAGCGCAG
TTGGTAGCGCGCCTGCTTTGGGAGCAGGATGTCGGGAGTTCGAGTCTCCCCACTCCGACCATTTTAATAATAGGTAAATAGGATGGATAATAAATGG
ATATCATGGGAACATCAAATTATAGGAACAGCTCTTTACGCTATTCTTAGTGACCCTGAATTAACTAATATTCAATTAGCTCAAGGCTTACACTATC
TAACAGAAGCAAAGTCTTCTGTATTACATGTTTGTAATAACCATATTACATTCACTGTAACCTATCCACATGGCACATTTAGAACCAATGTAATTAG
AGAGTGCCCTGCTAGTGATACAAATACATTCAAATGGTCAGGTGTATTAGTCCGTCAAAAAGATGGAACATTCTTACCAGAATAAATAAAAAGGGCC
TATAGCTCAGTTGGTTAGAGCAGGCGACTCATAATCGCTTGGTCGCAGGTTCAAGTCCTGCTGGGCCCACCATATACTAGCCTCCCACTTGGGGGAG
GTTTTATACTGTCTCATTGAGGAAAACATGAATACAGTAATAATGTTGGTATTATCTACAAAGTTGGATTATTTGGTTTCATTTCGACTAATGAAA
GTAATATCCTATTTGAAAATAGGGAACAGTGTATTTCTCATCTGGATATTCTGAACATAAATACAAGTCTCTTGAAGTTATTCGAAATGAGAATAC
TCTAAAGATAACCGAAAGAGATAACCATTCTATTTATATTTTTAAATGTCTCTAGGAAAATACATGGAACATCAANAACAAAAAGAACTATTGAGAC
AACCATTACAAACACTTTATAATCTTACTTTTAGTCCCCGTTTACGTAATGGAGCGAAGGCTCCCGATTGGATTCACCTGACCGATGAAGTAACCCT
ATTCCCAAACGGATTAGATATTACAATCAACGCTGTTACACGTTGCATCAAATGGGAACTTATCGGCGAGGATGTAAGTAACATTACTTATGTTGAA
GCTATGTTCTTTAATAAAGGTCTTAAAGCAGTTAAAGCCTATCTCAAACATACGGAGTAAATATGATCATCTAACCCAACGCAGAGCGCTGTATA
TTTCACATTTATTAGCCCCTGAGTTTATAAAGCTAACTCTTGTTGAATCTTTTGTAGCGATCCACAAGAAACATCCAGAAGTAAAGCATTGCGTTAAG
AAAAAGATTAGTGCTAATGAAACGCAGTTTATCTTTATCTTCAAAGATGGGACTGATAATTTAATCATTACACGTAAAACTGAACCTTGCCCTGAAC
TGGATAGCCCAGTAGGCGATAGTATTAAGTTGTCCGGCGAAGAACTTAAAAATATTCTTGCTAAGTACGATCGTCCCAAGGATGGTAACTATTTCAA
GCACTGGACTGATCGCCCGTAATAAAATATTACTGGTTATGTAATACTATGTAGGAAGTCATGTCCATACGTTTGCGCTCATAGTTCAGTTGGTTAG
AATACCCGCCTGTCACGCGGGTGGTCAGGGGTTCGAGTCCCCTTGGGCGCGCATTTAATTCCGTGATAGCTCAGTCGGTAGAGCAAGTGACTGTTA
ATCACTGGGTTCCCTGGTTCGAGTCCAGGTCACGGAGCCATATTCTAAAGAGTAGCTTCGGCTACTCTTTTATGTTGCCATGGGTTATCTTATGAATT
AAAATGATTTACTTGAGAGCACACTCATGTTTGAATTACTATTATCNCCAGATATAGGCGAAGAGTTACCCTTGGTTGGATTTAATGAAATTATTAA
ATTAGGTGATCTACCTGTAGCGTTAGCTGGTACAATGTCATATGTGGATGGAAATACACTGTATGTTGGATCGGTCATCATACTGAAGGACAAACA
GCTGCAACTGTGTTCAGACGTTTTACCATATCGCCATTTGCCGATATAGGTGCAACTGCTTCTGGAACATTCTTACCAGGGGTATCTTTAGGATTTG
GGACATTACATAAGAATAACTTTATTGTTTATGGCGGTATTACTGGATGGAACTCGGCTGGTAATGGTGGTACGGGAACATCTAACTTTATACAACA
TTTTGATATAGCTACAGGCAATAAGGTTGAGCGATATAGTGGTCCCGTACCACTTTGGGGCACAGCCTCCGCATCAGATGGTAATGATCTTATTCTA
TGCGTTAACCCANTTGGGNGTAANNGCAATGCGNTTAAAACCATCNNGTAAGNCNTGGCCTTAGNGGNCAAGANTATTCAGGTGGTGCTCGTTCAGGTC
AACAGTTATTCTTTTATAATGGTTACTTTTACCATTTTGGTGGTTGGGATAATACAAAGAACATACCTAATCTTGAAGTTTATCGATATAATGCAAC
TACCTTAATATGGGAGCAAACACCTTGGATGATTATACCTGCTGATAAAGGAACAATCTGGCAAGGTAANGGTTATGTAGATGGNGACTATTTTAAT
TACCTTAACGCTGTTGATGTCGGCGGTGTAACTAAAAATGTTTGCACAACGTTTTAATATTAGGCGCCGGAAATGGGCTGAACCATTTGAACTAGGTA
TCGGATTCCTNAATATTTCATCTATAGCTAAAGGTCCGGATAATAGCATGATCATTGTAGGTGGATCTAAAATGCCAGTTGGTTGGTGGAGCANANAT
GTTGAAAAGCCAATTGTTATCAGGTNTCTATCAGGTAAAACTAGCACCATTAATCATTGATTAAAATAATAATATTTATAACTATTTAGATAATTAT
ACTGGCACGATGATATTATGTAAGAGTACTATANTAAAGTATTCTTAAATCTATCCACTAAACACACTCGGTGGTAGAACTTATTATAGAGTGTGTC
```

Figure 8(J)

```
TAAATGCCAGGGGTTTGCCACCCCTGGNTATATTCATTGTTACTATTATAAATTCATTTATAGATGAGAAAAGGTTTTATCACCTTTTCAAAATCGG
CATTTAATTCCAGTTAAAAAAACTGAATCTATGCTACATTGTAATAAAGGAGTCTATTATGACTAACTCTAATCCGTTTGTAAGAACTATTGTAAAG
TACCAAGATATCCTAGATGCTTTAATTCAAAAAACGAATGAGAACTGGGTTAATTATCGATCTAATTCTATTGGNCATATTGTTATTCGTGAATACA
GGACTGTTGGATTATTTGTAGGTCGGCAATGTGGTAGTACAACTGCATTGATTGAGTTTGCTAATCGTCANCCTGGCGAATGTCTAGCTGTATTTGT
AGAAGATAAAATTAAACAGGCTGTACTGGCTAAGTTCCAGAATGCTAAAGATAATATTGTTTCTTGTTTAATTACACACCAACTCCGNAAATATATT
CATCAACCTGAAGAATCATCTATTCAAAAAGATATTAAAGAAGAATTAATATCGTCTGTAAAATATATTCTTGTTGACAATGCCTCATTTAATCTGA
ACCTACGCGGTATCACTGATAAAGAATTTAACCAGTGGGTTGCAGATACTTTTGGTACAGAGGTAATGGTGGTTCGTTTTAGTTAGAATTAGTAACT
TTGATAGTTTCTAATAAGATTAACTACACGTTATTTACATAATGTCATAACAAGAAATAAATAATACTCAGATTGTAATAATATGTAGTTATTACAT
ATCTATATTAGGTTGTCAGTAACTCATCTCTAATATAAAATCGCCATAATTCTTCCGTGATAGCTCAGTCGGTAGAGCAAGTGACTGTTACGATTTC
ATTGGTAAGTACCCGAGTGGCAGCAGGGAGCGGACTGTTAATCCGTTGGCGAAAGCCCACCGTAGGTTCGAATCCTACCTTACCAGCCAAATTCTAA
AGAGTAGCCAGCTGGCTACTTTTATCTTGTTCTATAGATCGAACTAGCTATCTATTTTTAAACCCTAGGTTCGATATGAAAGAAAAAAATAATTAA
TGGTTATCGGGCTCTGTATTTACCTGAACATCGGCAGGCAAAAGCTAACCCCAAAATGTTTGGATGGGTATACGAACACCGTGTAGTCGGTGAAGAT
ACAATCGGAAGATCTCTTTACGATGACGAAGAGGTTCATCATTTGGATGAGAACAAACTCAATAACCATCCCGATAATCTTTTGATCCTCCCTCAAT
CACAGCATCTAAAACTACATGCATGGATGAAACGACTGGGCATTGATCCAAAGAACTATCCTACAAAACTTTGTGGTGCTTGTGGTAGGGTAATGAA
TCATAAATTGATTAAATTCTGTAACCCTGAGTGTTCTGCCAAAGGTCGACGTAAGGTTGATCGACCATCTAAAGAACAACTCGTCCTTGACGTTACA
TTGTTATCTCTTGTGAAAATAGGAGAAAAGTATGGGGTATCGGATAATGCAATTCGTAAATGGTGTCGGTCATACAAAATCAATATTCCAGCTAGGT
TTATTAGGGTCAGCACTAATGGGGGTATTAGCACCTTGGCCCCCACACAATAAAAATATACTCGATGTAGATTAATATACAAAAACATAATCACTGG
GTCCCTGGTTCNANNCCAGGTCACGGAGCCAATTCATAGTTTTAGATTTAGTTATATTTCACTACTATGTAAACTATAAAGGCAGCTAATGCTGCCT
TTATGTCGTCTTGTAAAAGTACCCAGTAGTTGAATCTTATAGCTGAATACAAATAGGGTAAAGACATGTCACTTAAAGCATTGCAAGATATAGTTAG
TAGTGTTCCTACAAATGAACAAAAGGAACGATTAGTTAAAGTTCGGAAAACGATGGAAGAGCTAAATGAGTCTATTAAGAATCAGATTCGTAATAAA
CGACCTAGTCAAGCTCTTCTCGACAAAACGATAAACTGGGGTACCAAGTATGGCTAAGACATTAGTTCGTGCAAAGCTGATTACTGAAGCTGGTCAA
TGGATGTCGTCTGACTGGGAATGTGGTTTCCGTGCATGTCGATTCGTGAAACTTGGTAATGATCATGTAAACATAAAAGACTTTGAGGCTATGATCA
CGGCATTCGAAGTTGGTGACATGTTAGTGATTTGGCCAAATGGGCTTAGAACTTCGTATAGTGTGGATAATTTCAATAAGTACTTTTCCCATATCAA
AGATGAATACCATGAGACTGATCTCCGTCCACTCTTTTACCCCAAGTAGTTGAGCTTATGATAACTATATTCGTGTATAAATACATTACATTCGTTA
TACCCTTTAATTGATTGAAATCAAGCTACATAAAAGTGATGAATACTTTAACCCAATGATGTATAAATTAAAAAGTATGCACACTAAAAATACAGAT
GGTGTTTATTTGATATTTTTACCAACGCCTACTATCGATGATCAAATTAACACCATGCAAGGGTATATTATCAATAAATCCGGTAATCTCATTAGGA
CTACTGTACAGTCATGGCGATTTGAGAAAATTGAATTCAAAGACTTAGCCAAACATGATAGACGTTGGTTATTTATTGAATATTACATTAATGTTAA
ACAAACGAAAATAATATAATCAAAGAGCAACAAGATGAATTAACTAAATTTATTTATTATAGTACTCTAAGTTAAAACAAATAAAAAAATAAATAT
AAGAGCTAGCCCCTAATGGGCTAGCTTTATGTTATCTTACTCTGCTACATCTTTTACATCAGGTTTATTATTCCAACGTACTGCTCTCGCAATACCA
TACGTAAGAATAAGAGCACCCACGGTGCCAATAGTGGTGCTAATAATAATGCCAAGAGTTTTTGGNTCNATATTCATATTTAGTNTCCTATTTACAA
TTAATAGAAAATATTACTTTTAGTAATATCANNTTNNTNATATACNNNTTTAAAAAATANGTTTGAATATAACTTTATTTATTATAATAAATTAAAATAAT
ACTTTCATATACACTATATGTAGAAGATTNCGCCGCTATAGCTCAGCTAGGTAGAGCAACGCACTTGTAATGCGTAGGTCCTCCGTTCGATTCGGAG
TGGCGGCACCAAATTTACTGAGGTTTAAACTATTCTTAAATATATTAGTTAGGATGGGATTGAACGNGAAAGACTCAGTAAATCATATTGCCCCTCC
ATATGGAGGGGCTTATGTTTGTCATTAATCAGGAAAATATAAAATGAGNCATCTATTATTTATCATCCAAGAATACATTACTAATAAATTTGAGATA
ACACGAATTGATATGAAGCCAGGTAATAGAATGTTACGTGTATGTTTATACGGTCAACATAAGGGAAAAGGTTTCGTCCGTATAGATTTATGGTCAG
TTGGTTATCGCATTACAAAGAAATAAATACTCCAGATTATTTAATATGTATTAATCAAAGGAGTTTATAATGAGTAATGAAACTAACTATCTAGGTTA
TGAATGGAAAACAGATATAACTACTTCAAATCTTAATAGAGTGGTTGATTTATATACACTTGAATTAACATGGTTAAAAGAAGATTTTAATGATACT
CTTTTTATAAAGTCTTATAAAGTGCTAGAGGGTCTATTAGAGGAACCGTCTAGGGCAATCCATGATGATACAGTACCATTCAAGATCAATTAGATG
AATTAAATACTGTTTTTAAATTAGTATTTGGAAAAGATAATAACGTAGAGTTATCAATTAATAATGATTCAATTATTGTGATCGGTGCTACAGATGC
AACTAAAGAAAAGTTAGAAGCAGAGGTGCGTGAGTTTGCATATAGAAAATCATTAATTGATGAACGTTATCCAGATATTGTAACGGATTAAAATACT
TACAGCTATCTAGTATGTAACTAGGCGGATTGCCATTTGTAAATTATCTATTTAATCGAACTGAGGAAATACTAATGAAACAATTCTTTCAACTACT
TCTAAGCCTACTTTTCAAACTACCGGTTCTATCATATTTTGCTGAGAAGAAAACAGATTAGAGAAAGAGAAAAAAGGGAAGAAAGAAGCGTCAGCAAGAA
CAACGTCAAAAAGAACTACTTGATGAACAACGTCGCGAACAAGAAGATCATTATCGAAAAACCGCTTACGATCGCCTAGCAAAACTTATTCATACTC
GGTGGTATGATGAGTTTAATGCATACGAAAAGAAACTAGTTGATCTTGCTGTATCGAGTGGTAAAGCAGTTAGTGTTAAGTATGGTAAAGTTACTAA
GATGCAGCACCCTCATCAATTTAAACTACTTAATGATTGGCTGGATGATATTCCAGTAGAAGATTATTCTAAGTGAAGAGGAGATATACAATGGTCT
TCACACTCGAAGATTTCGTTGGGGACTGGCGACAGACAGCCGGCTACAACCTGGACCAAGTCCTTGAACAGGGAGGTGTGTCCAGTTTGTTTCAGAA
TCTCGGGGTGTCCGTAACTCCGATCCAAAGGATTGTCCTGAGCGGTGAAAATGGGCTGAAGATCGACATCCATGTCATCATCCCGTATGAAGGTCTG
AGCGGCGACCAAATGGCCAGATCGAAAAAATTTTTAAGGTGGTGTACCCTGTGGATGATCATCACTTTAAGGTGATCCTGCACTATGGCACACTGG
TAATCACGGGGTTACGCCGAACATGATCGACTATTTCGGACGGCCGTATGAAGGCATCGCCGTGTTCGACGGCAAAAAGATCACTGTAACAGGGAC
CCTGTGGAACGGCAACAAATTATCGACGAGCGCCTGATCAACCCCGACGGCTCCCTGCTGTTCCGAGTAACCATCAACGGAGTGACCGGCTGGCGG
CTGTGCGAACGCATTCTGGCGTAAGTTTAAATAAAAGAAAATAAAGACGAAGTTTTCTTTACATGGAGAGGGGTTTATGCCGTAATTATACACTTA
CTTTGATAAGATTTTTAATATCAGTAAAATGGGTATATGTTGCCTTTTATCTTTGTGAACCAGTAAGCAACAGGTACCTTCATTTACTGTATTGGT
TTGTTTAATGGGATATTTAAAGCATATTCAAACAGATCATCCATCGATGGACTAAATACCATTATTGATAAGGACATGATCGAAATCAATTAAT
CCAATAAACGAATCGATCTCAGATTGATAATACTCTACAACCATTTTAGACCATTCTTTGTTTATCGCCTCAATGACATTAGGATTATTTATTTTAT
TAAATAACTCANTNCGTTCCTNAGTAGGTAAACTGAGGTAATAATTAATATTACTCCTAACGATATCTGGATTAGTGTATATCNATTTTTTCTGGTAA
GTTATATTTACTATCTACATAATTCTTAGTTTCTGGTGTCATTCCCAGCAACCATAATCAGCAGTAGTACTTGATGGATCTATTTTAGTCTCCACT
ACTTTAGAAAATACATCTACATATAAATTAACAGATTCGTATACATCAGGTCTGATTGGATTAAAGTTTAAACTTTTAATAAGACCCCTAACTGGCC
GAGTACCAATTAGACAATGCAATTCAAGCTTAACATTTTCCTCTTTAGCCATCTTAAATANATCAGCAAAACTGAGCTTTTCTGCCATTTAGAATAT
ACCTTTTATTAATTGGACAAATAGATTAGATACACATAGAAATAGAAACCATAAACCTAGTCTTTGTAATTTATCTATACGCTTAGCTTTTTGT
TTCCTCTTTAATCTAACTAATAATGTATTTTAATATCATTCATTAAATTATCTCAGATTTTTAGACGGTGTATAAACCCTCAGTATTACATGTTGT
TATGATATTGTAAAGACGATGCCAATAGCGATCATACGTATTTTTACGTTTGTAGCTATTGGTNCGGATGACTAGATTGGCGACCCAGTGATTCTGA
TCAATGGTCTCATGTAGATGCCCGAAATAAGCCCCAGTTCAATTTCGAATGGGATCTTACACTCACGCCCCTTACACATTGCTTCACGCAATAAAC
GCATTGCAGAATTCTCTGCATTGGTATCTTTAAATAAAAGACTAATGTATCCAGGGCTACCACCAGTTTCTTCATCAACATGGCCTGAACAGCAATA
AATAGTTGCAACATTGATAAATTGATTAAAACCATTTAATTAATGCCTACATGCTTCATCAATAAGATCTTCATATTCAGGTTTATACATTACTTTA
ACAGTATCATCTGCACGTTGTTTCACATGATGAAAATATTGCTCCCAATTTACATTAGTGTAATATAGCATATCCATATTAGAATTACTCATACAAA
TCAACCCCATATGTTATTGGCATATTCGCGGTCATTGAAAATGCGGGTAAGATCCATCCGCTTTTGAATGCGCGTAGTATCCATTTTAGTTGTTTA
GTTGATAGTTCTTGATTTTGCTTGTACTCACCTGTAGCATGGATGTAATAATCAAATTTACGACTTACAGTAGTAGTATGTGCACATGCAATAGCAA
ATGCTTCAAGTGCAGTTAGTTTGGTTGATCCATTATCATTACAATTAGGGATAAACTCAAGTACACTATTAACTGCATCTACACCACTACCCAAATG
AGCCCAATCTTCTTGGTGATGTTGATACCCATGTCTTTAAGAATAACTGTATATATGTCACCATTCTCCATAGTGAACATCATAGAAGTATTACCA
TTAAACAACCTGCGTTCTATGACTGGCAAGATATTTACTTCAACTTTAAACCAATCAGCTAAATCAACACCTGCGGTAAGGGCATTCAATAGATCAT
AAACATTATCTATAGTTCCAGCAAAAGCCATAGTTTTAACACGTTTACCTTGCCAAGTAACTGTCGGATGAAAAATTATCTTGTGGCAATCATTGTA
```

Figure 8(K)

```
ATATACATCTACACCTTCAGCTTTAGCAGTTAGATCAATATAACCGTTATCTAATACTGGAAGTCGCCCAATGCTATCAGTTGCATTATTCCGCTCA
ATTAATAGGCAGTCTGCAATCATGACTTTACCATCATTTACGATATATGTCATTTTCACTCCTTATAATAAAATAAATAGGCTTAAGCGAAATAAAG
CCCTCCCCGAAGGGAGGGCATTATCAATAGGTGGGATCTCGGCGGCACCTTCATTTGCGGACGGGAACGCTGAAGGGAGATAGTCCGGGAGATCCCG
ATTTGGGTATTCTTTACATATGGTATTACTGCAAGTATTTGTTCCCCGCAGTATAATCACCATTGATCCAATTTTTGATTACAACACTGATCCCTTC
ATTTTCTTTAACGGTAACCCCCAACTCAAGATCGATTGATTGATAAGCTACAGCCGCCAGTGTTAACCGAAGATAAACGGATCCATCTTTTTCGATA
TCGTAGGATACTACGAACCCGTCTTGTAGATTTGTAGCTGGAATGTATTAGCATGTTGTGGATGGAGACGATCCATATTGTACTCGACGACATCTAG
TAGATATTGCCGAGCATCAGCAGCATTATCAAATCCGAGANCGCACAGACCGATCGGATAGCGAGCTTGCGTGCATGTAACTTTCATAGATACTACA
CGATGTTGTTTGCACATTATATTTTCCTCTTAGATGTCAAAACCCTCCCGATCAGGGGAGGGTATCTCATTGGTACTTCTTCAGCAAAACTGAAACT
AAGATAAAAGAGCAATCGTAAAGGAACTACATAGAATAGTGTATTTCTTTTACTATTTTTACACAACCTCTTTAGATGGGGGTTCTTTATGAATCCA
GTCTAAAGTTGTTGGTAAACTATTATCTGATCTGAAGGTACACACCGTCCGGAACCGAGAGTGATCAACTACAGATAATTGCCCGTTAATCGCAGCC
TCATATTGCCTACACAACTTCACACACCTTTTCTCTAGATCAGTTGGTTCGTAACCTTCTTCTCTTGGTTCAGTGTATGGTCCATCCCAAAAGAATA
TTAATCTAAGATCAATCCCAGATTTATACTCCGCTTGGTATGAATATTGNTGAACATCAAAATCATCTAATTCTTCAACTAGATGTGATGTTATTGT
TCTAGGNTGTTCATGAGTTAATTCACTGTATATATGTTTATTTCTAGGGTTTTGTAAATCAACTACGATAAGTTGACTAGTCATTTTAACTTTTATC
CAGATGTCTATTACGAGTGCGTTCCACTGCTGTAGGTTCGACAGTGGCTCGCGGTAGATAAGTAATCTCCGGGAAAGTCTTATTAAGAGCATCTTCA
ATTAGCTCTTTAGCAATCTCTGCATCGATGTAATGGTTTAGAATAATACCACGATGATCAGGAAGAAGCTGTATTCATCATAACCATGGCGAAGAC
TTACTTTACCACGATACCCACCATAGGTTAGAGTATCTTCGTTAATTCATTCCGATAAATATCAAGTTGGATATTATTTTGAAGATGCATTTGAATG
AAGTCATTACTATCACCGCCGAATAGGGTTGGTCGTTTCCGACCAGTAACAACATCTTGGATGGAATCCATTAGTCGGTTAATGTCTGTTTCTAATC
GTTGGATATCACATTGAGAATTCATTGCTTCATGGAAACGAGTTACAACTGCATTGAATTCTTCTTCAGTCCAACCACTGGTACGTTTTCATAATCA
ACAATGATAATACCGAACCAGGCATAACCGTTAGAATGTTTACTTTAACACATAGATGAGGTACATTATCAGCACCTGACTGATGGTTAACAGTGTA
ATTATTATTACGGCTGATTACTAGTTTGATAAAAGGTAGACTAATGATTGACGCCATGGAAATATTCCTTTTGTATTTTTTAAATTAAAGTAGGAGT
TATTATTGAGTTTCAACTCAATACATCAATAACTCCATGTATGTTTTCAAAATTAAATACATGTATTTACAGTTACATTGTAACCAGTTAGTTTTGCC
AACAATACAAATTAGCGAACCTGTTCGATTTTTCAGAAACAATGAAAATATGTGCAATACGATCCTCATCAANATACCGATATCGAAATGAGGTAT
AACTAGATGACACATCCGTATCGTTTAAATAGGTGATATTAAAATCATCTACTTCCCTACCATTAGCAGCCGCAACGGTATTTAGAATGTTGAGTAG
ACTCATTTTACAGATTCCTTTTTAGTATATTAATATTTCAATAGACTATTGATAAAAGCATTAGGGTCATAACGGTTATTTGAAAAAGCCGCCATTA
CATCACACCCTGGCTGATCTTTAAATCTGATATCTTCAGGAATATCGAAGTCAGGGAACATTAGTTTAATATACTCCCTAACTTCTTGATCTCGTAG
ATATGGAATCTCCACCATGTAATCAACGCGACCTTTCCTTAGAAGTGCTTTATCAATATTCTCAGGATGGTTTGTAGTTAGAATGGTCATAGTCTCA
TCTAGTGGAACAATGCCATCTAGCCCATTTAATAGAGCTGACAAAGTTAATCCGCTAGCTGGTTGTTCATACGTGATTCCATTCTTCATGCATTTCT
TTAATTTCCACCATCGGCGAATTGTGGTAAATAATGGATCTTTTTCATCGGCCCATTTGAAACACCCAGTTCAGCCATAGCATAAGCACTTATCCCA
AAACCTTGATCATCGCTATTTTCATCAAAGATATAGATGGTGTCATTAACCCAACTACAGAGTATCCTTCATAGTCATCTTTAAGATCAACCCATGC
AGACGGATATTTTTCAATTAAATCAATAAAAGAATATTTCCTCTCTAATTCCTTTATCTCTTTATCTAGTTTTACAGGATCATTTAAAACACGATCT
TTAACTGCCGGGGTATCATCGAAATCTTCAATTAGAAGAATATTACCTTTAGGTAGTGTAGTGTAGATGCCCGCCTAAGACTATCATTGGTCATAGAGG
CTAATGACGTGCACTAACATTTTTATTAAAATGTGAGGCAATCGCTTTACTGATTGAGGTTTACCAGTACCAGGAGGACCTGTTAGAACACAAGTG
AATTTATAGGGTAGTCCACGATCATCGTACCATTTCCGATCAGAATAGAATTCTTCAATCTTATTAAGGAATTCTTCTTTGATCTCTTTACGCAAAA
TCACCGTGTTGATATCGCGTTTAGTAACTTCAATCTCATTGCCCCAACGGTTACCATCCCAATGTGAAATAGTCAGACCCCTTTCATTTGGGCGCCA
ATGGTAAGCATCTACTAAATCAATAATTAGTTTACTACTCCTAGATAATCCACGGATAGTAATATCCATTTGATCTCGACTGGCATTTTGACTATCC
CGGCGTGCTTTTACAAACCAGAATAACCTACCTTTAAACAGAAAGAAATGTAAGCCAAAACCAACACCAATTTCTGTTTAGTTGCACTATAACTTT
GCTCATCAACATTAGTTGAAAAACGTCGATTAAATCCAGCTAATGGCTGCTTAATATACCATTCCATGAAACAATCAAAGTTCTTCTCGTTCAGCCC
ATTACCCATGTTGGTAATATGTAGACTAACTGTAAACTGATTTAATGCGAACCTAGCTAGTTTACTTGGTAAGCCTCTTAGAGTGGTCCAGAATAAA
CCACCAATTGCCATTCCGATAGCTCCACCCATAACCATATTCTTCTGAGAGATATCGATGAACATGGCGTAATATTGCAATAAGGTTTCTATAATCA
TACTAGCATCCCTCTGGATAGCTTAGGAAATATTGTCCACAGATCATGTATTCACGTTCTAGAAATCTAGAGTATGACTTTCAAATATTTCACCTAC
ATCTTTACCATAGATTTCCGTATACCCATTTTTGAATACGGCCATTACATAAACATCAGACATAGTCATGCCGTAGTTATAAATTTGATTGTCTCTG
TATTTTGGATGAAATAGGTCATATAAAAAACGAGTCATTGAACTATTGGCAACAGTTGTCACCCCTTTCTGCTTTAAGGCATAACGTACTTGTTTAA
CCACATAGTTAACTTTAGAGCGCTCGCCAAATACCGTCAGTTTATCTACATTGCAATTACGATATCCCATAACACCAGGATTAGCTATCACGGTGTG
TTTTGGAACACGTACATCAAAGATAATGCCATTAGGGGATAGAATAATCTTTTCATGGTTAAATAGAACATGAAATAAATGTCGTTCTGGTTTAGTG
ATTTTGATACTTAACCCAATCACCCCACTAATCTTTCTTTCTAGATCTTCTAGTGACTGCATCACCATGTGATATTGATTGAAGAAAGCATTGTTCT
TATATTGATCTAATTCAAAGTATTTCCAACTTCCACGAAATGAATAGCATGGCTTTGGTATAACCTTTAGTTAATCGACACTTGAGTTTGTCAAACC
AGCTTTCAAGATAACTCTCGACTGTAAACCAAGTGGGTTATTATATAAGTTTATTGGAATATGATAAGCTAAATCTGTACATAGTTCGACGATGCAT
TTATATTCCTGCCAAATAAAGAAAAATAAAGGGCTCCGAAGAGCCCTTTATGTATTAGATTTTTACAGACCAACTTTGCTCGAATTCCTGATATAGG
AAATTGTCTGACGCATTATCCCAATTTTCTCGATCAGTTACACCATAATAATGGAATTCTAGTTCAGTAGGTCCACCAACAAACCATTCTTAGCAT
AGCTATAAACTTGCCATTGGTTAGCTTAATCAGTGTATCCACATAGAAACTATTACGGTTCCATATTTCATTGTGGATGTACTTAAATACCACACTG
TNGATATACTTAAATTGCGCACTTGGTTTTCCGAGTACACTCCAATAGAATTTACGGATACCTATTTCGGTCTTGAAATTAAACTCTCCGTTGCGAA
TGTTGTTAGAAACAATACGTGCGCAGTTTATTAACCCGATTTCTTCACCGATAGATATCCCGGAACACTACATCCATCTCCTATTGATCCATTA
TTAACTAGTGGATCAACACCATATTCATCAGTGAAAATGGTTTTGATAACCTCTTTACCTTCTCGACGCATAACATATTCAGGTGACCATCTTCGA
TATATGACATATGGCTAGGCTGAATATATTCACTTGTATCGACGTAACATCATTCGCCATTACATTAAACTGTAGATGGTTACCAGATCACTAAT
ACCTTTAAAACGAATGGCTTGGTTCGCTGTATTTAGATCGACATACACCACGACATCAATAATGCCTTGTTTTAGTGATTTGTCATCTTTGTCAGTA
GTTGTATCAATTTTACGTAATTTTGATATAGTTCACTAAAACAAGATATGATGTCATCATGTAGTTTAATTACATCAGATCCATTTCGTTCAAGCGC
TTTAAGCGATACGTTAAACAATACGAATTTTATTAGAACGACGTGCCATGGTTTATATCACCTATGTTAAATTAATGAATTATTTATTCAATTACCG
TACTACATCTGTGATTAGAATAAGTTCACCATCACTATTGATAACACTATAGCTTTTACAATTTCGATGCGCTTACTAATAATCTTATTCTCTAGAT
CTACTTTTACGATATTAACACGAATTACCTTATTCGATTGATCATGCATTTCTTTAAAATGCATTCGATATTTACCAATGACAGCTTTTAATTTTC
AATGCTGTCAATGGATGAATATTTAAAACTATATGCTTCTGCCAGGGTTTTGCATTACCCACAACCGTAGTTAGGGTACCCAATAATCATAAACAT
ACAACGCAGTATCACTATTGGGATTATCGATAATTTCAATTATAAATCCACTTGTATCACTCCTATTAGTTTATTGATAGTACACTTGTAATATAGA
TCTTAAATAAATTATGATCTAACCATTTAAAATAGATAAAGCCTCTATATGCCAATGGTGTATTAGTTCTTCTTTACTAATAATATTATTGAAGTAG
TTTAACCGATGTGATACCATTAATTTAGAATGCATATCGACTTCACTTACCTTAATCACCCCAGTCTCTAATAATTGCAGAATTCACTACACG
CAAATAAAGTTGGTTTTAAATACCAGTGTTCCCTATATTGTTTTTGATCAGGTACATTTCCTATAATGTAGTCAGTAGAATTACTTCGGTATGCGTA
AATAGTTGATTTAGAACCAAGTAAATTAAGATCGATATCATAACTCCCGCTTTTAGCTGCAATACATTCAATAACTGATGGGGCCACACATATACGG
TTGGTTACACTGTCTTCGCCATCAGCTCTATTACTTGGAATATATGGCCTTAATAAACATAATCCCCAAGGTATACTGTCGATATGTGATACATAAT
TAACCTATTTAATTAAAACAGATAACGCTCTGTTACTGAACGATATTGTGACATGATGTTTAATGGATCAACATCCACTGGTGCTTTAGTGACAGTT
AAGCGAGCCACCTTTTAAAAATCACCAATATCTAATTTCCTTACAGTAACATCATGGATAGTGTTTTTCGTAATCCACTCAGTATCAATGCTATTGTG
AGGATATTATTCTTAATCCATTTGTCAGAGTCCCTAAATGGAATGGTATAAACATACACAACCATTTTAAAATATCACTTTTATCGATATTATTTGA
CAATAGATTGTAATATCCCTATCAACAGTAGCCATATCTATCACTATCAAATAACTTTTCGATAGCGCTACCAATACCTAAATAAGATGCATCTTTTT
CAGATGACGTTGCATATAGGTATTGGTTAGACTCAATACCATCCCACATAACAAGTTCACCAGATCTTTTAAATCCTGGCATTAATTCATCTTGTTT
```

Figure 8(L)

```
ATAAAGAGAACCATGGTAAGTAATTCTGGTTTATTCATAATAAAATCCACTATGCTTTATAAGAGTTATGGTTATCAATTAACTTCAAGGTAGTAGT
GTGGCAGTATTGAAGTGATTGGTTACTGCTTCGATCAGCATTTGCTCGATGTTGATTTTGTAGTATTCTGGTTCTTCGTTCAATTCCCAATAATAGT
CGCACGTAATAGTGCAGGTGCTATGAATCTAACTACCTTACCATGTGTGTCAAACTCTACATGAACATTGCATATTGTTCAGTAGTATGATTTTATA
GAAATGAATTACCAGCGTAACTGCGACCTCTATTTCACCATGAATACTGGAGTAGGGTTTCCTGGTGGAATACTTTACCTTTAAGGCGTGTATTCTCT
TCAATGATATTACCAATTCTTTCAATTTGTCTTATCTAGTTGCATTTGTAGGTTCCTATTAATAAATGTATACGATGGATATCTTTTACGATTTCCG
GTGCTTATCCATATCTAGTTTTATATCAGTATATATCTTGAATCTATTAGATAGGCTATCCATATCTACGTGCAATGCCCGAATATGCATATCAGTA
TCTTTTGGTTTACCTTCAGACTCCCATACGGCCTTTGCGATATCAAATGCTACATTGTTCAAATAGTATTCGACTTCATGTTCATCAAGCAAAAGAG
CATCATGGAAACCAATACGTGATAGAATGGCGTAATCACGCTGATTAACATCTCTCCAATCTTTACGCACTAAGTAACTTTTACCAATTCCATCTTT
TTTACAACTTTTACTAATAATTTCTATAATGAACTTATCATGCCATTTATAATCCATAATCATTACTCCTTTATTTAATCAGCTTCATTACTAGAGG
AACAGATAGACTTATGCCATTAGCCATTTTAGCTAGAATATGATAGACATCGTCTGCTTCTTGATTATTGTACAAGGTATAGAAATGGCATCACCAT
AGTAAGGACTGTAGTTAATACGGTCGCCATACACACCACTCACAAAACTATAATCTAATCCATCCGTGGTAGTCATAATAACTACAACATGATCATC
CCCAACTATACCGGATTCTAAATCCTCACATAGTTCTAGTTTTGTTGCACACCTCGTTGACAGATCCATACTTCACGGTATTGATGATGAGGATATG
GATTACATGCTACATCATTTTCACTAACGAAGTACATAGTCCCCCAGTTGTAAGACTGGAATTGGGTTGTTGTTTGTGGGCTTCCCATACCTCTTCC
ATACAAAGGTATGTTGTTAACCCATAGACCATCGTTATTAAGACTATCAACGATCCATCACGGACACGTACTACACGGAGTGTTTTTGCCATTTTTA
ATTATCCTAAATACATAAAGGAATCACTTAGTAAACACCATTGACAATAGCATCGCGGAAACGAGACCATTCCGTTTGACCAACTACGAATACTCGT
TCTTTAGGACGCCATAGATGATCACCGCAGTCAAGACCCAAGTAAAGCATATTGGTTTTCCATGATTGCGATGAACACGTAGTTTAGCTGATACACT
GAACTCACACATTACTTCATTTACATCAAGATGTGTAGTGTATCACTATCATACCTGACATACTGATACCAATTGATTTACGAACTCGGATTAGATC
CTCAGTCATCACCCGCCAAGTTACCAGATGCTCGTAATACTCATCTGGTGTCATGTTGTTTTATAATTCAGTGCACCTGGAGTCATTGACATCAGT
TAGTGAACTGGAAGTCATGTAATACATCCAATCACTATTATGACGGAGTTCTTTAAGCTTCTCTGTATTACGATATTAGTAGTTGCTTTAGTCATCT
ACGTACCCTCATCAGATACATAAGTACGTTCAGGCTGAACACATATTTGATGTTATTAATTACAGCTGTGATATAAACCTGATATTCTTTTGAAATA
GATTCCATCAGTTCAATAGATACGGAATTGAACTCTGAATAAGTTATTTACTTTCTTAGTTCATCAATTCTACCGACCGTAATTACACCAACATCTC
TGAAACTGATAACTGGATAGTGTTTCCAATATAACAATTCAGTTTACCAAGATGAATTACTTGAATTGTTTCATCGCACCATTGTTTCTTTTCTATT
GTAGTATTCAACACGACGTTCGATGAAGACGCGAGTACCAGAAACAGAGGTGTACGCATTCAGTCATAACCATACTTATGGTACGTTATTTGGATCT
TGGCGCCATTTTGGATGAATGCTTTCATTTGTATTTTCCTTTTACGAAATAGAAGCCCTCCCGAAGGAGGGCAATTACCATTATTAAATTACGAGTC
TATTACTTCTTTTAATTTTCACCAGGGGTAGCTAGATAATCTACATTATATTTAATAGCAATTACACCACAAGTTCTTTTTCATAGCTGTTCTACCT
GATCGCATATTTATCAATAGCTCCATCTTCTACATCCTCGTATAATGGATATTGACTATAATATTATCAGGTGTAAGTACAGACAGTTTCAATCCCA
TCTTTACCAATGACTGGGTGATATGTCTGTTTAAGACCTTTACAATGATAGTGATAGGTATGCGCTGTGTTTAGGTGGTCATGTAAAGATACCTCAT
AAACCGTTGGGTAGTCCGTCTTTAAGACAGTTAGTTGATTAACATCTTTCAATGATTATCTGCAATATTCTTAGCCAATAACAGTAGATCATTGGTG
ATATGTTTTAATGAGAACTTAAGCCTCTCCCTTTGTTTATATCGGAACCTTATTATCACAGTAACTCCATCCGGTTATTTTTATAATTCAGTACAGT
GATTGGTGTATTCGGTACAAAGACGGCTAGTTCGTCATCGAATACAATGTAAACCATCACTTTATAATTATTAACCGATTCTTGGAATTGTTCTGTG
ATTACATTATAGTCTTTTGTGCGATGGCTAAGAAAACAGCTCACTATTAGCTCGGCAGAAACTATGTCGCGCTTTTTATCAGCACTCATAACAGCGAT
ACCACGGATAATGAATTTATTATCTAAGGTATATTTTCTTTGAGACATCGCATAGTCGACTACATCAACATCGCCGCCAAATAGCACGGCATTTTCA
CCGTATCCACAAATAAGAGCCATTTATAATTACCTGTTTAAAAATTATATTCAATAAATTGAGAGTGAATAGTTCACTACATTCCCATGTACGACTT
GCTAATTTATATTTACCTTTAACAGGTAAGTCAAATAACGTAATGCTTTTCTACTGAACCAGCCTCATGATTAACCAATAGAACATTCCTAGCCTTC
AGAATATTTGAACAATTTACAAGTTCATAATCATCTCGCTTAGGTGTCAATAGCTACATTAGTGCCTGGTTTCTAGCATACCAGAGCACCTCATGAC
CCTCTGGATTAATAATAGAGATATAGCTGACGTTCAGCGGGTAACCACAAGTTACGTGGATCATANTCTCCATTAACATCAAAGAATTTAAATATCA
TAGAGTTGGAACGGTTTTGATGGATCAGCAATTANTGCAGATTCNTCTACATAAACCATTGCNAAGTTTTCACCTTCTTTACGAATACCAGTAGAA
GGTGTTTTCGATGGATCATAACGATAATTGGCACTGCTGTCCAGCTGTTAAATAAGTTGGGCCAGTTAATGCATTGGGTTTTGGATGAGGAATATCA
ATTTTAGTAATACAATATTGACCAGTACGAAACTCACGCATTATATTAACCTCTTAATGAATAACTGTTGCAGAAGGACGACATTTCATAGTTTTAA
AAATGTCAGTAGGATAGATATTACCAGCTTGTCCGAAAGGTTTATCGGCTAGAAGAAACTGCGGACAAACTGTTTGTAGATAACCACTATCAGTGGG
TAGGAATCCTTCAATATCACTGATGAGAATTTGCCAGATGGGCAATTGGTTATAATAGTCATCCATATTGTAGTATGCGTGGAGTTTACCACCGAAC
CCATATACAAACTGATGAGTATCAATTAGACGAATACCAAATTTAGGTTGTCGTCCCATCCTT
```

RECOMBINANT B11 BACTERIOPHAGES AND USES THEREOF

CROSS-REFERENCE TO RELATED APPLICATION

This application is a divisional application of U.S. patent application Ser. No. 15/908,197, filed on Feb. 28, 2018 and titled "RECOMBINANT B11 BACTERIOPHAGES AND USES OF THEREOF," which is incorporated by reference in its entirety.

SEQUENCE LISTING

The instant application contains a Sequence Listing which has been submitted electronically in ASCII format and is hereby incorporated by reference in its entirety. Said ASCII copy, created on Feb. 27, 2018, is named 102590-0610_SL.txt and is 277,834 bytes in size.

TECHNICAL FIELD

The present technology relates generally to compositions including recombinant B11 bacteriophages, methods for making the same, and uses thereof. The recombinant B11 bacteriophages disclosed herein are useful for the identification and/or antibiotic susceptibility profiling of specific bacterial strains/species present in a sample.

BACKGROUND

The following description of the background of the present technology is provided simply as an aid in understanding the present technology and is not admitted to describe or constitute prior art to the present technology.

Bacterial infections may complicate a patient's existing medical condition, and in some cases, may lead to death. Patients suffering from various bacterial infections often present with similar symptoms, thus making it difficult to accurately identify and characterize the bacterial species or strain responsible for the infection. Accurate identification of the bacteria through conventional lab tests can be challenging and may require incubation periods of up to several days. Additionally, some bacterial strains are not amenable to culturing and in vitro analysis in light of their fastidious nature. In other situations, the observable behavior of some bacterial strains is not readily distinguishable from others. Moreover, individual strains of a particular bacterial species may exhibit resistance to otherwise effective antibiotics.

Early and accurate identification of the bacterial strain(s) responsible for a patient's illness and determining its susceptibility to various antibiotics is an important aspect of the treatment selection decision process.

SUMMARY OF THE PRESENT TECHNOLOGY

In one aspect, the present disclosure provides a recombinant B11 bacteriophage nucleic acid sequence, wherein the nucleic acid sequence between (a) position 65,939 and position 65,940 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In certain embodiments, the open reading frame of the heterologous nucleic acid sequence is operably linked to an expression control sequence that is capable of directing expression of the reporter protein. The expression control sequence may be an inducible promoter or a constitutive promoter. Additionally or alternatively, in some embodiments, the recombinant B11 bacteriophage nucleic acid sequence comprises a sequence selected from the group consisting of SEQ ID NO: 2, SEQ ID NO: 3, SEQ ID NO: 4, and SEQ ID NO: 12.

Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa. Examples of chemiluminescent protein include, but are not limited to, β-galactosidase, horseradish peroxidase (HRP), or alkaline phosphatase. Examples of bioluminescent protein include, but are not limited to, Aequorin, firefly luciferase, *Renilla* luciferase, red luciferase, luxAB, or nanoluciferase. In some embodiments, the bioluminescent protein is nanoluciferase.

In one aspect, the present disclosure provides a vector comprising any of the recombinant B11 bacteriophage nucleic acid sequences disclosed herein, as well as bacterial host cells comprising the vectors of the present technology. The bacterial host cell may be a natural or non-natural host for B11 bacteriophage.

In another aspect, the present disclosure provides a recombinant B11 bacteriophage comprising any of the recombinant B11 bacteriophage nucleic acid sequences of the present technology. Also provided herein are recombinant B11 bacteriophages comprising a nucleic acid sequence selected from the group consisting of SEQ ID NO: 2, SEQ ID NO: 3, SEQ ID NO: 4, and SEQ ID NO: 12.

In one aspect, the present disclosure provides a bacterial host cell comprising a recombinant B11 bacteriophage disclosed herein. The bacterial host cell may be a natural or non-natural host for B11 bacteriophage.

In one aspect, the present disclosure provides a method for identifying at least one bacterial strain or species in a test sample obtained from a subject comprising (a) contacting the test sample comprising bacterial cells with a recombinant B11 bacteriophage of the present technology; and (b) detecting the expression of the reporter protein of the recombinant B11 bacteriophage, wherein detection of the reporter protein indicates the presence of at least one bacterial strain or species in the test sample. In some embodiments of the method, the expression of the reporter protein is measured in about 5, 10, 15, 20, 25, 30, 35, 40, 45, 50, 55, 60, 65, 70, 75, 80, 85, 90 or 120 minutes after contacting the test sample comprising bacterial cells with the recombinant B11 bacteriophage.

In another aspect, the present disclosure provides a method for determining the antibiotic susceptibility of a bacterial strain or species in a test sample obtained from a subject comprising (a) infecting a plurality of test samples comprising bacterial cells with a recombinant B11 bacteriophage of the present technology and an antibiotic, wherein the plurality of test samples is derived from the subject; (b) detecting the expression of the reporter protein of the recombinant B11 bacteriophage in the plurality of test samples; and (c) determining that the antibiotic is effective in inhibiting the bacterial strain or species in a test sample when the reporter protein expression levels of the recombinant B11 phage infected bacterial cells in the test sample are reduced relative to that observed in an untreated control sample comprising bacterial cells, wherein the untreated control sample is derived from the subject and is infected with the recombinant B11 bacteriophage of the present technology. The expression of the reporter protein may be measured in about 5, 10, 15, 20, 25, 30, 35, 40, 45, 50, 55, 60, 65, 70, 75, 80, 85, 90 or 120 minutes after infecting the plurality of test samples comprising bacterial cells with the recombinant B11 bacteriophage.

Additionally or alternatively, in some embodiments of the methods disclosed herein, the test sample is blood, sputum, mucus, lavage, saliva, or a swab obtained from the subject. In some embodiments, the subject is human.

In certain embodiments of the method, the antibiotic is selected from the group consisting of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In one aspect, the present disclosure provides methods for making a recombinant B11 bacteriophage of the present technology in a bacterial host cell. In some embodiments, the method comprises (a) contacting a first B11 bacteriophage genome with a first sgRNA-CRISPR enzyme complex and a second sgRNA-CRISPR enzyme complex in vivo under conditions where (i) the first sgRNA-CRISPR enzyme complex cleaves a first protospacer sequence 5' AGAAGATCATTATCGAAAGA 3' (SEQ ID NO: 5) within the first B11 bacteriophage genome; and (ii) the second sgRNA-CRISPR enzyme complex cleaves a second protospacer sequence 5' AGACATAGCCCCTCTCCACA 3' (SEQ ID NO: 6) within the first B11 bacteriophage genome to produce a cleaved first B11 bacteriophage genome; and (b) recombining in vivo the cleaved first B11 bacteriophage genome with a heterologous nucleic acid sequence in the presence of a recombination system under conditions to produce the recombinant B11 bacteriophage genome, wherein the bacterial host cell is infected with the first B11 bacteriophage genome, and wherein the heterologous nucleic acid sequence comprises an open reading frame that encodes a bioluminescent protein, a fluorescent protein, a chemiluminescent protein, or any combination thereof. In some embodiments, the first sgRNA-CRISPR enzyme complex comprises Cas9 and a first sgRNA having the sequence of 5'AGAAGAUCAUUAUCGAAAGAGUUUUAGAGCUA-GAAAUAGCAAGUUAAAAUAA GGCUAGU-CCGUUAUCAACUUGAAAAAGUGGCACCGAGUCG-GUGCUUUUUUU 3' (SEQ ID NO: 7). Additionally or alternatively, in certain embodiments, the second sgRNA-CRISPR enzyme complex comprises Cas9 and a second sgRNA having the sequence 5' AGACAUAGCCCCUCUC-CACAGUUUUAGAGCUA-GAAAUAGCAAGUUAAAAUAA GGCUAGU-CCGUUAUCAACUUGAAAAAGUGGCACCGA GUCGGUGCUUUUUUU 3' (SEQ ID NO: 8). The recombination system may be endogenous or non-endogenous. The first B11 bacteriophage genome may be recombinant or non-recombinant.

Additionally or alternatively, in some embodiments of the methods disclosed herein, the cleaved first B11 bacteriophage genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

Additionally or alternatively, in some embodiments of the methods disclosed herein, the recombination system is a non-endogenous recombination system that is induced in the bacterial host cell. The non-endogenous recombination system may comprise lambda Red proteins Gam, Exo, and Beta operably linked to an inducible promoter. In some embodiments of the methods disclosed herein, the inducible promoter is araB and the non-endogenous recombination system is induced by the addition of arabinose.

Additionally or alternatively, in some embodiments of the methods disclosed herein, the bacterial host cell comprises a non-endogenous CRISPR expression vector comprising a nucleic acid sequence that encodes a first sgRNA, a second sgRNA, and a CRISPR enzyme. In some embodiments, the first sgRNA and the second sgRNA are operably linked to a constitutive promoter. In certain embodiments, the CRISPR enzyme is a Cas protein selected from the group consisting of Cas1, Cas1B, Cas2, Cas3, Cas4, Cas5, Cash, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The CRISPR enzyme may be operably linked to an inducible promoter, such as a tetracycline-inducible promoter.

In another aspect, the present disclosure provides sgRNAs that are useful for making the recombinant B11 bacteriophages disclosed herein. In some embodiments, the sgRNA sequence is selected from the group consisting of SEQ ID NO: 7 and SEQ ID NO: 8.

Also disclosed herein are kits comprising one or more coded/labeled vials that contain the recombinant B11 bacteriophage of the present technology, instructions for use, and optionally at least one antibiotic.

BRIEF DESCRIPTION OF THE DRAWINGS

FIG. 1 shows the heterologous nucleic acid sequence that was inserted into B11 phage genomic DNA between position 65,939 and position 65,940 of SEQ ID NO: 1 using single guide RNAs (sgRNAs) sgRNA 6.3A and sgRNA 6.3B (SEQ ID NO: 2). The underlined sequences represent the homologous 5' and 3' flanking regions of the heterologous nucleic acid sequence.

FIG. 5(A) shows a general schematic of a first B11 bacteriophage genome (i.e., intact B11 bacteriophage genome) and a cleaved first B11 bacteriophage genome. The cleaved first B11 bacteriophage genome comprises a first cleaved bacteriophage genomic fragment and a second cleaved bacteriophage genomic fragment.

FIGS. 7(A)-7(L) show the B11 contig-6 genome sequence of non-recombinant B11 phage (SEQ ID NO: 1).

FIGS. 8(A)-8(L) show the B11 contig-6 genome sequence of the recombinant NanoLuc®B11 phage that was cleaved with sgRNA 6.3A and sgRNA 6.3B (SEQ ID NO: 12).

DETAILED DESCRIPTION

Figure 2A:
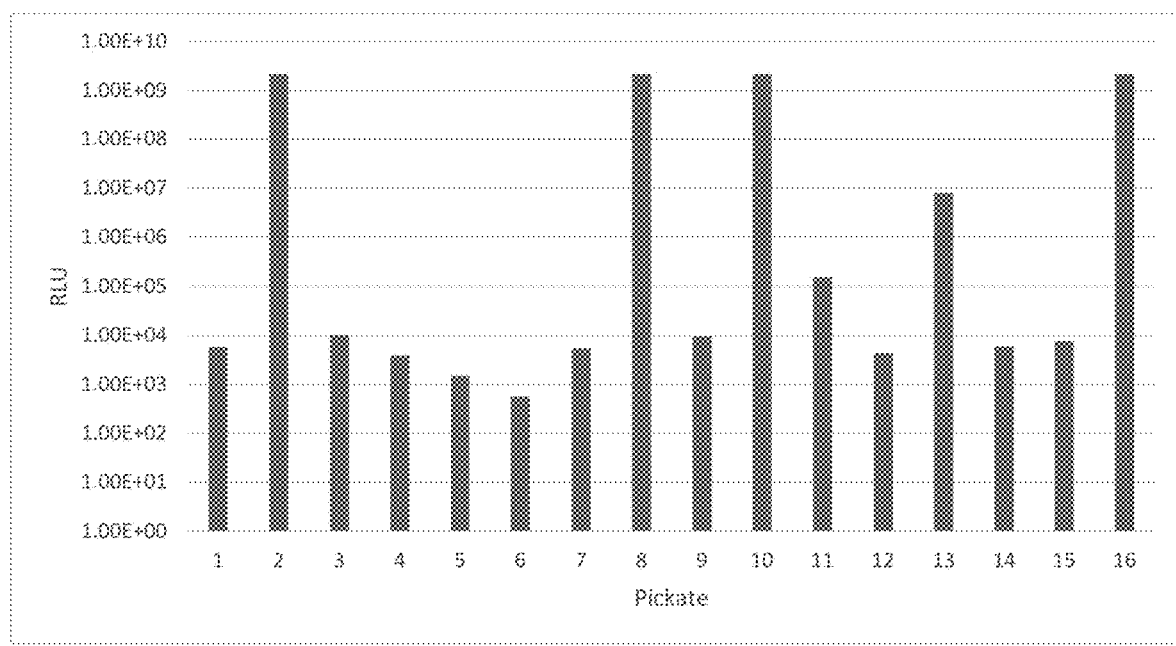
FIG. 2(A) shows the luminescence activity profile of individual plaques that were generated from the recombination experiments in *P. aeruginosa* PAO1 strain harboring crR-B11 6 (site 6.3 cutting plasmid) and pBBR1-B11 6 (site 6.3 donor plasmid).

It is to be appreciated that certain aspects, modes, embodiments, variations and features of the present methods are described below in various levels of detail in order to provide a substantial understanding of the present technology.

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation*; *Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology*.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both).

Figure 5B:
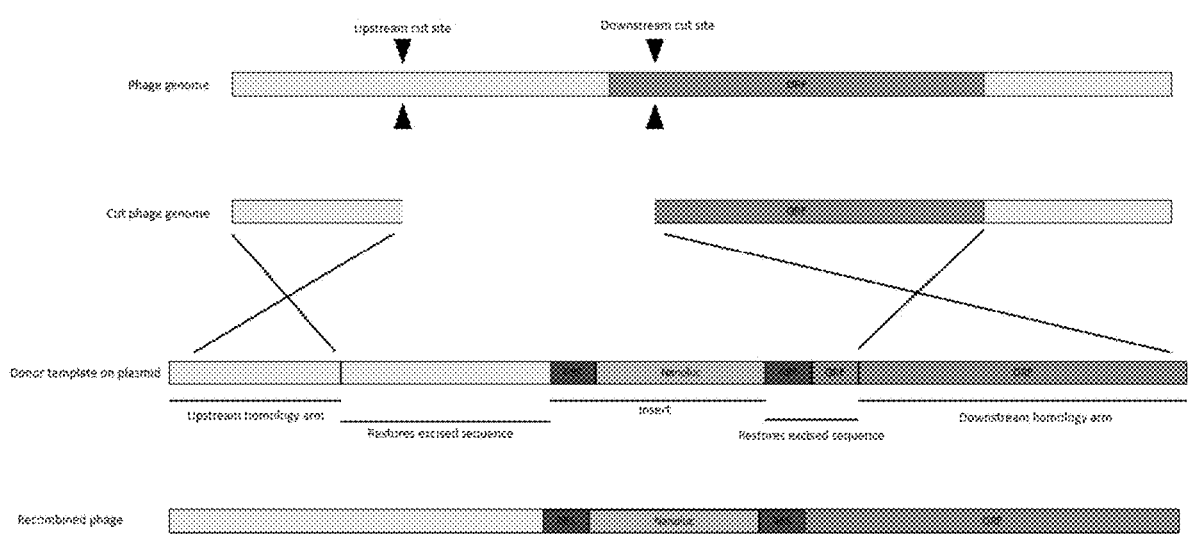
FIG. 5(B) shows a general schematic of the donor template design and recombination between a cleaved phage genome and the donor template. Two double-stranded breaks are generated by Cas9 at sites specified by the two sgRNAs. In some instances, Cas9 cleavage excises a phage DNA sequence that is important for phage viability. The donor template contains any exogenous reporter gene inserts like nanoluciferase, but must also restore the function of excised phage sequences. The 5' and 3' flanking regions of the donor template are homologous to the DNA sequences immediately adjacent to the two cleavage sites in the phage genome, and are necessary for repairing double-stranded breaks via homologous recombination.

As used herein, a "cleaved first B11 bacteriophage genome" refers to the B11 bacteriophage genome fragments that are formed after a first B11 bacteriophage genome has undergone enzymatic cleavage with one or two sgRNA-CRISPR enzyme complexes. When a first B11 bacteriophage genome is cleaved with two sgRNA-CRISPR enzyme complexes, the "cleaved first B11 bacteriophage genome" excludes the shortest nucleic acid sequence that lies between the cleavage site of the first sgRNA-CRISPR enzyme complex and the second sgRNA-CRISPR enzyme complex. See FIGS. 5(A)-5(B).

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease or condition, a positive control (a compound or composition known to exhibit the desired therapeutic effect) and a negative control (a subject or a sample that does not receive the therapy or receives a placebo) are typically employed.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences.

As used herein, a "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+ PDB+GenBank CDS translations+SwissProtein+SPupdate+ PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, *E. coli* may be the natural host cell for a particular type of phage, but *Klebsiella pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/ or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to a nucleic acid of interest to initiate, regulate or otherwise control transcription of the nucleic acid of interest.

As used herein, a "phage genome" or "bacteriophage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion or an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it. A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome. A "recombinant bacteriophage" means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, a "recombinant B11 bacteriophage" or "recombinant B11 phage" means a B11 bacteriophage whose genomic DNA comprises a heterologous nucleic acid sequence that encodes a bioluminescent protein, a fluorescent protein, a chromogenic protein, or any combination thereof.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

As used herein, "a sub-sample" refers to one or more samples containing bacterial cells that are derived from a test sample obtained from a subject. In some embodiments, the sub-sample is void of non-bacterial cells (e.g., human cells). In some embodiments, the sub-sample contains lysed human cells.

As used herein, "test sample" refers to a sample taken from a subject that is to be assayed for the presence of bacteria and/or for the antibiotic susceptibility of bacteria present in the sample. In some embodiments, the test sample is blood, sputum, mucus, lavage, or saliva. In certain embodiments, the test sample is a swab from a subject.

As used herein, the terms "subject," "individual," or "patient" are used interchangeably and refer to an individual organism, a vertebrate, a mammal, or a human. In certain embodiments, the individual, patient or subject is a human.

As used herein, a "vector" refers to a nucleic acid molecule capable of transporting another nucleic acid to which it has been linked. One type of vector is a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors").

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances no more than 500,000 bp. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

Recombinant B11 Phage Compositions of the Present Technology

In one aspect, the present disclosure provides a recombinant B11 bacteriophage nucleic acid sequence, wherein the nucleic acid sequence between position 65,939 and position 65,940 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof. In some embodiments, the heterologous nucleic acid sequence further comprises at least one segment that corresponds to at least part of the excised endogenous phage genome sequence between position 65,939 and position 65,940 of SEQ ID NO: 1.

The present disclosure also provides a recombinant B11 bacteriophage nucleic acid sequence, wherein the nucleic acid sequence (a) between position 65,469 and position 65,470 of SEQ ID NO: 1, or (b) between position 66,001 and 65,002 of SEQ ID NO: 1 is replaced with a heterologous nucleic acid sequence comprising an open reading frame that encodes a reporter protein, wherein the reporter protein is a bioluminescent protein, a fluorescent protein, a chemiluminescent protein, or any combination thereof.

Also disclosed herein are recombinant B11 bacteriophages that comprise any recombinant B11 bacteriophage nucleic acid sequence disclosed herein. In some embodiments, the reporter protein(s) encoded by the heterologous nucleic acid sequence produces a detectable signal upon exposure to the appropriate stimuli, and the resulting signal permits detection of bacterial host cells infected by a recombinant B11 phage of the present technology.

In certain embodiments, the open reading frame encodes a reporter protein that serves as a marker that can be identified by screening bacterial host cells infected by a recombinant B11 phage of the present technology. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome.

In some embodiments, the length of the heterologous nucleic acid sequence is at least 100 bases, at least 200 bases, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the B11 phage genome with no loss of endogenous B11 phage genomic sequence. In some embodiments, the heterologous nucleic acid sequence replaces an endogenous B11 phage genomic sequence. In some embodiments, the heterologous nucleic acid sequence includes an endogenous B11 phage genomic sequence that was previously excised from the phage genome.

In certain embodiments, the heterologous nucleic acid sequence replaces an endogenous B11 phage genomic sequence that is less than the length of the heterologous nucleic acid sequence. Accordingly, in some embodiments, the length of the recombinant B11 phage genome is longer than the length of the wild-type B11 phage genome. In some embodiments, the heterologous nucleic acid sequence replaces an endogenous B11 phage genomic sequence that is greater than the length of the heterologous nucleic acid sequence. Thus, in some embodiments, the length of the recombinant B11 phage genome is shorter than the length of the wild-type B11 phage genome. In certain embodiments, the heterologous nucleic acid sequence replaces an endogenous B11 phage genomic sequence that is equal to the length of the heterologous nucleic acid sequence.

In certain embodiments, the open reading frame of the heterologous nucleic acid sequence encodes a reporter protein that confers a phenotype of interest on a host cell infected by a recombinant B11 phage of the present technology. In some embodiments, the phenotype of interest is the expression of the gene product encoded by the open reading frame of the heterologous nucleic acid sequence.

In certain embodiments, the open reading frame of the heterologous nucleic acid sequence is operably linked to an expression control sequence that is capable of directing expression of the open reading frame, wherein the open reading frame encodes a reporter protein (e.g., a bioluminescent protein, a fluorescent protein, a chemiluminescent protein, or any combination thereof). In some embodiments, the expression control sequence is located within the heterologous nucleic acid sequence. In other embodiments, the expression control sequence is located in the endogenous B11 phage genome sequence. For example, the open reading frame may be inserted into the B11 phage genome downstream of or in the place of an endogenous B11 phage open reading frame sequence. In some embodiments, the expression control sequence is an inducible promoter or a constitutive promoter (e.g., sarA promoter or lpp promoter). See e.g., Djordjevic & Klaenhammer, *Methods in Cell Science* 20(1):119-126 (1998). The inducible promoter or constitutive promoter may be an endogenous B11 phage promoter sequence, a phage promoter sequence that is non-endogenous to B11 phage, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include, but are not limited to, blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOK, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nano-luciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid sequence comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type B11 bacteriophage and the bacterial host cell. Accordingly, detection of the epitope in a sample demonstrates the presence of a bacterial host cell infected by a recombinant B11 phage comprising a heterologous nucleic acid sequence, wherein the open reading frame of the heterologous nucleic acid sequence comprises the epitope. In other embodiments, the open reading frame of the heterologous nucleic acid sequence comprises a polypeptide tag sequence, such that the expression product of the open reading frame comprises the tag fused to a polypeptide or protein encoded by the open reading frame (e.g., poly-histidine, FLAG, Glutathione S-transferase (GST) etc.).

In some embodiments, the open reading frame of the heterologous nucleic acid sequence comprises a biotin binding protein such as avidin, streptavidin, or neutrAvidin that can be detected with a biotin molecule conjugated to an enzyme (e.g., β-galactosidase, horseradish peroxidase (HRP), and alkaline phosphatase) or an antibody. In some embodiments, an antibody conjugated to a biotin molecule may be directly linked to a signal generating moiety (such as by covalent attachment of a chemiluminescent or fluorescent protein), or can be detected using at least one additional binding reagent such as a secondary antibody, directly linked to a signal generating moiety.

Also disclosed herein are recombinant B11 bacteriophages comprising any of the recombinant B11 bacteriophage nucleic acid sequences disclosed herein. In some embodiments, the recombinant B11 bacteriophages comprise a nucleic acid sequence selected from the group consisting of SEQ ID NO: 2, SEQ ID NO: 3, SEQ ID NO: 4 and SEQ ID NO: 12.

In another aspect, the present disclosure provides a vector comprising any of the recombinant B11 bacteriophage nucleic acid sequences disclosed herein, as well as bacterial host cells comprising the vectors of the present technology. The bacterial host cell may be a natural or non-natural host for B11 bacteriophage.

The present disclosure also provides a bacterial host cell comprising a recombinant B11 bacteriophage disclosed herein. The bacterial host cell may be a natural or non-natural host for B11 bacteriophage.

Methods of Making Recombinant B11 Bacteriophage of the Present Technology

In one aspect, the present disclosure provides methods for making a recombinant B11 bacteriophage of the present technology in a bacterial host cell. The bacterial host cell may be a non-natural bacterial host cell or a natural bacterial host cell for B11 bacteriophage.

In some embodiments, the method comprises (a) contacting a first B11 bacteriophage genome with a first sgRNA-CRISPR enzyme complex and a second sgRNA-CRISPR enzyme complex in vivo under conditions where (i) the first sgRNA-CRISPR enzyme complex cleaves a first protospacer sequence 5' AGAAGATCATTATCGAAAGA 3' (SEQ ID NO: 5) within the first B11 bacteriophage genome; and (ii) the second sgRNA-CRISPR enzyme complex cleaves a second protospacer sequence 5' AGACATAGCCCCTCTCCACA 3' (SEQ ID NO: 6) within the first B11 bacteriophage genome to produce a cleaved first B11 bacteriophage genome; and (b) recombining in vivo the cleaved first B11 bacteriophage genome with a heterologous nucleic acid sequence in the presence of a recombination system under conditions to produce the recombinant B11 bacteriophage genome, wherein the bacterial host cell is infected with the first B11 bacteriophage genome, and wherein the heterologous nucleic acid sequence comprises an open reading frame that encodes a bioluminescent protein, a fluorescent protein, a chemiluminescent protein, or any combination thereof. In some embodiments, the first sgRNA-CRISPR enzyme complex comprises Cas9 and a first sgRNA having the sequence of 5' AGAAGAUCAUUAUCGAAAGAGUUUUAGAGCUA-GAAAUAGCAAGUUAAAAUAA GGCUAGU-CCGUUAUCAACUUGAAAAGUGGCACCGA GUCGGUGCUUUUUUU 3' (SEQ ID NO: 7). Additionally or alternatively, in certain embodiments, the second sgRNA-CRISPR enzyme complex comprises Cas9 and a second sgRNA having the sequence of 5' AGACAUAGCCCCU-CUCCACAGUUUUAGAGCUA-GAAAUAGCAAGUUAAAAUAA GGCUAGU-CCGUUAUCAACUUGAAAAGUGGCACCG AGUCGGUGCUUUUUUU 3' (SEQ ID NO: 8). The recombination system may be endogenous or non-endogenous. The first B11 bacteriophage genome may be recombinant or non-recombinant.

The cleaved first B11 bacteriophage genome comprises a first cleaved bacteriophage genomic fragment and a second cleaved bacteriophage genomic fragment. In certain embodiments of the methods disclosed herein, the heterologous nucleic acid sequence comprises a 5' flanking region that is homologous to the 3' end of the first cleaved bacteriophage genomic fragment, and a 3' flanking region that is homologous to the 5' end of the second cleaved bacteriophage genomic fragment.

In some embodiments of the methods disclosed herein, the homologous 5' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the homologous 3' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the recombination system is a non-endogenous recombination system that is induced in the bacterial host cell. The non-endogenous recombination system may include a recombination expression vector that comprises lambda Red proteins Gam, Exo, and Beta operably linked to an inducible promoter. In some embodiments of the methods disclosed herein, the inducible promoter is araB and the non-endogenous recombination system is induced by the addition of arabinose. In some embodiments, the recombination expression vector further comprises the heterologous nucleic acid sequence. In other embodiments, the expression vector comprising the heterologous nucleic acid sequence is separate and distinct from the recombination expression vector comprising lambda Red proteins.

In other embodiments of the methods disclosed herein, the recombination system is a non-endogenous recombination system that includes a recombination expression vector comprising RecET (RecE, RecT) operons operably linked to an inducible promoter, and optionally the heterologous nucleic acid sequence. In some embodiments, the inducible promoter is araB and the non-endogenous recombination system is induced by the addition of arabinose. In other embodiments, the expression vector comprising the heterologous nucleic acid sequence is separate and distinct from the recombination expression vector comprising RecET.

In another embodiment of the methods disclosed herein, the recombination system is a non-endogenous recombination system that includes a recombination expression vector comprising RecA recombinase or a RecA gain-of-function variant operably linked to an inducible promoter and optionally the heterologous nucleic acid sequence. In some embodiments, the inducible promoter is araB and the non-endogenous recombination system is induced by the addition of arabinose. In other embodiments, the expression vector comprising the heterologous nucleic acid sequence is separate and distinct from the recombination expression vector comprising RecA recombinase or the RecA gain-of-function variant.

Additionally or alternatively, in some embodiments of the methods disclosed herein, the bacterial host cell comprises a non-endogenous CRISPR expression vector comprising a nucleic acid sequence that encodes a first sgRNA, a second sgRNA, and a CRISPR enzyme. In some embodiments, the first sgRNA and the second sgRNA are operably linked to a constitutive promoter. In some embodiments, the sequence of the first sgRNA and the second sgRNA is SEQ ID NO: 7 and SEQ ID NO: 8, respectively.

A variety of CRISPR enzymes are available for use in conjunction with the disclosed methods of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any variants, homologs or orthologs thereof. Non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or variants thereof. The CRISPR enzyme may be operably linked to an inducible promoter, such as a tetracycline-inducible promoter. In some embodiments, the CRISPR enzyme cleaves both strands of the target nucleic acid at the Protospacer Adjacent Motif (PAM) site.

In another aspect, the present disclosure provides sgRNAs that are useful for making the recombinant B11 bacteriophages disclosed herein. In some embodiments, the sgRNA sequence is selected from the group consisting of SEQ ID NO: 7 and SEQ ID NO: 8. The design of sgRNAs that are capable of cleaving at the other B11 genomic positions described herein, is within the scope of one of ordinary skill in the art.

Bacterial Identification and Antibiotic Susceptibility Profiling Methods of the Present Technology Accurate identification of bacterial species within a biological sample informs the selection of suitable therapies for treating bacterial infections. The recombinant B11 bacteriophages disclosed herein may be used to identify bacteria present within a biological sample (e.g., whole blood, plasma, serum). Such methods entail contacting the biological sample with a recombinant B11 bacteriophage disclosed herein, and detecting the presence of bacterial host cells infected by the recombinant B11 phage, wherein the recombinant B11 phage comprises a heterologous nucleic acid sequence that encodes a detectable gene product, thereby leading to the identification of bacteria present within the biological sample.

Additionally or alternatively, the recombinant B11 bacteriophages disclosed herein, may be used in methods for profiling antibiotic susceptibility of bacteria present within a biological sample (e.g., whole blood, plasma, serum). These methods include (a) infecting the biological sample with an antibiotic and a recombinant B11 bacteriophage disclosed herein, (b) detecting the presence of bacterial host cells infected by the recombinant B11 phage, wherein the recombinant B11 phage comprises a heterologous nucleic acid sequence that encodes a detectable gene product, and (c) determining that the antibiotic is effective in inhibiting the bacteria present in the biological sample when the levels of recombinant B11 phage infected bacterial host cells is reduced relative to that observed in an untreated control sample.

In one aspect, the present disclosure provides a method for identifying at least one bacterial strain or species in a test sample obtained from a subject comprising (a) separating bacterial cells isolated from the test sample into one or more sub-samples, (b) infecting each sub-sample with at least one recombinant B11 bacteriophage disclosed herein, wherein each recombinant B11 bacteriophage comprises a heterologous nucleic acid sequence encoding one or more reporter genes, and (c) identifying at least one bacterial strain or species in the test sample by detecting the expression of the one or more reporter genes of the at least one recombinant B11 bacteriophage. In certain embodiments, the at least one B11 bacteriophage comprises a nucleic acid sequence selected from the group consisting of SEQ ID NO: 2, SEQ ID NO: 3, SEQ ID NO: 4 and SEQ ID NO: 12. In certain embodiments, the method for identifying at least one bacterial strain or species in a test sample does not require the culturing of bacterial cells from the test sample or a sub-sample.

In some embodiments, identification of at least one bacterial strain or species includes detecting the expression of the one or more reporter genes of the at least one recombinant B11 bacteriophage, e.g., detectable expression of green fluorescence indicates the presence of bacterial species A in a test sample or sub-sample. In some embodiments, the absence of at least one bacterial strain or species is identified by the lack of detectable expression of the one or more reporter genes of the at least one recombinant B11 bacteriophage, e.g., undetectable expression of green fluorescence indicates the lack of bacterial species A in a test sample or sub-sample.

In some embodiments, the at least one recombinant B11 bacteriophage infects a single species of bacteria. In certain embodiments, the at least one recombinant B11 bacteriophage infects two or more species of bacteria.

In some embodiments, detection of the expression of the reporter gene is detection of the gene product itself, e.g., a fluorescent protein. In some embodiments, detection of the expression of the reporter gene is detection of an enzymatic reaction requiring the expression of the reporter gene, e.g., expression of luciferase to catalyze luciferin to produce light.

In some embodiments, the expression of the one or more reporter genes is detected in about 5, 10, 15, 20, 25, 30, 35, 40, 45, 50, 55, 60, 65, 70, 75, 80, 85, 90, 120 minutes or any time between any two of the preceding values after infecting a sub-sample with the at least one recombinant B11 bacteriophage disclosed herein.

The present disclosure also provides a method for identifying at least one bacterial strain or species in a test sample obtained from a subject comprising (a) infecting the test sample comprising bacterial cells with a recombinant B11 bacteriophage of the present technology; and (b) detecting the expression of the reporter protein of the recombinant B11 bacteriophage, wherein detection of the reporter protein indicates the presence of at least one bacterial strain or species in the test sample. In some embodiments of the method, the expression of the reporter protein is measured in about 5, 10, 15, 20, 25, 30, 35, 40, 45, 50, 55, 60, 65, 70, 75, 80, 85, 90 or 120 minutes after infecting the test sample comprising bacterial cells with the recombinant B11 bacteriophage.

Additionally or alternatively, in some embodiments of the methods disclosed herein, the test sample is blood, sputum, mucus, lavage, saliva, or a swab obtained from the subject. In some embodiments, the subject is human.

In another aspect, the present disclosure provides a method for determining the antibiotic susceptibility of a bacterial strain or species in a test sample obtained from a subject comprising (a) separating bacterial cells isolated from the test sample into a plurality of sub-samples, (b) infecting the plurality of sub-samples with a recombinant B11 bacteriophage disclosed herein and at least one antibiotic, wherein the recombinant B11 bacteriophage comprises a heterologous nucleic acid sequence encoding a reporter gene, and (c) detecting the expression of the reporter gene of the recombinant B11 bacteriophage in the presence of each antibiotic. In some embodiments, the method further comprises determining that the bacterial strain or species in the test sample is susceptible to an antibiotic if the reporter gene expression of the recombinant B11 bacteriophage in the antibiotic treated sub-sample is decreased relative to that observed in a control sub-sample that is not treated with the antibiotic. In other embodiments, the method further comprises determining that the bacterial strain or species in the test sample is resistant to an antibiotic if the reporter gene expression of the recombinant B11 bacteriophage in the antibiotic treated sub-sample is comparable to that observed in a control sub-sample that is not treated with the antibiotic. In certain embodiments, the method for determining the antibiotic susceptibility of a bacterial strain or species in a test sample does not require the culturing of bacterial cells from a test sample or a sub-sample.

Additionally or alternatively, in some embodiments of the recombinant B11 bacteriophages of the present technology, the reporter gene is nanoluciferase. In certain embodiments, recombinant B11 bacteriophage comprises a nucleic acid sequence selected from the group consisting of SEQ ID NO: 2, SEQ ID NO: 3, SEQ ID NO: 4 and SEQ ID NO: 12.

Examples of antibiotics include one or more of rifampicin, tetracycline, levofloxacin, ampicillin, penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

In some embodiments of the method, the differences in the reporter gene expression of the recombinant B11 bacteriophage observed in the antibiotic treated sub-sample and the untreated control sub-sample is defined as µ.

Additionally or alternatively, in some embodiments of the method, the expression of the reporter gene is detected in about 5, 10, 15, 20, 25, 30, 35, 40, 45, 50, 55, 60, 65, 70, 75, 80, 85, 90, 120 minutes or any time between any two of the preceding values after infecting a sub-sample with a recombinant B11 bacteriophage disclosed herein.

In some embodiments, two or more sub-samples are tested for antibiotic susceptibility in series. In some embodiments, two or more sub-samples are tested for antibiotic susceptibility in parallel. In some embodiments, one or more sub-samples are tested for antibiotic susceptibility in a running assay (where resistance or sensitivity to one antibiotic is determined and the resistance or sensitivity to a second, third, fourth, fifth, etc., antibiotic is being assayed).

In some embodiments of the methods disclosed herein, isolating bacterial cells from a test sample includes incubating the test sample with distilled water to form a mixture, centrifuging the mixture to form a pellet that includes bacterial cells, and re-suspending the pellet to form a bacterial suspension comprising isolated bacterial cells after discarding the supernatant. The pellet may be re-suspended in a phosphate buffer. In some embodiments, the bacterial suspension is divided into one or more sub-samples.

In certain embodiments of the methods disclosed herein, mixing the test sample with distilled water will lead to the lysis of cells that lack cell walls (e.g., mammalian cells and red blood cells) while leaving cells with cell walls (e.g., bacteria) intact. Without wishing to be bound by theory, in some embodiments, the removal of cells that lack cell walls enhances the detection of reporter gene expression in bacterial cells infected with a recombinant B11 bacteriophage, as intact non-bacterial cells (e.g., red blood cells) may quench reporter gene expression. In some embodiments of the methods of the present technology, the mixture is about 90% distilled water and 10% test sample, about 80% distilled water and 20% test sample, about 70% distilled water and 30% test sample, about 60% distilled water and 40% test sample, about 50% distilled water and 50% test sample, about 40% distilled water and 60% test sample, about 30% distilled water and 70% test sample, about 20% distilled water and 80% sample, or about 10% distilled water and 90% test sample. In some embodiments of the methods disclosed herein, the mixture is incubated for 1, 2, 3, 4, 5, 6, 7, 8, 9, 10, 11, 12, 13, 14, or 15 minutes, or any time between two of the previously listed time points. Additionally or alternatively, in certain embodiments of the methods disclosed herein, the mixture is centrifuged for 1, 2, 3, 4, 5, 6, 7, 8, 9, 10, 11, 12, 13, 14, or 15 minutes, or any time between two of the previously listed time points.

Additionally or alternatively, in certain embodiments of the methods disclosed herein, each of the one or more sub-samples comprise between about 5 to 500, about 10 to 400, about 20 to 300, about 30 to 300, about 40 to 200 or about 50 to 100 bacterial cells. In some embodiments of the methods disclosed herein, each of the one or more sub-samples comprises between about 100 to 10,000, about 200 to 9,000, about 300 to 8,000, about 400 to 7,000, about 500 to 6,000, about 600 to 5,000, about 700 to 4,000, about 800 to 3,000, about 900 to 2,000, or about 1,000 to 1,500 bacterial cells.

In another aspect, the present disclosure provides a method for determining the antibiotic susceptibility of a bacterial strain or species in a test sample obtained from a subject comprising (a) infecting a plurality of test samples comprising bacterial cells with a recombinant B11 bacteriophage of the present technology and an antibiotic, wherein the plurality of test samples is derived from the subject; (b) detecting the expression of the reporter protein of the recombinant B11 bacteriophage in the plurality of test samples; and (c) determining that the antibiotic is effective in inhibiting the bacterial strain or species in a test sample when the reporter protein expression levels of the recombinant B11 phage infected bacterial cells in the test sample are reduced relative to that observed in an untreated control sample comprising bacterial cells, wherein the untreated control sample is derived from the subject and is infected with the recombinant B11 bacteriophage of the present technology. The expression of the reporter protein may be measured in about 5, 10, 15, 20, 25, 30, 35, 40, 45, 50, 55, 60, 65, 70, 75, 80, 85, 90 or 120 minutes after infecting the plurality of test samples comprising bacterial cells with the recombinant B11 bacteriophage. In other embodiments, the method further comprises determining that the bacterial strain or species in the test sample is resistant to the antibiotic when the reporter protein expression levels of the recombinant B11 bacteriophage infected bacterial cells in the test sample are comparable to that observed in an untreated control sample comprising recombinant B11 phage infected bacterial cells, wherein the untreated control sample is derived from the subject and is infected with the recombinant B11 bacteriophage of the present technology.

In any of the above embodiments of the methods of the present technology, the test sample is blood, sputum, mucus, lavage, saliva, or a swab obtained from the subject. In some embodiments of the methods disclosed herein, the test sample is obtained from a mammalian subject, including, for example, farm animals, such as sheep, pigs, cows, and horses; pet animals, such as dogs and cats; and laboratory animals, such as rats, mice and rabbits. In one embodiment, the mammal subject is a human.

Kits

The present technology provides kits including the recombinant B11 bacteriophages disclosed herein for bacteria identification and antibiotic susceptibility profiling.

In one aspect, the kits of the present technology comprise one or more coded/labeled vials that contain a plurality of the recombinant B11 bacteriophages disclosed herein, and instructions for use. In some embodiments, each coded/labeled vial corresponds to a different recombinant B11 bacteriophage. In other embodiments, each coded/labeled vial corresponds to the same recombinant B11 bacteriophage. In some embodiments, the kits of the present technology comprise one or more coded/labeled vials that contain at least one recombinant B11 bacteriophage comprising a nucleic acid sequence selected from the group consisting of SEQ ID NO: 2, SEQ ID NO: 3, SEQ ID NO: 4 and SEQ ID NO: 12.

In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the bacteriophage genomes for extended periods, such as under bacteriophage-specific, controlled temperature, moisture, and pH conditions.

Additionally or alternatively, in some embodiments, the kits further comprise vials containing natural or non-natural bacterial host cells. In some embodiments, the bacterial host cells are *Pseudomonas aeruginosa*.

The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids of the recombinant B11 bacteriophages disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, the kits disclosed herein may also include coded and labeled vials that contain a plurality of antibiotics. In some embodiments, the plurality of antibiotics comprises one or more of rifampicin, tetracycline, levofloxacin, and ampicillin. Other examples of antibiotics include penicillin G, methicillin, oxacillin, amoxicillin, cefadroxil, ceforanid, cefotaxime, ceftriaxone, doxycycline, minocycline, amikacin, gentamicin, levofloxacin, kanamycin, neomycin, streptomycin, tobramycin, azithromycin, clarithromycin, erythromycin, ciprofloxacin, lomefloxacin, norfloxacin, chloramphenicol, clindamycin, cycloserine, isoniazid, rifampin, teicoplanin, quinupristin/dalfopristin, linezolid, pristinamycin, ceftobiprole, ceftaroline, dalbavancin, daptomycin, mupirocin, oritavancin, tedizolid, telavancin, tigecycline, ceftazidime, cefepime, piperacillin, ticarcillin, virginiamycin, netilmicin, paromomycin, spectinomycin, geldanamycin, herbimycin, rifaximin, loracarbef, ertapenem, doripenem, imipenem/cilastatin, meropenem, cefazolin, cefalotin, cephalexin, cefaclor, cefamandole, cefoxitin, cefprozil, cefuroxime, cefixime, cefdinir, cefditoren, cefoperazone, cefpodoxime, ceftibuten, ceftizoxime, lincomycin, dirithromycin, roxithromycin, troleandomycin, telithromycin, spiramycin, aztreonam, furazolidone, nitrofurantoin, posizolid, radezolid, torezolid, azlocillin, carbenicillin, cloxacillin, dicloxacillin, flucloxacillin, mezlocillin, nafcillin, penicillin V, temocillin, bacitracin, colistin, polymyxin B, enoxacin, gatifloxacin, gemifloxacin, moxifloxacin, nalidixic acid, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (Co-trimoxazole) (TMP-SMX), sulfonamidochrysoidine, demeclocycline, oxytetracycline, clofazimine, dapsone, capreomycin, ethambutol, ethionamide, pyrazinamide, rifabutin, rifapentine, arsphenamine, fosfomycin, fusidic acid, metronidazole, platensimycin, thiamphenicol, tinidazole, trimethoprim(Bs) and vancomycin.

Additionally or alternatively, in some embodiments, the kits comprise one or more sgRNA sequences selected from the group consisting of SEQ ID NO: 7 and SEQ ID NO: 8.

EXAMPLES

Example 1: Design and Methods for Generating the Recombinant B11 Bacteriophages of the Present Technology This Example demonstrates that the methods of the present technology are useful for making the recombinant B11 bacteriophages disclosed herein in a bacterial host cell.

The recombinant *P. aeruginosa* B11 bacteriophage of the present technology were engineered using a 'break and recombine' (BAR) phage engineering method. The BAR method relies on (1) cleaving a phage genome in vivo at one or two locations using an RNA-guided endonuclease (e.g., Cas9)-sgRNA complex, and (2) providing a heterologous nucleic acid sequence comprising the nanoluciferase gene with an upstream ribosome binding site as well as 5' and 3' flanking regions that are homologous to a portion of the initial B11 phage genome (collectively, referred to as the donor template region). The donor template region also contains sequences that restore the function of any B11 phage DNA that was excised by the sgRNA-CRISPR enzyme complexes. The 5' and 3' flanking regions (about several hundred base pairs in length) are homologous to the DNA sequences immediately adjacent to the two cleavage sites in the phage genome (FIGS. 5(A)-5(B)), and are necessary for repairing double-stranded breaks via homologous recombination.

The desired insertion site (site 6.3) was immediately downstream of an open reading frame (ORF) of unknown function. The sequence of the initial B11 contig-6 genome is shown in FIGS. 7(A)-7(L) and is represented by SEQ ID NO: 1. The 20 bp protospacer site, along with the accompanying 3 bp protospacer adjacent motif (PAM) were identified near 'site 6.3.' The B11 protospacer sequences along with their adjacent PAM sites (PAM site underlined) are provided below:

```
Protospacer 6.3A  5' AGAAGATCATTATCGAA/AGACGG 3' (SEQ ID NO: 9)

Protospacer 6.3B  5' AGACATAGCCCCTCTCC/ACATGG 3' (SEQ ID NO: 10)

cleavage sites marked with a '/'
```

The complete sequences of sgRNA 6.3A, and sgRNA 6.3B are provided below:

```
sgRNA 6.3A RNA sequence:
                                      (SEQ ID NO: 7)
5' AGAAGAUCAUUAUCGAAAGAGUUUUAGAGCUAGAAAUAGCAAGUUAA
AAUAAGGCUAGUCCGUUAUCAACUUGAAAAAGUGGCACCGAGUCGGUGCU
UUUUUU 3' sgRNA 6.3B RNA sequence:
                                      (SEQ ID NO: 8)
5' AGACAUAGCCCCUCUCCACAGUUUUAGAGCUAGAAAUAGCAAGUUAA
AAUAAGGCUAGUCCGUUAUCAACUUGAAAAAGUGGCACCGAGUCGGUGCU
UUUUUU 3'.
```

The CRISPR expression vector (crR) was assembled for CRISPR-Cas9 mediated cleavage in in *P. aeruginosa*. The crR plasmid is a shuttle vector containing a pUC origin of replication, a pRO1600 origin of replication, a kanamycin resistance cassette, and an *S. pyogenes* Cas9 gene (codon-optimized for expression in *P. aeruginosa*) operably linked to a pTet (tetracycline) promoter. The crR plasmid also contains a scaffold into which a segment of synthetic DNA can be inserted so as to permit the transcription of two sgRNAs (e.g., using a dual-guide cassette) by the lipoprotein (lpp) promoter. The nucleic acid sequences of the 'dual-guide cassettes' for sgRNAs 6.3A and 6.3B are provided below:

```
Dual-guide cassette (sgRNAs 6.3A and 6.3B):
                                     (SEQ ID NO: 11)
AGCAGTGGTAAGGTCTCTTAACAGAAGATCATTATCGAAAGAGTTTTAGA

GCTAGAAATAGCAAGTTAAAATAAGGCTAGTCCGTTATCAACTTGAAAAA

GTGGCACCGAGTCGGTGCTTTTTTTGCTAACTGATACCGACTACGCCTGA

ACAGTCGAATCTTCACCTCGTCTGGTACCGACGCGGTCCCAAATATTGAC
```

-continued

AACATAAAAAACTTTGTGTTATACTTGTAACAGACATAGCCCCTCTCCAC

AGTTTTGAGACCAGCTCGTAGG

The 'dual-guide cassette' for sgRNAs 6.3A and 6.3B was PCR amplified, digested with the restriction enzyme BsaI, and ligated into a BsaI-digested crR plasmid to create the crR-B11 6' CRISPR expression vector.

The donor template vector was designed as follows. FIG. 1 shows the donor template sequence for B11 phage genomic DNA that was cleaved with sgRNA 6.3A and sgRNA 6.3B (SEQ ID NO: 2). The donor template sequences contain the nanoluciferase reporter gene with an upstream ribosome binding site (RBS), as well as the region of the B11 phage genome between the two CRISPR cleavage sites that is to be excised, such that the original sequence and function is restored. Specifically, the donor template sequences included 5' and 3' flanking regions (about 300 bp in length) that were perfectly homologous to the cleaved ends of the wild-type B11 phage genome so as to facilitate strand invasion and homologous recombination between the cleaved phage genome and the donor sequence, thereby repairing the double-stranded breaks and incorporating the nanoluciferase reporter gene. The protospacers/PAM sequences within the donor templates were modified such that the CRISPR system would not recognize and cleave the donor template, and would only target the wild-type phage genome. For example, the regions internal to the two cleavage sites (i.e., right of the upstream cut site and left of the downstream cut site) were either codon-reassigned or otherwise changed by single-base pair substitutions that were not expected to detrimentally affect phage function.

The recombination plasmid was assembled by PCR amplification of the plasmid 'pBBR1-Gent' with primers 5' CAGGTTCATCATGCCGTTTGTG 3' (SEQ ID NO: 13) and 5' TATTTGCCCATGGACGCACAC 3' (SEQ ID NO: 14) followed by a Gibson assembly reaction between the amplified plasmid and the donor template. The assembled recombination plasmid was designated as 'pBBR1-B11 6'.

The *P. aeruginosa* strain PAO1 was transformed with the crR-B11 6 and pBBR1-B11 6' plasmids. The strain was maintained in kanamycin at 250 μg/mL and gentamicin at 50 μg/mL. A 5 mL culture of this strain was grown to early-log phase and then treated with 1 μg/mL anhydrotetracycline (aTc) for two hours to induce Cas9 expression. The culture was then infected with wild-type B11 phage overnight. It was observed that aTc induction did not reduce phage titer/plaque formation.

Results.

PCR assays of the overnight lysate revealed that most transformants were wild-type non-recombinant B11 phage. To reduce contamination due to nanoluciferase protein and plasmid DNA, the lysate was purified by multiple rounds of size-exclusion filtration. The purified lysate was then subject to a large screen (automated brute force methodology) to enrich for recombinant B11 phage. Once determined to be reasonably pure, the sample was diluted and plated on a PAO1 overlay, such that single plaques could be recovered for genotypic and phenotypic analysis.

Figure 2B:
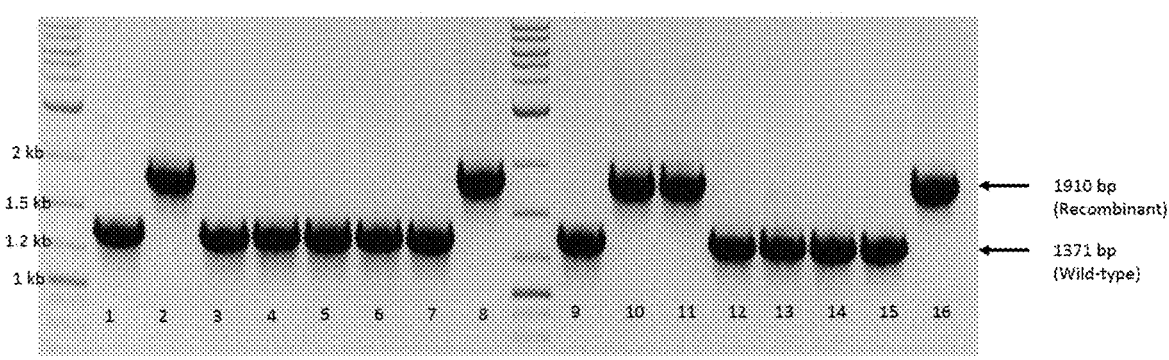
FIG. 2(B) shows flanking PCR assays that tested for the presence of recombinant NanoLuc®B11 bacteriophage using primer sets that flank site 6.3.
Figure 3A:
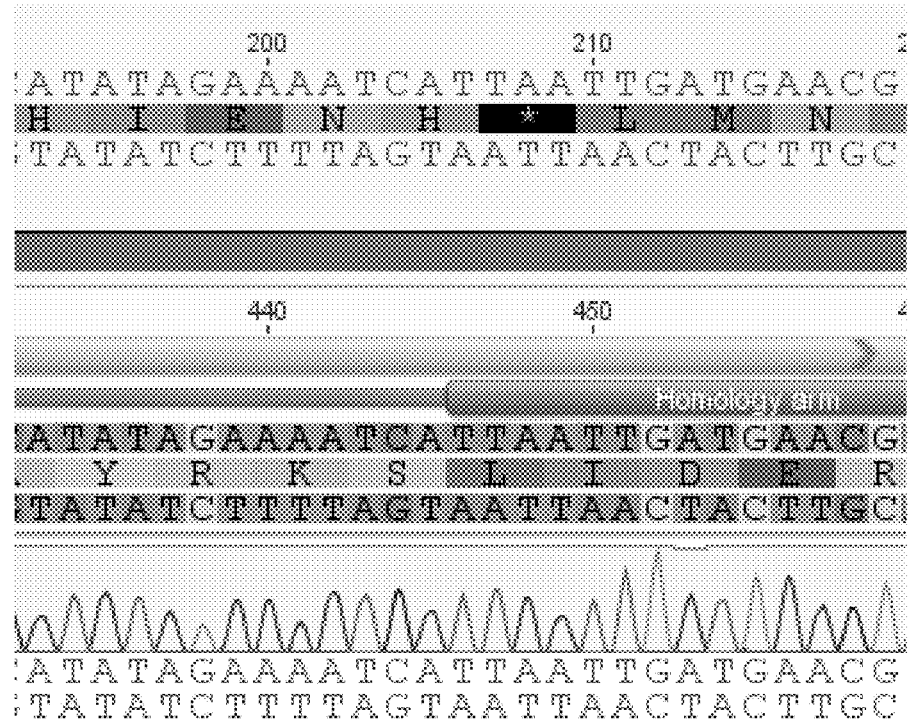
FIG. 3(A) shows the upstream junction sequence where the region of B11 phage genome intersects with the 5' homologous region of the donor plasmid. Figure discloses SEQ ID NOS 15, 16, 15, 17, and 15, respectively, in order of appearance.
Figure 3B:
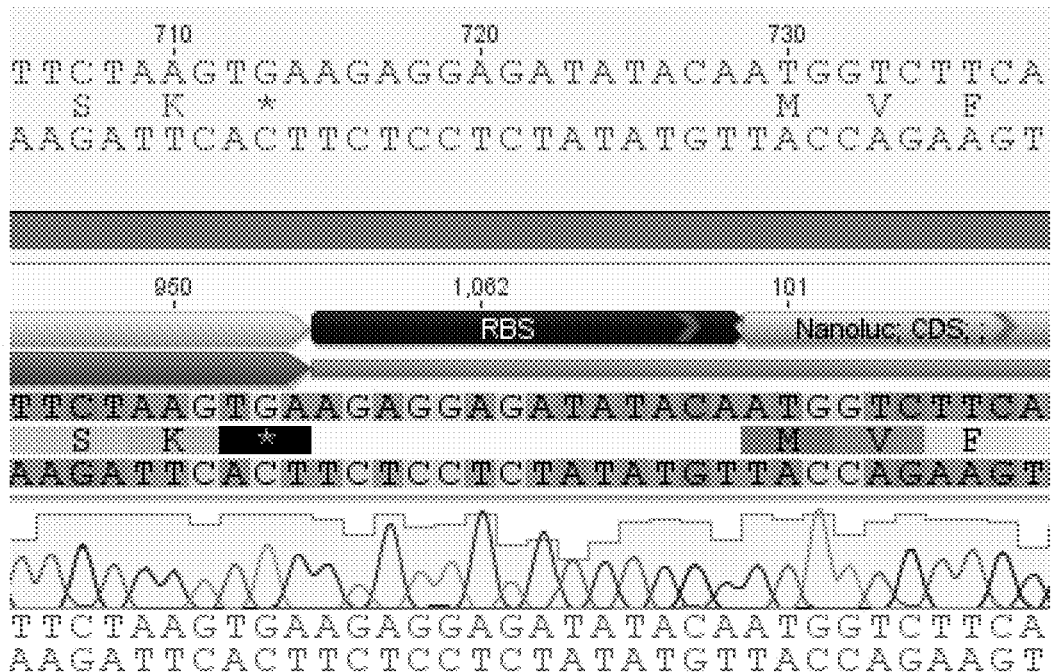
FIG. 3(B) shows the upstream junction sequence of the nanoluciferase insertion in the recombinant B11 phage genome cleaved by sgRNA 6.3A and sgRNA 6.3B: 5' TTCTAAGTGAAGAGGAGATATACAATGGTCTTCA 3' (SEQ ID NO: 3).
Figure 3C:
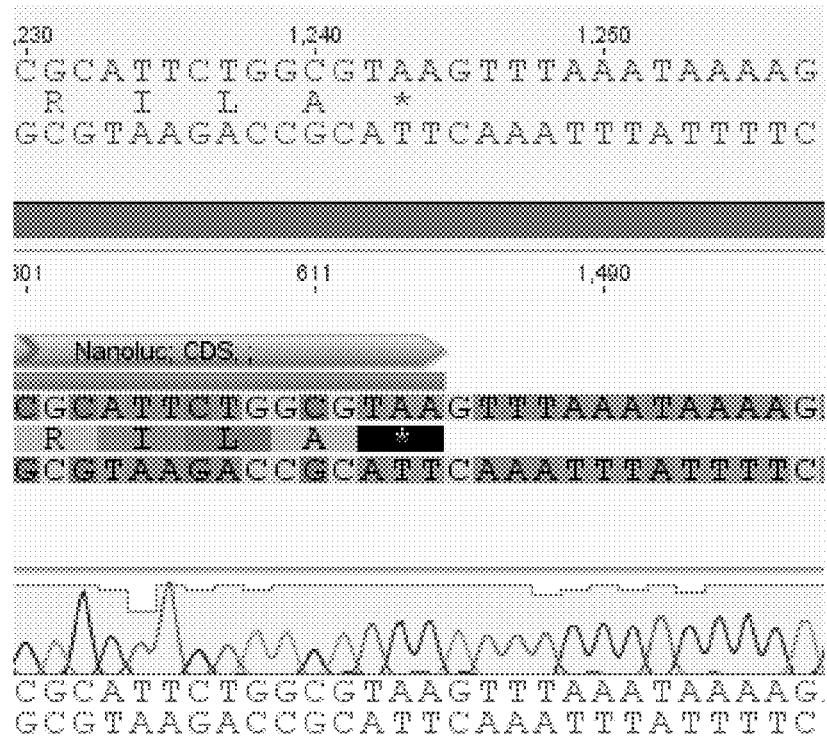
FIG. 3(C) shows the downstream junction sequence of the nanoluciferase insertion in the recombinant B11 phage genome cleaved by sgRNA 6.3A and sgRNA 6.3B: 5' CGCATTCTGGCGTAAGTTTAAATAAAAG 3' (SEQ ID NO: 4)). Figure discloses the protein sequence as SEQ ID NO: 18.
Figure 3D:
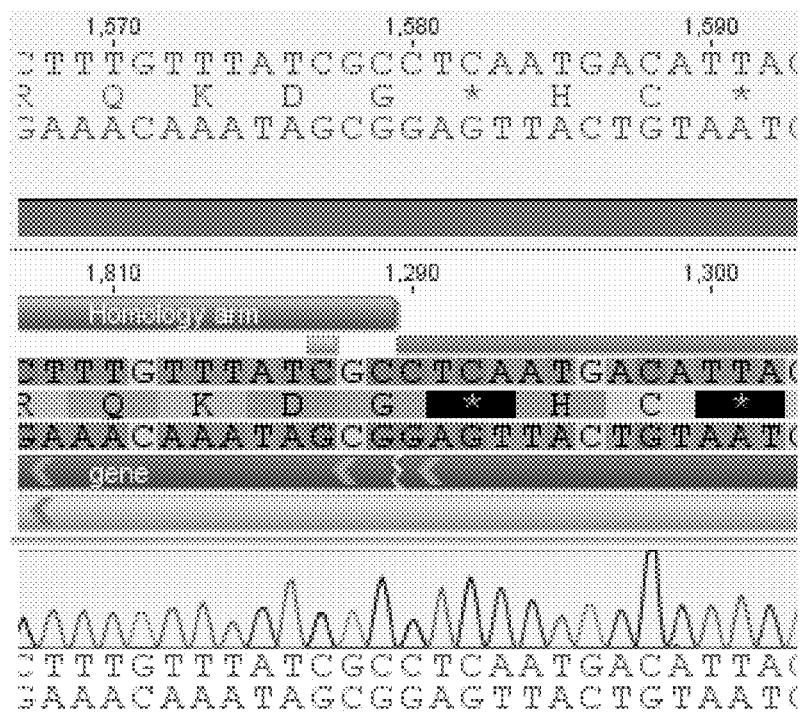
FIG. 3(D) shows the downstream junction sequence where the region of B11 phage genome intersects with the 3' homologous region of the donor plasmid. Figure discloses SEQ ID NOS 19, 20, 19, 20, and 19, respectively, in order of appearance.

16 single plaques were picked into 25 μl of Tris buffer, and 1 μl of each 'pickate' was used to infect 150 μl of mid-log PAO1 overnight. Relative luminescence units (RLU) readings were then recorded. The infections were also analyzed via PCR reaction using primers that flank the intended nanoluciferase insertion site. FIGS. 2(A)-2(B) demonstrate that pickates 2, 8, 10, and 16 were both genotypically and phenotypically positive for nanoluciferase insertion. The PCR product from pickate 2 was then sequenced. FIGS. 8(A)-8(L) show the B11 contig-6 genome sequence of the recombinant NanoLuc®B11 phage that was cleaved with sgRNA 6.3A and sgRNA 6.3B (SEQ ID NO: 12). FIGS. 3(B)-3(C) show the upstream and downstream junction sequences of the nanoluciferase insertions at site 6.3 within the recombinant B11 phage. FIG. 3(A) shows the upstream junction sequence where the region of B11 phage genome intersects with the 5' homologous region of the donor plasmid. FIG. 3(D) shows the downstream junction sequence where the region of B11 phage genome intersects with the 3' homologous region of the donor plasmid.

These results demonstrate that the methods of the present technology are useful for making the recombinant B11 bacteriophages disclosed herein in a bacterial host cell. Accordingly, the methods disclosed herein are useful for generating recombinant B11 bacteriophages that can be used in the identification and/or antibiotic susceptibility profiling of specific *P. aeruginosa* strains present in a sample.

Example 2: Functional Activity of the Recombinant B11 Bacteriophages of the Present Technology This Example demonstrates that the recombinant B11 bacteriophages of the present technology are useful for the identification and/or antibiotic susceptibility profiling of specific *P. aeruginosa* strains present in a sample.

Figure 4:
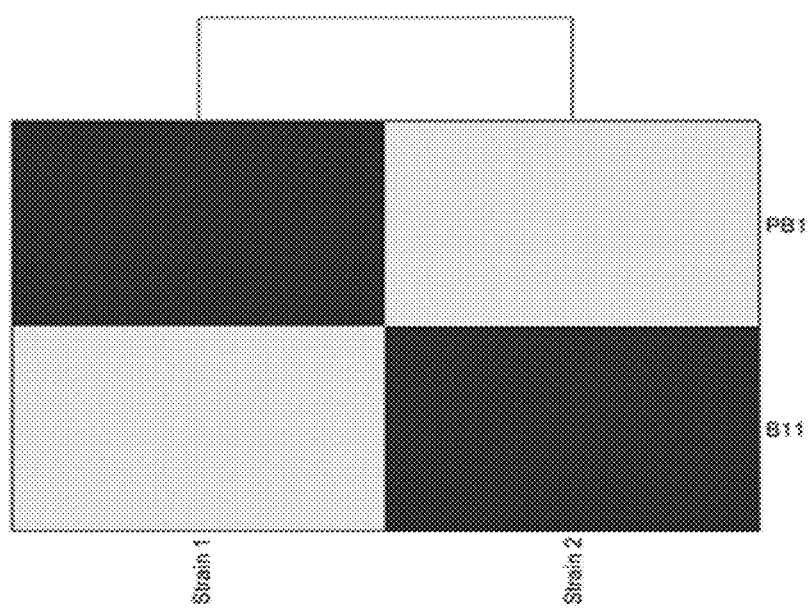
FIG. 4 shows a comparison of the host ranges of recombinant NanoLuc® B11 phage, and recombinant NanoLuc®PB1 phage. Grey means the given strain is infected by the indicated phage, whereas black means a given strain is not infected by the indicated phage.

*P. aeruginosa* clinical isolates (designated as strains 1-2) were infected with the recombinant NanoLuc®B11 phages disclosed herein and a recombinant NanoLuc® PB1 phage for 1 hour. FIG. 4 shows that the recombinant NanoLuc®B11 phages of the present technology successfully infected a *P. aeruginosa* clinical isolate (strain 1) that was incapable of being infected with a recombinant nanoluciferase expressing PB1 phage.

These results demonstrate that the methods of the present technology are useful for making the recombinant B11 bacteriophages disclosed herein in a bacterial host cell. Accordingly, the methods disclosed herein are useful for generating recombinant B11 bacteriophages that can be used in the identification and/or antibiotic susceptibility profiling of specific *P. aeruginosa* strains present in a sample.

Example 3: Antibiotic Susceptibility Profiling Using the Recombinant B11 Bacteriophages of the Present Technology Antibiotics were prepared by performing eleven 2-fold serial dilutions in Mueller Hinton Broth (Sigma, St. Louis, Mo.) in 96 well microtiter plates at a final volume of 100 μl. One column contained broth only and served as a no drug control.

Cells from an overnight growth blood culture in 25% human blood and 75% Tryptic Soy Broth TSB were diluted 1:10 in Mueller Hinton Broth. From this dilution, 5 μl of cells was added to each well of the antibiotic plate. Cells were pretreated with antibiotics (meropenem) for 120 minutes at 37° C. After the 120 minute pretreatment, 10 μl of phage suspension comprising the recombinant B11 phage of the present technology (1E6 pfu/reaction well) was added to each well and incubated at 37° C. for 45 minutes. After infection with the phage, 50 μl of the reaction was added to 50 μl Nano Glo Luciferase Substrate (Promega, Madison, Wis.) in a luminescent plate and read in a luminometer. The minimal inhibitory concentration (MIC) of each sample was determined using the ETEST® method (Biomerieux, St.

Louis, Mo.) according to the manufacturer's instructions. The differences in the reporter gene expression of the recombinant B11 bacteriophage observed in the antibiotic treated samples and the untreated control samples is defined as µ.

Figure 6:
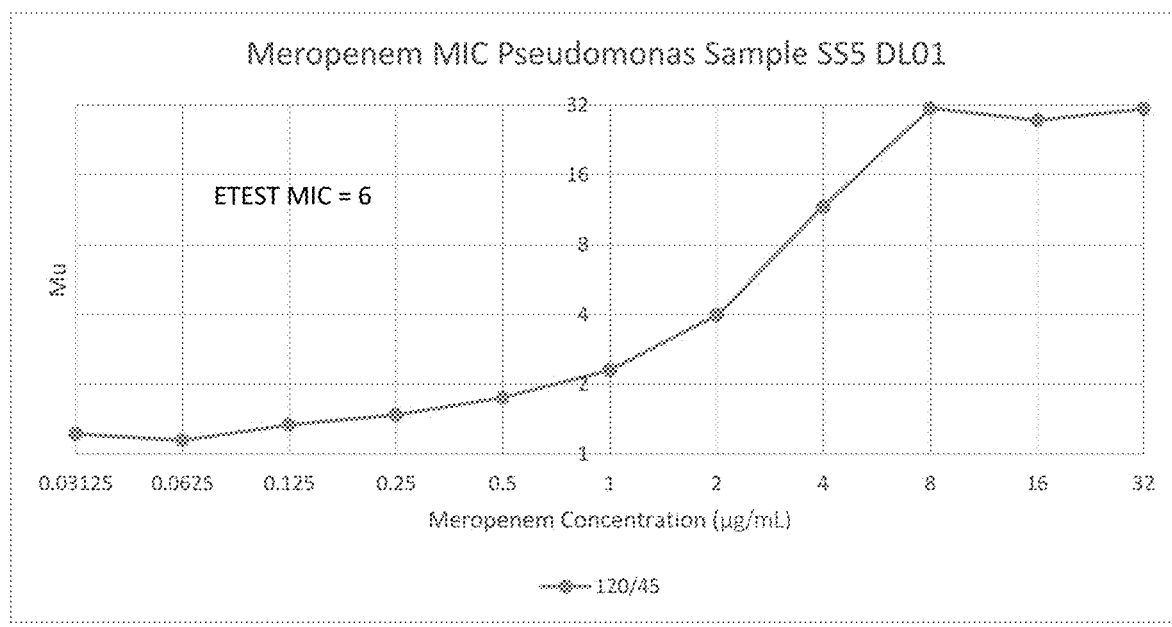
FIG. 6 shows the antibiotic susceptibility profile of a *P. aeruginosa* strain to meropenem using the recombinant B11 phages of the present technology.

FIG. 6 demonstrates that the recombinant B11 bacteriophages of the present technology were effective in determining the antibiotic susceptibility profile of *P. aeruginosa* strain SS5 DL01.

These results demonstrate that the recombinant B11 bacteriophages of the present technology are useful for determining the antibiotic susceptibility of a bacterial strain or species in a test sample. Accordingly, the recombinant B11 bacteriophages disclosed herein are useful for the identification and/or antibiotic susceptibility profiling of specific *P. aeruginosa* strains present in a sample.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for making a recombinant B11 bacteriophage in a bacterial host cell comprising
   (a) contacting a first B11 bacteriophage genome with a first sgRNA-CRISPR enzyme complex and a second sgRNA-CRISPR enzyme complex in vivo under conditions where
      (i) the first sgRNA-CRISPR enzyme complex cleaves a first protospacer sequence 5' AGAAGATCAT-TATCGAAAGA 3' (SEQ ID NO: 5) within the first B11 bacteriophage genome; and
      (ii) the second sgRNA-CRISPR enzyme complex cleaves a second protospacer sequence 5' AGACAT-AGCCCCTCTCCACA 3' (SEQ ID NO: 6) within the first B11 bacteriophage genome
   to produce a cleaved first B11 bacteriophage genome; and
   (b) recombining in vivo the cleaved first B11 bacteriophage genome with a heterologous nucleic acid sequence in the presence of a recombination system under conditions to produce the recombinant B11 bacteriophage genome,
   wherein the bacterial host cell is infected with the first B11 bacteriophage genome, and wherein the heterologous nucleic acid sequence comprises an open reading frame that encodes a bioluminescent protein, a fluorescent protein, a chemiluminescent protein, or any combination thereof.

2. The method of claim 1, wherein the recombination system is a non-endogenous recombination system that is induced in the bacterial host cell.

3. The method of claim 2, wherein the non-endogenous recombination system comprises lambda Red proteins Gam, Exo, and Beta operably linked to an inducible promoter.

4. The method of claim 3, wherein the inducible promoter is araB and the non-endogenous recombination system is induced by the addition of arabinose.

5. The method of claim 1, wherein the bacterial host cell comprises a non-endogenous CRISPR expression vector comprising a nucleic acid sequence that encodes a first sgRNA, a second sgRNA, and a CRISPR enzyme.

6. The method of claim 5, wherein the first sgRNA and the second sgRNA are operably linked to a constitutive promoter and wherein the CRISPR enzyme is operably linked to an inducible promoter.

* * * * *

SEQUENCE LISTING

```
<160> NUMBER OF SEQ ID NOS: 20

<210> SEQ ID NO 1
<211> LENGTH: 78879
<212> TYPE: DNA
<213> ORGANISM: Pseudomonas phage B11
<220> FEATURE:
<221> NAME/KEY: modified_base
<222> LOCATION: (203)..(203)
<223> OTHER INFORMATION: a, c, t, g, unknown or other
<220> FEATURE:
<221> NAME/KEY: modified_base
<222> LOCATION: (212)..(212)
<223> OTHER INFORMATION: a, c, t, g, unknown or other
<220> FEATURE:
<221> NAME/KEY: modified_base
<222> LOCATION: (223)..(224)
<223> OTHER INFORMATION: a, c, t, g, unknown or other
<220> FEATURE:
<221> NAME/KEY: modified_base
<222> LOCATION: (226)..(226)
<223> OTHER INFORMATION: a, c, t, g, unknown or other
<220> FEATURE:
<221> NAME/KEY: modified_base
<222> LOCATION: (236)..(238)
<223> OTHER INFORMATION: a, c, t, g, unknown or other
<220> FEATURE:
<221> NAME/KEY: modified_base
<222> LOCATION: (242)..(242)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
```

-continued

```
<222> LOCATION: (250)..(251)
<223> OTHER INFORMATION: a, c, t, g, unknown or other
<220> FEATURE:
<221> NAME/KEY: modified_base
<222> LOCATION: (256)..(256)
<223> OTHER INFORMATION: a, c, t, g, unknown or other
<220> FEATURE:
<221> NAME/KEY: modified_base
<222> LOCATION: (281)..(281)
<223> OTHER INFORMATION: a, c, t, g, unknown or other
<220> FEATURE:
<221> NAME/KEY: modified_base
<222> LOCATION: (285)..(285)
<223> OTHER INFORMATION: a, c, t, g, unknown or other
<220> FEATURE:
<221> NAME/KEY: modified_base
<222> LOCATION: (293)..(293)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (419)..(419)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (509)..(509)
<223> OTHER INFORMATION: a, c, t, g, unknown or other
<220> FEATURE:
<221> NAME/KEY: modified_base
<222> LOCATION: (513)..(513)
<223> OTHER INFORMATION: a, c, t, g, unknown or other
<220> FEATURE:
<221> NAME/KEY: modified_base
<222> LOCATION: (522)..(522)
<223> OTHER INFORMATION: a, c, t, g, unknown or other
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (564)..(564)
<223> OTHER INFORMATION: a, c, t, g, unknown or other
<220> FEATURE:
<221> NAME/KEY: modified_base
<222> LOCATION: (569)..(570)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other
<220> FEATURE:
```

```
<221> NAME/KEY: modified_base
<222> LOCATION: (3627)..(3627)
<223> OTHER INFORMATION: a, c, t, g, unknown or other
<220> FEATURE:
<221> NAME/KEY: modified_base
<222> LOCATION: (3636)..(3636)
<223> OTHER INFORMATION: a, c, t, g, unknown or other
<220> FEATURE:
<221> NAME/KEY: modified_base
<222> LOCATION: (3639)..(3639)
<223> OTHER INFORMATION: a, c, t, g, unknown or other
<220> FEATURE:
<221> NAME/KEY: modified_base
<222> LOCATION: (3642)..(3642)
<223> OTHER INFORMATION: a, c, t, g, unknown or other
<220> FEATURE:
<221> NAME/KEY: modified_base
<222> LOCATION: (3675)..(3675)
<223> OTHER INFORMATION: a, c, t, g, unknown or other
<220> FEATURE:
<221> NAME/KEY: modified_base
<222> LOCATION: (3681)..(3681)
<223> OTHER INFORMATION: a, c, t, g, unknown or other
<220> FEATURE:
<221> NAME/KEY: modified_base
<222> LOCATION: (3684)..(3684)
<223> OTHER INFORMATION: a, c, t, g, unknown or other
<220> FEATURE:
<221> NAME/KEY: modified_base
<222> LOCATION: (3692)..(3692)
<223> OTHER INFORMATION: a, c, t, g, unknown or other
<220> FEATURE:
<221> NAME/KEY: modified_base
<222> LOCATION: (4080)..(4080)
<223> OTHER INFORMATION: a, c, t, g, unknown or other
<220> FEATURE:
<221> NAME/KEY: modified_base
<222> LOCATION: (4182)..(4182)
<223> OTHER INFORMATION: a, c, t, g, unknown or other
<220> FEATURE:
<221> NAME/KEY: modified_base
<222> LOCATION: (4212)..(4212)
<223> OTHER INFORMATION: a, c, t, g, unknown or other
<220> FEATURE:
<221> NAME/KEY: modified_base
<222> LOCATION: (4314)..(4314)
<223> OTHER INFORMATION: a, c, t, g, unknown or other
<220> FEATURE:
<221> NAME/KEY: modified_base
<222> LOCATION: (4323)..(4323)
<223> OTHER INFORMATION: a, c, t, g, unknown or other
<220> FEATURE:
<221> NAME/KEY: modified_base
<222> LOCATION: (5079)..(5079)
<223> OTHER INFORMATION: a, c, t, g, unknown or other
<220> FEATURE:
<221> NAME/KEY: modified_base
<222> LOCATION: (5190)..(5190)
<223> OTHER INFORMATION: a, c, t, g, unknown or other
<220> FEATURE:
<221> NAME/KEY: modified_base
<222> LOCATION: (6180)..(6180)
<223> OTHER INFORMATION: a, c, t, g, unknown or other
<220> FEATURE:
<221> NAME/KEY: modified_base
<222> LOCATION: (6252)..(6252)
<223> OTHER INFORMATION: a, c, t, g, unknown or other
<220> FEATURE:
<221> NAME/KEY: modified_base
<222> LOCATION: (6273)..(6273)
<223> OTHER INFORMATION: a, c, t, g, unknown or other
<220> FEATURE:
<221> NAME/KEY: modified_base
<222> LOCATION: (6279)..(6279)
<223> OTHER INFORMATION: a, c, t, g, unknown or other
<220> FEATURE:
<221> NAME/KEY: modified_base
<222> LOCATION: (6612)..(6612)
<223> OTHER INFORMATION: a, c, t, g, unknown or other
```

-continued

```
<220> FEATURE:
<221> NAME/KEY: modified_base
<222> LOCATION: (6621)..(6621)
<223> OTHER INFORMATION: a, c, t, g, unknown or other
<220> FEATURE:
<221> NAME/KEY: modified_base
<222> LOCATION: (6627)..(6627)
<223> OTHER INFORMATION: a, c, t, g, unknown or other
<220> FEATURE:
<221> NAME/KEY: modified_base
<222> LOCATION: (6783)..(6783)
<223> OTHER INFORMATION: a, c, t, g, unknown or other
<220> FEATURE:
<221> NAME/KEY: modified_base
<222> LOCATION: (6792)..(6792)
<223> OTHER INFORMATION: a, c, t, g, unknown or other
<220> FEATURE:
<221> NAME/KEY: modified_base
<222> LOCATION: (6800)..(6801)
<223> OTHER INFORMATION: a, c, t, g, unknown or other
<220> FEATURE:
<221> NAME/KEY: modified_base
<222> LOCATION: (6819)..(6819)
<223> OTHER INFORMATION: a, c, t, g, unknown or other
<220> FEATURE:
<221> NAME/KEY: modified_base
<222> LOCATION: (6840)..(6840)
<223> OTHER INFORMATION: a, c, t, g, unknown or other
<220> FEATURE:
<221> NAME/KEY: modified_base
<222> LOCATION: (6846)..(6846)
<223> OTHER INFORMATION: a, c, t, g, unknown or other
<220> FEATURE:
<221> NAME/KEY: modified_base
<222> LOCATION: (6945)..(6945)
<223> OTHER INFORMATION: a, c, t, g, unknown or other
<220> FEATURE:
<221> NAME/KEY: modified_base
<222> LOCATION: (9573)..(9573)
<223> OTHER INFORMATION: a, c, t, g, unknown or other
<220> FEATURE:
<221> NAME/KEY: modified_base
<222> LOCATION: (9576)..(9576)
<223> OTHER INFORMATION: a, c, t, g, unknown or other
<220> FEATURE:
<221> NAME/KEY: modified_base
<222> LOCATION: (9578)..(9578)
<223> OTHER INFORMATION: a, c, t, g, unknown or other
<220> FEATURE:
<221> NAME/KEY: modified_base
<222> LOCATION: (9582)..(9583)
<223> OTHER INFORMATION: a, c, t, g, unknown or other
<220> FEATURE:
<221> NAME/KEY: modified_base
<222> LOCATION: (9603)..(9603)
<223> OTHER INFORMATION: a, c, t, g, unknown or other
<220> FEATURE:
<221> NAME/KEY: modified_base
<222> LOCATION: (9606)..(9606)
<223> OTHER INFORMATION: a, c, t, g, unknown or other
<220> FEATURE:
<221> NAME/KEY: modified_base
<222> LOCATION: (9609)..(9609)
<223> OTHER INFORMATION: a, c, t, g, unknown or other
<220> FEATURE:
<221> NAME/KEY: modified_base
<222> LOCATION: (9661)..(9661)
<223> OTHER INFORMATION: a, c, t, g, unknown or other
<220> FEATURE:
<221> NAME/KEY: modified_base
<222> LOCATION: (9854)..(9854)
<223> OTHER INFORMATION: a, c, t, g, unknown or other
<220> FEATURE:
<221> NAME/KEY: modified_base
<222> LOCATION: (10379)..(10379)
<223> OTHER INFORMATION: a, c, t, g, unknown or other
<220> FEATURE:
<221> NAME/KEY: modified_base
<222> LOCATION: (10382)..(10382)
```

-continued

```
<223> OTHER INFORMATION: a, c, t, g, unknown or other
<220> FEATURE:
<221> NAME/KEY: modified_base
<222> LOCATION: (10385)..(10385)
<223> OTHER INFORMATION: a, c, t, g, unknown or other
<220> FEATURE:
<221> NAME/KEY: modified_base
<222> LOCATION: (10388)..(10388)
<223> OTHER INFORMATION: a, c, t, g, unknown or other
<220> FEATURE:
<221> NAME/KEY: modified_base
<222> LOCATION: (10397)..(10397)
<223> OTHER INFORMATION: a, c, t, g, unknown or other
<220> FEATURE:
<221> NAME/KEY: modified_base
<222> LOCATION: (10400)..(10400)
<223> OTHER INFORMATION: a, c, t, g, unknown or other
<220> FEATURE:
<221> NAME/KEY: modified_base
<222> LOCATION: (10403)..(10403)
<223> OTHER INFORMATION: a, c, t, g, unknown or other
<220> FEATURE:
<221> NAME/KEY: modified_base
<222> LOCATION: (10415)..(10415)
<223> OTHER INFORMATION: a, c, t, g, unknown or other
<220> FEATURE:
<221> NAME/KEY: modified_base
<222> LOCATION: (10488)..(10488)
<223> OTHER INFORMATION: a, c, t, g, unknown or other
<220> FEATURE:
<221> NAME/KEY: modified_base
<222> LOCATION: (10556)..(10556)
<223> OTHER INFORMATION: a, c, t, g, unknown or other
<220> FEATURE:
<221> NAME/KEY: modified_base
<222> LOCATION: (10580)..(10580)
<223> OTHER INFORMATION: a, c, t, g, unknown or other
<220> FEATURE:
<221> NAME/KEY: modified_base
<222> LOCATION: (10598)..(10598)
<223> OTHER INFORMATION: a, c, t, g, unknown or other
<220> FEATURE:
<221> NAME/KEY: modified_base
<222> LOCATION: (10610)..(10610)
<223> OTHER INFORMATION: a, c, t, g, unknown or other
<220> FEATURE:
<221> NAME/KEY: modified_base
<222> LOCATION: (10835)..(10835)
<223> OTHER INFORMATION: a, c, t, g, unknown or other
<220> FEATURE:
<221> NAME/KEY: modified_base
<222> LOCATION: (10837)..(10837)
<223> OTHER INFORMATION: a, c, t, g, unknown or other
<220> FEATURE:
<221> NAME/KEY: modified_base
<222> LOCATION: (10850)..(10850)
<223> OTHER INFORMATION: a, c, t, g, unknown or other
<220> FEATURE:
<221> NAME/KEY: modified_base
<222> LOCATION: (10853)..(10853)
<223> OTHER INFORMATION: a, c, t, g, unknown or other
<220> FEATURE:
<221> NAME/KEY: modified_base
<222> LOCATION: (10913)..(10913)
<223> OTHER INFORMATION: a, c, t, g, unknown or other
<220> FEATURE:
<221> NAME/KEY: modified_base
<222> LOCATION: (11051)..(11051)
<223> OTHER INFORMATION: a, c, t, g, unknown or other
<220> FEATURE:
<221> NAME/KEY: modified_base
<222> LOCATION: (11108)..(11108)
<223> OTHER INFORMATION: a, c, t, g, unknown or other
<220> FEATURE:
<221> NAME/KEY: modified_base
<222> LOCATION: (11117)..(11117)
<223> OTHER INFORMATION: a, c, t, g, unknown or other
<220> FEATURE:
<221> NAME/KEY: modified_base
```

```
<222> LOCATION: (11244)..(11244)
<223> OTHER INFORMATION: a, c, t, g, unknown or other
<220> FEATURE:
<221> NAME/KEY: modified_base
<222> LOCATION: (11246)..(11246)
<223> OTHER INFORMATION: a, c, t, g, unknown or other
<220> FEATURE:
<221> NAME/KEY: modified_base
<222> LOCATION: (11450)..(11450)
<223> OTHER INFORMATION: a, c, t, g, unknown or other
<220> FEATURE:
<221> NAME/KEY: modified_base
<222> LOCATION: (11453)..(11453)
<223> OTHER INFORMATION: a, c, t, g, unknown or other
<220> FEATURE:
<221> NAME/KEY: modified_base
<222> LOCATION: (11549)..(11549)
<223> OTHER INFORMATION: a, c, t, g, unknown or other
<220> FEATURE:
<221> NAME/KEY: modified_base
<222> LOCATION: (11585)..(11585)
<223> OTHER INFORMATION: a, c, t, g, unknown or other
<220> FEATURE:
<221> NAME/KEY: modified_base
<222> LOCATION: (11606)..(11606)
<223> OTHER INFORMATION: a, c, t, g, unknown or other
<220> FEATURE:
<221> NAME/KEY: modified_base
<222> LOCATION: (12014)..(12014)
<223> OTHER INFORMATION: a, c, t, g, unknown or other
<220> FEATURE:
<221> NAME/KEY: modified_base
<222> LOCATION: (12058)..(12058)
<223> OTHER INFORMATION: a, c, t, g, unknown or other
<220> FEATURE:
<221> NAME/KEY: modified_base
<222> LOCATION: (12112)..(12112)
<223> OTHER INFORMATION: a, c, t, g, unknown or other
<220> FEATURE:
<221> NAME/KEY: modified_base
<222> LOCATION: (12125)..(12125)
<223> OTHER INFORMATION: a, c, t, g, unknown or other
<220> FEATURE:
<221> NAME/KEY: modified_base
<222> LOCATION: (12145)..(12145)
<223> OTHER INFORMATION: a, c, t, g, unknown or other
<220> FEATURE:
<221> NAME/KEY: modified_base
<222> LOCATION: (12200)..(12200)
<223> OTHER INFORMATION: a, c, t, g, unknown or other
<220> FEATURE:
<221> NAME/KEY: modified_base
<222> LOCATION: (12262)..(12262)
<223> OTHER INFORMATION: a, c, t, g, unknown or other
<220> FEATURE:
<221> NAME/KEY: modified_base
<222> LOCATION: (12266)..(12266)
<223> OTHER INFORMATION: a, c, t, g, unknown or other
<220> FEATURE:
<221> NAME/KEY: modified_base
<222> LOCATION: (12308)..(12308)
<223> OTHER INFORMATION: a, c, t, g, unknown or other
<220> FEATURE:
<221> NAME/KEY: modified_base
<222> LOCATION: (12311)..(12311)
<223> OTHER INFORMATION: a, c, t, g, unknown or other
<220> FEATURE:
<221> NAME/KEY: modified_base
<222> LOCATION: (12356)..(12356)
<223> OTHER INFORMATION: a, c, t, g, unknown or other
<220> FEATURE:
<221> NAME/KEY: modified_base
<222> LOCATION: (12389)..(12389)
<223> OTHER INFORMATION: a, c, t, g, unknown or other
<220> FEATURE:
<221> NAME/KEY: modified_base
<222> LOCATION: (12422)..(12422)
<223> OTHER INFORMATION: a, c, t, g, unknown or other
<220> FEATURE:
```

-continued

```
<221> NAME/KEY: modified_base
<222> LOCATION: (12630)..(12630)
<223> OTHER INFORMATION: a, c, t, g, unknown or other
<220> FEATURE:
<221> NAME/KEY: modified_base
<222> LOCATION: (12663)..(12663)
<223> OTHER INFORMATION: a, c, t, g, unknown or other
<220> FEATURE:
<221> NAME/KEY: modified_base
<222> LOCATION: (12674)..(12674)
<223> OTHER INFORMATION: a, c, t, g, unknown or other
<220> FEATURE:
<221> NAME/KEY: modified_base
<222> LOCATION: (12686)..(12686)
<223> OTHER INFORMATION: a, c, t, g, unknown or other
<220> FEATURE:
<221> NAME/KEY: modified_base
<222> LOCATION: (12693)..(12693)
<223> OTHER INFORMATION: a, c, t, g, unknown or other
<220> FEATURE:
<221> NAME/KEY: modified_base
<222> LOCATION: (12723)..(12723)
<223> OTHER INFORMATION: a, c, t, g, unknown or other
<220> FEATURE:
<221> NAME/KEY: modified_base
<222> LOCATION: (12777)..(12777)
<223> OTHER INFORMATION: a, c, t, g, unknown or other
<220> FEATURE:
<221> NAME/KEY: modified_base
<222> LOCATION: (12822)..(12822)
<223> OTHER INFORMATION: a, c, t, g, unknown or other
<220> FEATURE:
<221> NAME/KEY: modified_base
<222> LOCATION: (14712)..(14712)
<223> OTHER INFORMATION: a, c, t, g, unknown or other
<220> FEATURE:
<221> NAME/KEY: modified_base
<222> LOCATION: (14904)..(14904)
<223> OTHER INFORMATION: a, c, t, g, unknown or other
<220> FEATURE:
<221> NAME/KEY: modified_base
<222> LOCATION: (14906)..(14906)
<223> OTHER INFORMATION: a, c, t, g, unknown or other
<220> FEATURE:
<221> NAME/KEY: modified_base
<222> LOCATION: (14910)..(14910)
<223> OTHER INFORMATION: a, c, t, g, unknown or other
<220> FEATURE:
<221> NAME/KEY: modified_base
<222> LOCATION: (14916)..(14916)
<223> OTHER INFORMATION: a, c, t, g, unknown or other
<220> FEATURE:
<221> NAME/KEY: modified_base
<222> LOCATION: (15003)..(15003)
<223> OTHER INFORMATION: a, c, t, g, unknown or other
<220> FEATURE:
<221> NAME/KEY: modified_base
<222> LOCATION: (15088)..(15088)
<223> OTHER INFORMATION: a, c, t, g, unknown or other
<220> FEATURE:
<221> NAME/KEY: modified_base
<222> LOCATION: (15091)..(15091)
<223> OTHER INFORMATION: a, c, t, g, unknown or other
<220> FEATURE:
<221> NAME/KEY: modified_base
<222> LOCATION: (15102)..(15102)
<223> OTHER INFORMATION: a, c, t, g, unknown or other
<220> FEATURE:
<221> NAME/KEY: modified_base
<222> LOCATION: (15105)..(15105)
<223> OTHER INFORMATION: a, c, t, g, unknown or other
<220> FEATURE:
<221> NAME/KEY: modified_base
<222> LOCATION: (15108)..(15108)
<223> OTHER INFORMATION: a, c, t, g, unknown or other
<220> FEATURE:
<221> NAME/KEY: modified_base
<222> LOCATION: (15180)..(15180)
<223> OTHER INFORMATION: a, c, t, g, unknown or other
```

-continued

```
<220> FEATURE:
<221> NAME/KEY: modified_base
<222> LOCATION: (16845)..(16845)
<223> OTHER INFORMATION: a, c, t, g, unknown or other
<220> FEATURE:
<221> NAME/KEY: modified_base
<222> LOCATION: (16852)..(16852)
<223> OTHER INFORMATION: a, c, t, g, unknown or other
<220> FEATURE:
<221> NAME/KEY: modified_base
<222> LOCATION: (17294)..(17294)
<223> OTHER INFORMATION: a, c, t, g, unknown or other
<220> FEATURE:
<221> NAME/KEY: modified_base
<222> LOCATION: (17399)..(17399)
<223> OTHER INFORMATION: a, c, t, g, unknown or other
<220> FEATURE:
<221> NAME/KEY: modified_base
<222> LOCATION: (17648)..(17648)
<223> OTHER INFORMATION: a, c, t, g, unknown or other
<220> FEATURE:
<221> NAME/KEY: modified_base
<222> LOCATION: (17673)..(17674)
<223> OTHER INFORMATION: a, c, t, g, unknown or other
<220> FEATURE:
<221> NAME/KEY: modified_base
<222> LOCATION: (17982)..(17983)
<223> OTHER INFORMATION: a, c, t, g, unknown or other
<220> FEATURE:
<221> NAME/KEY: modified_base
<222> LOCATION: (17993)..(17993)
<223> OTHER INFORMATION: a, c, t, g, unknown or other
<220> FEATURE:
<221> NAME/KEY: modified_base
<222> LOCATION: (18008)..(18008)
<223> OTHER INFORMATION: a, c, t, g, unknown or other
<220> FEATURE:
<221> NAME/KEY: modified_base
<222> LOCATION: (18020)..(18020)
<223> OTHER INFORMATION: a, c, t, g, unknown or other
<220> FEATURE:
<221> NAME/KEY: modified_base
<222> LOCATION: (18029)..(18029)
<223> OTHER INFORMATION: a, c, t, g, unknown or other
<220> FEATURE:
<221> NAME/KEY: modified_base
<222> LOCATION: (18041)..(18041)
<223> OTHER INFORMATION: a, c, t, g, unknown or other
<220> FEATURE:
<221> NAME/KEY: modified_base
<222> LOCATION: (18110)..(18111)
<223> OTHER INFORMATION: a, c, t, g, unknown or other
<220> FEATURE:
<221> NAME/KEY: modified_base
<222> LOCATION: (18309)..(18309)
<223> OTHER INFORMATION: a, c, t, g, unknown or other
<220> FEATURE:
<221> NAME/KEY: modified_base
<222> LOCATION: (18401)..(18401)
<223> OTHER INFORMATION: a, c, t, g, unknown or other
<220> FEATURE:
<221> NAME/KEY: modified_base
<222> LOCATION: (18405)..(18405)
<223> OTHER INFORMATION: a, c, t, g, unknown or other
<220> FEATURE:
<221> NAME/KEY: modified_base
<222> LOCATION: (18450)..(18450)
<223> OTHER INFORMATION: a, c, t, g, unknown or other
<220> FEATURE:
<221> NAME/KEY: modified_base
<222> LOCATION: (18458)..(18458)
<223> OTHER INFORMATION: a, c, t, g, unknown or other
<220> FEATURE:
<221> NAME/KEY: modified_base
<222> LOCATION: (18574)..(18574)
<223> OTHER INFORMATION: a, c, t, g, unknown or other
<220> FEATURE:
<221> NAME/KEY: modified_base
<222> LOCATION: (18641)..(18641)
```

-continued

```
<223> OTHER INFORMATION: a, c, t, g, unknown or other
<220> FEATURE:
<221> NAME/KEY: modified_base
<222> LOCATION: (18740)..(18740)
<223> OTHER INFORMATION: a, c, t, g, unknown or other
<220> FEATURE:
<221> NAME/KEY: modified_base
<222> LOCATION: (18779)..(18779)
<223> OTHER INFORMATION: a, c, t, g, unknown or other
<220> FEATURE:
<221> NAME/KEY: modified_base
<222> LOCATION: (18881)..(18881)
<223> OTHER INFORMATION: a, c, t, g, unknown or other
<220> FEATURE:
<221> NAME/KEY: modified_base
<222> LOCATION: (19177)..(19177)
<223> OTHER INFORMATION: a, c, t, g, unknown or other
<220> FEATURE:
<221> NAME/KEY: modified_base
<222> LOCATION: (19326)..(19326)
<223> OTHER INFORMATION: a, c, t, g, unknown or other
<220> FEATURE:
<221> NAME/KEY: modified_base
<222> LOCATION: (19349)..(19349)
<223> OTHER INFORMATION: a, c, t, g, unknown or other
<220> FEATURE:
<221> NAME/KEY: modified_base
<222> LOCATION: (19370)..(19370)
<223> OTHER INFORMATION: a, c, t, g, unknown or other
<220> FEATURE:
<221> NAME/KEY: modified_base
<222> LOCATION: (19616)..(19616)
<223> OTHER INFORMATION: a, c, t, g, unknown or other
<220> FEATURE:
<221> NAME/KEY: modified_base
<222> LOCATION: (19732)..(19732)
<223> OTHER INFORMATION: a, c, t, g, unknown or other
<220> FEATURE:
<221> NAME/KEY: modified_base
<222> LOCATION: (19749)..(19749)
<223> OTHER INFORMATION: a, c, t, g, unknown or other
<220> FEATURE:
<221> NAME/KEY: modified_base
<222> LOCATION: (19756)..(19756)
<223> OTHER INFORMATION: a, c, t, g, unknown or other
<220> FEATURE:
<221> NAME/KEY: modified_base
<222> LOCATION: (19758)..(19758)
<223> OTHER INFORMATION: a, c, t, g, unknown or other
<220> FEATURE:
<221> NAME/KEY: modified_base
<222> LOCATION: (19760)..(19760)
<223> OTHER INFORMATION: a, c, t, g, unknown or other
<220> FEATURE:
<221> NAME/KEY: modified_base
<222> LOCATION: (20043)..(20043)
<223> OTHER INFORMATION: a, c, t, g, unknown or other
<220> FEATURE:
<221> NAME/KEY: modified_base
<222> LOCATION: (20053)..(20053)
<223> OTHER INFORMATION: a, c, t, g, unknown or other
<220> FEATURE:
<221> NAME/KEY: modified_base
<222> LOCATION: (20085)..(20085)
<223> OTHER INFORMATION: a, c, t, g, unknown or other
<220> FEATURE:
<221> NAME/KEY: modified_base
<222> LOCATION: (20152)..(20152)
<223> OTHER INFORMATION: a, c, t, g, unknown or other
<220> FEATURE:
<221> NAME/KEY: modified_base
<222> LOCATION: (20170)..(20170)
<223> OTHER INFORMATION: a, c, t, g, unknown or other
<220> FEATURE:
<221> NAME/KEY: modified_base
<222> LOCATION: (20176)..(20176)
<223> OTHER INFORMATION: a, c, t, g, unknown or other
<220> FEATURE:
<221> NAME/KEY: modified_base
```

```
<222> LOCATION: (20251)..(20251)
<223> OTHER INFORMATION: a, c, t, g, unknown or other
<220> FEATURE:
<221> NAME/KEY: modified_base
<222> LOCATION: (20257)..(20257)
<223> OTHER INFORMATION: a, c, t, g, unknown or other
<220> FEATURE:
<221> NAME/KEY: modified_base
<222> LOCATION: (20269)..(20269)
<223> OTHER INFORMATION: a, c, t, g, unknown or other
<220> FEATURE:
<221> NAME/KEY: modified_base
<222> LOCATION: (20296)..(20296)
<223> OTHER INFORMATION: a, c, t, g, unknown or other
<220> FEATURE:
<221> NAME/KEY: modified_base
<222> LOCATION: (20299)..(20299)
<223> OTHER INFORMATION: a, c, t, g, unknown or other
<220> FEATURE:
<221> NAME/KEY: modified_base
<222> LOCATION: (20302)..(20302)
<223> OTHER INFORMATION: a, c, t, g, unknown or other
<220> FEATURE:
<221> NAME/KEY: modified_base
<222> LOCATION: (20305)..(20305)
<223> OTHER INFORMATION: a, c, t, g, unknown or other
<220> FEATURE:
<221> NAME/KEY: modified_base
<222> LOCATION: (20313)..(20313)
<223> OTHER INFORMATION: a, c, t, g, unknown or other
<220> FEATURE:
<221> NAME/KEY: modified_base
<222> LOCATION: (20416)..(20416)
<223> OTHER INFORMATION: a, c, t, g, unknown or other
<220> FEATURE:
<221> NAME/KEY: modified_base
<222> LOCATION: (20488)..(20488)
<223> OTHER INFORMATION: a, c, t, g, unknown or other
<220> FEATURE:
<221> NAME/KEY: modified_base
<222> LOCATION: (21006)..(21006)
<223> OTHER INFORMATION: a, c, t, g, unknown or other
<220> FEATURE:
<221> NAME/KEY: modified_base
<222> LOCATION: (21012)..(21012)
<223> OTHER INFORMATION: a, c, t, g, unknown or other
<220> FEATURE:
<221> NAME/KEY: modified_base
<222> LOCATION: (21019)..(21019)
<223> OTHER INFORMATION: a, c, t, g, unknown or other
<220> FEATURE:
<221> NAME/KEY: modified_base
<222> LOCATION: (21024)..(21024)
<223> OTHER INFORMATION: a, c, t, g, unknown or other
<220> FEATURE:
<221> NAME/KEY: modified_base
<222> LOCATION: (21173)..(21173)
<223> OTHER INFORMATION: a, c, t, g, unknown or other
<220> FEATURE:
<221> NAME/KEY: modified_base
<222> LOCATION: (21175)..(21175)
<223> OTHER INFORMATION: a, c, t, g, unknown or other
<220> FEATURE:
<221> NAME/KEY: modified_base
<222> LOCATION: (21182)..(21182)
<223> OTHER INFORMATION: a, c, t, g, unknown or other
<220> FEATURE:
<221> NAME/KEY: modified_base
<222> LOCATION: (21184)..(21184)
<223> OTHER INFORMATION: a, c, t, g, unknown or other
<220> FEATURE:
<221> NAME/KEY: modified_base
<222> LOCATION: (21423)..(21423)
<223> OTHER INFORMATION: a, c, t, g, unknown or other
<220> FEATURE:
<221> NAME/KEY: modified_base
<222> LOCATION: (21425)..(21429)
<223> OTHER INFORMATION: a, c, t, g, unknown or other
<220> FEATURE:
```

```
<221> NAME/KEY: modified_base
<222> LOCATION: (21432)..(21432)
<223> OTHER INFORMATION: a, c, t, g, unknown or other
<220> FEATURE:
<221> NAME/KEY: modified_base
<222> LOCATION: (21435)..(21435)
<223> OTHER INFORMATION: a, c, t, g, unknown or other
<220> FEATURE:
<221> NAME/KEY: modified_base
<222> LOCATION: (21440)..(21440)
<223> OTHER INFORMATION: a, c, t, g, unknown or other
<220> FEATURE:
<221> NAME/KEY: modified_base
<222> LOCATION: (21454)..(21454)
<223> OTHER INFORMATION: a, c, t, g, unknown or other
<220> FEATURE:
<221> NAME/KEY: modified_base
<222> LOCATION: (21456)..(21457)
<223> OTHER INFORMATION: a, c, t, g, unknown or other
<220> FEATURE:
<221> NAME/KEY: modified_base
<222> LOCATION: (21471)..(21472)
<223> OTHER INFORMATION: a, c, t, g, unknown or other
<220> FEATURE:
<221> NAME/KEY: modified_base
<222> LOCATION: (21474)..(21474)
<223> OTHER INFORMATION: a, c, t, g, unknown or other
<220> FEATURE:
<221> NAME/KEY: modified_base
<222> LOCATION: (21478)..(21478)
<223> OTHER INFORMATION: a, c, t, g, unknown or other
<220> FEATURE:
<221> NAME/KEY: modified_base
<222> LOCATION: (21496)..(21496)
<223> OTHER INFORMATION: a, c, t, g, unknown or other
<220> FEATURE:
<221> NAME/KEY: modified_base
<222> LOCATION: (21517)..(21517)
<223> OTHER INFORMATION: a, c, t, g, unknown or other
<220> FEATURE:
<221> NAME/KEY: modified_base
<222> LOCATION: (21533)..(21534)
<223> OTHER INFORMATION: a, c, t, g, unknown or other
<220> FEATURE:
<221> NAME/KEY: modified_base
<222> LOCATION: (21544)..(21544)
<223> OTHER INFORMATION: a, c, t, g, unknown or other
<220> FEATURE:
<221> NAME/KEY: modified_base
<222> LOCATION: (21559)..(21559)
<223> OTHER INFORMATION: a, c, t, g, unknown or other
<220> FEATURE:
<221> NAME/KEY: modified_base
<222> LOCATION: (21570)..(21570)
<223> OTHER INFORMATION: a, c, t, g, unknown or other
<220> FEATURE:
<221> NAME/KEY: modified_base
<222> LOCATION: (21574)..(21574)
<223> OTHER INFORMATION: a, c, t, g, unknown or other
<220> FEATURE:
<221> NAME/KEY: modified_base
<222> LOCATION: (21583)..(21583)
<223> OTHER INFORMATION: a, c, t, g, unknown or other
<220> FEATURE:
<221> NAME/KEY: modified_base
<222> LOCATION: (21660)..(21660)
<223> OTHER INFORMATION: a, c, t, g, unknown or other
<220> FEATURE:
<221> NAME/KEY: modified_base
<222> LOCATION: (21684)..(21684)
<223> OTHER INFORMATION: a, c, t, g, unknown or other
<220> FEATURE:
<221> NAME/KEY: modified_base
<222> LOCATION: (21710)..(21710)
<223> OTHER INFORMATION: a, c, t, g, unknown or other
<220> FEATURE:
<221> NAME/KEY: modified_base
<222> LOCATION: (21778)..(21778)
<223> OTHER INFORMATION: a, c, t, g, unknown or other
```

```
<220> FEATURE:
<221> NAME/KEY: modified_base
<222> LOCATION: (21789)..(21789)
<223> OTHER INFORMATION: a, c, t, g, unknown or other
<220> FEATURE:
<221> NAME/KEY: modified_base
<222> LOCATION: (21798)..(21798)
<223> OTHER INFORMATION: a, c, t, g, unknown or other
<220> FEATURE:
<221> NAME/KEY: modified_base
<222> LOCATION: (21823)..(21823)
<223> OTHER INFORMATION: a, c, t, g, unknown or other
<220> FEATURE:
<221> NAME/KEY: modified_base
<222> LOCATION: (21874)..(21874)
<223> OTHER INFORMATION: a, c, t, g, unknown or other
<220> FEATURE:
<221> NAME/KEY: modified_base
<222> LOCATION: (21876)..(21876)
<223> OTHER INFORMATION: a, c, t, g, unknown or other
<220> FEATURE:
<221> NAME/KEY: modified_base
<222> LOCATION: (21880)..(21880)
<223> OTHER INFORMATION: a, c, t, g, unknown or other
<220> FEATURE:
<221> NAME/KEY: modified_base
<222> LOCATION: (21889)..(21889)
<223> OTHER INFORMATION: a, c, t, g, unknown or other
<220> FEATURE:
<221> NAME/KEY: modified_base
<222> LOCATION: (21894)..(21894)
<223> OTHER INFORMATION: a, c, t, g, unknown or other
<220> FEATURE:
<221> NAME/KEY: modified_base
<222> LOCATION: (22844)..(22844)
<223> OTHER INFORMATION: a, c, t, g, unknown or other
<220> FEATURE:
<221> NAME/KEY: modified_base
<222> LOCATION: (22907)..(22907)
<223> OTHER INFORMATION: a, c, t, g, unknown or other
<220> FEATURE:
<221> NAME/KEY: modified_base
<222> LOCATION: (22914)..(22914)
<223> OTHER INFORMATION: a, c, t, g, unknown or other
<220> FEATURE:
<221> NAME/KEY: modified_base
<222> LOCATION: (23167)..(23167)
<223> OTHER INFORMATION: a, c, t, g, unknown or other
<220> FEATURE:
<221> NAME/KEY: modified_base
<222> LOCATION: (23348)..(23348)
<223> OTHER INFORMATION: a, c, t, g, unknown or other
<220> FEATURE:
<221> NAME/KEY: modified_base
<222> LOCATION: (23351)..(23351)
<223> OTHER INFORMATION: a, c, t, g, unknown or other
<220> FEATURE:
<221> NAME/KEY: modified_base
<222> LOCATION: (23406)..(23406)
<223> OTHER INFORMATION: a, c, t, g, unknown or other
<220> FEATURE:
<221> NAME/KEY: modified_base
<222> LOCATION: (23647)..(23647)
<223> OTHER INFORMATION: a, c, t, g, unknown or other
<220> FEATURE:
<221> NAME/KEY: modified_base
<222> LOCATION: (23806)..(23806)
<223> OTHER INFORMATION: a, c, t, g, unknown or other
<220> FEATURE:
<221> NAME/KEY: modified_base
<222> LOCATION: (24617)..(24617)
<223> OTHER INFORMATION: a, c, t, g, unknown or other
<220> FEATURE:
<221> NAME/KEY: modified_base
<222> LOCATION: (24853)..(24853)
<223> OTHER INFORMATION: a, c, t, g, unknown or other
<220> FEATURE:
<221> NAME/KEY: modified_base
<222> LOCATION: (25080)..(25080)
```

```
<223> OTHER INFORMATION: a, c, t, g, unknown or other
<220> FEATURE:
<221> NAME/KEY: modified_base
<222> LOCATION: (25108)..(25108)
<223> OTHER INFORMATION: a, c, t, g, unknown or other
<220> FEATURE:
<221> NAME/KEY: modified_base
<222> LOCATION: (25371)..(25371)
<223> OTHER INFORMATION: a, c, t, g, unknown or other
<220> FEATURE:
<221> NAME/KEY: modified_base
<222> LOCATION: (25397)..(25397)
<223> OTHER INFORMATION: a, c, t, g, unknown or other
<220> FEATURE:
<221> NAME/KEY: modified_base
<222> LOCATION: (25411)..(25411)
<223> OTHER INFORMATION: a, c, t, g, unknown or other
<220> FEATURE:
<221> NAME/KEY: modified_base
<222> LOCATION: (25507)..(25507)
<223> OTHER INFORMATION: a, c, t, g, unknown or other
<220> FEATURE:
<221> NAME/KEY: modified_base
<222> LOCATION: (25692)..(25692)
<223> OTHER INFORMATION: a, c, t, g, unknown or other
<220> FEATURE:
<221> NAME/KEY: modified_base
<222> LOCATION: (25712)..(25713)
<223> OTHER INFORMATION: a, c, t, g, unknown or other
<220> FEATURE:
<221> NAME/KEY: modified_base
<222> LOCATION: (25718)..(25718)
<223> OTHER INFORMATION: a, c, t, g, unknown or other
<220> FEATURE:
<221> NAME/KEY: modified_base
<222> LOCATION: (25728)..(25728)
<223> OTHER INFORMATION: a, c, t, g, unknown or other
<220> FEATURE:
<221> NAME/KEY: modified_base
<222> LOCATION: (25742)..(25742)
<223> OTHER INFORMATION: a, c, t, g, unknown or other
<220> FEATURE:
<221> NAME/KEY: modified_base
<222> LOCATION: (25774)..(25774)
<223> OTHER INFORMATION: a, c, t, g, unknown or other
<220> FEATURE:
<221> NAME/KEY: modified_base
<222> LOCATION: (27450)..(27450)
<223> OTHER INFORMATION: a, c, t, g, unknown or other
<220> FEATURE:
<221> NAME/KEY: modified_base
<222> LOCATION: (29480)..(29480)
<223> OTHER INFORMATION: a, c, t, g, unknown or other
<220> FEATURE:
<221> NAME/KEY: modified_base
<222> LOCATION: (29507)..(29507)
<223> OTHER INFORMATION: a, c, t, g, unknown or other
<220> FEATURE:
<221> NAME/KEY: modified_base
<222> LOCATION: (31101)..(31101)
<223> OTHER INFORMATION: a, c, t, g, unknown or other
<220> FEATURE:
<221> NAME/KEY: modified_base
<222> LOCATION: (32562)..(32562)
<223> OTHER INFORMATION: a, c, t, g, unknown or other
<220> FEATURE:
<221> NAME/KEY: modified_base
<222> LOCATION: (32840)..(32840)
<223> OTHER INFORMATION: a, c, t, g, unknown or other
<220> FEATURE:
<221> NAME/KEY: modified_base
<222> LOCATION: (32855)..(32855)
<223> OTHER INFORMATION: a, c, t, g, unknown or other
<220> FEATURE:
<221> NAME/KEY: modified_base
<222> LOCATION: (32865)..(32865)
<223> OTHER INFORMATION: a, c, t, g, unknown or other
<220> FEATURE:
<221> NAME/KEY: modified_base
```

```
<222> LOCATION: (32922)..(32922)
<223> OTHER INFORMATION: a, c, t, g, unknown or other
<220> FEATURE:
<221> NAME/KEY: modified_base
<222> LOCATION: (32988)..(32988)
<223> OTHER INFORMATION: a, c, t, g, unknown or other
<220> FEATURE:
<221> NAME/KEY: modified_base
<222> LOCATION: (32991)..(32991)
<223> OTHER INFORMATION: a, c, t, g, unknown or other
<220> FEATURE:
<221> NAME/KEY: modified_base
<222> LOCATION: (33295)..(33295)
<223> OTHER INFORMATION: a, c, t, g, unknown or other
<220> FEATURE:
<221> NAME/KEY: modified_base
<222> LOCATION: (33364)..(33364)
<223> OTHER INFORMATION: a, c, t, g, unknown or other
<220> FEATURE:
<221> NAME/KEY: modified_base
<222> LOCATION: (35517)..(35517)
<223> OTHER INFORMATION: a, c, t, g, unknown or other
<220> FEATURE:
<221> NAME/KEY: modified_base
<222> LOCATION: (35526)..(35526)
<223> OTHER INFORMATION: a, c, t, g, unknown or other
<220> FEATURE:
<221> NAME/KEY: modified_base
<222> LOCATION: (35718)..(35718)
<223> OTHER INFORMATION: a, c, t, g, unknown or other
<220> FEATURE:
<221> NAME/KEY: modified_base
<222> LOCATION: (36058)..(36058)
<223> OTHER INFORMATION: a, c, t, g, unknown or other
<220> FEATURE:
<221> NAME/KEY: modified_base
<222> LOCATION: (36064)..(36064)
<223> OTHER INFORMATION: a, c, t, g, unknown or other
<220> FEATURE:
<221> NAME/KEY: modified_base
<222> LOCATION: (36607)..(36607)
<223> OTHER INFORMATION: a, c, t, g, unknown or other
<220> FEATURE:
<221> NAME/KEY: modified_base
<222> LOCATION: (36622)..(36622)
<223> OTHER INFORMATION: a, c, t, g, unknown or other
<220> FEATURE:
<221> NAME/KEY: modified_base
<222> LOCATION: (36667)..(36667)
<223> OTHER INFORMATION: a, c, t, g, unknown or other
<220> FEATURE:
<221> NAME/KEY: modified_base
<222> LOCATION: (36679)..(36679)
<223> OTHER INFORMATION: a, c, t, g, unknown or other
<220> FEATURE:
<221> NAME/KEY: modified_base
<222> LOCATION: (36985)..(36985)
<223> OTHER INFORMATION: a, c, t, g, unknown or other
<220> FEATURE:
<221> NAME/KEY: modified_base
<222> LOCATION: (37006)..(37006)
<223> OTHER INFORMATION: a, c, t, g, unknown or other
<220> FEATURE:
<221> NAME/KEY: modified_base
<222> LOCATION: (37249)..(37249)
<223> OTHER INFORMATION: a, c, t, g, unknown or other
<220> FEATURE:
<221> NAME/KEY: modified_base
<222> LOCATION: (37267)..(37267)
<223> OTHER INFORMATION: a, c, t, g, unknown or other
<220> FEATURE:
<221> NAME/KEY: modified_base
<222> LOCATION: (37306)..(37306)
<223> OTHER INFORMATION: a, c, t, g, unknown or other
<220> FEATURE:
<221> NAME/KEY: modified_base
<222> LOCATION: (37351)..(37351)
<223> OTHER INFORMATION: a, c, t, g, unknown or other
<220> FEATURE:
```

```
<221> NAME/KEY: modified_base
<222> LOCATION: (37429)..(37429)
<223> OTHER INFORMATION: a, c, t, g, unknown or other
<220> FEATURE:
<221> NAME/KEY: modified_base
<222> LOCATION: (37432)..(37432)
<223> OTHER INFORMATION: a, c, t, g, unknown or other
<220> FEATURE:
<221> NAME/KEY: modified_base
<222> LOCATION: (37504)..(37504)
<223> OTHER INFORMATION: a, c, t, g, unknown or other
<220> FEATURE:
<221> NAME/KEY: modified_base
<222> LOCATION: (37507)..(37507)
<223> OTHER INFORMATION: a, c, t, g, unknown or other
<220> FEATURE:
<221> NAME/KEY: modified_base
<222> LOCATION: (37510)..(37510)
<223> OTHER INFORMATION: a, c, t, g, unknown or other
<220> FEATURE:
<221> NAME/KEY: modified_base
<222> LOCATION: (37550)..(37550)
<223> OTHER INFORMATION: a, c, t, g, unknown or other
<220> FEATURE:
<221> NAME/KEY: modified_base
<222> LOCATION: (37579)..(37579)
<223> OTHER INFORMATION: a, c, t, g, unknown or other
<220> FEATURE:
<221> NAME/KEY: modified_base
<222> LOCATION: (37630)..(37631)
<223> OTHER INFORMATION: a, c, t, g, unknown or other
<220> FEATURE:
<221> NAME/KEY: modified_base
<222> LOCATION: (37642)..(37646)
<223> OTHER INFORMATION: a, c, t, g, unknown or other
<220> FEATURE:
<221> NAME/KEY: modified_base
<222> LOCATION: (37841)..(37841)
<223> OTHER INFORMATION: a, c, t, g, unknown or other
<220> FEATURE:
<221> NAME/KEY: modified_base
<222> LOCATION: (37856)..(37856)
<223> OTHER INFORMATION: a, c, t, g, unknown or other
<220> FEATURE:
<221> NAME/KEY: modified_base
<222> LOCATION: (37859)..(37859)
<223> OTHER INFORMATION: a, c, t, g, unknown or other
<220> FEATURE:
<221> NAME/KEY: modified_base
<222> LOCATION: (37970)..(37970)
<223> OTHER INFORMATION: a, c, t, g, unknown or other
<220> FEATURE:
<221> NAME/KEY: modified_base
<222> LOCATION: (38051)..(38051)
<223> OTHER INFORMATION: a, c, t, g, unknown or other
<220> FEATURE:
<221> NAME/KEY: modified_base
<222> LOCATION: (38198)..(38198)
<223> OTHER INFORMATION: a, c, t, g, unknown or other
<220> FEATURE:
<221> NAME/KEY: modified_base
<222> LOCATION: (38216)..(38216)
<223> OTHER INFORMATION: a, c, t, g, unknown or other
<220> FEATURE:
<221> NAME/KEY: modified_base
<222> LOCATION: (38243)..(38243)
<223> OTHER INFORMATION: a, c, t, g, unknown or other
<220> FEATURE:
<221> NAME/KEY: modified_base
<222> LOCATION: (38306)..(38306)
<223> OTHER INFORMATION: a, c, t, g, unknown or other
<220> FEATURE:
<221> NAME/KEY: modified_base
<222> LOCATION: (38367)..(38367)
<223> OTHER INFORMATION: a, c, t, g, unknown or other
<220> FEATURE:
<221> NAME/KEY: modified_base
<222> LOCATION: (38498)..(38498)
<223> OTHER INFORMATION: a, c, t, g, unknown or other
```

```
<220> FEATURE:
<221> NAME/KEY: modified_base
<222> LOCATION: (38624)..(38624)
<223> OTHER INFORMATION: a, c, t, g, unknown or other
<220> FEATURE:
<221> NAME/KEY: modified_base
<222> LOCATION: (38921)..(38921)
<223> OTHER INFORMATION: a, c, t, g, unknown or other
<220> FEATURE:
<221> NAME/KEY: modified_base
<222> LOCATION: (38933)..(38933)
<223> OTHER INFORMATION: a, c, t, g, unknown or other
<220> FEATURE:
<221> NAME/KEY: modified_base
<222> LOCATION: (38960)..(38960)
<223> OTHER INFORMATION: a, c, t, g, unknown or other
<220> FEATURE:
<221> NAME/KEY: modified_base
<222> LOCATION: (39092)..(39092)
<223> OTHER INFORMATION: a, c, t, g, unknown or other
<220> FEATURE:
<221> NAME/KEY: modified_base
<222> LOCATION: (39113)..(39113)
<223> OTHER INFORMATION: a, c, t, g, unknown or other
<220> FEATURE:
<221> NAME/KEY: modified_base
<222> LOCATION: (39149)..(39149)
<223> OTHER INFORMATION: a, c, t, g, unknown or other
<220> FEATURE:
<221> NAME/KEY: modified_base
<222> LOCATION: (39151)..(39151)
<223> OTHER INFORMATION: a, c, t, g, unknown or other
<220> FEATURE:
<221> NAME/KEY: modified_base
<222> LOCATION: (39227)..(39227)
<223> OTHER INFORMATION: a, c, t, g, unknown or other
<220> FEATURE:
<221> NAME/KEY: modified_base
<222> LOCATION: (39240)..(39240)
<223> OTHER INFORMATION: a, c, t, g, unknown or other
<220> FEATURE:
<221> NAME/KEY: modified_base
<222> LOCATION: (39324)..(39324)
<223> OTHER INFORMATION: a, c, t, g, unknown or other
<220> FEATURE:
<221> NAME/KEY: modified_base
<222> LOCATION: (39347)..(39347)
<223> OTHER INFORMATION: a, c, t, g, unknown or other
<220> FEATURE:
<221> NAME/KEY: modified_base
<222> LOCATION: (39545)..(39545)
<223> OTHER INFORMATION: a, c, t, g, unknown or other
<220> FEATURE:
<221> NAME/KEY: modified_base
<222> LOCATION: (39575)..(39575)
<223> OTHER INFORMATION: a, c, t, g, unknown or other
<220> FEATURE:
<221> NAME/KEY: modified_base
<222> LOCATION: (39665)..(39665)
<223> OTHER INFORMATION: a, c, t, g, unknown or other
<220> FEATURE:
<221> NAME/KEY: modified_base
<222> LOCATION: (39707)..(39707)
<223> OTHER INFORMATION: a, c, t, g, unknown or other
<220> FEATURE:
<221> NAME/KEY: modified_base
<222> LOCATION: (39731)..(39731)
<223> OTHER INFORMATION: a, c, t, g, unknown or other
<220> FEATURE:
<221> NAME/KEY: modified_base
<222> LOCATION: (39782)..(39782)
<223> OTHER INFORMATION: a, c, t, g, unknown or other
<220> FEATURE:
<221> NAME/KEY: modified_base
<222> LOCATION: (39820)..(39820)
<223> OTHER INFORMATION: a, c, t, g, unknown or other
<220> FEATURE:
<221> NAME/KEY: modified_base
<222> LOCATION: (39976)..(39976)
```

-continued

```
<223> OTHER INFORMATION: a, c, t, g, unknown or other
<220> FEATURE:
<221> NAME/KEY: modified_base
<222> LOCATION: (44407)..(44407)
<223> OTHER INFORMATION: a, c, t, g, unknown or other
<220> FEATURE:
<221> NAME/KEY: modified_base
<222> LOCATION: (46542)..(46542)
<223> OTHER INFORMATION: a, c, t, g, unknown or other
<220> FEATURE:
<221> NAME/KEY: modified_base
<222> LOCATION: (49791)..(49791)
<223> OTHER INFORMATION: a, c, t, g, unknown or other
<220> FEATURE:
<221> NAME/KEY: modified_base
<222> LOCATION: (54345)..(54345)
<223> OTHER INFORMATION: a, c, t, g, unknown or other
<220> FEATURE:
<221> NAME/KEY: modified_base
<222> LOCATION: (58249)..(58249)
<223> OTHER INFORMATION: a, c, t, g, unknown or other
<220> FEATURE:
<221> NAME/KEY: modified_base
<222> LOCATION: (59537)..(59537)
<223> OTHER INFORMATION: a, c, t, g, unknown or other
<220> FEATURE:
<221> NAME/KEY: modified_base
<222> LOCATION: (60478)..(60478)
<223> OTHER INFORMATION: a, c, t, g, unknown or other
<220> FEATURE:
<221> NAME/KEY: modified_base
<222> LOCATION: (60929)..(60929)
<223> OTHER INFORMATION: a, c, t, g, unknown or other
<220> FEATURE:
<221> NAME/KEY: modified_base
<222> LOCATION: (60934)..(60934)
<223> OTHER INFORMATION: a, c, t, g, unknown or other
<220> FEATURE:
<221> NAME/KEY: modified_base
<222> LOCATION: (60939)..(60940)
<223> OTHER INFORMATION: a, c, t, g, unknown or other
<220> FEATURE:
<221> NAME/KEY: modified_base
<222> LOCATION: (60949)..(60949)
<223> OTHER INFORMATION: a, c, t, g, unknown or other
<220> FEATURE:
<221> NAME/KEY: modified_base
<222> LOCATION: (60961)..(60962)
<223> OTHER INFORMATION: a, c, t, g, unknown or other
<220> FEATURE:
<221> NAME/KEY: modified_base
<222> LOCATION: (60968)..(60968)
<223> OTHER INFORMATION: a, c, t, g, unknown or other
<220> FEATURE:
<221> NAME/KEY: modified_base
<222> LOCATION: (60970)..(60970)
<223> OTHER INFORMATION: a, c, t, g, unknown or other
<220> FEATURE:
<221> NAME/KEY: modified_base
<222> LOCATION: (60979)..(60979)
<223> OTHER INFORMATION: a, c, t, g, unknown or other
<220> FEATURE:
<221> NAME/KEY: modified_base
<222> LOCATION: (60982)..(60982)
<223> OTHER INFORMATION: a, c, t, g, unknown or other
<220> FEATURE:
<221> NAME/KEY: modified_base
<222> LOCATION: (60988)..(60988)
<223> OTHER INFORMATION: a, c, t, g, unknown or other
<220> FEATURE:
<221> NAME/KEY: modified_base
<222> LOCATION: (61180)..(61180)
<223> OTHER INFORMATION: a, c, t, g, unknown or other
<220> FEATURE:
<221> NAME/KEY: modified_base
<222> LOCATION: (61195)..(61195)
<223> OTHER INFORMATION: a, c, t, g, unknown or other
<220> FEATURE:
<221> NAME/KEY: modified_base
```

-continued

```
<222> LOCATION: (61315)..(61315)
<223> OTHER INFORMATION: a, c, t, g, unknown or other
<220> FEATURE:
<221> NAME/KEY: modified_base
<222> LOCATION: (61397)..(61397)
<223> OTHER INFORMATION: a, c, t, g, unknown or other
<220> FEATURE:
<221> NAME/KEY: modified_base
<222> LOCATION: (61399)..(61399)
<223> OTHER INFORMATION: a, c, t, g, unknown or other
<220> FEATURE:
<221> NAME/KEY: modified_base
<222> LOCATION: (61427)..(61427)
<223> OTHER INFORMATION: a, c, t, g, unknown or other
<220> FEATURE:
<221> NAME/KEY: modified_base
<222> LOCATION: (61532)..(61532)
<223> OTHER INFORMATION: a, c, t, g, unknown or other
<220> FEATURE:
<221> NAME/KEY: modified_base
<222> LOCATION: (61623)..(61623)
<223> OTHER INFORMATION: a, c, t, g, unknown or other
<220> FEATURE:
<221> NAME/KEY: modified_base
<222> LOCATION: (61864)..(61864)
<223> OTHER INFORMATION: a, c, t, g, unknown or other
<220> FEATURE:
<221> NAME/KEY: modified_base
<222> LOCATION: (61957)..(61957)
<223> OTHER INFORMATION: a, c, t, g, unknown or other
<220> FEATURE:
<221> NAME/KEY: modified_base
<222> LOCATION: (62071)..(62071)
<223> OTHER INFORMATION: a, c, t, g, unknown or other
<220> FEATURE:
<221> NAME/KEY: modified_base
<222> LOCATION: (63256)..(63256)
<223> OTHER INFORMATION: a, c, t, g, unknown or other
<220> FEATURE:
<221> NAME/KEY: modified_base
<222> LOCATION: (63258)..(63259)
<223> OTHER INFORMATION: a, c, t, g, unknown or other
<220> FEATURE:
<221> NAME/KEY: modified_base
<222> LOCATION: (64474)..(64474)
<223> OTHER INFORMATION: a, c, t, g, unknown or other
<220> FEATURE:
<221> NAME/KEY: modified_base
<222> LOCATION: (64477)..(64477)
<223> OTHER INFORMATION: a, c, t, g, unknown or other
<220> FEATURE:
<221> NAME/KEY: modified_base
<222> LOCATION: (64493)..(64493)
<223> OTHER INFORMATION: a, c, t, g, unknown or other
<220> FEATURE:
<221> NAME/KEY: modified_base
<222> LOCATION: (64537)..(64538)
<223> OTHER INFORMATION: a, c, t, g, unknown or other
<220> FEATURE:
<221> NAME/KEY: modified_base
<222> LOCATION: (64541)..(64542)
<223> OTHER INFORMATION: a, c, t, g, unknown or other
<220> FEATURE:
<221> NAME/KEY: modified_base
<222> LOCATION: (64544)..(64544)
<223> OTHER INFORMATION: a, c, t, g, unknown or other
<220> FEATURE:
<221> NAME/KEY: modified_base
<222> LOCATION: (64551)..(64552)
<223> OTHER INFORMATION: a, c, t, g, unknown or other
<220> FEATURE:
<221> NAME/KEY: modified_base
<222> LOCATION: (64561)..(64561)
<223> OTHER INFORMATION: a, c, t, g, unknown or other
<220> FEATURE:
<221> NAME/KEY: modified_base
<222> LOCATION: (64632)..(64632)
<223> OTHER INFORMATION: a, c, t, g, unknown or other
<220> FEATURE:
```

```
<221> NAME/KEY: modified_base
<222> LOCATION: (64766)..(64766)
<223> OTHER INFORMATION: a, c, t, g, unknown or other
<220> FEATURE:
<221> NAME/KEY: modified_base
<222> LOCATION: (64845)..(64845)
<223> OTHER INFORMATION: a, c, t, g, unknown or other
<220> FEATURE:
<221> NAME/KEY: modified_base
<222> LOCATION: (65260)..(65260)
<223> OTHER INFORMATION: a, c, t, g, unknown or other
<220> FEATURE:
<221> NAME/KEY: modified_base
<222> LOCATION: (65454)..(65454)
<223> OTHER INFORMATION: a, c, t, g, unknown or other
<220> FEATURE:
<221> NAME/KEY: modified_base
<222> LOCATION: (65978)..(65979)
<223> OTHER INFORMATION: a, c, t, g, unknown or other
<220> FEATURE:
<221> NAME/KEY: modified_base
<222> LOCATION: (66038)..(66038)
<223> OTHER INFORMATION: a, c, t, g, unknown or other
<220> FEATURE:
<221> NAME/KEY: modified_base
<222> LOCATION: (66079)..(66079)
<223> OTHER INFORMATION: a, c, t, g, unknown or other
<220> FEATURE:
<221> NAME/KEY: modified_base
<222> LOCATION: (66089)..(66089)
<223> OTHER INFORMATION: a, c, t, g, unknown or other
<220> FEATURE:
<221> NAME/KEY: modified_base
<222> LOCATION: (66101)..(66101)
<223> OTHER INFORMATION: a, c, t, g, unknown or other
<220> FEATURE:
<221> NAME/KEY: modified_base
<222> LOCATION: (66143)..(66143)
<223> OTHER INFORMATION: a, c, t, g, unknown or other
<220> FEATURE:
<221> NAME/KEY: modified_base
<222> LOCATION: (66165)..(66165)
<223> OTHER INFORMATION: a, c, t, g, unknown or other
<220> FEATURE:
<221> NAME/KEY: modified_base
<222> LOCATION: (66207)..(66207)
<223> OTHER INFORMATION: a, c, t, g, unknown or other
<220> FEATURE:
<221> NAME/KEY: modified_base
<222> LOCATION: (66228)..(66228)
<223> OTHER INFORMATION: a, c, t, g, unknown or other
<220> FEATURE:
<221> NAME/KEY: modified_base
<222> LOCATION: (66272)..(66272)
<223> OTHER INFORMATION: a, c, t, g, unknown or other
<220> FEATURE:
<221> NAME/KEY: modified_base
<222> LOCATION: (66315)..(66315)
<223> OTHER INFORMATION: a, c, t, g, unknown or other
<220> FEATURE:
<221> NAME/KEY: modified_base
<222> LOCATION: (66317)..(66317)
<223> OTHER INFORMATION: a, c, t, g, unknown or other
<220> FEATURE:
<221> NAME/KEY: modified_base
<222> LOCATION: (66325)..(66325)
<223> OTHER INFORMATION: a, c, t, g, unknown or other
<220> FEATURE:
<221> NAME/KEY: modified_base
<222> LOCATION: (66386)..(66386)
<223> OTHER INFORMATION: a, c, t, g, unknown or other
<220> FEATURE:
<221> NAME/KEY: modified_base
<222> LOCATION: (66655)..(66655)
<223> OTHER INFORMATION: a, c, t, g, unknown or other
<220> FEATURE:
<221> NAME/KEY: modified_base
<222> LOCATION: (66949)..(66949)
<223> OTHER INFORMATION: a, c, t, g, unknown or other
```

```
<220> FEATURE:
<221> NAME/KEY: modified_base
<222> LOCATION: (68575)..(68575)
<223> OTHER INFORMATION: a, c, t, g, unknown or other
<220> FEATURE:
<221> NAME/KEY: modified_base
<222> LOCATION: (69069)..(69069)
<223> OTHER INFORMATION: a, c, t, g, unknown or other
<220> FEATURE:
<221> NAME/KEY: modified_base
<222> LOCATION: (69123)..(69123)
<223> OTHER INFORMATION: a, c, t, g, unknown or other
<220> FEATURE:
<221> NAME/KEY: modified_base
<222> LOCATION: (70063)..(70063)
<223> OTHER INFORMATION: a, c, t, g, unknown or other
<220> FEATURE:
<221> NAME/KEY: modified_base
<222> LOCATION: (72804)..(72804)
<223> OTHER INFORMATION: a, c, t, g, unknown or other
<220> FEATURE:
<221> NAME/KEY: modified_base
<222> LOCATION: (78300)..(78300)
<223> OTHER INFORMATION: a, c, t, g, unknown or other
<220> FEATURE:
<221> NAME/KEY: modified_base
<222> LOCATION: (78367)..(78367)
<223> OTHER INFORMATION: a, c, t, g, unknown or other
<220> FEATURE:
<221> NAME/KEY: modified_base
<222> LOCATION: (78377)..(78377)
<223> OTHER INFORMATION: a, c, t, g, unknown or other
<220> FEATURE:
<221> NAME/KEY: modified_base
<222> LOCATION: (78395)..(78395)
<223> OTHER INFORMATION: a, c, t, g, unknown or other

<400> SEQUENCE: 1
cgatttgctt agtacattca ttacatttac tattcatcct tatttacctt taataaattt      60
gcttatcaaa agagcaatta attgggatag tgataacttc attagtaact acatgtttgc     120
ctgtcttttt aaagaattgg gcaaattttg aagtagctgg aattacaaag gtatcatccc     180
gatcattatt tgacatattg tanaaagtaa anttaccgtc tanntnaaac ctaatnnncc     240
antnaatatn ncgtantttg aaatctatac caaatcttaa ntgancatca atnaattcag     300
aaccaccgta ntcataagct ccggtgaaat tccaattaat ttctgcgaat tggaaagtta     360
caggatgttc gccatgttca tcttgtatgt agtaaccatc atgagctttc caatagatna     420
ctaaatcatg catgctacca gcctcaaaga aataatagggg gagtctagac tcccctatta     480
atttattttg cttttagcca ntcttctant ggnggtaaat anttctcatg ngcccantta     540
atnattgttt ctacaacagg accntgtann tcaaggttnc ctgagatttc atgnggttca     600
tcaatagata gaacccacgt ntgtggcgca atgcgttcag ttgctttngt tagatacaca     660
tcaggcatta acgtaagatt caattgatcg ccgtcaaaat cagccgtatt gttcagtatc     720
agtcgttaat tgatacccgc accattacgt gcagctctag ctttcactag aagaccagac     780
tatatcttca cccttccttt cggagtgggg tgtctcccat ttcgagtcac ttgaccctac     840
atcctatttc taggaccggt gcacctgata ccgtgatagt cgttgaacct tctcctattc     900
ctaaatggaa tgttacggag cttggctgct gattgaccct acctaatctt tttcaaacct     960
tggctttgtc tttcgactcg cagtggtaga ttagtttaac aggatatccc agcaattaga    1020
gagaactcaa cccaacgatt actcattggg ggaactagat ttgattaact taataaggta    1080
tttatcaagc accccattct tttcaaagat tgctcttcga acagtattcg gatgcttaat    1140
accgacatct cttgcaaagt gtggaatact cggatacact ttggtagtgt tcaagatggt    1200
```

```
gtcagttact tcaattggag tacctttcc attactaggt tttccaaatg aggcttcaat      1260
ttctttttga gtgtatttag ggaaatcttc aggattagcg gtatatgaga ataccaaacc      1320
atccatgatt tccttactac ctctaactag atggtaatag gctttattac gtttagtacc      1380
tagtgcaagt tccatttctg ctaagttatg aaacacatgt aatgtcttag tcttatagtc      1440
taaaacataa actgtcttgg tactatctcg atcagcaatc ttagtctcac cggtaataaa      1500
ttcaaatgtg aatctatttc tatacggctt agtcttatga tcacgtataa taacccaaac      1560
cgtattttta ttaactccta atgcccgagc aagttcattc atcgagtaat aagtagtctt      1620
ttcaccagtg gtaacgtcag ttgcaattac ccgtctattt tcttttctta atccattttt      1680
gtaagcatgc tcaatgtttt caccacgagt catccactcc aaattagatg gtaagttatt      1740
atgtttgttg ccgtctttat gattgacttc ataatctggt ccaggtgatg gaccatggaa      1800
agctaaacag attaatatat gaactccctt actcttagat gttttttcat catttttgc       1860 accaatattg agatatgtcc caatcgatgt tttagtaagg aagaaattac atattctatt      1920
taaccgctta tgacgaattg ttcctaagtt actagcttca tatgctgagt atccaggaat      1980
atcccgccat tcaattttaa atgaagccgg atcaaagacg gacactactc cgttttgttc      2040
cattgttttt accctttattt agttattcaa ttgtccatta ggcgctttaa ggcataaaac      2100
tgacatgctg atagaattat cattaatgtc atcttttact ttagtaataa agaactgctg      2160
cgtagatcca cgttgaagcg ttggcaatat cttcagatag ttcgttaggc tatcccgcac      2220
cattacgtgc agctctagtt ctcactagat gttgagacta tatcttcacc tttggcttta      2280
tccagtaagg tgcttcccac ttcgatttaa gggattctat acccaccccac ttgggcccta      2340 ctctactccc tctaccttac ggcatggttt cgatagtcgt tgaggattcc tcatactcct      2400
tttaattaag aaggttagag gctttcctgc tgattgactc tattcaatac ttttcgaact      2460
tttccgtatt agctttcgct atccgtttca gtgtattgac ctagcgagtt atcccagcat      2520
ttcaagaagt tttgtcgagt atcattctg atacaaggaa accattatta agttgatcca      2580
ctacactaag attacttagg tggtatgtag cttctcttta cgcgctttgt atcggttata      2640
ttcgtcaatg gatttattaa ccatctcttg agttaattta gaaacgtatt cgaatagccg      2700
ttccttatct tcaactctac agatgacata tccattaaat aatctcagtt ctggtttctt      2760
caagatgtct tgcactgacc ccttgattaa tccagtccta agttgcaatt gtgttaagtt      2820
ctcatacctg ccaaaggtgt tagttttgaa gtctatgcaa taaacttcaa tagcgttctt      2880
ccgcttctgt ggatgataat ccccagttac ttcaaacacg tacttaccat tgtaaggttt      2940
agttagatgc gccatgacta catgcagccc tttaccatga cctagctcta agaactctgc      3000
aacttctttc atcgagatga agttatacac ctcacccgtg gttacatcag tgcatttaac      3060
agctaatgcg tgtttgtttg caccggttat aaatgcatgt tttacattac cactgcgagt      3120
ttcccactct aggttaaggt aatggttatg atgcttattg gtgtctttat ggttaacgtc      3180
caaggataca taattctcag gtaatccatg gaaagccata catacgaaac gatgcacgta      3240
tcgtattttg cgaacaccct catcattgtg gatattaacc gtcaggtaag tacccttaga      3300
tgttttgttc tcatgttgag aaatcaactc acctttaagg ttccttactt gaccatggtc      3360
actgacttca tagttactga aaccaggtat acttcgccat cttatttctt cattcatatt      3420
tcctcattag agattcttgg ttaccacacc cagaatctgt agcgctacga cttaataaat      3480
taatttcggt gaaaagtaca acccatccct ttataagggg ctgcttctgc aattagctct      3540
ttaaatagat ctgcaatgat ttggttatat tgaagtacat tctcatatac aaatgagaat      3600
```

```
gcttcacgag ttgtcatgtt aaacttngct tttagnttnt tngttagatg atactttaat    3660
aattgacaac ctacncccca nggnatatgt anttcatcat aatcatgcgg gtcactaata    3720
gaagtgatta ctgcacgtgc cgtagcgttg agacgagcac caaacatgtg acgccgagca    3780
agaccaggct tttgagcaat tcgtgatttt gcgtagatct cgtagaactg gccatatagt    3840
cttagtcctc gcatagtcct attctgagct ttaattggac taagtggtac agatgatgca    3900
tcaatactag cgaaggttaa ggtagcatca attgctgctt caattggttt atctaagtaa    3960
gtaccagatg tggttgattc tgctacgaaa cagagtttag aaggaactgg taaatattta    4020
gggaataact tatctttatt ctgagcaacg aattgagcga attcggattt attattagan    4080
ataatatttg catctagtag gaattggaag atctcattga aattatcaat gaagtgattt    4140
aatcctcttt caaatcctcg atgcagtagc ctatctactt tnctgcgtgt ttctttagaa    4200
ccaatagatt cnacatcgta tcgataagaa gtatcagtta gatatgctaa gaaatcgaat    4260
tctttagtta ctagatatcc ggttagcata atgattaaac gtgggttaat tagnctacgt    4320
acntgttttg gtgtacgaac ccacattgat ggttcgatag gacggctaga agtattgaca    4380
actggagtat tacaaatatc acagattact ccgagtttat gtgcgtcttc gattgctcga    4440
caatcacagc ttacactact ttcaattgct tctgaatctt ggaaatgaga atagaaatgc    4500
ctatcaaatt cttctttctc atctgagtta ctcgtattgt aatcattggc ataaattcgt    4560
ttacccgtaa attgatcatg aacttcatta tgatcaacaa ctttggcata aagacccata    4620
ccaaactcct atttatcgat taacaaaaaa ggagatataa gcggcccccg aaggagccgc    4680
tatatcagtt tttacaatgg accaccaacg gagcctggcc cgatcctagc gtcatctaca    4740
aagcttaacc tccgctcttc tctgtagcat accggcacta gtatcattta ccatccattg    4800 tagttttga tcacacgtca ccttttgagt aactccttc ggttaagtga tctatcatcc    4860
tcgtgtagtg ataggtcgac ctagactaag tccactagtc gattacttca cggaacctac    4920
tcctaaccgt tatcaccgaa gtgaaccagg gtcgcagtat tagaatcggg atgttactta    4980
tttaacatcc ctatctaccg aggtatttcc tattagtacc aggtacccgg tgcattatag    5040
gaaggagcgc cgtaagtttg acccatgctg ccagccatnc caacttgtgc actaccagaa    5100
acagccatgt tacccatacc ggtgtaacca gcgaagcgct gttgaccgaa gttggtaatt    5160
aggttttcca tggttacagt tacaccagcn gctgctgctg cggcatccat tgcggtgatg    5220
aatttcgggt taaaggttag acgacgagca cgaccagtat aggtaacgtt acctaggtac    5280
atcttgtcga agcctttact gttattcata cgacgcacaa tgtggtcatt acctacctga    5340
gtagcatacc aggtcttcca ctcttggtca ttaccttcag acatgttcat ggcacctaga    5400
acgtcgagat cacgacggtc gcttagttca ccatgctcat cagtgtagtg accgaggtct    5460
acttcatgat ggttgtcaaa gataatcgga ccagcttcag ctagattata gaactgacgg    5520
aaatcagtgc cgtataggtt agttagagct tggaagatca gactaactgc acgagcttgg    5580
tttacgccac cagctgcatc taggacgact tgctcaatag ctgagttgtc tcccattgga    5640
tcgacatcga tctggaatgc agggttctgg ttaaccatct tgttcattag cattacgaag    5700
ttgctgtcgt ctgccatgaa tgcttcggtg cgagtttcaa tcgctttacc tagctctgag    5760
taataaccaa gtgcaccaat atcacgcatc ttactagtag cgatcttcgg cattagagta    5820
cgagcccatg cctgagatgc agttgcacga tacgcgttac caagcgcgaa cagccacatt    5880
tctagagtcc atgcttggat ccaggacgcc ttacgaacgt cagtaataac gatgtaagga    5940
```

```
gtgaactgcg gaggtagaac tgcaccaggt agagttacgc caaacatgcc ttgttgctgg      6000
ccagtggtcg gagtccaatg tagatctacg aatagactaa cttggtttag ctggctatcg      6060
gtatcataga actcgttctc aggtacgttg gttttcttac cacggctagt ggagatgacc      6120
aggtcagaac ggatcggatt accacagcta tctttaaccg gaataccatt gtagtctagn      6180
ttgcaggtaa gctgttcgtt ttctgctttg atgtgggtcg caatagagaa cggagtctca      6240
ttgttacgac gngcaatagc atcttcacag atnttaacng attcaactag taggttctta      6300
acagctagtt catctttgaa gtcgaagtca gcatacactg cacgtggacc ggcagatagt      6360
acttctagac cagggatgtt gtaacggttc cgtaggaact cgccgatctt gctccagtat      6420
tgagcagtga atacatcacg cggtagtacc ttctcttcaa tgatgtcatc agttagacca      6480
ttgttgattt tgtgggtacg gggacggatg cgagtaccag gtaggttatc gagtactaga      6540
gtacgaacga atgccttcat ggaaccattg atatctttag ctagtttaac aatgagtaga      6600
ccagccatac cnacttgttg ngcatcncga tcgaaacgat ggatatcgaa gtcatcaggt      6660
aggtcctgat ggcggattgc ttcttctttt actttagtga atacttgtag ggcatctgct      6720
gaacgagcat cagagccatc tagccgacca gagcgacgca ttagatggtt aatgccagta      6780
gtngacccag gngcgccagn nggacgttga gcttgacgnt gtgcagtggg ttgcggagcn      6840
ggagcngtag cttgagtttg aacggtgccg atttcgtttt cgttaacagc catttttaaat     6900 acctttacga ttatggtttc ttgatcaaga agaacctaag tactnagtat actagattca      6960
atttagtaat ataaatctca aatttttttc attacaacat agacgctata atctgctatc      7020
agcagatcgt aacgaacact atgttcacta catattatta caatctgagt attatttatt      7080
tttcatctta caatttccat atcttctttt ttgagtttat gggtataaag tttgaatcca      7140
gaaactaatt tacgtcagtc ctgtattaaa taataactat cagtattttt ataaaatgca      7200
gttatcattt acttcgcata tacttacgaa ctgttccaaa aagagaatga tacagtttgt      7260
atagtttact aactggatca actttattat tatcagttgt atcaaattta gcaataaatg      7320
gtgaatgtgc cgaagcagat gtttcattta ctttaactac actaccaaat cgatatgcga      7380
ctaataccct tattaattcc tcatggagtt tagtagcagt tgctaatgga ttgggatcat      7440
taggatctat cttaatccta cgctcgacat tgaaaaagtt tactacaatt tctttgctag      7500
tcatgtatac agtaagatct ttgttattac ctaaatatag tggcggatct tcaacattat      7560
ttttagccat tgtatattcc tatttgtaat tactactgtt gttaccaaac tatgatatag      7620
atctcaatta attttaatc ggataataac catgtataat ttatttaaga atgctccgtc      7680
acgtaaattg gggcaggtgg ttgatcctaa catccattat atccgacgaa tctacgctga      7740
gcaaattagg gacgttaaaa gttattatag acgggcaccg aagtatgttg aatctaaaaa      7800
catattagca caaatgattc gacatttaa cgtagagtta ctaagtgatg atgctacttt      7860
tataaagaac gtggacgatc gttcacgtgc tattattcgt tcatttggta ttacatcatc      7920
tttaaataaa ggtaaggttc atgtaggtgg tgttacactt ggtcctcaaa ctgaagaagt      7980
tctagtatcc acatcagaga gctttgatct aaaagatcta aataaaacat ggtataaact      8040
ttcccctgtt acgtatctgt atcatacacg tactgatact aatttaccta tcatgaacaa      8100
taccacacag ggtagaggct atggtgtaac tctagtaaat ataccaatgc ttcttgtgat      8160
gtaccgttac tggtatcgat ggcaagttga gaagaatcct gatgaagtag aagacactta      8220
taggtttata ggatcatttg tattgccaaa tatggttgac tcttatttag atatttcttt      8280
ctttaatagg ttagcaagga atgctttaga tattaaaaat ccaacattcc ctataccgca      8340
```

```
tccatttttac atcactgata tgaatccacg tattgataaa ctatgtacaa ctatcaatag    8400
agaatccata ttaaaaggtg tagacatgga aggtttatca tggataacac cagctatcgt    8460
acaatctaat ttgttcgata tgatgcggct cccacgagaa cctattaaca ggaataatga    8520
atgggcttat gtattggctc gcacacccct cattaagtat cttgtagggc agcttttaaa    8580
gaatactggt tatgatcaat cttctgttaa cactgtatta attgatctta tagaagcatc    8640
taatgatcaa gcatttaagc aacaagcaaa tagtgagttt gtaaaagctc aacaggcaca    8700
agttgattgg atgatagatg cacttaaaag aaaagaaatg tgacataaac cccctcctaa    8760
attggagggg gttatatgcc gttttattag aaattacctt tcttcatttt agaaagtaat    8820
tttctacgtt cagctcggtt aattcctggg atagctggta atagcatttt attactaaac    8880
ttacctggct tgcggtcatg atttagtaat tgatcaacta cagcttggtc actgcttta    8940 actccattat ccatttcatc taatgggtcc ataatagctt tagcagtcaa tcttagatga    9000
gtaactagtg catcaaatga actatcggta ttaataagtt gtttatcaac accttcttta    9060
agagcttgtt taatagttac gtcttttacc aggatattat cacattccca aagagttgta    9120
tgatgggtat ttaacattaa ttcaagtgag acattattgt aatcgttgtc agcacttgag    9180
tgccaattga attcatcaat atagtcattt agactcatta actttggtgg ttcgttacta    9240
gaggtaatta aaccaattgg ttgaacatca tctagtgaac ttttatcact agtaattgca    9300
gttgtttcag tagtaacatc aacttctttt aattcgttgg tataagttac atatactaat    9360
tcttcactac cgtcatccaa aagaacatag gctgttgctt tggtggaatc atcaggtgct    9420
aatccatgga tcctaatacg attatcattt actaatttac tataatcatt ccagtgatta    9480
cacgaacttc attagtcttt tccattatca tctacctctt ttaatttatc tttaatatat    9540
ttcggataaa gctcgttttc ttcacgagtt aanccngntg gnncggttgg taatgtgata    9600
gtnccnctnt taattgcctt cttcatccga tctaagtcaa aattaaattc ggtatgattt    9660
ntcattatat tgaaccatat taagttagta attggcaatc agactatata aatcttaatt    9720
attttttagt atataagcct cccactaggg gaggctatat ttcttaatag aagtcagaga    9780
tgagtcgatc gttattttta tcaataagga aaataccctag ggactctaag gttagataga    9840
atacacccat agtnttttcca atgatagttc taacgtcagc aacacgcgta ataacttctg    9900
gaatacgacc agtttctact actgtactcg ggatatggaa atcaccaata ctggttttat    9960
tttcttcagt aacccatgct tgaatacgag cagctaattt cttatcttcg ataccatcaa    10020
tccattcttt gatcgcagtt ttattattaa gagtaactga gatctttaca tgtgaataag    10080
gtggatcacc agcgtcacca aatgatggag caaatacagt cttccacact aatccctttt    10140
tatgggttga gttatcttca gatttataag actcaggtcg tttagtttga ccacttgtca    10200
gatactcagc tttaccactt ctaacagact caataatttc tctttcgata tcaccaactt    10260
cttttagaat tgaagccaag tcgatttcct cttcagtctt tacagtttta atgatatctt    10320
ccatgagtgt tttagcacga ctattaatct tcttaggtac tttactatcc cttagtccna    10380
cnccnttnat ctccatncgn gantcattaa acatnacccc ttcttgggca tcctgtgatg    10440
caaagtaatg tttagaacga gtagttaagg ccagtactgc gaaataaaat tcgttcttca    10500
ttgcaaatag acgaagctta tctttagata cacccatatt agcggattga atcgcnaaga    10560
tatgcataac tacttcagan actagaaaca ctagtgcnaa tactagtcgn ttagcttcat    10620
tgctaaaagt tactttacca aagaattcct caacccacca ttgtaatgta aacatagtgg    10680
```

```
agtcagtatc tgaaataaca gcagctcgtc tatacacagt tggaaaagca tgaatgcttg    10740
atggtacaca tttagtcaag aagaaagctt caatcaatag acgatattca ttaagagttt    10800
cagcgatatt tcgaccagtg gcataaactt ggttnantgt atctggatcn gantctttta    10860
gtttagcttt agatcgacct ttaacagtat caaagcaaat aaagctagcc aanagatcca    10920
tatcaccatc ataagttgaa tattcttctt cagtgatgat ttgttctttt gttccaacct    10980
ggcttaattt aattagaaag ctcttgatta attctttatt gtatttatat aagtgatata    11040
gatcacctac ntacataact gctgctcgtt cgactggtgt catcccagta gctagtttta    11100
aaatctgngc cgtgtantac ttattttgcc aatagtgttt agttgaataa agaaccatat    11160
caactacttc ttctggcgtt gggcaatgta gattaaaatt agttactgct ttttgaatta    11220
actccatatc agctacatta atantnttta ctaaattagc ttttgtgatt tctggagtat    11280
aataatgcct attacccata atgaattttt cattatttga gttagcataa gaggtaccag    11340
ttctacaggt agatgttaaa ctagagtgtg tggacttata ataaagaata gtggcagcag    11400
atacagtacc gcctgaatat gagttattgt taattttgaa gttttcttgn tcnccttttac   11460 gtacttgtgc aagttctgtt ttaatttgtg aattctcttt atcgccggcc tgtaggaaag    11520
cagctgcttc acgttcagcc tgcatctgnt caccttaaac acgcttacgg tttttcacac    11580
cttcngcaat atagatggag tgcgtngact gtctaacaga ctctggtaaa tatgcggtca    11640
ttgatggaga taataataga ttctgtttct taacacggtt aagaaaagcc ataaatgaaa    11700
ccgtctttaa ttccctatca ccaaacttat ttttatctag aatagttgct aatggattac    11760
gaagtgcata ttcgccattt tgacgtaatt gttctttaac aaattcttta cattcttcta    11820
aactaatatt taattcatct tttgtcatta attgaagata tttggcatta tcatcaagac    11880
atgcattaat gatatcaata tcacgatggt aatcattgac atcttttaaa aacggatttg    11940
gttgggcaaa tgcggtcatt tcacatatct ctcagtatac ttattttta attatagtga    12000 atgatttctc tctntttaac taaaaaagaa aggaaagaa tgggtaccct atacgggnac     12060
cctaaattga gaggtagcac atcaacttac attcacatta gatgatgtaa gnaagtaaaa    12120
ataanacaac ataaaaggag ccatnatggc tcctttatag ttattcatat gtcactgaag    12180
ttggtggtgc attattttgn cgcactgcca atagaatgcg atcatacatt ttattatcga    12240
catcatccca tactaatgtc anacgnttac catctcacg ttctaatgta ttcgcaacaa     12300
tccaaggnat nccaataaac atcacacttt cattattggc cattcgtaca cgaatntaat    12360
tgtattgtgt tggatcaact ggagctganc ctgctggtaa acttggatat acttgctgcc    12420
cngcagcagc tacatcaaaa cccattgcag atgctacaga cgcagtaaca ataccttcga    12480
ctgtaacgtt cttaaaatta gtacctagga tagcatatgg atagacctcg aatgagatcc    12540
tatcacctgc ttgaatgtct cgaatattaa cagccatggt aatacctaa aatagttggt     12600 tacatagggt attactcatc tagtaatacn actacaccaa acagaccttt cgtatccatt    12660
ggnactgtaa tgantacatg tccatntgga tantttctt taaagctatt gataaagtcg     12720
gtncaatatt caataacata tcctttagta gaataattct ctaactcaat atcttcntca    12780
ggatcatcaa atgagtcatg tccatacatc agcatatgga tntatatgtc attattaagc    12840
gtatccatat aacttaactt acgtgattct tcaaataaat caagtggtgt tggacaatct    12900
ggatatatca ttcgttttgt atattcacga agcaaatgtt gcgaatatac ttctgactct    12960
ttagatttaa atacgataaa tactcgtttt tccatatcgg ttcctagtag gaagcctatg    13020
tgaaccgata ggctttccta tttgcgtcaa ttgttaatat gtgtcactta atccacatca    13080
```

```
ttgtaacagt ccataccaaa gtcttcacct tctagaatat aaccctgatt atgttgatca   13140
actgctattg attggattct ttctacacca tatccattct gatagagatg tgctatttca   13200
gattgtagtt tgctagccaa tgttttacac acggtcgcaa accacatatt aagaatactc   13260
aatgcatatt tatcttgcat aatcacaggt gctaccgatg gaaagtattc ttgtaaataa   13320
tagtcaaccc ctataattgg ttgagtaggc tgttgcgcta gaaattcaat atatgaatta   13380
attgcctgat accataattg ttctatagac tggtgttcag tatatgggta agggtattgt   13440
aagacttatt gacaactaca tcagccattt tattaacaat gggccagata tcactgatgt   13500
taataactac gaaactcgtc attccttgtt gacctggagt tatgttatta gcatcattta   13560
tccgctgcat ttcttgttgt ctataaagaa gtggatgcat catgtttgag acctcataac   13620
taatttagtt accatcttat atttatctac ttctatacat ttaagactag taataagatt   13680
acctgcttga ataacttgtt tttggattat ctctaggaaa tcagttccaa ataaatccaa   13740 tacccttcg ataatctcag cagatcttaa gtgccaattg atggtattag gatttccctg   13800
atgatcaaat accatcatac tcgtcggtct atccggttct atataggtat cgcttaagta   13860
atcttctaac cattgctcta aaaaggtagg ccaatctaat ctctgccagt ggttaaaata   13920
ttcacatatg ctgctagaag tctattgata caccacagta caaagtcagt cggttcatct   13980
acacctagct cttccgtaaa agaacgcggt ttcaaaatta gcaacaattg catattgact   14040 ccactctta ccagtgacta tagttaatag aacaactttg ttatctatta cactaatgaa   14100
cttatagtct attaaattct tcggtgttct atgtagtaat tggattccag ttgtatagaa   14160
caaattaatg aactcatccc aatctggacc atttcctagt tgtattgata tatccacaaa   14220
aggaataacc gtattatcct gttgtaattt agacatcatc ttaacaaccc attgagttaa   14280
taagacgatg actgtagctt catctttatt tgttaggtaa gtaaatttct ttatcaatgt   14340
gattaattgt gggaatacca cttcgattgg caatacatat accagacgtt gtacttcctc   14400
cgatgtacaa tccatctcgt gcttctgttt cataccacag ttccttagta tttgttggaa   14460
tgaggtgcat gatctgctca gcaccctcat cgagaagttc tattagttta tgcatgaaat   14520
gaatgtcttt agcatattca tagaacattt cttctttaac gaccatttgc ataagcttct   14580
gttctgccaa tgcaacaagc aaatgcattg cttcgatata actaatatct aaaaagtcca   14640
atacaaatct tagatagtta tcatcttaa taagtttact tttagtcgct cttagtaaaa   14700
aacgaggttg tngtgtgggt aatggtgacg tatagatctt ctggtttctc agtatcataa   14760 ataccctat ttaactggat gttaccagct gatggtagaa ctacccggtt agaacaatta   14820
tacagataag ttgttaaatc aatatcacaa atatccctat aacccagcat ctgattaatt   14880
agttctatga catcattaga tgtncnaccn gatgcnctct cagacgctgc tgccaataca   14940
attgttaatg catattctgc accaatacta ttttttatag atttccaaat atcagaatgt   15000
tgntcttgta caaagatct tacttccatt ctgatacaca ttgatgtgtc tttatcatta   15060
gatatgttca ttataaaaac cttataancg ntataaagcc cnccntangg agggctttat   15120
ttagtataga ttattttcta aaatgtatcg ctcagcttgc gctcgctgat catcaggtan   15180
ataatcacca cgttgatatt caaatactaa tttctcaata ggataagttg cattcttatt   15240
cttgtataca gaaattacat agctatgata ctctagttca tacttaacat catgctcaat   15300
tctggttgaa aaataagcca tgttaataga actaactaga gggctaatat atttctcttc   15360
aaatagtaat aaattatcaa gtcctaaact tgcaaagaaa tcatggttaa ccttaggtat   15420
```

```
taggtaagat actttaatat tactatattg tttaacaatt acgccaataa gtaatgcagt    15480
taactgttct tgaatatatt ctactgcgat gttgtatgca tggttagtgg tgatgtggtc    15540
tttatttaaa gtatagctac cgccattggt aatagatggc tgagttttac gtctagattc    15600
gtagatacta taacctagtg tttgtaaatt aattttgtca aagccatgga agaaagtccg    15660
tagaaattca ctaaataaat agtttaatgg gttcagtagg ttaagtgata ccactgcatg    15720
atcatcacca ttatcaatcc catggacacg atcatattct gcgattcgat aatctttacc    15780
actgattaaa gttataactg aaccagcttt aactacatcc cattggatcc atgtaccgct    15840
atcgatatat tttgctactt gcttatagat atctagatag atagtttcta gataaggtag    15900
tttcattaga ttttctaccc aagcaacttt attactatct acgtcagtta cagcacaatt    15960
aaaaatagct gcggccatct taagattggt gtactggtct ttggctgttt tatatgaaac    16020
taaactctct actatatttt caaccattag atgtaaaaac tgttgagcca catctttact    16080
caatttcacc ccaatcgctt catcaattga agctgaagct gtaagctgac ctagtaaatc    16140
gtatattgct ttttcttggt ggcgcgtatc aagtacaatg agcttattcg acattatatt    16200
tctccaatta attttttgga atagcgatcc aaactgtgtt ctttaaccga tagaatatta    16260
caaacttacc tgcatttact ctaggtataa ttttttaatat atcccaaaga tcagatgcgg    16320
cctcatgatt atcatgaaac cattggattt cttgaggggt gttatttatt ggattatatc    16380
cagtagtata catgaattca aaagagtcaa tagagtattt aaagaagtca tcaattaagc    16440
tgtcctctac tgatttaaat atatgctcta atgtaccata gtcatctgga tgtattccaa    16500
agctttggca cctaatcgct aaacgcgtat ttattaactc ttttggcgat cttggtacta    16560
acttggctat caccctcgtt acatctatta catacaggtc agccacttgg ggagtagtca    16620
cagtacaatc tctcgttaaa tgttcaggaa catgatatag atctaaaaat attttttagtc    16680 aaatctgttc gtggtaagcc gatgtatatt ataccttagt tgggtattat ctccatcgaa    16740
aaaacgcgta cagcgcatta taggacgttt ttatgaatcc aattactaag gctttacgtg    16800
atatttcttt taagatccca aaacagatat taaatactgt tttcntatct ancgaaatgt    16860
caggctgtgg tgcagctatc tcactagaaa ccaggatacg cgaagctgtt attgaaccac    16920
gtgttatgtt agatattgat ttagtcggtg gttcaaaagt attcattcca ctagattttc    16980
cagtgcaagc agaatatgtt gacccttata cagtggttta ttacattcca gacgaataca    17040
ctcagcaacg cccaattatc caatgttaca gtatccattt tggagtatta ggattccata    17100
ctgctggcta tgctatgcac tataatgaat caagtatggg tgcattaaca cgacgtgtac    17160
tagattcagc tagacagtta ccagtcgccc aaacagcata tatcaactta attaacccac    17220
acactgtcat ggtcaggtat atcaatatcc ctaactactc atcattcctt gcctgtcgcg    17280
taggtaatga tgangagcta aataccatac gacctacagc catacctgca ttttcaaaac    17340
tcattgagta tgctgttaag tcatacatct acaatgagtt atttgtatct atgggtgang    17400
cacagttatc aggtggtgct gagttaggtg tattccgtga taaggtttat gaatatgccg    17460
atgctgaaga actatatcag gaacaattaa tgcgttggat gaaaatatcc aggcagttca    17520
atgatcctga aggtaagcga catcatattc ggacaatcac agccgctcaa taaaaaaata    17580
aaaaaaagac atattgccct cccattgcgg gagggcttat gccattaagg taatatctaa    17640
ataacacnat atttaaaaac atactggtat aanncatcat caattaacac tgttgagaat    17700 cttttttgatg agatcaccag gtgcgatacc aatgcctgaa caataccgtc taaagttatt    17760
acacggttga catgctttct tttcaacgat atttaattca aagcaaatat tgccacgtga    17820
```

```
atctagaatg gatataaatg ctttgttacc tgttacgcga tatgtcttac cgaatacaac   17880
agttgtttta tatgcaaggc tattcatgat tattccttta acatggatta ttatcatgtt   17940
tgtaatatag cctttaaatg tatttaaata tttattaaac cnnatagcga tgngctatat   18000
atgttttnaa tacctcatan gccttatcng ttgccatgga nctattgaca aaatcagaat   18060
gatcaatctt aataatctta ccgaatgaat cataatcgat agttgtaacn nctattcgat   18120
cactatcacg gatcaatagt ttattttatt taaaacaaaa atattccatt tctcgccatc   18180
ggctaaaata acatcctcat ctttaagatt aagacgaaca aactgtttta cataaatact   18240
taactgagca actgttgaca taatgatttc tcgatatctg ttaatgaact aatcatatct   18300
cggacattna tggtaataac attttttataa gttaaataag ttggatatga acccataaat   18360
gtaatagtcc cacagatatg attttttatat ctaatatcaa nacanccgtc atatctccag   18420
ataaaatcaa atgatccttt agtgtggtgn tcaagtgnaa gaatagaacc actaactaat   18480
ttaggatatt gttcaaattc agacattaca taatctgcca gttccttaac ctcaggataa   18540
tcaatcaata atagcatata cgtaaatctc aatnagttaa tataacaccc catccagggt   18600
ggactctttc gaaaaatggt aatgtattat ttcgtatact ntctgcatca atatttggaa   18660
tgtggatggt acaacagtgg gggttactgt caatcttgaa atagaaatta tcttttaaat   18720
cttcaacctt ggatgtttgn aatggatata aaataccatt cccccaaaca taccaacgnc   18780
tatacagctt atcgtttaac cgcttctcaa taaccgaatg cgatttgaaa cgaggaactc   18840
gcaaacgcat cccgtttact tcagcccatt tgtctacccg ntcatagcta ataattccat   18900
ccttaaccat tacaaagata aatccctcaa ctatgttggg gagacgaact acgtgtttca   18960
gaaccatagt aaacggagat aacgtcagat caagttcagc tgccatttgc tcgtcgagct   19020
ttttagcagt gttctttgcc atcggttatc tcctaatata cagattatta attatcgcta   19080
gttatttaat atctgcaaaa ttctgattta ctttacccat aaaaatacca tcggctctat   19140
cgtcataata aagcttccct gctttagcat tacatanaac tccataaatg tgaccattgt   19200
aaccatcaaa attaaataaa gatggattat gcggtacatg aatgaatccc attttatcgc   19260
acagaaactt agctacagca gccgatcggc taatacctgc ctcacagtgt acgaataggt   19320
gttgancctt accaagagct tcacagaang aaataatacg ttgtgcatgn cgatgatcaa   19380
atagatcata agaagaatca acataatcct caatgtcatc aacattgata cgtaaataat   19440
taagatgttt tgctgaataa agtgggactc tacctttctc cagtagacag atcatatttc   19500
taggggaata aaatgattca gccacatgca aaggaatata agtaactgta tttactggct   19560
tcatattaca cctcgttaca aaaaaataaa aggagccccg aagggctcca gtatangtta   19620
atcgaataca agaccactac tagttgcttg gtcatccaca tctagagtag actgacgctt   19680
acgcatatta gctttggctc gattcatcat ttcacgacgt tcttctaatc gnttacgaat   19740
atcttcaana gatagncnan tgatcacaaa atgcatttga tcgaaatcat atttctcggg   19800
atcagcataa ccagtggtac gagttaaaac agtgttaatg gatacttcgc gatcagggtc   19860
agtgtatagc gaagcaatag aaattgggtc cagaatagcc tgggcttctt gacgatcaaa   19920
acacacgtgt aattggacag tctgtacagg tacatcatgg tgtttatgga agtgtgccca   19980
gttagtgata tccattagat caagactttg gtgttcttga ttaaatagag ttactagtgc   20040
atntagtact tcnagaatgt tttggttcac cattgactgc ggtanacctt caacattctc   20100
atgatagtta ataatcatcg gaactttact aacagaggaa accccttcaa angtcttaag   20160
```

```
gctaccactn ctattncgaa gactaatatc actgtcgtaa gatccaatga ccacacttac   20220
aactacttca ccttgttgtt gtagatgact nacaagngaa ggaccaatng ttgaaccaga   20280
agcaccaccc attgantana cnacnatgtt agnatccccct gctgggaaat gatgggcaat   20340
ggcaggaata tgtgcagaga ttagttctgc ggctgcctta cgatctttac ccataccgat   20400
agcacgttta cgtgcngtct ggtcagctag cttagtatcc gcttcaataa tgatcgtatt   20460
atcgtcagta ttgtgtttgt gtttattntg tacactggta tcaatgtagc aaacatcctc   20520
atgataacca tggaatagtt caccaatacg gaaaccagca ccaccacaaa agtaaattcg   20580
agttttactt tagacatcat tacacctcat tgtgattaat ataattcata taccaacttg   20640
taaatggtat cagtgcttaa aagtaacgat ctcttcatga gttcgttctt gatgaacatt   20700
aattcattaa ccactttacc agtatcagat ttaaattcga ttaccatctt atctcgacac   20760
atgtatgttt gccaagtacc accagactta acacaatcaa taatcatgtt aagtacattc   20820
ttaacttcaa tcttactaac tttataacga taaacgttta gaagttcagt aagccatttc   20880 gttttttggga ttttggcatt tttacgttct tttgaaatat caaaaggaat tagtgcaatg   20940
atctcaccat ctttgttggt gaattcaaat accattcctt ttgagttagc taaaggacga   21000
atgttntaat tnccttttanc actncatact tcttcagata acttaactaa cctatctagt   21060
tgaacatcag atgcatgaat gttatcttct ttaaatgctt tctttagttc atcatgagtt   21120
agtggagtac gtactagagt gtaatctttc tgttcagtca ttttttcattt ttncnatttt   21180 cnanttcaaa ttaaacggta ttggcttta tagccaatcc cttattacta aaagtaatag   21240
attctcgaac taaggatggt tataccccctt ctctaataat aaggaatatt atatgggacc   21300
ccccaaaggg tccccccaca taatatacta tttatataat ttcttttaga agaaaagaga   21360
taaataagag aaatacagtc tattaaagta atgaatttct caaaaattaa atagtacacc   21420
gcncnnnnnt tncgncggan ggtcctgccg gacnanngtc cggatgtgcg nnantagngg   21480 gttttttcaaa aatacntgca tcgcggttga attgagnggt tgattataac gtnngatctt   21540
aatngtaaat agaacttcnt caacatctgn atgncatcct tcnaaactaa aatatacttc   21600
agtccgatca ataaactgat acatttctac agctggttca gctggatctt taaaggccan   21660
cttattagcg aaataatcag tatngggctag aattaattct tttacattan ttgcattctt   21720
cttatcaaca aggaattcaa actcttcaag gttatctgtt ttgaaaatac cttgatanga   21780
tgacgactng attagttnat cactgatatc atcaacatga acncctggca taaattcaat   21840
gactggtaga ataagcttgt tacctcctac gccntnagcn atatgaatnc caancacatt   21900
accatcacta atgtattcgt cattaccgca aataacggca ccagccgcta gatataaatt   21960
atcaacatat ttcagattat cggcaataat gcgagatagt acatattctc gcaccatggc   22020
atcatctgga cttgactgcg gtttaaaagt atagtgggtg ttatgactac tcatggtcgc   22080
acatgtaaca aaaactgaaa tatctactgg attaaatacc caatgaacgg agatatcctc   22140
taatttatgt ggatgatgta aaccatctag cttagatagg gcttggagtt gttcttccca   22200
ggtgatgtta aattgagtca ttttttctaac ctcttcattt attaaaaata atacacttat   22260
tttactttag cagttgatac ttcacataca ttaactaatt gttcaaataa cggttcatta   22320
tctggatcat taactaattt gatgtattaa taataatacc agaatacagc atatcagctg   22380
catctcgatc acttgttta attctggtta caccttccca cttccatcca tagtaaatta   22440
aatcaaatga tgaaccaatg ttaaaggttg attgaataaa tttgcatgta ccattttctt   22500
ttaaccaatc aggcctatat ggttcatttt tataaaattc atgcatgagt actttaaaat   22560
```

```
cagtttaat gttttcatga ataatgcaat caatagaatt aagagcttca tcaagagctg    22620
atttagactc aataatgatt tctaatacat tggcagattt tagtgtaatc atacctagtt    22680
catctgagtg tgctcttccg atttgaaata cattgagctt accaattggt aaggtggctt    22740
ttaatggcag attagtatag tgagatacat cgcttttata actgtcttca tatgactcaa    22800
ttaaattaag ccatgctctt tcaatacgtg tattctcaaa atgntgttct tcttctagta    22860
gtctagaaat tagatgatta atgtattgaa cattatggcc agtaccngta attnaattat    22920
atttcgtatt accggtaatt ccccatttat tattttcttt atttatccaa ccgtagatta    22980
cactgttttt aggatattta tttttaaaat tatcgtatat ttcttttaga tgtggattag    23040
gggtaaaact aaaagtagtt gattcagtca ttatagatac ctatttgaat attgtttatt    23100
attgcaaatt agtaatatag atcttaaact tttttaactc agcataaagc ctcccctagg    23160
ggaggcnata tgttcattta tctatttcag cgtttggatc ataccaaggt aataaactta    23220
gtagtgccgg ttgttgtttc ttcatatcct ctaagattgt tgcttcactt gcaccttcta    23280
acatagtggt gaaagtaatc atgttcttag agttatatat cggacgtaga ccattaccaa    23340
agaatttnac ntgttgaacc attatttga aatcagggtt atcgactaca tctgggatat    23400
agatancagg tggcgcactg aaataacgtt taattaactc aatagcccaa tacgttggta    23460
aatcaccaaa ctgtgatttc actgtagcta ggtttaattg gaatgcttta ggttcttcag    23520
gcggcggttc caccggatca attggatcag tgggttcttc agggccagta ggttcagtag    23580
gctcttcagg atcctctgga tcgccttctg ttggcttttc ttcagatgtg ccaccatcag    23640
ggtcacntga accatcatca tcttcaacgg gctcctcagg cgtttctata ggctccttcg    23700
gatcttcctg attctccgat agatcgggct cttctgattc cccatctcca tttgcttcag    23760
tagaagacgt gtcttctgat tcttcatctg ttgtcgagtc agttgnggct gtgttttctg    23820
aatcggcagt ggtatttcat tttcacttga ttcagtagaa acaatttcag taggagtggt    23880
ttcaagttca ttgacactat cctctgcatt agttacttca ttagggattt cactaatttc    23940
tgataatgtt actggtgcac ttactgcgcg agcttttcgt ttagccatgg ttgtaccta    24000 gatagaatag tattatggta agtgactaat tcaggatcag ttaaattgat actttgaata    24060
gtcatattca gaattacata ggagtccatt gttctccggg tatatccagt taattccatc    24120
ttgttatatt tctgtacatg atctggaacc caatcaccaa agataacacc cagtttatga    24180
aaacgataca ccaatctgga taatgcacgt tgggtttcag ttgggaatat atcgggaaca    24240
ttttcgggaa cagtacattt atcactaaat ggagtaataa taggaccacg atgaatggtg    24300
tagctaagct taaagataac agcaccaagt tcgtcattaa tacgcctaag tatacgataa    24360
ccataatcgg tacgctcaag tttatataca ttactaggat cagcatctgc taaccttcta    24420
gcatgtcgtc tagtgcacgt ttgataccac ggttatagat gagttcacgt tctatgtaat    24480
ctctctcaaa agcggcctga gggctttctt tctcaaattc cttagttact gaccaagaaa    24540
ttgtttcacc agttaattca tcagttaaaa catacagata tgtcatagag tcaacgtatg    24600
aatactggat agagtancgt gataaatcac atggcttagc atttaatcgt tcttcttta    24660 aatagaaaaa catatcttgt aaatgattat aagtttggca gccaccacca agatgatcaa    24720
tatcaataga cgtatctggc ttgactggag ctttgcagca actcattaca cacctctaca    24780
attatatttg agttattgta ctacagatga taaagagaaa atacatcata agccctctcc    24840
ttatggagag ggnattatat ttcatagtg ttaaaacacg cattaaattt agataatgag    24900
```

```
cagccagtat aaattaatga ttgctctagt tgtatgatga catcgccatt actatcaaaa   24960
tcagcagcaa taaaagtaga ttcagttatc ttaaaagtag atggcagcat ttctaaataa   25020
ttaaatattg cttgattatc gatgtcatga ggatttaaat ccatatgtta cctatacatn   25080
gatagttatg gaccaaatat taacaggnct gcataagaca attgtgatta aatctccatg   25140
agttctctga taatggttga aacacataac tttgattaac tttaattttt tagtttcttt   25200
attttgaatt tctttgataa gtgattcaat aagatcagta gtaataagtg aatgaccatc   25260
aataaatggt tttatactta ctagcgaatc tttgttaaat agaattgcat catcatattc   25320
acatgtagat gcggtcttgt atatggatgc aactttatta actttgtcat nagtgactat   25380
agaaaaatta aattcantct tagttttact naacgatgtt tcaaataatt tatatttatc   25440
aataatagtt ttattatcaa taaatgattt cattccaata tttaaatcta tgtccagggt   25500
ataagantta tgtattaatc caactgatag ttgagtttca ttaccactat tgttaaactt   25560
aatattatta actgaacata tctgattatt aataaacgat aataaatagtt tagaaatagt   25620 tttaataaca ttaacttcat aatcattatt agtacaagca agtgcagttg tcatgtatcg   25680
actaacttga cnaacatcta gtttctgata gnnactanca ctatctancc atgggtcaat   25740
anttaaaaaa atccttagac tagctagaat atcngaagat gtttcagaat aaatgaaaaa   25800
cacattatta ttaagatcat cttttagcca accactagtt ctaagatttt ctagatcttt   25860
ttcattagat accgattgac ttaattgctg aattaaacta gggttagcta ggtttaataa   25920
actaatcatt ttataaacca ttttattatc ctctaattta tgtaattaca tggaataaat   25980
aacataagta cttttatgac ttatgatttg attctccagg aggttttccc aatggcaact   26040
attaaagaag tccttgatag aaattttaag gatgttcaat ttgatcgcga tttatgtaaa   26100
agaattattg acttactat cagttttatg aataggaatg ctgatcactc tgctttcttt    26160
ggtggtgtat tactaggtgt acaacaagtt aaattcttcg atacggatcg tgagatttgg   26220
tatgatgatg ttttacgaat tgatgaagcg ctgttagtcc aagattttaa gtcagttgaa   26280
ttcattgacc ctaaccatcg tgtaatgtca gatgtattca atcatcttcc tgcctatatt   26340
tgttctaggc ttttaaaaac aactaatgtt cctttgaata ttagacatga agcaatggtt   26400
agttgtttca tggtgttgca ttttaaatat ctaacatctt tacttgtacc acgctttaaa   26460
tatcctgcac gtaaagaagt agccgaagct gcattcgccg cactcaatta tcgatttgac   26520
attaagacaa ttgggtcatg ggagaaacta tttaggcaac gggctgaagg tatcattgca   26580
cctgattcta tttatgcacc tttcttaact ggtaaaacac aagaactgga ttattggtct   26640
ggtcgtgtgg tatctgatac tcaaacacgt ctacgtgaat taatcaacaa gtactatgat   26700
gtttatatca gaacactgca atcaggtggt aaattagtta tttcatcgga tatggctgtt   26760
aattctgatg gtgagcagat tctacgcgat aagtctactg ggtatcgctc atatcttact   26820
tatatccatc aagttgcgca acaagaacaa aatttcatta gacctgagtt agtcggtatt   26880
attgaaaaga taatgcccac aatgccacca gaaatgttca tggcgacact tagacacctt   26940
tcccgtaaca tcggtcaacc tagggcacaa aagcttgaga aactcgtaga tgagtgctta   27000
ttgtatgctt tcgattatat gcaatcactc cgtacaatgg ttgctagaaa taatgatcta   27060
caaacattgc ttgtaaaaat acgagcaaag ataatggcat ctaaaacaga aaatgctcaa   27120
gttattttca tgcgtgaaga aggtgagaag ttagttaggg atgcgactaa ttctagggta   27180
cctgcatata tcgcagcaac taggactggg ttgatgttgt atttaattct acgtgctatg   27240
actaagaatt actatacaaa acaaaataaa cataatgccc tcccgcaatg ggagggctta   27300
```

```
tgctgttaag taacattagc tagattgatc attacataaa ttttcagag catcgtaaat    27360 agccacataa gtaaaatagt taaactatct ttaatttcct tacgtggggt gccactgaat    27420
ccaccccatg atacatttgt attactaacn catacagtgc taatagctgg ctcatgatag    27480
ccaccatcta ctttacgctt tgcataaacc ttagccgtaa tttctccacg taacttttg     27540 aagaaaacta gagcacccgg aacgactata cgtttattac caatcttcgt aataaattct    27600
ttacgattag taaagtgctc ttttaataaa tcattaataa ttttagttaa actatcaatt    27660
tcattcttca tcgacacgtt gttagttcct tacaaataaa cttgataacg tgatcactta    27720
caaatttcaa tggaccagaa caattagatt tctcaatagc ggtttcagtg tatgaaatta    27780
tttgatttcc acttaaggat aatgaatcaa ataattcata agagttatta ttttattctt    27840
aaaggatact gcatattgac tatttcacta ttgatgcaaa ataggttaat agctgggata    27900
gatacagagt tatctgaagt atggctattt ccgtaatat tccaattact gtatacagtg     27960
aaaatatttg cagctagtaa aaggttggca ttaaccgttt ctaaactaac atactccaca    28020
gaagtacctt tatgccaata tagttcaatt ggattaaccc aagtataccc aatggttta     28080 tagaaggcat gcattacata ttctcgccaa cgtgtgggtt tcttattatc agttaaaaca    28140
cacgtaatat tgcctgacgg ataaatgtgg tggatgctac atgcattaat ttcatctcta    28200
acattagttg tttcagtaat attagaatga tcctgtttga atagccattt taaatgacta    28260
ttagttgtgt catcaccttc cccatttgca atgtcatttt ctaaccactt tcaaatgta    28320 gcttgtctat caggtgttgg cattccccaa taggtagcta atgaaacga taatagtatc    28380 gaataatatc atcatcgtta agaatatttt atccagtttc cagtgatgtt gatactcgta    28440
tacttcgctt ggaatattat ttacttgata ccatgtatta attaactctt gaattgttaa    28500
ttgccgaata ctctcacttg ttagagtgta atattccctg ctatgcggct cttcaattgt    28560
cacttcttga tcagtataac caatgtattt aggtttacca tcgatgagtg caaaattaac    28620
attccatgat gtatcattac taaagtgat attaataaaa ccttgttcaa agctaggctt    28680
cactacgaaa ctgacatcat ccttctgata tgtcatttgc gttagaatac caaaattaat    28740
tttagatgta aattctttat cgaagttatg tttataaagt aatcctagta aacaatcaat    28800
tttattaata gtgtggtttt ctaataataa atcagtattt gtaagttcat taattttcat    28860
tttaacctct ctaaaattta caatctagtt ttacttattg aataagcaaa catgtaatat    28920
atatcttaat tatttttagc atagttttta acaacataaa gcctccccga agggaggcga    28980
tatgctttag ctttttggtt agtaccgaca gtctgctcat tcttttcagt ttgagcattt    29040
cgccgaagtt gactaaccag accattgcca gccgcaacta catcgggaga aaagaatgca    29100
ttgatatcaa agttctgatc ttggttgcga gtcttcccag gtgggaccat cggatatact    29160
tttgccatta gcttaatcct acaccgtcgt aagttacccg attccaact gcacgttcaa     29220 tctggtcttg aataccatta cgtgcacgta gtacgtcagc agataaacca ccccagtcta    29280
atttctggtt attggggttc ataccgcgaa tgtttagttt acggaacatt tgacgagcgt    29340
attcttgtac accttcagaa acatcagtca gtgcagagaa ctcaacgttt agatcaaggt    29400
tctgaccaat ctgtgatgca tctttacggt ttccccaagg accagtagtt aatgggaaca    29460
tgttggtgca aagataagcn ttaacgcaat cctggaaggt aggatcnggt tctacgaata    29520
gaacagtcat accgtagaag gtagcgtcgt atttctcaac cggtacaatg ccatctgata    29580
caatacgcgg tactttggta ttctcatctg caataccata gttgatccac cattgtaaga    29640
```

```
aacgttggat agcgcggttt tgtaattccc agcaaccaaa gtttgggtta gaccgggcac    29700
gggttacgtt agtagccgtt tggataactt caccagaacc accccagggt gcttcagcgt    29760
tatctacagt aagcgtacgt tgtaaaccat cgatggtacg agtatgcgtt tcaacgaaag    29820
ccttaagaca tgcaactaac cagttagtat tactagcata cttaaagaat cgtggagcat    29880
ctagtaggaa cggcactaag ttacgtgcca catatggcgt gttagtagcc aggttagcta    29940
agtcaggccg aaatacgtta gtaccagcct gagcaaggtt tacagtgtta cgggcaccac    30000
cagcaccata accagtctcg ggtgccatcg gatcattata gcgagccatt taacttttcc    30060
tcattctgaa agccacccac tcattgctga gcaggtgggg tttcaatacg aacagtttcc    30120
agattgaagt tcaacgtggt ccgcgggtta ttagcctcaa cagttacgtt gcaagtccag    30180
ctggtgccgt tatttgcgtc aatcggagtg atctctgtac gcgggataat gttgacacga    30240
gtaccgaaca tatcacgtac tagatcgaga atatactcgt cacaacgctc aactaattgt    30300
tcaggtgtta gtgtagcatt accgctaaat tgagcgtgta ctttatggat cagtcggatt    30360
aatacacagc aaatattaac agtaatcggt gatagaagta cagatgtatc atctagcatt    30420
actgaacgta ggcacggata ataggagcta cgatggtcat atgactgact ccaagtagca    30480
ccattcgccc aagcttgtgc ccgtacacga tcatcaaaga atttaacatt tagatcttta    30540
acaaaagtaa cacggttatt aggacttaca tccatttcca tacctggaac tagattacca    30600
gttccagcac ctgcatagcg tgcccatgac atagctacga ctaaaagctg cggtacatat    30660
ttacgatagg taccatccat tagtttgcca gattgcatta caatcatagc gcgacaaaca    30720
ccagttccgt atagagtgga ttctgggaaa gcttttaggc gagtgataat ctgttgaaca    30780
cgacttagct cagtagcttc atcaggtaga cgactatcag tttctacgaa tgtagtgaag    30840
aaatattgta gatcacgccg cgcacttagt acgcgcattg cccgatattt tgattccatc    30900
ggaaggccag tgtcataaag aacaccgaac tgatattctg caatgttatt atagcgatca    30960
tttaatttgc caaagttaat attttcaata tcaactaatt tggcatattc ttctagatca    31020
gttgtaccgt cagtaccacc actagcatag atgttaccat cttacctaa cgtaatgccg    31080 ccatctagtg gaccgagtac ntgaataccc tggtaaggat caccatcaac agctaagaag    31140
gttaggaagt caatttcacc aggtgcagta gtatgcgcag cagcggctgg gttaactcgc    31200
atctcagtgt cataaatcat ctgacgaaca agatcaatgt tctcatgata gacgtagaac    31260
tgagagaacg gtgaataaag tggacttagg ccagagacta caccatcatc tgagtaagaa    31320
tcaactaata catcaccaac ataaaggtca gcgttataca tatcgctgta aacaccttta    31380
tcaaatgtaa tgtttagata atcttgctgg tcagcagttt tgacaataac tggactagtg    31440
cctacttcag gcttctcaat taactgaata cggaattgac gagttttaaa cttcgccata    31500
gctgcttcat cgaactcttc gatatcagca gttgtagtac tccatacacg cataccgtta    31560
gaatcaccta atttaccaaa gaaggaaacc ggtgcttcaa ataacggata tactagtgat    31620
tgagatccat ctttatctga tactaaagta cctggtagta cacgttgtgt acctacttca    31680
gaggtattat cttcaataag aataatacgt gcctttagac catcaacttt atcagcagtc    31740
gggactggtg cattaccaat gtcacgaaca ctgtttggat agttgaaacc actaagacga    31800
cgaatcgtaa gtgggatttc atcttccaca atttcaatag caacaattaa ccgagatgga    31860
ttagctgcat cttcaggacg tagacgttta acataaaacc attaccacgg ccaagaaggt    31920
taagtgctaa tagtgattgt gtattgaaaa acttactacg tggatcaagc gatgcttgac    31980
catagatgga tgcaaaacca tcatcagaat caccgacata agtggtttca gtcggtcctg    32040
```

```
tctcagtgaa gagacgtaat agcggacagt gttgtgcgaa cgtgatgtcc ggacggatca   32100
ggggccggcg gctacgatcc cggataccat taaacacaac cctagggaca gcgttgtaat   32160
atgccatctt tttgattctc ccaagttgga gctttgaact cgatgttatg agtgttaact   32220
aacagtcaat catagatatt aatcatagtt gaccatacta gttattttt actatccatt    32280 taaggagtag cggtaatgtt tttgctaccg tatgaaacta cagtttgtaa aactctatac   32340
aatcccaccg gcggtggaaa attatatcct aaacaatatg ttgatcaaat tgaaaatgcg   32400
atcaagaaag ccaatgtgta tctacccatt ccacctgttg atgcacgtaa tggtgaaacg   32460
ctagagcata gtggacagat taccccagtt gatgattttg aggatattaa gaaatttact   32520
caaattgtca atatcggtga tcgtgataat cctaagctag tngttgatgc tcgtctatat   32580
aaaaagattg aacagcgtac tggtattcct aggattattc agcagaatga gtggcaattc   32640
caatatattc ggatggcact taatatcaaa ctattacgtg aaggcccgga cttcctccat   32700
cgcttaggtg atatcccagt taaagttttc tataattgga tctcaggcat cctaacacaa   32760
aaatacagcc taccacctga atcaacccaa gctatttggg taatctgtgc tgtttattac   32820
tttgctatgc aagatgatgn tctaacagaa ccagntcagg aacgngatcg gttaatacca   32880
attatttccc gtcttacata tattccagct ggttttattg cngatgttat tgatacatta   32940
ggtccacttc ataatgccgg tgatctagct tatgagattt caactaangg ncgttcgatc   33000
aggatgggta aactaaaatt cagtgatcta caattattag tatcaccgag ttggtttggt   33060
accgcttccc gtgaaaacgt aggtgtggca ctagaacaca tgccaactta catcacactg   33120
atctacatgg cattagctga tcgctcatac cgtaaaacag ttttaagtca gaaagttgaa   33180
atgatttcac gttctgatga tgcaagtcgt tttattaatc tagtgaatga agctgtaagt   33240
agccaattcg ttaagtaaat ataggggtga atcaatgaac gcatatctat tgcgncatgc   33300
gattgataac gtttggtgta acccagccca ggaccgacag tttgtttatg aactgaaaca   33360 gctnaccccca cgctacggcg tgagggtaaa ctgggtggtt gattcacccc ggtataagct   33420
accagtccaa agtacacgtg attattggca tctttatcaa attggtaaaa tgattcctaa   33480
acacctgggc ttgcctaagg tttacaataa gtggatgagc ctaaatgagt tggctcaaaa   33540
ccatttaaat ttagcagacg tttatgtaaa tagtggtatt aattattcac gtaatgatac   33600
atacgtttta ataaccagtt cgcaaaatct tttaattgct gttaagatag atccattatt   33660
ccctgatctc gatgaaaatc aaccctatct tcatgtttat aacaatgctt actttcaatc   33720
aaatagatcg gatgtagctg gacatagatg gttagtttct gaatcgtatc gagttaaaac   33780
aatatctgaa ttaactcaat ttcagattaa gataatggat accatagcat ctaaaggtgg   33840
tgttcctaaa tactttgtaa atggtagata tgttaatgag atatctcctg ttacagcaac   33900
agtcggtgat gtttgtgatt tcattctaga tccatccatt aaaaggatgg tagattttga   33960
tctacgtaca ttacctgttt tcatgtcaga aatagatagt gaaagaaata tattttacac   34020
tacactgata agactgtgca aacaattgag ttctttgatg atgttgaagc atatatctat   34080
cagccattag gtaataatcg ttatactggt gttaattacc atcataacga gagccgttgg   34140
atgcggatgc ttacacataa agattattct ataccaactg cacgaattga tcagtttaaa   34200
gcacttcatc cagaagatcc tcgacgtggt gctgatccta ctcgttggcc aagtcaaaac   34260
tggaaagcat tagataatct agtatttaga atctacatac atcattctgg ttatgatcgc   34320
ccattagttg ctgattcaca tcgtattcaa attctgtatc gtttaaaatc agaagatatc   34380
```

```
ataagggcta tgactggtgc agattctggt aatcctttat ggcgagctga aaatctagag    34440
caatcaccat attgctggtt catgtcagca ccatctagtt tcgtataccc attaacattc    34500
aatctacctg aagaaacatc gcctagtaag gtagaagcgc agaatatggc tggtgatgtt    34560
tttggttatt atgaagcagc taatattcaa ggttataatc cagcttgggt ttataatgat    34620
gctggtctaa agaccgctga tttacgatac aactactggc tagatgcaac tgtatttgag    34680
tatgatgaga aaggtatctt attaggttat aattatcata cagcaggtcg caaatatttc    34740
cctaaagata gtcgttgtgc atatgttgaa tgcattaatg gtaaaggaag tgtagatcta    34800
catgaagcat atgggaatga tcccgtgcct ttacgtgatg gtgacaactg gcgagtttat    34860
gttagtcctg tttgggctgg cgtaccaact ggcgaatggc aagatataac agaccatcca    34920
gatcgaaaca actgggtttt ttatgatgat accactgatg ataaacgttg ggtttggata    34980
gctaagtcaa atgagtggta tggcctagta agaaccgatg agtacttcta tctaaaagaa    35040
ttaaagttta ataaaactga tggtatcatt aaatggagta tacgtaatac tgaaactcat    35100
aatggtgtaa aagtcgataa attgatggag ataccatttg gtcagtatga tgtgtttgta    35160
aatggtcggc ctatcattga aggtcttgat tacacgcgtg aatggcctca aactgtatta    35220
tgtaatctgg aatattttaaa tgcagatcca aatgcagtta atacgattct tctacgtgga    35280
acaggtttcc caacaccaga tttaaaacca tacgaacctg gcgagattgg tttcattgag    35340
tatggcgtat tgtctaatga tggtatttat aaagtacatt caaataaaca atcacgcata    35400
atcattgatg gtcattatcg tgaccctgct gatcttgaat ccaagaaga tcaaggcact    35460 actgttatca ctgatgaacg caatggtgca ccattccaaa tacaaacacc acaggcncgc    35520
ttccgngatg tttataatga tgattaccaa gctaggatta aggatgatgc acgggataaa    35580
caagtcactg attttatgac tgaatatttc ccaatgaaac ctcaacctaa tccggacaag    35640
atcgattata gataccaggt gctttcagcg ttttcatgta agatcattca tgatatcgta    35700
aaagaatata tcaaaccncc atatcaaaat ggacggtata gtgacgatga tattgttaag    35760
cagctaaaag attacgagtg gttagcagct tatgacatta tcaataaagg ctacaacaaa    35820
aataaagttg tagtttatcc acattggtat actgaacctg tagaactaga tatttccaat    35880
gggaatattt aaatcgtatt ctatcgatat atctacgtga agtaccgcca ctatccttgt    35940
tcgttaagat taaaggaat caaccatgac aacgtcatat gaaagtagcc agtaccaacc    36000
accacagcat aaaaaccatt tctggtttag aggtgatatt gtctcatatg ctggtganac    36060
tggnaaagca atccctgcta aaggagattt agtatttgac gcagcacaag ttggtttat    36120 tgttcgtgaa gttgatgaaa caactggggt atctatctta gatccatggt acatgcccca    36180 aaaccaggc aatgaaaatg aacaaaacct actagttgct gtaggtccag gatatagctc    36240
agaatcttat cggttattcc tagatcagtc tgtaacacca tttaatattt gcccagaccg    36300
gcgattacat tttatggat caatggtgca tggctataaa gttttcctag gttcagatat    36360
atcagaaata catggtaaag tgatttccct gttctatgat aatgctggta attatctagg    36420
gccaactata ccagttgaat cagtacccga tccattgact caacagaatg ttgttaaagc    36480
gttaatgaat ggtaggactg ctgagaaat gcaaaatggt gaacgtgtaa ctctagtagc    36540
ttatgatgac gtgggtgggc ctgtttcgat tgctcaactc gttgtaatga atactgaagt    36600
tatagcncaa gaggatacct cnaagaaata tgtaggtggt atcactattg aatcaccatt    36660
catctcncca gctgatccna agttattga gttcccatta aacgtaccag ttgaatcatt    36720
accgatgatg ggtgctgttc attaccgtga tggtaagaag catgtgatga atattgatgg    36780
```

```
tacggcaatg gcaatttatg gtttacgtaa ctatattgcc actgaggaag gacaagagtt   36840
taaattaact ctatcttacc aattagcaca agatgagtta tcatacttat cgactccttc   36900
ggctaaccgt cgtattcagg agacatatac agcgcgtacc acgcctgtac agggtgctta   36960
cagttgtcgt atgtttgttt atccngcttg ggttaatgag gcagtnggtt acagattaga   37020
attctggtta gccaatattg atcgtcaaca aatttggaat attacccat atgttgaatt    37080 aggtgcaaac tcagcaccct ttaacccacg tggttatggt actatccaaa cactaacata   37140
tgcggttaac ctaaaccaag ttgatggacg attcctacca gttcgatttg catctacttt   37200
ccaagtagca ctattgagcg ctggtaataa tcggaatgct aactgggana tctattcacg   37260
ccctgancaa ggtgaagcat atggtcgtga tcttaaagcc gatatngaat ttatcaatgg   37320
taatctttgg gatctccggt tagctaatgg ngcacagtca caagctgcct ggcttaagaa   37380
aatgtacttt gctgctgagc cattaactgg tccaatggaa gctactccnc cnacacctac   37440
gcatttccgg gtgcgtacag tgcataacga gtatgagtat acggtaagtc aatggaatac   37500
tgcnttncgn attaatgctc aagatatggc cgatggtgct ttactacaan tcacctggat   37560
tcgtcgtgag tatgatacng acctacagtt agccattacc gcattacctt gtttacaacg   37620
ttaaatatan ngcccctag gnnnnnccta gggggcttta taacgtcttt taacacatta   37680
tccatatgag actatacttt acaattgccg ttcaatacgg ctttattatg gcacattaaa   37740
ataagtacct taaagggcag tgtatggacg ttatacttt caatagtgat tgggataaat    37800
actacagcgc tagtgttgat cttactacta aaaataaatc ntttataaag ttagcnttna   37860
cttataaaaa gatgggtatt aaaaattaca aatttatact agctatattg gaccaaggtt   37920
taattggggt ggatccatat gaccctaatc ttagcgaaga aatgaagttn cgtattaaca   37980
tggaatgcaa atataatcct tggtattttt ttagggaagt ggcaagaatc cccctaact    38040 cgggtaataa nccaattcca ttccaagcta accgtggtaa tattgcttta ttctggtgtt   38100
atttcaatca cgtagatttt ggtttattac agcctcgtca gacaggtaag tccgtatcaa   38160
ctgacgtgct caatacaggc atgatgtata tctggggnga gaacactaag attaanctta   38220
ttactaaaga taacaaacta cgnaatgcta acatcgagcg tctaaaagta atgcgtgatt   38280
tgttaccaga gtatatccac tatacngatc cattagatgc ggataactcc gaattgatga   38340
catgtattag attaggtaat aggtatntaa cagctgttgg tcgaaatgat gttaacgcag   38400
ctgataaatt aggtcgtggt cttactgtac caaatatgca ctttgacgaa cttgcctata   38460
ttaacttaat tggtgtttca ctacctgttg cacttgcntc aggttcagca gctcgtgatg   38520
aagctcgccg tgagaaccag ccttatggta acatctatac aactacagct ggtaacatca   38580
ctacccgtga tggtgaattt gcatatcact tcttaacagg tggntgccca tggtcagagg   38640
aattctttga tctaccagat cagaaaactc tacatcgtgt tgtagaaaaa ggcactactg   38700
gaaagaaacc tctagtttat ggtgcattta accaccgtca attaggacgt accgatgagt   38760
ggttatataa cacacttcgt gaatcaggtt cattcggtga aattgccgat agggacttct   38820
tcaatatctg gacagttggt ggtgaaggtt caccttatc atcagatgag aaagataaac    38880
ttaaaaacaa tatgcgtgag ccaagctgga cagaaatcac ngatgatggt tanacacttc   38940
gttggtatat accaaaagan gaagtagcct cacggatgat gaagggtagg ttcgttatgg   39000
gtaccgaccc atctgaactt cttggtgaag ataatgacgc cactggcaca gttgtagttg   39060
acgtagaaac acatgaggtt atgtgtgttg gnagatacaa tgaatcatca gtnccatcaa   39120
```

```
tgggtaatttt ctttgcaaca atgctattna natatcctaa tattctttgg ataccagaac    39180
gtaaatcaat aggtatatcg ttaattgacc atgttatctt gattctncat actaaaggan    39240
tagatccatt ccggcgtatc tttaacagaa ttgtcaatga atcatcagaa agagaaaatg    39300
atttcagaga cattcaaact ccgntatcag caagacaacc atcgttntat gataggttta    39360
aacgttattt tggctatgca acgtcaggta ctggcgagta ttctcgtgat aatctattta    39420
aggtggcatt accatcagca atgcattatg gggtaaggac catctatgat aaaccactta    39480
gcacggagtt attagcactt actatccgta atggtagaat tgaccatgct aaggggaacc    39540
atgangactt agtggtatca ttattattag cccantggtt attaatacaa ggtaagaatt    39600
tatcttatta tggtatcaat gttcccatct taggtaaatc aaaattacgt gataaagaac    39660
caagncaact tgaaaaatat catgaagaga aagaacagca aggtcgnaaa gaatttgaag    39720
agataattga ncagcttcgc ggtgaaaaga acccgatgat tgcagctaaa ttagaaatgc    39780
gnttgaaaca attgtctaaa cgtgttaata ttgatgatan cagtggtgta ggtattgatg    39840
ccatgttaaa tcaagctcgt gcagagcgta cacgtagagt gcgtattaac agatattcta    39900
gaaatagttg gtattaaaca aaaaaaataa taatacgtta ccctcttcgc aatgaagagg    39960
gtatttgaag ttaagnaact ctagcgaaca aaagattact ggagttagaa ttaatatgat    40020
agttagacga tccgtcaatc catttagcat cggaaatctt gtttacaagc tgaccattgc    40080
caatgtaacc taggaaagtt ttattatcat atacagcaat tttgattagc tcatttcgtc    40140
cgtagactag tggcttacca ttgaatgctg ttacttctaa accagacatg tatccataaa    40200
ttggatcagg tctggaactt gtttcaaaga ctttcattcg aagtctcatc tgcaagaaag    40260 cccatttttgg gcaaaaaatg tcaagcttaa acttgacgac atatagccct cctggtgcga    40320
caggagggct aatctttttca gaacgtacgg tgttgttata atactgctag cgaaaatacc    40380
catgataggt aagtagctaa tccgcagttc tcttggatga tacctactga cagtgtagtt    40440
gcaaatgtgc tgtttggaac cccactggtt tagcggccag tgggaattcc ttttatgccg    40500 cttttttcttt ctttactgga tatttcttat atttacaaac ccacgttctt acgctggtag    40560
gtatcttcct tcttattata ttcgtagttc tcgatgaggc acttgttgct gaactcgacc    40620
atcgaacaca tcttgtccat gatgacttca gatatttacc atgttcataa attcggcgta    40680
gttgtagccg gtattcatgt cgagatagtc ttgttcgacc atatcgtcat tcaggtactt    40740
gacgtaagcc tcggcgtgag cagtggctac cgacttggtg aagaagtaac gagcgtgctg    40800
acggttctgt tcgaactgac gcagattagt agtggcctga ccgccgaaac cattgacctc    40860
cattaccccg taaacagtac gatcatccag agtagtgatc tgtgcaatca ctacacgaga    40920 agcatttttcc gaatggtcga tgaacgtcat actgtaaatc tcgatttctt tgaagtcttc    40980
cattagaatt tcctgttaaa aaaatgaata dacaacccct accttcgggt aggggcttta    41040
tgccgtcaac cgacaataag gtcccgaatc gttacgatct aggtatcaga tgcaggttta    41100
gtcaaacgag ttacacgaat ataaaccatg tagtcactca gagatagaac tttttcactt    41160
atacatcttc cagcgtcatg attacgacat gataaggact atcagcattg tgacccatgc    41220
acgtctcgca tttgaagatc cgccacatgc catacgaagg cagctcgcgg tttttcacat    41280
aaacgtagtc gtgcgctgcc acgaggtatt tttgttgaat cgagaattca caagtgatgt    41340 aaccttttttc acggatgaat tcttgagtca tctgatcaaa agtctgtttg agttcatcag    41400
taagagcgac ttgggtttcg aacattgaaa tattcctttt gatatattaa atagtttga    41460 ttatttcgga gttattgaat atttaggtta ccatctgctc tatatagact cggctgattt    41520
```

-continued

```
catttaagta agcgagtgcc aatagaatac cagcccaaat aacaattttt cgagtagtct    41580
gtttttctat tacacctggg tgtgattcac gaatactacg gtgacaaaat acataaaaca    41640
gacacagact cattgtaaca aagataatgg taaaccatcc tagatagatc attttcttca    41700
cctattttta taaatagagt ttatagttta gtcaggcgga tgatttcttc taaagctgca    41760
tcaacttgat aatacggcca tgaatcaaca cgaggttcgt tatcaaagta tgtccaaagt    41820
tgaatacctt ggagtttatt gtagaataca ttgattctga ttccttcatg gccaacaaga    41880
ccttcaatgt aagctgcacc atgcacatac gtaacatgta gtgcgtactc gctatcttca    41940
ccagcgtatt gcataggtct ggagtagatg aaggaataag gattaaatgg atcagcctga    42000
gtgatatgtt cgaagaattc tttcaaacta gattttttca tattggacat tatattttcc    42060
tcatgattta ttaagtctat cttctaggag gtagacttaa tactattcga tgttatttta    42120
agacgcctgc cttgtaacct ttaacaacag ttctagcttc taatgcactg atttcgccaa    42180
tgtgtttacg cagtgcttta atagcgttga tggtaggttc attatccgcg atatgtcgcc    42240
agtttccctt acccttaatg agttcaacat cctggacata tagaccatct ttaactagat    42300
ccattgtttc taccaacttt tcgacttctt tagttagatg cgtatgaaga ctggcgaggg    42360
acatgtcagt catttgatgc acatcataga gaaatcccta ttatcagaag acgataaaat    42420
ttctttggtg agtttattta cagtgtcaat gtttgctgca attgaaacta gcagtgcagc    42480
atatttctct gcattataat tcattaatac gtattcctat ttaaaattgg atttagtgta    42540
atgcggtaat actgcgaata tctaattcat gtaaatcata tttctttagg aactcattca    42600
ccgcttgctg aatggtgtac ccactcggag attcccactg agtaccatta aaagcaataa    42660
tacgataacc taccattttt tattcctcta atcacaaaat aaatacccte ccgaaggagg    42720 gtatttatat cgttaccaat tgattacagc gacaaactca aatacccgac acaattcttt    42780
atcacgatgg gcatgatgaa aagatttacc ttcaataccg caatacggat aaaacaattt    42840
tcggtgttcc gtgtcgccga accagaaggt ggtgttattg gaatcaacca caccatggat    42900
agccacatca cgaatgtact gaaatacatg aactgcctta tcagtgatca ctcgaagttc    42960
tacaccgtgt tccttcatca tagccaggat gtcttccttg gtgtaatctg cttgttcagc    43020
attggtcatg atcttgtgag tcagagaacg cttttccttg tcaccgaaac agatacagac    43080
caattgcacc aactgacctt ctaccttgag accactggtc ggttttagta gaacgaactc    43140
atcatatttg taatcattgg tgacaatcag tgccgactta ttgcgagtga caatgcctag    43200
gttatacgac ataattaatc ttcctcattt tagaatatgt tgaaccttgt ggatgtcttc    43260
caggctatga ccaagaccag tggctttgta agaatgttcc tgatcaacac gcttgtgata    43320
tgcaagcagt gcatctactg gatgttcagc gaagaagtat tcagtgttgt tgcagtccca    43380
agcgaactcc cattcaccat cacgaatctc tattttgtta gcactgaggt aagtgatatt    43440
gatggtattt acagtggcat taccaccaat gaggtagtac gatccttcat tgctacgaac    43500
atcgatcctg ccgccatcga tagtatcctg atagtagaaa ccacggtcga agaataactt    43560
cagcatcgaa gtgaagtagc tgttcaatac agcttgagca tctttctctt cgaccaccca    43620
ttttccatca acgatgttat tcaggtaatt acgatcatga ttgatcccga cattatccac    43680
gatgtcagcg tagttcttat ggaacttagc aatctcgtac aaacgttcca gagcagcaaa    43740
acggaaaggg ctggtgggat gcagagccag aatgatccga cctacgctcc acaaaccggt    43800
cccgttgacc tcgtaacttt cttcgaggta acctttgata ccacagttaa cttcaagttc    43860
```

```
atctgctggg aaaccggtgc ggagccgcct acggatagcc aatagtaccg attcggattc   43920
ttccggatcg aacaggtcta tgccgaaagt aatccagcta ccacgtactt tgtgctggta   43980
tgccaggcgt acagtatcac cgaatggaga aatgaaccag cgttcgtctt ccgatacgac   44040
caaatggcaa ccacattgcc acagggtact tagaggatcg ttagaggcga gaatgcgctt   44100
ggtgtcgttc atatccgacg aagtagcatc tggactgcca tgtaggtgtg tcagaataaa   44160
cagaagcgat gattctgtag tttgagcact caacattgcg cgagtgatgg ttgcattgat   44220
gatcatgaga tatcttcctt tttacagttt atgaatatat tgctaaataa aaaaatatta   44280
cgatgtagaa aataaaaggg agtccgaaga ctcccattat tgcgtgtaat ctatttgatg   44340
ataaccgctt tagaaagagt ttccatactt ccaataacta atttggattt ctcttcttca   44400
gggttcncca ttgcttcacg caggagttca ccaatagttt tgggttgaac atcatcactg   44460
atttcacgcg agcatgccga gtcgtcgtac atatcaaaca cattcagatc atcatcatcc   44520
aggggcgtgc tgtcattcca tgaatagctt gattcatccg aggtatcatc agactcacca   44580
tactgttcac tgaggtcacg gtccagttca gcctcataca tctcgctaat tgctttatcg   44640
tcttcttctt gcgccttacg acgagaagtc ttgtagaacg gaagcaggcg ttgcaggact   44700
ttatggaact tcttcttgct gatcaaccag ctaacagagt agcgagacag ctttacttca   44760
gctgctttga tagtcggatc ggagtacagc gccatgacta gcttgtccag tttgtgcaga   44820
tgatctttaa acgagtttgc ataagcagga tgttcccgaa gagtgaacat cacaaacgaa   44880
cgcatgtcag tgatatagta ctgactgtga tgtttgttga tttcgatgta taccggatct   44940
actgcgcggt tataatcgaa ttcctctgcc caggtaaggc tacgtacttt agtaggacga   45000
ggaccttctg cccaacgaac agtcggatgt ttctcacgga tgttccaacc atgattgcga   45060
tcatactcgg ttgactcttc tttgaaccag gtgaaattac cttcaccgcg cgatacaata   45120
ccacggcacc aactgacgtt gattgccttg ttacggcttt cagtaagatc acagggcatg   45180
tccagaatag cgacataact gttatgacca ttggccacaa cgccgagaac agtagcttcg   45240
aatgtctcgt agcgctgtcc aggatacaca cgttcattct catccaggta acgaagggag   45300
caggattcga agatagcacg agtaccggca gggaaatggg cacgaccgaa aggttgttcg   45360 gccttcttt ctttacgacg gctgataacc cattccagtt tttctttggt cagacgggtt   45420
acgggttcac gatactgttt catggtaatt tcctttttac gattgattgg gttgagtaca   45480
tctcaatgca tccttttcaa gacgcattga gatggggtct ccgaagagac ccatctatta   45540
ttcttgggtc agttccccaa gacgaccttc ggctttcatg cgacggattt ccagagatgga   45600 tttaccgtac atttttggcca gttctttcac agtaccttca ggcacaggtt tgttcatgtc   45660
gcggaagttc tgcttagcga tattgtaacg ctgatgttga agagtcttca gttccgaacg   45720
taccagagcg ttaccggcac attgggagat gaatgtaacc atgaaggtct tcagcttgcc   45780
acggtagacg ttgacccaag cacaggactc atccacgtgg atgttcttgt actcggaaac   45840
cttggcgtat tccagcaggc cgacggcatc gggaccgttg tcctgataaa ccatcttgtt   45900
gaacaggccc agggcgatat cggaggaacg ctcacctttt atgaaggcga tggcgtcttc   45960
gatgatcttg gttccaggt cttgtgtactt gaccgggtcg ttcttgatca acagtagcat   46020
ggcgtcgacc ttgacagtca aacccatgtc ggcaccgcgt cgatcgatca actcgttgtg   46080
ctgtttctgc gtgaacacgg gatctatgtt cttgaaagct ttcaggagac gctgttccat   46140
ttacttgtcc tcttttgacgt tgaatgcata catggtacat ttcggcttag ccgggtgttg   46200
gcaccactct ttagatacct tgccctcagg tttagtgaga tcgtaataga actcaccacc   46260
```

```
tgcggcagcg ataccatca gtactgcaat gaatcccatt ccgatcttta ctttcatttg    46320
gcaatgatcc gttgtacgaa gtgttgaagg ttggctacca ggcgttcgaa ttcttcttcg    46380
gttacctggt cacgatgcga ttccagaagt acttctactt ccggcaggac gttcatggcg    46440
atatccaact ggatacggct gatgaactct tccgttgtga tatttcgatc acgacgaata    46500
cgacttacca gcttgcgatg ttgttcgctg ttgcggtagg tngagatctt atcgataaga    46560
atatcagaga tactgctttc gatctgttcg gctacagcct gaccgtcttc ctttacgtta    46620
gctttgaccg cgaggatggc agcaacggct gttgcgccaa ctgccagtgc aataagacca    46680
agtgcgtttt ctttgatgaa gttcatattg attatccttt caaagttgca tcatcattga    46740
agatatcagg acccaccgag agacttccca gaagatccgg agcaatgtaa acagagttga    46800
gggtttcgta tacaccggta acagcatcta cgttaaccag gctagaactg cgcatgggta    46860
cccattcacc gttacggaag gcttcaccga ccagtacacg aacatcatct acgtcagtgc    46920
ggttcggcca tagatcctta ccttctacta ttttacatt acgagcatgg tagaccagtt     46980
taccattcat gcgagcaacg atattcggac ggcacatgtt gtcgattact ttaactgcta    47040
cggacttttc catttttatt tctctattta gttacgagca tttcttgacc attgggaccg    47100
atacgatgac cgaggataac agtttcatta gaaatagttt gctcttcaaa cttagcgttt    47160
acaaacagtc caccaaaagt caaaccaata accactagtg cgaatgcttt catttttaaa    47220
gtcccttttt acattaattg aaggttaaat atcaagttag taatatactg tttaaatatg    47280
gtttgaataa gggagtagta gttattacat atcgtgcagg taggtctcat caatgatggc    47340
acgggctagc tcaatgagac tatcttcatc aacaacaatg ttaccatctt tccaggtagc    47400
gctatgggat aaccagttac ggtaatcctt acctcgtaca ggattgatgc atacctgacg    47460
agtagctgca tcacggtcac cacggaaacc catgatagca cgtgcacgac ggattgcttc    47520
tttctccaag tcttcgtcag atttaaaagt caggaaagtt gtcatagttt gattccttt     47580 tactgattta ataggtttaa ttacactgtt gtgatatact ggttaaaatg gtttgaatgt    47640
attatttcat ttccacagac gacaatagtc atctacatgt cgagtgattt ctgcaacagc    47700
cctgagtcgc cggcggccag ttaatttaga gcagtgttta ttaactaatg tatcaacagt    47760
tttacgtaac ctaacacagc gttcttcatt aggtatatct tgttcgataa acaggctagt    47820
taatttatgg atttccatat ggattttctt acatacatcg ttagccgatt tcttcatttt    47880
aatttgttgt atgattcgac taacttaaca atagttgtag caacagtagt tgcggcaaca    47940
aaaatttgaa taccattgat aaaattttta ttaaacattt ttaaactcca actaatgtat    48000
taaaaaaata tgtctatatt gaaaataaag ccctccccga agggagggtg tatgtcgcca    48060
ataagtgtta ctaattttatt tagttagttt gaccatacgt tctttcaaag ttgtttacat    48120
cataacctga gtggtgtgtt gcagaaccac ctgaagtagt atctataatc ttaactacca    48180
cttcatcatt ttcaatgtaa accgacagtt tatctcgcat aaaatccacg tggtcatttc    48240
gataacgtag atatttcatt acagcttcgc cactgatttt actgttagcc attattattt    48300
cctcgattga ttccagttaa aattatcttt tgcatttta gtgaagaacc cgttaccccca    48360 accaaatgag tatctaaagt ccttgattac accaacatcc gaatcgataa ccttatattc    48420
aatgacttta tcactattct ccagaatgac taagatcgcg ataagatctt taggatcacc    48480
tacagtcaat tcatgtcttt cagactcgtc tctgtggata acgatgtaca tggtacttta    48540
tcctctaatt atacccattt agttactggg agttcgaagg tttcacacaa gtcgagtact    48600
```

```
ttacgatgtt ccaagttatt ttctggatag aaggtaatgg gtgtagtcgg actacccaa   48660 ttaacacgac atccagtttc tttatggatt tcgccaagta cagtatatgc acctgcccca   48720
tctgcataac ccatttgatt agggttaacg cagatttgag taaaacgctc cgtcaatact   48780
cgattaatag tgatggtcaa gagacgaacg aactcacgag tcttctcgat gtcgtctacc   48840
cagaattcca gaaggatcca tttcccatga gggttatcat gcccaccttg aagaataca   48900 cagaaacctt cttttgcctt ataaaactcg tgattggtaa tgttacattc aaccatttgt   48960
ttcactgcat gccatacacg ctcggtgaca taatcaccat aaagttcgat gcagtgacca   49020
cggccaggga attgttcttt tttagaaaat ttaatttcga acatggtata gattccttt   49080 tacattaatt gaaggttaaa tatcaagtta gtaatatact gtttaaaatg gtttgaatgt   49140
attatcggta ggggagggtt acccttttaa cttttaata ctattggata agtacatgac   49200
actacggaaa atttttgaatc ttgaaaagta ttcacgtact tctttttag tcaatacaag   49260 tcttccatct ttgtttacat tatcaccaaa gacaatttcc tgagtattct tccataaaga   49320
tctataaaga taacagccat gtggtgcatc acaccaatca tagatcttaa gttcaaattc   49380
aactttgtcg acaatatcat catcaaataa aatagtattt cctttactat ttaattccat   49440
taactcattt gcacaattta ttgcaaactc aaccgctgcc caggttctac caccgctgaa   49500
catatcttta cttaatttat ttagatcgat agcattataa gttgtttct tagtgttttt   49560 catggactgc accctcaat aataaataga ataatctgta tttaattcac ctttgtaata   49620
tactttaaat acatttgaat acatgacata aagccttccc ctggggaagg ctattattat   49680
gttttaatcc aatgggtata tgtacatagg tcagtttctt taataatggt tgatttccat   49740
ttatcccatt taatgatttc tttagggaaa taaacacaac tactattatc natttccatc   49800
ttgacagtag taatgtacat ttcgtctaaa atatcctttt caatgacttc tttataaagt   49860
tgagaaccgc caatgatcca tacatccttt ccagtttctt tattgaaatg agtggcataa   49920
acaatagctg cacttagatt agggagtaca cctaatttat tatcataggc tactggataa   49980
ttaccgttac gatataaact tgatgataca acaatgttat tacgattagg taacggttta   50040
ctacctaagg ataagaaagt atttttaccc atgataacac agcaaccagt tgtcatttct   50100
ttaaagaaag ctaaatcctc aggtatatgc caaggtaata gattattata tccaatgaca   50160
ccatttaggt catgggcaac gattaatta atagccatta attttcctta ggccagaatt   50220
tacaagatac ttcattatct ttaaattcaa tagcccaact acagcaagtg aaattagttt   50280
taaacttaaa tgtagacgct aataggtaat taatttgagc catttgtaat agcgttaatt   50340
caccatatac tttctcatca atcaatacac caggtctttt atgtttaata actaattcat   50400
tcaacttaat atcttgttca atatagaggt attccacttc gccttttct agtataggca   50460 tgtcccaaag aatcagacta atctgttgtg tgaattcctc aatactagtt gtaatatcta   50520
gtccttcata acctatcaat agatttataa gtacttgtag actaatcaga ttaacaggta   50580
agtcttttaa atcgtcttct ttaatagttg ttctaaaata aacagtgcca tctaagtttt   50640
taactaataa tctatttaat agatgattga cttctgattt aatctgataa tccagtttga   50700
tcattagcta actccttgag tctagtcatg ccattactaa cttcaataat gtaactaaag   50760
tcaaaactat atttcatcat tttgaattct tctttaaagt tagcgatatt tccagacaga   50820
gcaatttgtt caaatcgact aaaatcagta atagtttcat cgaacattag ttctcttgcg   50880
gtaatatctg gatcatagtt aggatgatca actcagtac cttcgtggtt taaagtacct   50940
tgaaaattca aagtcttttt aacatggtct acagttattt tccaactagt tgcaatatac   51000
```

```
cgagctttaa ctaaattagg agcatacctg taaatacacc attgtaatgg agtgccaaca    51060
gtttgcgtat catgcgtggc ttttataact ttaataaaat tctcaagttg atcaaatgta    51120
acattcctag ttacaccatc attagtggtt atattaagag atggtcgaag accagtacca    51180
agatcattgg tgatgattat atcctcaact aaagcttcat ataactttag tccttctttt    51240
ctggatccaa catcattacc cattgtttag cttcctcttt tgttaccagt tgataaagtt    51300
tattaaattc acgttgacgc attaatttgt aatctagtat acgcccatta tttttacgaa    51360
ttaaaataat aaaatcaccc ggacagacaa ttttatcttt atctgggcct acacgtaaaa    51420
taccatgact agattcagtt agattacata atgggcaaat cgcattacta agagtagact    51480
ctttagtagg tatagcataa ccaacaatag caccttggtt gatattattg ataacgccat    51540
caccaggtat atcaccgttc ttttccatt cgattgcttc aattggatcg gtgtatttcg    51600
gtagataaaa agacattctt aattaactcc gataaataat agtagtatag taaaaagcac    51660
ttaggtatat ttctatttta agctatattg ttgataaaat aaaacctaag ggtacatagt    51720
gggttattat ttaaagctct taaatagcat ggtagaacga tattggacta tatagctgta    51780
acccttaagg cactaaggct acagaggttt ttaagataaa gatatccaat gtaccataat    51840
atgcttttac aatagatcaa ctaaattcat ttaaatggg tcgtaaaaat acttagttga    51900
tctaaagata tgttgaatac tttttcacat gaacttacga ctcacaattg gaaattaaca    51960
atgttaaaaa ctatcattaa actagacggt actgaagaag catactcacc tgctaagatt    52020
aatggttggg gtgaatgggc agcccaacat cttggcgata aggtggattg gagtagtgtt    52080
gtgatggatg ctgttcaagc tcttggtgat aaaacttcat cacaagaact acaattacaa    52140
cttattgaag aatgtttaaa tcgtaagaca tggtcttatt atctaatggc tggtagacta    52200
tatgcgattt atcttcgtaa gaagttctat ggtctaaatg gcatcccaac tgttaaagcg    52260 cttcaaaacca ggatgcgtaa agatggtatc attgttaaat tagattatag tagtaaagaa    52320
tacgctcaga ttgaaaagat cattgatcac gatcttgacc tactttgtcc gcattttca    52380 cttcatcaca ttcgtggaaa gtatgctcta cgtaatcgta aaactggtca agaatatgag    52440
actgcccagt ttgtatatat gcgaatggca atggctctag ctgaaaaaga gccagctgaa    52500
actcgcatga ctcatgtgga gaattactat aaactacttt ctaataaaat tcttagtgcg    52560
ccaacaccta actacgttaa cctaggtact aagcttcgtg gttttgcatc atgttgccta    52620
tttgcttctg gtgataatgg tgtatcactg gcaatgggcg attatattgc taacatcatg    52680
acccaatcat cagcaggcat aggtgttaac ttaatgacta ggtcaattgg tgatcctatc    52740
cgtaatggcc taatcattca ccaaggtaag aaaccataca tcgatgtaat tggtaaagca    52800
gtaagggcta acctacaaaa tggtcgaggt ggtgctgtta cgtgttacta cagtgctttc    52860
gatcctgaag cagatatgat tactcagcta cgtaatccac gttctactga ggataggaag    52920
aaccgtgatc ttcactatgc attcctaagt aataagttct ttgctaagaa agcagctcag    52980
aaagatggta tgatctttgt attcaatcca tttactgctc cagatctaca tgatgctttc    53040
tatagtggtg atattgataa gtttattaag ctttatgaaa aatatgaagc ggatcctaaa    53100
tttgagaaaa cttatgtaaa tgctcgggat cttctcaaat caatgctagt tgaagcatat    53160
gagactggaa ccatctattc agctcaaatt gatgaactca atcatcatac accatttaaa    53220
gaacctattt acagttctaa cctatgcctt gaaatcgcag aacccactaa gccttactat    53280
cgaatggaag atctttattc tagtgaggat cacgggcgcg gtgagattgc tacttgttca    53340
```

```
ctggctgcta ttgcagtgga taacgttcct gataagcaaa cttatgaaat ggcggcttac   53400
tacgcactta agatgattga ctattgtatc cttaatgcag agtatgcttt cccacacctt   53460
gcactaaccg ctaagaatcg aatgagtgct ggtgttggta tcatgggtct agccacacat   53520
atggcacgtg ctggccttaa atatagcagc gatgctggta agctgaaat ccacttcatt    53580 gctgaacggc atatgtactt ccttatcaag gcgtcactta agatttctaa agaacgcggg   53640
aatgcgcctt ggattcataa gactaaatgg ccagagggat ggactccacg taagacttat   53700
aataagtcag tggatactat cattgaaggt ggctttgaag aactttatcc atgggatgag   53760
ctagagaaag aaattaagga gaatggtggt attgcacact ccgtactagc tgcatacatg   53820
cctggtgagg catcatctaa agcactaggg tcaactaatg gtccatatcc ggtacgtcgt   53880
ctaattctga ataagactga taatggcgca cgtgtgttat gggctgctcc atatggagat   53940
gatgattcct atgtgtatga atcagcttat gatatcccca ctaaagatct tattgactgc   54000
tatgccatta ttcaaaagtg gactgatcaa acaatcagtg cagacctcta tcgacgcatt   54060
gtaggttcgg aaaagatctc ttctaatgaa atgctaagta atcacttcta catggtgaaa   54120
cgtggaatga aaacccggta ttatgtaaat ctagaaacag cggcaggact tgacattaaa   54180
tcacttgaac gtgctgttga ggtaactaat actgaagttg ggtgtgcagg tggttcgtgc   54240
actctttaag tgtatacacc ctcccttaat tgggagggtg ttattcccaa tttatactaa   54300
cctctattat ttattgtaag aaatattttt aaattgtaaa ggaantaaca tgtctactaa   54360
atctcaacta ccaaagaaaa tcttcaatgt tgctaagagt gattatcatc taccggaaat   54420
tattcttgga gatgatccag gtctactaga ttcaatccac actcattatc ctaaaatgtg   54480
ggagctatat aagcgtctaa agatgcttga ttgggatgag ctagaatttg acttttccac   54540
ttgtctagta gaatttgaaa cgtgtgataa atcaacttat gacatgatga ttaagacact   54600
ggcctggcaa tgggaagctg actctgtagc cagtcgttcc attgttaata ttctatcacc   54660
tgtcatgaca gattcacgag tatgggcggg atatgtacgt attaatgata tgaagacgt    54720 acatgcttta acttattctg aaattgtacg taatagcttt aaagatccta agttattct    54780 agacgaaatt cttagggtag aagaagcaca agaacgaatg gttgcagtag cccgcactat   54840
gggtgaagca catgacgcag ttcatgcgta tgctcttaat caggtaccca atgatcaaga   54900
actttacaat aaagtattca tgttcttcat cgctctatat ttcctagaac gtatccagtt   54960
catggcatcc tttgcagtaa cctttgctat tggtcgtact ggtgcattcc agcaaattgc   55020
aaccgctgtt aagaaaattg cccaagacga attcgaaatc catgcacaat atggacaaga   55080
agttattcgt gcactactgg caactgaacg cggtaaactc gcttacagtc aatgtaaaga   55140
taaaatcatt gaactactat gggaaattgt aaagactgaa gttacctgga ttaattatct   55200
attctctgaa ggtcgtgaac taactggtgt taatgcgact aaacttatta actgggtact   55260
tttcaatgct aatgccgcag caacattcct aagtattgaa aatgatgttg tagaacagta   55320
tcaagtggag tttaaagaat cagctggatt tgattttgtt tggccagaga agaacccact   55380
tctttatatg gaagactacc tagatatttc atcaacccaa gcatctcctc aggaagaaga   55440
gaagcctgat tacatggtca acgttgtaaa tgatgttggt gaagaagaag atttgaggt    55500 tgacttctta tgattaagat tatcgcattc gtagttttaa tgtggtccac tgtcctattt   55560
gcagcaactg aagtaaaatc aactacagat ggtattattg cacattcaga atgtcagcta   55620
gttgctaaag atagtagtgt tgtcggcact actgttggag gtgcggttgg agccaccgca   55680
ggcgctgtat taggtcgagc aatctttggt aaatctggag gttgggtagg tggtttaatc   55740
```

| | | | | |
|---|---|---|---|---|
| ggtggtgccg | caggcggcgc | agtcggtaat | aatgttagtg | ctactgaaac | atttcaatgt | 55800 |
| aaactgattg | ttaatacaga | tggcaagcag | tacatggttc | aaacagttac | caatgaaaaa | 55860 |
| ccaaaggttg | gtgataaagt | cactgttgtt | gaaatgaatg | atggtacacg | agatataatg | 55920 |
| tagacataat | gaccctccct | taattgggag | ggtttatgct | aacaattcta | tagcactctt | 55980 |
| attaacagtc | atcaacgaga | gagtagacat | gaataaaatg | ctaaacttcc | taaaccgtac | 56040 |
| gctatatagc | ggtactgaaa | aagtatcttc | aaaagctaca | ccaagtctag | aacactttaa | 56100 |
| aacaaatgtt | gaacaagtag | ataaaaagat | tctacaaccc | tttagtacta | aatttaaaac | 56160 |
| cattctaaaa | gaatgttaca | gtaatgagga | gtgggttgaa | gaacaatcat | ttattgaaga | 56220 |
| acctattgat | cttggttcag | ctgcacgcgg | tcttaccgag | cgcggtatta | tgcgtggtga | 56280 |
| ttggggacgc | ttagcgcatt | ccactattaa | agaagcagaa | ggtatgatgc | gtacttatag | 56340 |
| tggtcgtcta | aatgaagata | tggaggcatc | tgaaattaat | gaagtaattc | aagatatgcc | 56400 |
| ttataacttc | acagctggct | cagctaatac | tagccgttta | gaagaagatg | actctatttt | 56460 |
| tgttgaagca | gatacaactg | tagttgaacc | tctgtctaag | cagactctgc | caaaagtagc | 56520 |
| agagcttact | aatcaattag | tggaagtcta | taaccgaatt | actgaagaat | ttacagaaac | 56580 |
| tggtattgct | aaagttgaac | aagttgaaca | gccagcagtt | cttgtagcac | ttggtgagat | 56640 |
| cattagtagt | tttaataaac | taattgattt | atcttgcggt | gctctaccag | tggaagaaac | 56700 |
| tgttattgta | gaggaggatc | cgttacctgc | cattgttact | ggtccaacta | ctgaacccat | 56760 |
| tgatggtgaa | attctaccgg | ttgatgctat | taataattct | gcggcattag | aagaattcat | 56820 |
| tgaagaagta | ttaagtacta | atccagaatt | cattaaatat | caaagtatga | atgatagtaa | 56880 |
| tattgattca | tatctaactg | gggatgactg | gattatactg | aaattcaaag | atggttctta | 56940 |
| ttatttatac | aatgcccaaa | gtgccggtga | aacgaatata | gaaatcatga | aagatatggc | 57000 |
| cgaaactggt | agtggtctta | atggttttat | aaatcgggtt | attcgtggcg | ggtatgtaga | 57060 |
| gaagtccatc | attaatactc | ccggttttat | acaagtctca | aatgaaggtc | ttatcgattc | 57120 |
| aatcaaaaaa | gttcttggca | tttctaatcg | aggtgatcag | aaacgtatct | ggcgttcatc | 57180 |
| gtccagtgca | agaggatttc | tggaacaact | agaatctaca | tttggcaatc | cacaatggct | 57240 |
| taataagcag | gtattcgtta | ctggcgatat | caatagtaat | ggtatagcta | acgtactgag | 57300 |
| tattaatggt | aaagtcagta | tcgaggatgc | cattcgtgca | gtagaaccat | tcttcaaact | 57360 |
| cgaagaaaag | tctaatcgcg | aaatggagtc | ttacaggcag | aagactaaac | ctgcattgga | 57420 |
| tctactcatt | aagaatgcac | ataacctaga | cgctaacgta | tacaaagaag | caaaggctat | 57480 |
| cgtagacaag | gcacgtgctg | gattcaagac | tagtgttaaa | tggcctgccg | gtactattac | 57540 |
| aggtaagggt | acctataatt | cacctcgcac | cgtggtcgcg | aaatatccat | ctactgatag | 57600 |
| taaactcaaa | gctcttactg | aagaagaagc | agctaaggcc | atgaacttaa | ttatatcggc | 57660 |
| attgaacgt | cagataactc | ttagcttcaa | gttccctgat | ttaccagatc | cactggaagg | 57720 |
| actaatctac | gatatgttgg | ataaccctag | tccaatagct | ggtatcgatt | actatgattg | 57780 |
| gaatgatttg | ttattcgcat | gctttggccc | tgggattgat | gatgatgtga | tggaagttaa | 57840 |
| taaaatgcga | caataccact | cattcattga | tatcatggag | gccgccgcaa | aatgggtaga | 57900 |
| tcggtctata | aaaggtaggt | tagcaatggg | taatgaaaac | taccagtaat | gtatctaata | 57960 |
| ttatgtagaa | ataatccctc | cccttgttt | ctacattagt | cataatagat | cggagccagt | 58020 |
| cccccttcca | actggctccc | agagagtaaa | actctttgct | gggcattaat | gacgatatat | 58080 |

```
cgcctcccct cggggaggct ttatattttg tttttacgta tgtatattaa aatatgtata   58140
aacaacatag agtaattata aaatgatcaa aaatgaactt ttaccagggc taatctatgc   58200
ccaaaaagaa tttgataaaa ttgcagctaa tgtaaaagac tatgataant ataaaagacg   58260
cgaagctggt agggcaagtg ccgtttaag aagtctagtg agcaatattg taaatcagaa    58320
taaaccatcc tcacttgaac atgaaggcaa agttagtact actaatacta atgaatattt   58380
agaagaagtt aataattact tcttaacat taataatatt aaattaattt ctcctaaact    58440
cataaaagag aaattaacaa ttgatctaat gaatatttat gttaaatgga atatgattgg   58500
agtggctggc cgaaatgatg ttccaattat tgaacacaga attaatgatt ggtgcgaagt   58560
gaccgatgtc tacattaatg gtaataagat aacttcttta caatggccac gttgaattta   58620
aaataagttg taataaaata cctagcatta catgttatgt attgaagcac aatgcccgaa   58680
tggtgaaatt ggtaaacaca gaagacttaa aatcttccgg ctacggtctt gtcggttcga   58740
atccgacttc gggcaccaat ttaaatacgg agtgtagcgc agttggtagc gcgcctgctt   58800
tgggagcagg atgtcgggag ttcgagtctc cccactccga ccatttaat aataggtaaa    58860 taggatggat aataaatgga tatcatggga acatcaaatt ataggaacag ctctttacgc   58920
tattcttagt gaccctgaat taactaatat tcaattagct caaggcttac actatctaac   58980
agaagcaaag tcttctgtat tacatgtttg taataaccat attacattca ctgtaaccta   59040
tccacatggc acatttagaa ccaatgtaat tagagagtgc cctgctagtg atacaaatac   59100
attcaaatgg tcaggtgtat tagtccgtca aaaagatgga acattcttac cagaataaat   59160
aaaaagggcc tatagctcag ttggttagag caggcgactc ataatcgctt ggtcgcaggt   59220
tcaagtcctg ctgggcccac catatactag cctcccactt gggggaggtt ttatactgtc   59280
tcattgagga aaacatgaat acagtaataa tgttggtatt atctatcaaa gttggattat   59340
ttggtttcat ttcgactaat gaaagtaata tcctatttga aaatagggaa cagtgtattt   59400
ctcatctgga tattctggaa cataaataca agtctcttga agttattcga aatgagaata   59460
ctctaaagat aaccgaaaga gataaccatt ctatttatat ttttaaatgt ctctaggaaa   59520
atacatggaa catcaanaac aaaaagaact attgagacaa ccattacaaa cactttataa   59580
tcttactttt agtccccgtt tacgtaatgg agcgaaggct cccgattgga ttcacctgac   59640
cgatgaagta accctattcc caaacggatt agatattaca atcaacgctg ttacacgttg   59700
catcaaatgg gaacttatcg gcgaggatgt aagtaacatt acttatgttg aagctatgtt   59760
ctttaataaa ggtcttaaag cagttaaagc ctatctcaaa catacggagt aaatatggat   59820
catctaaccc caacgcagag cgctgtatat ttcacattta ttagccctga gtttataaag   59880
ctaactcttg ttgaatcttt tgtagcgatc cacaagaaac atccagaagt aaagcattgc   59940
gttaagaaaa agattagtgc taatgaaacg cagtttatct ttatcttcaa agatgggact   60000
gataatttaa tcattacacg taaaactgaa ccttgccctg aactggatag cccagtaggc   60060
gatagtatta agttgtccgg cgaagaactt aaaaatattc ttgctaagta cgatcgtccc   60120
aaggatggta actatttcaa gcactggact gatcgcccgt aataaaatat tactggttat   60180
gtaatactat gtaggaagtc atgtccatac gtttgcgctc atagttcagt tggttagaat   60240
acccgcctgt cacgcgggtg gtcagggggtt cgagtcccct tgggcgcgcc atttaattcc   60300
gtgatagctc agtcggtaga gcaagtgact gttaatcact gggtccctgg ttcgagtcca   60360
ggtcacggag ccatattcta aagagtagct tcggctactt ttttatgttg ccatgggtta   60420
tcttatgaat taaaatgatt tacttgagag cacactcatg tttgaattac tattatcncc   60480
```

```
agatataggc gaagagttac ccttggttgg atttaatgaa attattaaat taggtgatct   60540
acctgtagcg ttagctggta caatgtcata tgtggatgga aatacactgt atgttggatc   60600
tggtcatcat actgaaggac aaacagctgc aactgtgttc agacgtttta ccatatcgcc   60660
atttgccgat ataggtgcaa ctgcttctgg aacattctta ccaggggtat ctttaggatt   60720
tgggacatta cataagaata actttattgt ttatggcggt attactggat ggaactcggc   60780
tggtaatggt ggtacgggaa catctaactt tatacaacat tttgatatag ctacaggcaa   60840
tagggttgag cgatatagtg gtcccgtacc actttgggc acagcctccg catcagatgg   60900
taatgatctt attctatgcg ttaacccant tggngtaann gcaatgcgnt taaaaccatc   60960
nngtaagncn tggcttagng gncaaganta ttcaggtggt gctcgttcag gtcaacagtt   61020
attcttttat aatggttact tttaccattt tggtggttgg gataatacaa agaacatacc   61080
taatcttgaa gtttatcgat ataatgcaac taccttaata tgggagcaaa caccttggat   61140
gattatacct gctgataaag gaacaatctg gcaaggtaan ggttatgtag atggngacta   61200
ttttaattac cttaacgctg ttgatgtcgg cggtgtaact aaaatgtttg cacaacgttt   61260
taatattagg cgccggaaat gggctgaacc atttgaacta ggtatcggat tcctnaatat   61320
ttcatctata gctaaaggtc cggataatag catgatcatt gtaggtggat ctaaaatgcc   61380
agttggtggt ggagcanana tgttgaaaag ccaattgtta tcaggtntct atcaggtaaa   61440
actagcacca ttaatcattg attaaaataa taatatttat aactatttag ataattatac   61500
tggcacgatg atattatgta agagtactat antaaagtat tcttaaatct atccactaaa   61560
cacactcggt ggtagaactt attatagagt gtgtctaaat gccaggggtt tgccacccct   61620
ggntatattc attgttacta ttataaattc atttatagat gagaaaaggt tttatcacct   61680
tttcaaaatc ggcatttaat tccagttaaa aaaactgaat ctatgctaca ttgtaataaa   61740
ggagtctatt atgactaact ctaatccgtt tgtaagaact attgtaaagt accaagatat   61800
cctagatgct ttaattcaaa aaacgaatga gaactgggtt aattatcgat ctaattctat   61860
tggncatatt gttattcgtg aatacaggac tgttggatta tttgtaggtc ggcaatgtgg   61920
tagtacaact gcattgattg agtttgctaa tcgtcancct ggcgaatgtc tagctgtatt   61980
tgtagaagat aaaattaaac aggctgtact ggctaagttc cagaatgcta aagataaatat  62040 tgtttcttgt ttaattacac accaactccg naaatatatt catcaacctg aagaatcatc   62100
tattcaaaaa gatattaaag aagaattaat atcgtctgta aaatatattc ttgttgacaa   62160
tgcctcattt aatctgaacc tacgcggtat cactgataaa gaatttaacc agtgggttgc   62220
agatactttt ggtacagagg taatggtggt tcgttttagt tagaattagt aactttgata   62280
gtttctaata agattaacta cacgttattt acataatgtc ataacaagaa ataaataata   62340
ctcagattgt aataatatgt agttattaca tatctatatt aggttgtcag taactcatct   62400
ctaatataaa atcgccataa ttcttccgtg atagctcagt cggtagagca agtgactgtt   62460
acgatttcat tggtaagtac ccgagtggca gcagggagcg gactgttaat ccgttggcga   62520
aagcccaccg taggttcgaa tcctacctta ccagccaaat tctaaagagt agccagctgg   62580 ctactttat cttgttctat agatcgaact agctatctat tttttaaacc ctaggttcga   62640
tatgaaagaa aaaaataatt aatggttatc gggctctgta tttacctgaa catcggcagg   62700
caaaagctaa ccccaaaatg tttggatggg tatacgaaca ccgtgtagtc ggtgaagata   62760
caatcggaag atctctttac gatgacgaag aggttcatca tttggatgag aacaaactca   62820
```

```
ataaccatcc cgataatctt ttgatcctcc ctcaatcaca gcatctaaaa ctacatgcat    62880
ggatgaaacg actgggcatt gatccaaaga actatcctac aaaactttgt ggtgcttgtg    62940
gtagggtaat gaatcataaa ttgattaaat tctgtaaccc tgagtgttct gccaaaggtc    63000
gacgtaaggt tgatcgacca tctaaagaac aactcgtcct tgacgttaca ttgttatctc    63060
ttgtgaaaat aggagaaaag tatggggtat cggataatgc aattcgtaaa tggtgtcggt    63120
catacaaaat caatattcca gctaggttta ttagggtcag cactaatggg ggtattagca    63180
ccttggcccc cacacaataa aaatatactc gatgtagatt aatatacaaa aacataatca    63240
ctgggtccct ggttcnannc caggtcacgg agccaattca tagttttaga tttagttata    63300
tttcactact atgtaaacta taaaggcagc taatgctgcc tttatgtcgt cttgtaaaag    63360
tacccagtag ttgaatctta tagctgaata caaatagggt aaagacatgt cacttaaagc    63420
attgcaagat atagttagta gtgttcctac aaatgaacaa aaggaacgat tagttaaagt    63480
tcggaaaacg atggaagagc taatgagtc tattaagaat cagattcgta ataaacgacc    63540
tagtcaagct cttctcgaca aaacgataaa ctggggtacc aagtatggct aagacattag    63600
ttcgtgcaaa gctgattact gaagctggtc aatggatgtc gtctgactgg gaatgtggtt    63660
tccgtgcatg tcgattcgtg aaacttggta atgatcatgt aaacataaaa gactttgagg    63720
ctatgatcac ggcattcgaa gttggtgaca tgttagtgat ttggccaaat gggcttagaa    63780
cttcgtatag tgtggataat ttcaataagt acttttccca tatcaaagat gaataccatg    63840
agactgatct ccgtccactc ttttacccca gtagttgag cttatgataa ctatattcgt    63900
gtataaatac attacattcg ttataccctt taattgattg aaatcaagct acataaaagt    63960
gatgaatact ttaacccaat gatgtataaa ttaaaaagta tgcacactaa aaatacagat    64020
ggtgtttatt tgatatttt accaacgcct actatcgatg atcaaattaa caccatgcaa    64080
gggtatatta tcaataaatc cggtaatctc attaggacta ctgtacagtc atggcgattt    64140
gagaaaattg aattcaaaga cttagccaaa catgatagac gttggttatt tattgaatat    64200
tacattaatg ttaaacaaac gaaaaataat ataatcaaag agcaacaaga tgaattaact    64260
aaatttattt attatagtac tctaagttaa aacaaataaa aaaataaata taagagctag    64320
cccctaatgg gctagcttta tgttatctta ctctgctaca tctttacat caggtttatt    64380 attccaacgt actgctctcg caataccata cgtaagaata agagcaccca cggtgccaat    64440
agtggtgcta ataataatgc caagagtttt tggntcnata ttcatattta gtntcctatt    64500
tacaattaat agaaaatatt acttttagta atatcannt nntnatatac nntttaaata    64560
ngtttgaata taactttatt tattataata aattaaaata atactttcat atacactata    64620
tgtagaagat tncgccgcta tagctcagct aggtagagca acgcacttgt aatgcgtagg    64680
tcctccgttc gattcggagt ggcggcacca aatttactga ggtttaaact attcttaaat    64740
atattagtta ggatgggatt gaacgngaaa gactcagtaa atcatattgc ccctccatat    64800
ggaggggctt atgtttgtca ttaatcagga aaatataaaa tgagncatct attatttatc    64860
atccaagaat acattactaa taaatttgag ataacacgaa ttgatatgaa gccaggtaat    64920
agaatgttac gtgtatgttt atacggtcaa cataagggaa aaggtttcgt ccgtatagat    64980
ttatggtcag ttggttatcg cattacaaag aaataatact ccagattatt taatatgtat    65040
taatcaaagg agtttataat gagtaatgaa actaactatc taggttatga atggaaaaca    65100
gatataacta cttcaaatct taatagagtg gttgattta atacacttga attaacatgg    65160
ttaaaagaag attttaatga tactcttttt ataaagtctt ataaagtgct agagggtcta    65220
```

```
ttagaggaac cgtctagggc aatccatgat gatacagtan ccattcaaga tcaattagat    65280
gaattaaata ctgtttttaa attagtattt ggaaaagata ataacgtaga gttatcaatt    65340
aataatgatt caattattgt gatcggtgct acagatgcaa ctaaagaaaa gttagaagca    65400
gaggtgcgtg agtttgcata tagaaaatca ttaattgatg aacgttatcc aganattgta    65460
acggattaaa atacttacag ctatctagta tgtaactagg cggattgcca tttgtaaatt    65520
atctatttaa tcgaactgag gaaatactaa tgaaacaatt ctttcaacta cttctaagcc    65580 tactttcaa actaccggtt ctatcatatt ttgctgagaa gaaacgatta gagaaagaga    65640 aaaggaaga agaaaagcgt cagcaagaac aacgtcaaaa agaactactt gatgaacaac    65700
gtcgcgaact agaagatcat tatcgaaaga cggcttacga tcgcctagca aaacttattc    65760
atactcggtg gtatgatgag tttaatgcat acgaaaagaa actagttgat cttgctgtat    65820
cgagtggtaa agcagttagt gttaagtatg gtaaagttac taagatgcag cacccctcatc   65880 aatttaaact acttaatgat tggctggatg atattccagt agaagattat tctaagtgag    65940
tttaaataaa agaaaataaa gacatagccc ctctccannt ggagaggggt ttatgccgta    66000
attatacact tactttgata agatttttaa tatcagtnaa atgggtatat gttgcctttt    66060
tatctttgtg aaccagtang caacaggtnc cttcatttac ngtattggtt tgttttaatg    66120
ggatatttaa agcatattca aanagatcat ccatccagtt aaatnccatg aacttattga    66180
taaggacatg atcgaaatca attaatncaa taaacgaatc gatctcanat tgataatact    66240
ctacaaccat tttagaccat tctttgttta tngcctcaat gacattagga ttatttattt    66300
tattaaataa ctcantncgt tcctnagtag gtaaactgag gtaataatta atattactcc    66360
taacgatatc tggattagtg atatcnattt tttctggtaa gttatattta ctatctacat    66420
aattcttagt ttctggtgtc attctccagc aaccataatc agcagtagta cttgatggat    66480
ctattttagt ctccactact ttagaaaata catctacata taaattaaca gattcgtata    66540
catcaggtct gattggatta aagtttaaac ttttaataag accccctaact ggccgagtac    66600 caattagaca atgcaattca agcttaacat tttcctcttt agccatctta aatanatcag    66660
caaaactgag cttttctgcc atttagaata tacctttat taattggaca aatagattag    66720
atacacatag caatagaata aaccataaac ctagtctttg taatttatct atacgcttag    66780 cttttttgttt cctctttaat ctaactaata atgtattttt aatatcattc attaaattat    66840
ctcagatttt tagacggtgt ataaaccctc agtattacat gttgttatga tattgtaaag    66900
acgatgccaa tagcgatcat acgtattttt acgtttgtag ctattggtnc ggatgactag    66960
attggcgacc cagtgattct gatcaatggt ctcatgtaga tgcccgaaat aagccccag    67020 ttcaatttcg aatgggatct tacactcacg ccccttacac attgcttcac gcaataaacg    67080
cattgcagaa ttctctgcat tggtatcttt aaataaaaga ctaatgtatc cagggctacc    67140
accagtttct tcatcaacat ggcctgaaca gcaataaata gttgcaacat tgataaattg    67200
attaaaccat ttaattaatg gcctacatgc ttcatcaata agatcttcat attcaggttt    67260
atacattact ttaacagtat catctgcacg ttgtttcaca tgatgaaaat attgctccca    67320
atttacatta gtgtaatata gcatatccat attagaatta ctcatacaaa tcaacccccat   67380 atgttattgg catattcgcg gtcattgaaa atgcgggtaa gatccatccg cttttgaatg    67440
cgcgctagta tccattttag ttgtttagtt gatagttctt gattttgctt gtactcacct    67500
gtagcatgga tgtaataatc aaatttacga cttacagtag tagtatgtgc acatgcaata    67560
```

```
gcaaatgctt caagtgcagt tagtttggtt gatccattat cattacaatt agggataaac   67620
tcaagtacac tattaactgc atctacacca ctacccaaat gagcccaatc tttcttggtg   67680
atgttgatac ccatgtcttt aagaataact gtatatatgt caccattctc catagtgaac   67740
atcatagaag tattaccatt aaacaacctg cgttctatga ctggcaagat atttacttca   67800
actttaaacc aatcagctaa atcaacacct gcggtaaggg cattcaatag atcataaaca   67860
ttatctatag ttccagcaaa agccatagtt ttaacacgtt taccttgcca agtaactgtc   67920
ggatgaaaaa ttatcttgtg gcaatcattg taatatacat ctacaccttc agctttagca   67980
gttagatcaa tataaccgtt atctaatact ggaagtcgcc caatgctatc agttgcatta   68040
ttccgctcaa ttaataggca gtctgcaatc atgactttac catcatttac gatatatgtc   68100
attttcactc cttataataa aataaatagg cttaagcgaa ataaagccct ccccgaaggg   68160
agggcattat caataggtgg gatctcggcg gcaccttcat ttgcggacgg gaacgctgaa   68220
gggagatagt ccgggagatc ccgatttggg tattctttac atatggtatt actgcaagta   68280
tttgttcccc gcagtataat caccattgat ccaattttg attacaacac tgatcccttc   68340
attttcttta acgtaacccc ccaactcaag atcgattgat tgataagcta cagccgccag   68400
tgttaaccga agataaacgg atccatcttt ttcgatatcg taggatacta cgaacccgtc   68460
ttgtagattt gtagctggaa tgtattagca tgttgtggat ggagacgatc catattgtac   68520
tcgacgacat ctagtagata ttgccgagca tcagcagcat tatcaaatcc gagancgcac   68580
agaccgatcg gatagcgagc ttgcgtgcat gtaactttca tagatactac acgatgttgt   68640
ttgcacatta tattttcctc ttagatgtca aaaccctccc gatcagggga gggtatctca   68700
ttggtacttc ttcagcaaaa ctgaaactaa gataaaagag caatcgtaaa ggaactacat   68760
agaatagtgt atttctttta ctattttttac acaacctctt tagatggggg ttctttatga   68820
atccagtcta aagttgttgg taaactatta tctgatctga aggtacacac cgtccggaac   68880
cgagagtgat caactacaga taattgcccg ttaatcgcag cctcatattg cctacacaac   68940
ttcacacacc ttttctctag atcagttggt tcgtaacctt cttctcttgg ttcagtgtat   69000
ggtccatccc aaaagaatat taatctaaga tcaatcccag atttatactc cgcttggtat   69060
gaatattgnt gaacatcaaa atcatctaat tcttcaacta gatgtgatgt tattgttcta   69120
ggntgttcat gagttaattc actgtatata tgtttatttc tagggttttg taaatcaact   69180
acgataagtt gactagtcat tttaactttt atccagatgt ctattacgag tgcgttccac   69240
tgctgtaggt tcgacagtgg ctcgcggtag ataagtaatc tccgggaaag tcttattaag   69300
agcatcttca attagctctt tagcaatctc tgcatcgatg taatggttta gaataatacc   69360
acgatgatac aggaagaagc tgtattcatc ataaccatgg cgaagactta ctttaccacg   69420
atacccacca taggttagag tatcttcgtt aattcattcc gataaatatc aagttggata   69480
ttattttgaa gatgcatttg aatgaagtca ttactatcac cgccgaatag ggttggtcgt   69540
ttccgaccag taacaacatc ttggatggaa tccattagtc ggttaatgtc tgtttctaat   69600
cgttggatat cacattgaga attcattgct tcatggaaac gagttacaac tgcattgaat   69660
tcttcttcag tccaaccact ggtacgtttt cataatcaac aatgataata ccgaaccagg   69720
cataaccgtt agaatgttta ctttaacaca tagatgaggt acattatcag cacctgactg   69780
atggttaaca gtgtaattat tattacggct gattactagt ttgataaaag gtagactaat   69840
gattgacgcc atgaaaatat tccttttgta ttttttaaat taaagtagga gttattattg   69900
agtttcaact caatacatca ataactccag tatgttttca aaattaaata catgtattta   69960
```

```
cagttacatt gtaaccagtt agttttgcca acaatacaaa ttagcgaacc tgttcgattt      70020
tttcagaaac aatgaaaata tgtgcaatac gatcctcatc aanataccga tatcgaaatg      70080
aggtataact agatgacaca tccgtatcgt ttaaataggt gatattaaaa tcatctactt      70140
ccctaccatt agcagccgca acggtattta gaatgttgag tagactcatt ttacagattc      70200 cttttttagta tattaatatt tcaatagact attgataaaa gcattagggt cataacggtt      70260
atttgaaaaa gccgccatta catcacaccc tggctgatct ttaaatctga tatcttcagg      70320
aatatcgaag tcagggaaca ttagtttaat atactcccta acttcttgat ctcgtagata      70380
tggaatctcc accatgtaat caacgcgacc tttccttaga agtgctttat caatattctc      70440
aggatggttt gtagttagaa tggtcatagt ctcatctagt ggaacaatgc catctagccc      70500
atttaataga gctgacaaag ttaatccgct agctggttgt tcatacgtga ttccattctt      70560
catgcatttc tttaatttcc accatcggcg aattgtggta ataatggat cttttcatc       70620 ggcccatttg aaacacccag ttcagccata gcataagcac ttatcccaaa accttgatca      70680
tcgctatttt catcaaagat atagatggtg tcattaaccc aactacagag tatccttcat      70740
agtcatcttt aagatcaacc catgcagacg atatttttc aattaaatca ataaaagaat       70800
atttcctctc taattccttt atctctttat ctagttttac aggatcattt aaaacacgat      70860
ctttaactgc cggggtatca tcgaaatctt caattagaag aatattacct ttaggtagtg      70920
tagtaaatgc ccgcctaaga ctatcattgg tcatagaggc taatgacagt gcactaacat      70980
ttttattaaa atgtgaggca atcgctttac tgattgaggt ttaccagtac caggaggacc      71040
tgttagaaca caagtgaatt tatagggtag tccacgatca tcgtaccatt tccgatcaga      71100
atagaattct tcaatcttat taaggaattc ttctttgatc tctttacgca aaatcaccgt      71160
gttgatatcg cgtttagtaa cttcaatctc attgccccaa cggttaccat cccaatgtga      71220
aatagtcaga ccccttttcat ttgggcgcca atggtaagca tctactaaat caataattag      71280
tttactactc ctagataatc cacgatagt aatatccatt tgatctcgac tggcattttg       71340
actatcccgg cgtgctttta caaccagaa taacctacct ttaaacagaa agaaatgtaa       71400
gccaaaacca acaccaattt tctgtttagt tgcactataa ctttgctcat caacattagt      71460
tgaaaaacgt cgattaaatc cagctaatgg ctgcttaata taccattcca tgaaacaatc      71520
aaagttcttc tcgttcagcc cattacccat gttggtaata tgtagactaa ctgtaaactg      71580
atttaatgcg aacctagcta gtttacttgg taagcctctt agagtggtcc agaataaacc      71640
accaattgcc attccgatag ctccacccat aaccatattc ttctgagaga tatcgatgaa      71700
catggcgtaa tattgcaata aggtttctat aatcatacta gcatccctct ggatagctta      71760
ggaaatattg tccacagatc atgtattcac gttctagaaa tctagagtat gactttcaaa      71820
tatttcacct acatctttac catagatttc cgtatacccca tttttgaata cggccattac      71880
ataaacatca gacatagtca tgccgtagtt ataaatttga ttgtctctgt attttggatg      71940
aaataggtca tataaaaaac gagtcattga actattggca acagttgtca cccctttctg      72000
ctttaaggca taacgtactt gtttaaccac atagttaact ttagagcgct cgccaaatac      72060
cgtcagttta tctacattgc aattacgata tcccataaca ccaggattag ctatcacggt      72120
gtgttttgga acacgtacat caaagataat gccattaggg gatagaataa tcttttcatg      72180
gttaaataga acatgaaaata aatgtcgttc tggtttagtg attttgatac ttaacccaat      72240 cacccccacta atctttcttt ctagatcttc tagtgactgc atcaccatgt gatattgatt      72300
```

```
gaagaaagca ttgttcttat attgatctaa ttcaaagtat ttccaacttc cacgaaatga    72360
atagcatggc tttggtataa cctttagtta atcgacactt gagtttgtca aaccagcttt    72420
caagataact ctcgactgta aaccaagtgg gttattatat aagtttattg gaatatgata    72480
agctaaatct gtacatagtt cgacgatgca tttatattcc tgccaaataa agaaaaataa    72540
agggctccga agagcccttt atgtattaga ttttttacaga ccaactttgc tcgaattcct   72600
gatataggaa attgtctgac gcattatccc aattttctcg atcagttaca ccataataat    72660
ggaattctag ttcagtaggt ccaccaacaa aaccattctt agcatagcta taaacttgcc    72720
attggttagc ttaatcagtg tatccacata gaaactatta cggttccata tttcattgtg    72780
gatgtactta aataccacac tgtngatata cttaaattgc gcacttggtt ttccgagtac    72840
actccaatag aatttacgga tacctatttc ggtcttgaaa ttaaactctc cgttgcgaat    72900
gttgttagaa acaatacgtg ccagtttatt aacccgattt cttcaccgat tagatagatc    72960
ccggaaacac tacatccatc tcctattgat ccattattaa ctagtggatc aacaccatat    73020
tcatcagtga aaatggtttt gataacctct ttaccttctc gacgcactaa catattcagg    73080
tgaccatctt cgatatatga catatggcta ggctgaatat attcacttgt atcgacgata    73140
acatcattcg ccattacatt aaactgtaga tggtttacca gatcactaat acctttaaaa    73200
cgaatggctt ggttcgctgt atttagatcg acatacacca cgacatcaat aatgccttgt    73260
tttagtgatt tgtcatcttt gtcagtagtt gtatcaattt tacgtaattt tgatatagtt    73320
cactaaaaca agatatgatg tcatcatgta gtttaattac atcagatcca tttcgttcaa    73380
gcgctttaag cgatacgtta aaccaatacg aattttatta gaacgacgtg ccatggttat    73440
atcacctatg ttaaattaat gaattatttta ttcaattacc gtactacatc tgtgattaga    73500
ataagttcac catcactatt gataacacta tagcttttac aatttcgatg cgcttactaa    73560
taatcttatt ctctagatct acttttacga tattaacacg aattaccttaa ttcgattgat    73620 catgcatttc tttaaaatgc attcgatatt ttaccaatga cagcttttaa ttttcaatgc    73680
tgtcaatgga tgaatattta aaactatatg cttctgccag ggttttgcat tacccacaac    73740
cgtagttagg gtaccccaat aatcataaac atacaacgca gtatcactat tgggattatc    73800
gataatttca attataaatc cacttgtatc actcctatta gtttattgat agtacacttg    73860
taatatagat cttaaataaa ttatgatcta accatttaaa atagataaag cctctatatg    73920
ccaatggtgt attagttctt ctttactaat aatattattg aagtagttta accgatgtga    73980
taccattaat ttagaatgca tatcgacttc actacttacc ttaatcaccc cagtctctaa    74040
taattgcaga gatccaacat acgcaaataa agttggtttt aaataccagt gttccctata    74100 ttgttttttga tcaggtacat ttcctataat gtagtcagta gaattacttc ggtatgcgta    74160
aatagttgat ttagaaccaa gtaaattaag atcgatatca taactcccgc ttttagctgc    74220
aatacattca ataactgatg gggccacaca tatacggttg gttacactgt cttcgccatc    74280
agctctatta cttggaatat atggccttaa taaacataat ccccaaggta tactgtcgat    74340
atgtgataca taattaacct atttaattaa aacagataac gctctgttac tgaacgatat    74400
tgtgacatga tgtttaatgg atcaacatcc actggtgctt tagtgacagt taagcgagca    74460 cctttttaaaa atcaccaata tctaatttcc ttacagtaac atcatggata gtgttttttcg   74520 taatccactc agtatcaatg ctattgtgag gatattattc ttaatccatt tgtcagagtc    74580
cctaaatgga atggtataaa catacacaac cattttaaaa tatcactttt atcgatatta    74640
tttgacaata gattgtaata tccctatcaa cagtagcata tctatcacta tcaaataact    74700
```

```
tttcgatagc gctaccaata cctaaataag atgcatctttt ttcagatgac gttgcatata    74760
ggtattggtt agactcaata ccatcccaca taacaagttc accagatctt ttaaatcctg    74820
gcattaattc atcttgttta taaagagaac catggtaagt aattctggtt tattcataat    74880
aaaatccact atgctttata agagttatgg ttatcaatta acttcaaggt agtagtgtgg    74940
cagtattgaa gtgattggtt actgcttcga tcagcatttg ctcgatgttg attttgtagt    75000
attctggttc ttcgttcaat tcccaataat agtcgcacgt aatagtgcag gtgctatgaa    75060
tctaactacc ttaccatgtg tgtcaaactc tacatgaaca ttgcatattg ttcagtagta    75120
tgattttata gaaatgaatt accagcgtaa ctgcgacctc tatttcacca tgaatactgg    75180
agtaggtttc ctggtggaat actttaccttt taaggcgtgt attctcttca atgatattac    75240
caattctttc aatttgtctt atctagttgc atttgtaggt tcctattaat aaatgtatac    75300
gatggatatc ttttacgatt tccggtgctt atccatatct agttttatat cagtatatat    75360
cttgaatcta ttagataggc tatccatatc tacgtgcaat gcccgaatat gcatatcagt    75420
atcttttggt ttaccttcag actcccatac ggcctttgcg atatcaaatg ctacattgtt    75480
caaatagtat tcgacttcat gttcatcaag caaaagagca tcatggaaac caatacgtga    75540
tagaatggcg taatcacgct gattaacatc tctccaatct ttacgcacta agtaacttttt   75600 accaattcca tcttttttac aactttttact aataatttct ataatgaact tatcatgcca    75660
tttataatcc ataatcatta ctcctttatt taatcagctt cattactaga ggaacagata    75720
gacttatgcc attagccatt ttagctagaa tatgatagac atcgtctgct tcttgattat    75780
tgtacaaggt atagaaatgg catcaccata gtaaggactg tagttaatac ggtcgccata    75840
cacaccactc acaaaactat aatctaatcc atccgtggta gtcataataa ctacaacatg    75900
atcatcccca actataccgg attctaaatc ctcacatagt tctagttttg ttgcacacct    75960
cgttgacaga tccatacttc acggtattga tgatgaggat atggattaca tgctacatca    76020
ttttcactaa cgaagtacat agtcccccag ttgtaagact ggaattgggt tgttgtttgt    76080
gggcttccca tacctcttcc atacaaaggt atgttgttaa cccatagacc atcgttatta    76140
agactatcaa cgatccatca cggacacgta ctacacggag tgttttttgcc atttttaatt    76200 atcctaaata cataaaggaa tcacttagta aacaccattg acaatagcat cgcggaaacg    76260
agaccattcc gtttgaccaa ctacgaatac tcgttcttta ggacgccata gatgatcacc    76320
gcagtcaaga cccaagtaaa gcatattggt tttccatgat tgcgatgaac acgtagttta    76380
gctgatacac tgaactcaca cattacttca tttacatcaa gatgtgtagt gtatcactat    76440
catacctgac atactgatac caattgattt acgaactcgg attagatcct cagtcatcac    76500
ccgccaagtt accagatgct cgtaatactc atctggtgtc atgttgtttt tataattcag    76560
tgcacctgga gtcattgaca tcagttagtg aactggaagt catgtaatac atccaatcac    76620
tattatgacg gagttctttta agcttctctg tattacgata ttagtagttg ctttagtcat    76680
ctacgtaccc tcatcagata cataagtacg ttcaggctga acacatattt gatgttatta    76740
attacagctg tgatataaac ctgatattct tttgaaatag attccatcag ttcaatagat    76800
acggaattga actctgaata agttatttac tttcttagtt catcaattct accgaccgta    76860
attacaccaa catctctgaa actgataact ggatagtgtt tccaatataa caattcagtt    76920
taccaagatg aattacttga attgtttcat cgcaccattg tttctttttct attgtagtat    76980 tcaacacgac gttcgatgaa gacgcgagta ccagaaacag aggtgtacgc attcagtcat    77040
```

```
aaccatactt atggtacgtt atttggatct tggcgccatt ttggatgaat gctttcattt    77100
gtattttcct tttacgaaat agaagccctc ccgaaggagg gcaattacca ttattaaatt    77160
acgagtctat tacttctttt aattttcacc aggggtagct agataatcta cattatattt    77220
aatagcaatt acaccacaag ttcttttca tagctgttct acctgatcgc atatttatca    77280
atagctccat cttctacatc ctcgtataat ggatattgac tataatatta tcaggtgtaa    77340
gtacagacag tttcaatccc atctttacca atgactgggt gatatgtctg tttaagacct    77400
ttacaatgat agtgataggt atgcgctgtg tttaggtggt catgtaaaga tacctcataa    77460
accgttgggt agtccgtctt taagacagtt agttgattaa catctttcaa tgattatctg    77520
caatattctt agccaataac agtagatcat tggtgatatg ttttaatgag aacttaagcc    77580
tctccctttg tttatatcgg aaccttatta tcacagtaac tccatccggt tatttttata    77640
attcagtaca gtgattggtg tattcggtac aaagacggct agttcgtcat cgaatacaat    77700
gtaaaccatc actttataat tattaaccga ttcttggaat tgttgtgtga ttacattata    77760
gtcttttgtg cgatggctaa gaaacagctc actattagct cggcagaaac tatgtcgcgc    77820
tttttatcag cactcataac agcgatacca cggataatga atttattatc taaggtatat    77880
tttctttgag acatcgcata gtcgactaca tcaacatcgc cgccaaatag cacggcattt    77940
tcaccgtatc cacaaataag agccatttat aattacctgt ttaaaaatta tattcaataa    78000
attgagagtg aatagttcac tacattccca tgtacgactt gctaatttat atttacctttt   78060 aacaggtaag tcaaataacg taatgctttt ctactgaacc agcctcatga ttaaccaata    78120
gaacattcct agccttcaga atatttgaac aatttacaag ttcataatca tctcgcttag    78180
gtgtcaatag ctacattagt gcctggtttc tagcatacca gagcacctca tgaccctctg    78240
gattaataat agagatatag ctgacgttca gcgggtaacc acaagttacg tggatcatan    78300
tctccattaa catcaaagaa tttaaatatc atagagttgg aaccggtttt gatggatcag    78360
caattantgc agattcntct acataaaacca ttgcnaagtt ttcaccttct ttacgaatac   78420
cagtagaagg tgttttcgat ggatcataac gataattggc actgctgtcc agctgttaaa    78480
taagttgggc cagttaatgc attgggtttt ggatgaggaa tatcaatttt agtaatacaa    78540
tattgaccag tacgaaactc acgcattata ttaacctctt aatgaataac tgttgcagaa    78600
ggacgacatt tcatagtttt aaaaatgtca gtaggataga tattaccagc ttgtccgaaa    78660
ggtttatcgg ctagaagaaa ctgcggacaa actgtttgta gataaccact atcagtgggt    78720
aggaatcctt caatatcact gatgagaatt tgccagatgg gcaattggtt ataatagtca    78780
tccatattgt agtatgcgtg gagtttacca ccgaacccat atacaaactg atgagtatca    78840
attagacgaa taccaaattt aggttgtcgt cccatcctt                          78879
```

<210> SEQ ID NO 2
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
ttaattgatg aacgttatcc agatattgta acggattaaa atacttacag ctatctagta     60
tgtaactagg cggattgcca tttgtaaatt atctatttaa tcgaactgag gaaatactaa    120
tgaaacaatt ctttcaacta cttctaagcc tactttttcaa actaccggtt ctatcatatt   180
```

-continued

```
ttgctgagaa gaaacgatta gagaaagaga aaaaggaaga agaaaagcgt cagcaagaac    240
aacgtcaaaa agaactactt gatgaacaac gtcgcgaaca agaagatcat tatcgaaaaa    300
ccgcttacga tcgcctagca aaacttattc atactcggtg gtatgatgag tttaatgcat    360
acgaaaagaa actagttgat cttgctgtat cgagtggtaa agcagttagt gttaagtatg    420
gtaaagttac taagatgcag caccctcatc aatttaaact acttaatgat tggctggatg    480
atattccagt agaagattat tctaagtgaa gaggagatat acaatggtct tcacactcga    540
agatttcgtt ggggactggc gacagacagc cggctacaac ctggaccaag tccttgaaca    600
gggaggtgtg tccagtttgt ttcagaatct cggggtgtcc gtaactccga tccaaaggat    660
tgtcctgagc ggtgaaaatg ggctgaagat cgacatccat gtcatcatcc cgtatgaagg    720
tctgagcggc gaccaaatgg gccagatcga aaaaattttt aaggtggtgt accctgtgga    780
tgatcatcac tttaaggtga tcctgcacta tggcacactg gtaatcgacg gggttacgcc    840
gaacatgatc gactatttcg gacggccgta tgaaggcatc gccgtgttcg acggcaaaaa    900
gatcactgta acagggaccc tgtggaacgg caacaaaatt atcgacgagc gcctgatcaa    960
ccccgacggc tccctgctgt tccgagtaac catcaacgga gtgaccggct ggcggctgtg   1020
cgaacgcatt ctggcgtaag tttaaataaa agaaaataaa gacgaagttt ttctttacat   1080
ggagaggggt ttatgccgta attatacact tactttgata agattttttaa tatcagtaaa   1140 atgggtatat gttgcctttt tatctttgtg aaccagtaag caacaggttc cttcatttac   1200
ggtattggtt tgttttaatg ggatatttaa agcatattca aacagatcat ccatccagtt   1260
aaatgccatg aacttattga taaggacatg atcgaaatca attaattcaa taaacgaatc   1320
gatctcagat tgataatact ctacaaccat tttagaccat tctttgttta tcgc          1374
```

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 3
ttctaagtga agaggagata tacaatggtc ttca                                 34

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 4
cgcattctgg cgtaagttta aataaaag                                        28

<210> SEQ ID NO 5
<211> LENGTH: 20
<212> TYPE: DNA
<213> ORGANISM: Pseudomonas phage B11

<400> SEQUENCE: 5
agaagatcat tatcgaaaga                                                 20

<210> SEQ ID NO 6
<211> LENGTH: 20

```
<212> TYPE: DNA
<213> ORGANISM: Pseudomonas phage B11

<400> SEQUENCE: 6
agacatagcc cctctccaca                                              20

<210> SEQ ID NO 7
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
agaagaucau uaucgaaaga guuuuagagc uagaaauagc aaguuaaaau aaggcuaguc    60
cguuaucaac uugaaaaagu ggcaccgagu cggugcuuuu uuu                     103

<210> SEQ ID NO 8
<211> LENGTH: 103
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
agacauagcc ccucuccaca guuuuagagc uagaaauagc aaguuaaaau aaggcuaguc    60
cguuaucaac uugaaaaagu ggcaccgagu cggugcuuuu uuu                     103

<210> SEQ ID NO 9
<211> LENGTH: 23
<212> TYPE: DNA
<213> ORGANISM: Pseudomonas phage B11

<400> SEQUENCE: 9
agaagatcat tatcgaaaga cgg                                           23

<210> SEQ ID NO 10
<211> LENGTH: 23
<212> TYPE: DNA
<213> ORGANISM: Pseudomonas phage B11

<400> SEQUENCE: 10
agacatagcc cctctccaca tgg                                           23

<210> SEQ ID NO 11
<211> LENGTH: 272
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
agcagtggta aggtctctta acagaagatc attatcgaaa gagttttaga gctagaaata    60
gcaagttaaa ataaggctag tccgttatca acttgaaaaa gtggaccga gtcggtgctt    120 tttttgctaa ctgataccga ctacgcctga acagtcgaat cttcacctcg tctggtaccg   180
acgcggtccc aaatattgac aacataaaaa actttgtgtt atacttgtaa cagacatagc   240
ccctctccac agttttgaga ccagctcgta gg                                 272
```

```
<210> SEQ ID NO 12
<211> LENGTH: 79409
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (203)..(203)
<223> OTHER INFORMATION: a, c, t, g, unknown or other
<220> FEATURE:
<221> NAME/KEY: modified_base
<222> LOCATION: (212)..(212)
<223> OTHER INFORMATION: a, c, t, g, unknown or other
<220> FEATURE:
<221> NAME/KEY: modified_base
<222> LOCATION: (223)..(224)
<223> OTHER INFORMATION: a, c, t, g, unknown or other
<220> FEATURE:
<221> NAME/KEY: modified_base
<222> LOCATION: (226)..(226)
<223> OTHER INFORMATION: a, c, t, g, unknown or other
<220> FEATURE:
<221> NAME/KEY: modified_base
<222> LOCATION: (236)..(238)
<223> OTHER INFORMATION: a, c, t, g, unknown or other
<220> FEATURE:
<221> NAME/KEY: modified_base
<222> LOCATION: (242)..(242)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
<222> LOCATION: (250)..(251)
<223> OTHER INFORMATION: a, c, t, g, unknown or other
<220> FEATURE:
<221> NAME/KEY: modified_base
<222> LOCATION: (256)..(256)
<223> OTHER INFORMATION: a, c, t, g, unknown or other
<220> FEATURE:
<221> NAME/KEY: modified_base
<222> LOCATION: (281)..(281)
<223> OTHER INFORMATION: a, c, t, g, unknown or other
<220> FEATURE:
<221> NAME/KEY: modified_base
<222> LOCATION: (285)..(285)
<223> OTHER INFORMATION: a, c, t, g, unknown or other
<220> FEATURE:
<221> NAME/KEY: modified_base
<222> LOCATION: (293)..(293)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (419)..(419)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (509)..(509)
<223> OTHER INFORMATION: a, c, t, g, unknown or other
<220> FEATURE:
<221> NAME/KEY: modified_base
<222> LOCATION: (513)..(513)
<223> OTHER INFORMATION: a, c, t, g, unknown or other
<220> FEATURE:
<221> NAME/KEY: modified_base
<222> LOCATION: (522)..(522)
<223> OTHER INFORMATION: a, c, t, g, unknown or other
```

-continued

```
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (564)..(564)
<223> OTHER INFORMATION: a, c, t, g, unknown or other
<220> FEATURE:
<221> NAME/KEY: modified_base
<222> LOCATION: (569)..(570)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other
<220> FEATURE:
<221> NAME/KEY: modified_base
<222> LOCATION: (3627)..(3627)
<223> OTHER INFORMATION: a, c, t, g, unknown or other
<220> FEATURE:
<221> NAME/KEY: modified_base
<222> LOCATION: (3636)..(3636)
<223> OTHER INFORMATION: a, c, t, g, unknown or other
<220> FEATURE:
<221> NAME/KEY: modified_base
<222> LOCATION: (3639)..(3639)
<223> OTHER INFORMATION: a, c, t, g, unknown or other
<220> FEATURE:
<221> NAME/KEY: modified_base
<222> LOCATION: (3642)..(3642)
<223> OTHER INFORMATION: a, c, t, g, unknown or other
<220> FEATURE:
<221> NAME/KEY: modified_base
<222> LOCATION: (3675)..(3675)
<223> OTHER INFORMATION: a, c, t, g, unknown or other
<220> FEATURE:
<221> NAME/KEY: modified_base
<222> LOCATION: (3681)..(3681)
<223> OTHER INFORMATION: a, c, t, g, unknown or other
<220> FEATURE:
<221> NAME/KEY: modified_base
<222> LOCATION: (3684)..(3684)
<223> OTHER INFORMATION: a, c, t, g, unknown or other
<220> FEATURE:
<221> NAME/KEY: modified_base
<222> LOCATION: (3692)..(3692)
<223> OTHER INFORMATION: a, c, t, g, unknown or other
<220> FEATURE:
<221> NAME/KEY: modified_base
<222> LOCATION: (4080)..(4080)
<223> OTHER INFORMATION: a, c, t, g, unknown or other
<220> FEATURE:
<221> NAME/KEY: modified_base
<222> LOCATION: (4182)..(4182)
<223> OTHER INFORMATION: a, c, t, g, unknown or other
<220> FEATURE:
<221> NAME/KEY: modified_base
<222> LOCATION: (4212)..(4212)
```

```
<223> OTHER INFORMATION: a, c, t, g, unknown or other
<220> FEATURE:
<221> NAME/KEY: modified_base
<222> LOCATION: (4314)..(4314)
<223> OTHER INFORMATION: a, c, t, g, unknown or other
<220> FEATURE:
<221> NAME/KEY: modified_base
<222> LOCATION: (4323)..(4323)
<223> OTHER INFORMATION: a, c, t, g, unknown or other
<220> FEATURE:
<221> NAME/KEY: modified_base
<222> LOCATION: (5079)..(5079)
<223> OTHER INFORMATION: a, c, t, g, unknown or other
<220> FEATURE:
<221> NAME/KEY: modified_base
<222> LOCATION: (5190)..(5190)
<223> OTHER INFORMATION: a, c, t, g, unknown or other
<220> FEATURE:
<221> NAME/KEY: modified_base
<222> LOCATION: (6180)..(6180)
<223> OTHER INFORMATION: a, c, t, g, unknown or other
<220> FEATURE:
<221> NAME/KEY: modified_base
<222> LOCATION: (6252)..(6252)
<223> OTHER INFORMATION: a, c, t, g, unknown or other
<220> FEATURE:
<221> NAME/KEY: modified_base
<222> LOCATION: (6273)..(6273)
<223> OTHER INFORMATION: a, c, t, g, unknown or other
<220> FEATURE:
<221> NAME/KEY: modified_base
<222> LOCATION: (6279)..(6279)
<223> OTHER INFORMATION: a, c, t, g, unknown or other
<220> FEATURE:
<221> NAME/KEY: modified_base
<222> LOCATION: (6612)..(6612)
<223> OTHER INFORMATION: a, c, t, g, unknown or other
<220> FEATURE:
<221> NAME/KEY: modified_base
<222> LOCATION: (6621)..(6621)
<223> OTHER INFORMATION: a, c, t, g, unknown or other
<220> FEATURE:
<221> NAME/KEY: modified_base
<222> LOCATION: (6627)..(6627)
<223> OTHER INFORMATION: a, c, t, g, unknown or other
<220> FEATURE:
<221> NAME/KEY: modified_base
<222> LOCATION: (6783)..(6783)
<223> OTHER INFORMATION: a, c, t, g, unknown or other
<220> FEATURE:
<221> NAME/KEY: modified_base
<222> LOCATION: (6792)..(6792)
<223> OTHER INFORMATION: a, c, t, g, unknown or other
<220> FEATURE:
<221> NAME/KEY: modified_base
<222> LOCATION: (6800)..(6801)
<223> OTHER INFORMATION: a, c, t, g, unknown or other
<220> FEATURE:
<221> NAME/KEY: modified_base
<222> LOCATION: (6819)..(6819)
<223> OTHER INFORMATION: a, c, t, g, unknown or other
<220> FEATURE:
<221> NAME/KEY: modified_base
<222> LOCATION: (6840)..(6840)
<223> OTHER INFORMATION: a, c, t, g, unknown or other
<220> FEATURE:
<221> NAME/KEY: modified_base
<222> LOCATION: (6846)..(6846)
<223> OTHER INFORMATION: a, c, t, g, unknown or other
<220> FEATURE:
<221> NAME/KEY: modified_base
<222> LOCATION: (6945)..(6945)
<223> OTHER INFORMATION: a, c, t, g, unknown or other
<220> FEATURE:
<221> NAME/KEY: modified_base
<222> LOCATION: (9573)..(9573)
<223> OTHER INFORMATION: a, c, t, g, unknown or other
<220> FEATURE:
<221> NAME/KEY: modified_base
```

```
<222> LOCATION: (9576)..(9576)
<223> OTHER INFORMATION: a, c, t, g, unknown or other
<220> FEATURE:
<221> NAME/KEY: modified_base
<222> LOCATION: (9578)..(9578)
<223> OTHER INFORMATION: a, c, t, g, unknown or other
<220> FEATURE:
<221> NAME/KEY: modified_base
<222> LOCATION: (9582)..(9583)
<223> OTHER INFORMATION: a, c, t, g, unknown or other
<220> FEATURE:
<221> NAME/KEY: modified_base
<222> LOCATION: (9603)..(9603)
<223> OTHER INFORMATION: a, c, t, g, unknown or other
<220> FEATURE:
<221> NAME/KEY: modified_base
<222> LOCATION: (9606)..(9606)
<223> OTHER INFORMATION: a, c, t, g, unknown or other
<220> FEATURE:
<221> NAME/KEY: modified_base
<222> LOCATION: (9609)..(9609)
<223> OTHER INFORMATION: a, c, t, g, unknown or other
<220> FEATURE:
<221> NAME/KEY: modified_base
<222> LOCATION: (9661)..(9661)
<223> OTHER INFORMATION: a, c, t, g, unknown or other
<220> FEATURE:
<221> NAME/KEY: modified_base
<222> LOCATION: (9854)..(9854)
<223> OTHER INFORMATION: a, c, t, g, unknown or other
<220> FEATURE:
<221> NAME/KEY: modified_base
<222> LOCATION: (10379)..(10379)
<223> OTHER INFORMATION: a, c, t, g, unknown or other
<220> FEATURE:
<221> NAME/KEY: modified_base
<222> LOCATION: (10382)..(10382)
<223> OTHER INFORMATION: a, c, t, g, unknown or other
<220> FEATURE:
<221> NAME/KEY: modified_base
<222> LOCATION: (10385)..(10385)
<223> OTHER INFORMATION: a, c, t, g, unknown or other
<220> FEATURE:
<221> NAME/KEY: modified_base
<222> LOCATION: (10388)..(10388)
<223> OTHER INFORMATION: a, c, t, g, unknown or other
<220> FEATURE:
<221> NAME/KEY: modified_base
<222> LOCATION: (10397)..(10397)
<223> OTHER INFORMATION: a, c, t, g, unknown or other
<220> FEATURE:
<221> NAME/KEY: modified_base
<222> LOCATION: (10400)..(10400)
<223> OTHER INFORMATION: a, c, t, g, unknown or other
<220> FEATURE:
<221> NAME/KEY: modified_base
<222> LOCATION: (10403)..(10403)
<223> OTHER INFORMATION: a, c, t, g, unknown or other
<220> FEATURE:
<221> NAME/KEY: modified_base
<222> LOCATION: (10415)..(10415)
<223> OTHER INFORMATION: a, c, t, g, unknown or other
<220> FEATURE:
<221> NAME/KEY: modified_base
<222> LOCATION: (10488)..(10488)
<223> OTHER INFORMATION: a, c, t, g, unknown or other
<220> FEATURE:
<221> NAME/KEY: modified_base
<222> LOCATION: (10556)..(10556)
<223> OTHER INFORMATION: a, c, t, g, unknown or other
<220> FEATURE:
<221> NAME/KEY: modified_base
<222> LOCATION: (10580)..(10580)
<223> OTHER INFORMATION: a, c, t, g, unknown or other
<220> FEATURE:
<221> NAME/KEY: modified_base
<222> LOCATION: (10598)..(10598)
<223> OTHER INFORMATION: a, c, t, g, unknown or other
<220> FEATURE:
```

-continued

```
<221> NAME/KEY: modified_base
<222> LOCATION: (10610)..(10610)
<223> OTHER INFORMATION: a, c, t, g, unknown or other
<220> FEATURE:
<221> NAME/KEY: modified_base
<222> LOCATION: (10835)..(10835)
<223> OTHER INFORMATION: a, c, t, g, unknown or other
<220> FEATURE:
<221> NAME/KEY: modified_base
<222> LOCATION: (10837)..(10837)
<223> OTHER INFORMATION: a, c, t, g, unknown or other
<220> FEATURE:
<221> NAME/KEY: modified_base
<222> LOCATION: (10850)..(10850)
<223> OTHER INFORMATION: a, c, t, g, unknown or other
<220> FEATURE:
<221> NAME/KEY: modified_base
<222> LOCATION: (10853)..(10853)
<223> OTHER INFORMATION: a, c, t, g, unknown or other
<220> FEATURE:
<221> NAME/KEY: modified_base
<222> LOCATION: (10913)..(10913)
<223> OTHER INFORMATION: a, c, t, g, unknown or other
<220> FEATURE:
<221> NAME/KEY: modified_base
<222> LOCATION: (11051)..(11051)
<223> OTHER INFORMATION: a, c, t, g, unknown or other
<220> FEATURE:
<221> NAME/KEY: modified_base
<222> LOCATION: (11108)..(11108)
<223> OTHER INFORMATION: a, c, t, g, unknown or other
<220> FEATURE:
<221> NAME/KEY: modified_base
<222> LOCATION: (11117)..(11117)
<223> OTHER INFORMATION: a, c, t, g, unknown or other
<220> FEATURE:
<221> NAME/KEY: modified_base
<222> LOCATION: (11244)..(11244)
<223> OTHER INFORMATION: a, c, t, g, unknown or other
<220> FEATURE:
<221> NAME/KEY: modified_base
<222> LOCATION: (11246)..(11246)
<223> OTHER INFORMATION: a, c, t, g, unknown or other
<220> FEATURE:
<221> NAME/KEY: modified_base
<222> LOCATION: (11450)..(11450)
<223> OTHER INFORMATION: a, c, t, g, unknown or other
<220> FEATURE:
<221> NAME/KEY: modified_base
<222> LOCATION: (11453)..(11453)
<223> OTHER INFORMATION: a, c, t, g, unknown or other
<220> FEATURE:
<221> NAME/KEY: modified_base
<222> LOCATION: (11549)..(11549)
<223> OTHER INFORMATION: a, c, t, g, unknown or other
<220> FEATURE:
<221> NAME/KEY: modified_base
<222> LOCATION: (11585)..(11585)
<223> OTHER INFORMATION: a, c, t, g, unknown or other
<220> FEATURE:
<221> NAME/KEY: modified_base
<222> LOCATION: (11606)..(11606)
<223> OTHER INFORMATION: a, c, t, g, unknown or other
<220> FEATURE:
<221> NAME/KEY: modified_base
<222> LOCATION: (12014)..(12014)
<223> OTHER INFORMATION: a, c, t, g, unknown or other
<220> FEATURE:
<221> NAME/KEY: modified_base
<222> LOCATION: (12058)..(12058)
<223> OTHER INFORMATION: a, c, t, g, unknown or other
<220> FEATURE:
<221> NAME/KEY: modified_base
<222> LOCATION: (12112)..(12112)
<223> OTHER INFORMATION: a, c, t, g, unknown or other
<220> FEATURE:
<221> NAME/KEY: modified_base
<222> LOCATION: (12125)..(12125)
<223> OTHER INFORMATION: a, c, t, g, unknown or other
```

```
<220> FEATURE:
<221> NAME/KEY: modified_base
<222> LOCATION: (12145)..(12145)
<223> OTHER INFORMATION: a, c, t, g, unknown or other
<220> FEATURE:
<221> NAME/KEY: modified_base
<222> LOCATION: (12200)..(12200)
<223> OTHER INFORMATION: a, c, t, g, unknown or other
<220> FEATURE:
<221> NAME/KEY: modified_base
<222> LOCATION: (12262)..(12262)
<223> OTHER INFORMATION: a, c, t, g, unknown or other
<220> FEATURE:
<221> NAME/KEY: modified_base
<222> LOCATION: (12266)..(12266)
<223> OTHER INFORMATION: a, c, t, g, unknown or other
<220> FEATURE:
<221> NAME/KEY: modified_base
<222> LOCATION: (12308)..(12308)
<223> OTHER INFORMATION: a, c, t, g, unknown or other
<220> FEATURE:
<221> NAME/KEY: modified_base
<222> LOCATION: (12311)..(12311)
<223> OTHER INFORMATION: a, c, t, g, unknown or other
<220> FEATURE:
<221> NAME/KEY: modified_base
<222> LOCATION: (12356)..(12356)
<223> OTHER INFORMATION: a, c, t, g, unknown or other
<220> FEATURE:
<221> NAME/KEY: modified_base
<222> LOCATION: (12389)..(12389)
<223> OTHER INFORMATION: a, c, t, g, unknown or other
<220> FEATURE:
<221> NAME/KEY: modified_base
<222> LOCATION: (12422)..(12422)
<223> OTHER INFORMATION: a, c, t, g, unknown or other
<220> FEATURE:
<221> NAME/KEY: modified_base
<222> LOCATION: (12630)..(12630)
<223> OTHER INFORMATION: a, c, t, g, unknown or other
<220> FEATURE:
<221> NAME/KEY: modified_base
<222> LOCATION: (12663)..(12663)
<223> OTHER INFORMATION: a, c, t, g, unknown or other
<220> FEATURE:
<221> NAME/KEY: modified_base
<222> LOCATION: (12674)..(12674)
<223> OTHER INFORMATION: a, c, t, g, unknown or other
<220> FEATURE:
<221> NAME/KEY: modified_base
<222> LOCATION: (12686)..(12686)
<223> OTHER INFORMATION: a, c, t, g, unknown or other
<220> FEATURE:
<221> NAME/KEY: modified_base
<222> LOCATION: (12693)..(12693)
<223> OTHER INFORMATION: a, c, t, g, unknown or other
<220> FEATURE:
<221> NAME/KEY: modified_base
<222> LOCATION: (12723)..(12723)
<223> OTHER INFORMATION: a, c, t, g, unknown or other
<220> FEATURE:
<221> NAME/KEY: modified_base
<222> LOCATION: (12777)..(12777)
<223> OTHER INFORMATION: a, c, t, g, unknown or other
<220> FEATURE:
<221> NAME/KEY: modified_base
<222> LOCATION: (12822)..(12822)
<223> OTHER INFORMATION: a, c, t, g, unknown or other
<220> FEATURE:
<221> NAME/KEY: modified_base
<222> LOCATION: (14712)..(14712)
<223> OTHER INFORMATION: a, c, t, g, unknown or other
<220> FEATURE:
<221> NAME/KEY: modified_base
<222> LOCATION: (14904)..(14904)
<223> OTHER INFORMATION: a, c, t, g, unknown or other
<220> FEATURE:
<221> NAME/KEY: modified_base
<222> LOCATION: (14906)..(14906)
```

-continued

```
<223> OTHER INFORMATION: a, c, t, g, unknown or other
<220> FEATURE:
<221> NAME/KEY: modified_base
<222> LOCATION: (14910)..(14910)
<223> OTHER INFORMATION: a, c, t, g, unknown or other
<220> FEATURE:
<221> NAME/KEY: modified_base
<222> LOCATION: (14916)..(14916)
<223> OTHER INFORMATION: a, c, t, g, unknown or other
<220> FEATURE:
<221> NAME/KEY: modified_base
<222> LOCATION: (15003)..(15003)
<223> OTHER INFORMATION: a, c, t, g, unknown or other
<220> FEATURE:
<221> NAME/KEY: modified_base
<222> LOCATION: (15088)..(15088)
<223> OTHER INFORMATION: a, c, t, g, unknown or other
<220> FEATURE:
<221> NAME/KEY: modified_base
<222> LOCATION: (15091)..(15091)
<223> OTHER INFORMATION: a, c, t, g, unknown or other
<220> FEATURE:
<221> NAME/KEY: modified_base
<222> LOCATION: (15102)..(15102)
<223> OTHER INFORMATION: a, c, t, g, unknown or other
<220> FEATURE:
<221> NAME/KEY: modified_base
<222> LOCATION: (15105)..(15105)
<223> OTHER INFORMATION: a, c, t, g, unknown or other
<220> FEATURE:
<221> NAME/KEY: modified_base
<222> LOCATION: (15108)..(15108)
<223> OTHER INFORMATION: a, c, t, g, unknown or other
<220> FEATURE:
<221> NAME/KEY: modified_base
<222> LOCATION: (15180)..(15180)
<223> OTHER INFORMATION: a, c, t, g, unknown or other
<220> FEATURE:
<221> NAME/KEY: modified_base
<222> LOCATION: (16845)..(16845)
<223> OTHER INFORMATION: a, c, t, g, unknown or other
<220> FEATURE:
<221> NAME/KEY: modified_base
<222> LOCATION: (16852)..(16852)
<223> OTHER INFORMATION: a, c, t, g, unknown or other
<220> FEATURE:
<221> NAME/KEY: modified_base
<222> LOCATION: (17294)..(17294)
<223> OTHER INFORMATION: a, c, t, g, unknown or other
<220> FEATURE:
<221> NAME/KEY: modified_base
<222> LOCATION: (17399)..(17399)
<223> OTHER INFORMATION: a, c, t, g, unknown or other
<220> FEATURE:
<221> NAME/KEY: modified_base
<222> LOCATION: (17648)..(17648)
<223> OTHER INFORMATION: a, c, t, g, unknown or other
<220> FEATURE:
<221> NAME/KEY: modified_base
<222> LOCATION: (17673)..(17674)
<223> OTHER INFORMATION: a, c, t, g, unknown or other
<220> FEATURE:
<221> NAME/KEY: modified_base
<222> LOCATION: (17982)..(17983)
<223> OTHER INFORMATION: a, c, t, g, unknown or other
<220> FEATURE:
<221> NAME/KEY: modified_base
<222> LOCATION: (17993)..(17993)
<223> OTHER INFORMATION: a, c, t, g, unknown or other
<220> FEATURE:
<221> NAME/KEY: modified_base
<222> LOCATION: (18008)..(18008)
<223> OTHER INFORMATION: a, c, t, g, unknown or other
<220> FEATURE:
<221> NAME/KEY: modified_base
<222> LOCATION: (18020)..(18020)
<223> OTHER INFORMATION: a, c, t, g, unknown or other
<220> FEATURE:
<221> NAME/KEY: modified_base
```

-continued

```
<222> LOCATION: (18029)..(18029)
<223> OTHER INFORMATION: a, c, t, g, unknown or other
<220> FEATURE:
<221> NAME/KEY: modified_base
<222> LOCATION: (18041)..(18041)
<223> OTHER INFORMATION: a, c, t, g, unknown or other
<220> FEATURE:
<221> NAME/KEY: modified_base
<222> LOCATION: (18110)..(18111)
<223> OTHER INFORMATION: a, c, t, g, unknown or other
<220> FEATURE:
<221> NAME/KEY: modified_base
<222> LOCATION: (18309)..(18309)
<223> OTHER INFORMATION: a, c, t, g, unknown or other
<220> FEATURE:
<221> NAME/KEY: modified_base
<222> LOCATION: (18401)..(18401)
<223> OTHER INFORMATION: a, c, t, g, unknown or other
<220> FEATURE:
<221> NAME/KEY: modified_base
<222> LOCATION: (18405)..(18405)
<223> OTHER INFORMATION: a, c, t, g, unknown or other
<220> FEATURE:
<221> NAME/KEY: modified_base
<222> LOCATION: (18450)..(18450)
<223> OTHER INFORMATION: a, c, t, g, unknown or other
<220> FEATURE:
<221> NAME/KEY: modified_base
<222> LOCATION: (18458)..(18458)
<223> OTHER INFORMATION: a, c, t, g, unknown or other
<220> FEATURE:
<221> NAME/KEY: modified_base
<222> LOCATION: (18574)..(18574)
<223> OTHER INFORMATION: a, c, t, g, unknown or other
<220> FEATURE:
<221> NAME/KEY: modified_base
<222> LOCATION: (18641)..(18641)
<223> OTHER INFORMATION: a, c, t, g, unknown or other
<220> FEATURE:
<221> NAME/KEY: modified_base
<222> LOCATION: (18740)..(18740)
<223> OTHER INFORMATION: a, c, t, g, unknown or other
<220> FEATURE:
<221> NAME/KEY: modified_base
<222> LOCATION: (18779)..(18779)
<223> OTHER INFORMATION: a, c, t, g, unknown or other
<220> FEATURE:
<221> NAME/KEY: modified_base
<222> LOCATION: (18881)..(18881)
<223> OTHER INFORMATION: a, c, t, g, unknown or other
<220> FEATURE:
<221> NAME/KEY: modified_base
<222> LOCATION: (19177)..(19177)
<223> OTHER INFORMATION: a, c, t, g, unknown or other
<220> FEATURE:
<221> NAME/KEY: modified_base
<222> LOCATION: (19326)..(19326)
<223> OTHER INFORMATION: a, c, t, g, unknown or other
<220> FEATURE:
<221> NAME/KEY: modified_base
<222> LOCATION: (19349)..(19349)
<223> OTHER INFORMATION: a, c, t, g, unknown or other
<220> FEATURE:
<221> NAME/KEY: modified_base
<222> LOCATION: (19370)..(19370)
<223> OTHER INFORMATION: a, c, t, g, unknown or other
<220> FEATURE:
<221> NAME/KEY: modified_base
<222> LOCATION: (19616)..(19616)
<223> OTHER INFORMATION: a, c, t, g, unknown or other
<220> FEATURE:
<221> NAME/KEY: modified_base
<222> LOCATION: (19732)..(19732)
<223> OTHER INFORMATION: a, c, t, g, unknown or other
<220> FEATURE:
<221> NAME/KEY: modified_base
<222> LOCATION: (19749)..(19749)
<223> OTHER INFORMATION: a, c, t, g, unknown or other
<220> FEATURE:
```

```
<221> NAME/KEY: modified_base
<222> LOCATION: (19756)..(19756)
<223> OTHER INFORMATION: a, c, t, g, unknown or other
<220> FEATURE:
<221> NAME/KEY: modified_base
<222> LOCATION: (19758)..(19758)
<223> OTHER INFORMATION: a, c, t, g, unknown or other
<220> FEATURE:
<221> NAME/KEY: modified_base
<222> LOCATION: (19760)..(19760)
<223> OTHER INFORMATION: a, c, t, g, unknown or other
<220> FEATURE:
<221> NAME/KEY: modified_base
<222> LOCATION: (20043)..(20043)
<223> OTHER INFORMATION: a, c, t, g, unknown or other
<220> FEATURE:
<221> NAME/KEY: modified_base
<222> LOCATION: (20053)..(20053)
<223> OTHER INFORMATION: a, c, t, g, unknown or other
<220> FEATURE:
<221> NAME/KEY: modified_base
<222> LOCATION: (20085)..(20085)
<223> OTHER INFORMATION: a, c, t, g, unknown or other
<220> FEATURE:
<221> NAME/KEY: modified_base
<222> LOCATION: (20152)..(20152)
<223> OTHER INFORMATION: a, c, t, g, unknown or other
<220> FEATURE:
<221> NAME/KEY: modified_base
<222> LOCATION: (20170)..(20170)
<223> OTHER INFORMATION: a, c, t, g, unknown or other
<220> FEATURE:
<221> NAME/KEY: modified_base
<222> LOCATION: (20176)..(20176)
<223> OTHER INFORMATION: a, c, t, g, unknown or other
<220> FEATURE:
<221> NAME/KEY: modified_base
<222> LOCATION: (20251)..(20251)
<223> OTHER INFORMATION: a, c, t, g, unknown or other
<220> FEATURE:
<221> NAME/KEY: modified_base
<222> LOCATION: (20257)..(20257)
<223> OTHER INFORMATION: a, c, t, g, unknown or other
<220> FEATURE:
<221> NAME/KEY: modified_base
<222> LOCATION: (20269)..(20269)
<223> OTHER INFORMATION: a, c, t, g, unknown or other
<220> FEATURE:
<221> NAME/KEY: modified_base
<222> LOCATION: (20296)..(20296)
<223> OTHER INFORMATION: a, c, t, g, unknown or other
<220> FEATURE:
<221> NAME/KEY: modified_base
<222> LOCATION: (20299)..(20299)
<223> OTHER INFORMATION: a, c, t, g, unknown or other
<220> FEATURE:
<221> NAME/KEY: modified_base
<222> LOCATION: (20302)..(20302)
<223> OTHER INFORMATION: a, c, t, g, unknown or other
<220> FEATURE:
<221> NAME/KEY: modified_base
<222> LOCATION: (20305)..(20305)
<223> OTHER INFORMATION: a, c, t, g, unknown or other
<220> FEATURE:
<221> NAME/KEY: modified_base
<222> LOCATION: (20313)..(20313)
<223> OTHER INFORMATION: a, c, t, g, unknown or other
<220> FEATURE:
<221> NAME/KEY: modified_base
<222> LOCATION: (20416)..(20416)
<223> OTHER INFORMATION: a, c, t, g, unknown or other
<220> FEATURE:
<221> NAME/KEY: modified_base
<222> LOCATION: (20488)..(20488)
<223> OTHER INFORMATION: a, c, t, g, unknown or other
<220> FEATURE:
<221> NAME/KEY: modified_base
<222> LOCATION: (21006)..(21006)
<223> OTHER INFORMATION: a, c, t, g, unknown or other
```

```
<220> FEATURE:
<221> NAME/KEY: modified_base
<222> LOCATION: (21012)..(21012)
<223> OTHER INFORMATION: a, c, t, g, unknown or other
<220> FEATURE:
<221> NAME/KEY: modified_base
<222> LOCATION: (21019)..(21019)
<223> OTHER INFORMATION: a, c, t, g, unknown or other
<220> FEATURE:
<221> NAME/KEY: modified_base
<222> LOCATION: (21024)..(21024)
<223> OTHER INFORMATION: a, c, t, g, unknown or other
<220> FEATURE:
<221> NAME/KEY: modified_base
<222> LOCATION: (21173)..(21173)
<223> OTHER INFORMATION: a, c, t, g, unknown or other
<220> FEATURE:
<221> NAME/KEY: modified_base
<222> LOCATION: (21175)..(21175)
<223> OTHER INFORMATION: a, c, t, g, unknown or other
<220> FEATURE:
<221> NAME/KEY: modified_base
<222> LOCATION: (21182)..(21182)
<223> OTHER INFORMATION: a, c, t, g, unknown or other
<220> FEATURE:
<221> NAME/KEY: modified_base
<222> LOCATION: (21184)..(21184)
<223> OTHER INFORMATION: a, c, t, g, unknown or other
<220> FEATURE:
<221> NAME/KEY: modified_base
<222> LOCATION: (21423)..(21423)
<223> OTHER INFORMATION: a, c, t, g, unknown or other
<220> FEATURE:
<221> NAME/KEY: modified_base
<222> LOCATION: (21425)..(21429)
<223> OTHER INFORMATION: a, c, t, g, unknown or other
<220> FEATURE:
<221> NAME/KEY: modified_base
<222> LOCATION: (21432)..(21432)
<223> OTHER INFORMATION: a, c, t, g, unknown or other
<220> FEATURE:
<221> NAME/KEY: modified_base
<222> LOCATION: (21435)..(21435)
<223> OTHER INFORMATION: a, c, t, g, unknown or other
<220> FEATURE:
<221> NAME/KEY: modified_base
<222> LOCATION: (21440)..(21440)
<223> OTHER INFORMATION: a, c, t, g, unknown or other
<220> FEATURE:
<221> NAME/KEY: modified_base
<222> LOCATION: (21454)..(21454)
<223> OTHER INFORMATION: a, c, t, g, unknown or other
<220> FEATURE:
<221> NAME/KEY: modified_base
<222> LOCATION: (21456)..(21457)
<223> OTHER INFORMATION: a, c, t, g, unknown or other
<220> FEATURE:
<221> NAME/KEY: modified_base
<222> LOCATION: (21471)..(21472)
<223> OTHER INFORMATION: a, c, t, g, unknown or other
<220> FEATURE:
<221> NAME/KEY: modified_base
<222> LOCATION: (21474)..(21474)
<223> OTHER INFORMATION: a, c, t, g, unknown or other
<220> FEATURE:
<221> NAME/KEY: modified_base
<222> LOCATION: (21478)..(21478)
<223> OTHER INFORMATION: a, c, t, g, unknown or other
<220> FEATURE:
<221> NAME/KEY: modified_base
<222> LOCATION: (21496)..(21496)
<223> OTHER INFORMATION: a, c, t, g, unknown or other
<220> FEATURE:
<221> NAME/KEY: modified_base
<222> LOCATION: (21517)..(21517)
<223> OTHER INFORMATION: a, c, t, g, unknown or other
<220> FEATURE:
<221> NAME/KEY: modified_base
<222> LOCATION: (21533)..(21534)
```

-continued

```
<223> OTHER INFORMATION: a, c, t, g, unknown or other
<220> FEATURE:
<221> NAME/KEY: modified_base
<222> LOCATION: (21544)..(21544)
<223> OTHER INFORMATION: a, c, t, g, unknown or other
<220> FEATURE:
<221> NAME/KEY: modified_base
<222> LOCATION: (21559)..(21559)
<223> OTHER INFORMATION: a, c, t, g, unknown or other
<220> FEATURE:
<221> NAME/KEY: modified_base
<222> LOCATION: (21570)..(21570)
<223> OTHER INFORMATION: a, c, t, g, unknown or other
<220> FEATURE:
<221> NAME/KEY: modified_base
<222> LOCATION: (21574)..(21574)
<223> OTHER INFORMATION: a, c, t, g, unknown or other
<220> FEATURE:
<221> NAME/KEY: modified_base
<222> LOCATION: (21583)..(21583)
<223> OTHER INFORMATION: a, c, t, g, unknown or other
<220> FEATURE:
<221> NAME/KEY: modified_base
<222> LOCATION: (21660)..(21660)
<223> OTHER INFORMATION: a, c, t, g, unknown or other
<220> FEATURE:
<221> NAME/KEY: modified_base
<222> LOCATION: (21684)..(21684)
<223> OTHER INFORMATION: a, c, t, g, unknown or other
<220> FEATURE:
<221> NAME/KEY: modified_base
<222> LOCATION: (21710)..(21710)
<223> OTHER INFORMATION: a, c, t, g, unknown or other
<220> FEATURE:
<221> NAME/KEY: modified_base
<222> LOCATION: (21778)..(21778)
<223> OTHER INFORMATION: a, c, t, g, unknown or other
<220> FEATURE:
<221> NAME/KEY: modified_base
<222> LOCATION: (21789)..(21789)
<223> OTHER INFORMATION: a, c, t, g, unknown or other
<220> FEATURE:
<221> NAME/KEY: modified_base
<222> LOCATION: (21798)..(21798)
<223> OTHER INFORMATION: a, c, t, g, unknown or other
<220> FEATURE:
<221> NAME/KEY: modified_base
<222> LOCATION: (21823)..(21823)
<223> OTHER INFORMATION: a, c, t, g, unknown or other
<220> FEATURE:
<221> NAME/KEY: modified_base
<222> LOCATION: (21874)..(21874)
<223> OTHER INFORMATION: a, c, t, g, unknown or other
<220> FEATURE:
<221> NAME/KEY: modified_base
<222> LOCATION: (21876)..(21876)
<223> OTHER INFORMATION: a, c, t, g, unknown or other
<220> FEATURE:
<221> NAME/KEY: modified_base
<222> LOCATION: (21880)..(21880)
<223> OTHER INFORMATION: a, c, t, g, unknown or other
<220> FEATURE:
<221> NAME/KEY: modified_base
<222> LOCATION: (21889)..(21889)
<223> OTHER INFORMATION: a, c, t, g, unknown or other
<220> FEATURE:
<221> NAME/KEY: modified_base
<222> LOCATION: (21894)..(21894)
<223> OTHER INFORMATION: a, c, t, g, unknown or other
<220> FEATURE:
<221> NAME/KEY: modified_base
<222> LOCATION: (22844)..(22844)
<223> OTHER INFORMATION: a, c, t, g, unknown or other
<220> FEATURE:
<221> NAME/KEY: modified_base
<222> LOCATION: (22907)..(22907)
<223> OTHER INFORMATION: a, c, t, g, unknown or other
<220> FEATURE:
<221> NAME/KEY: modified_base
```

```
<222> LOCATION: (22914)..(22914)
<223> OTHER INFORMATION: a, c, t, g, unknown or other
<220> FEATURE:
<221> NAME/KEY: modified_base
<222> LOCATION: (23167)..(23167)
<223> OTHER INFORMATION: a, c, t, g, unknown or other
<220> FEATURE:
<221> NAME/KEY: modified_base
<222> LOCATION: (23348)..(23348)
<223> OTHER INFORMATION: a, c, t, g, unknown or other
<220> FEATURE:
<221> NAME/KEY: modified_base
<222> LOCATION: (23351)..(23351)
<223> OTHER INFORMATION: a, c, t, g, unknown or other
<220> FEATURE:
<221> NAME/KEY: modified_base
<222> LOCATION: (23406)..(23406)
<223> OTHER INFORMATION: a, c, t, g, unknown or other
<220> FEATURE:
<221> NAME/KEY: modified_base
<222> LOCATION: (23647)..(23647)
<223> OTHER INFORMATION: a, c, t, g, unknown or other
<220> FEATURE:
<221> NAME/KEY: modified_base
<222> LOCATION: (23806)..(23806)
<223> OTHER INFORMATION: a, c, t, g, unknown or other
<220> FEATURE:
<221> NAME/KEY: modified_base
<222> LOCATION: (24617)..(24617)
<223> OTHER INFORMATION: a, c, t, g, unknown or other
<220> FEATURE:
<221> NAME/KEY: modified_base
<222> LOCATION: (24853)..(24853)
<223> OTHER INFORMATION: a, c, t, g, unknown or other
<220> FEATURE:
<221> NAME/KEY: modified_base
<222> LOCATION: (25080)..(25080)
<223> OTHER INFORMATION: a, c, t, g, unknown or other
<220> FEATURE:
<221> NAME/KEY: modified_base
<222> LOCATION: (25108)..(25108)
<223> OTHER INFORMATION: a, c, t, g, unknown or other
<220> FEATURE:
<221> NAME/KEY: modified_base
<222> LOCATION: (25371)..(25371)
<223> OTHER INFORMATION: a, c, t, g, unknown or other
<220> FEATURE:
<221> NAME/KEY: modified_base
<222> LOCATION: (25397)..(25397)
<223> OTHER INFORMATION: a, c, t, g, unknown or other
<220> FEATURE:
<221> NAME/KEY: modified_base
<222> LOCATION: (25411)..(25411)
<223> OTHER INFORMATION: a, c, t, g, unknown or other
<220> FEATURE:
<221> NAME/KEY: modified_base
<222> LOCATION: (25507)..(25507)
<223> OTHER INFORMATION: a, c, t, g, unknown or other
<220> FEATURE:
<221> NAME/KEY: modified_base
<222> LOCATION: (25692)..(25692)
<223> OTHER INFORMATION: a, c, t, g, unknown or other
<220> FEATURE:
<221> NAME/KEY: modified_base
<222> LOCATION: (25712)..(25713)
<223> OTHER INFORMATION: a, c, t, g, unknown or other
<220> FEATURE:
<221> NAME/KEY: modified_base
<222> LOCATION: (25718)..(25718)
<223> OTHER INFORMATION: a, c, t, g, unknown or other
<220> FEATURE:
<221> NAME/KEY: modified_base
<222> LOCATION: (25728)..(25728)
<223> OTHER INFORMATION: a, c, t, g, unknown or other
<220> FEATURE:
<221> NAME/KEY: modified_base
<222> LOCATION: (25742)..(25742)
<223> OTHER INFORMATION: a, c, t, g, unknown or other
<220> FEATURE:
```

```
<221> NAME/KEY: modified_base
<222> LOCATION: (25774)..(25774)
<223> OTHER INFORMATION: a, c, t, g, unknown or other
<220> FEATURE:
<221> NAME/KEY: modified_base
<222> LOCATION: (27450)..(27450)
<223> OTHER INFORMATION: a, c, t, g, unknown or other
<220> FEATURE:
<221> NAME/KEY: modified_base
<222> LOCATION: (29480)..(29480)
<223> OTHER INFORMATION: a, c, t, g, unknown or other
<220> FEATURE:
<221> NAME/KEY: modified_base
<222> LOCATION: (29507)..(29507)
<223> OTHER INFORMATION: a, c, t, g, unknown or other
<220> FEATURE:
<221> NAME/KEY: modified_base
<222> LOCATION: (31101)..(31101)
<223> OTHER INFORMATION: a, c, t, g, unknown or other
<220> FEATURE:
<221> NAME/KEY: modified_base
<222> LOCATION: (32562)..(32562)
<223> OTHER INFORMATION: a, c, t, g, unknown or other
<220> FEATURE:
<221> NAME/KEY: modified_base
<222> LOCATION: (32840)..(32840)
<223> OTHER INFORMATION: a, c, t, g, unknown or other
<220> FEATURE:
<221> NAME/KEY: modified_base
<222> LOCATION: (32855)..(32855)
<223> OTHER INFORMATION: a, c, t, g, unknown or other
<220> FEATURE:
<221> NAME/KEY: modified_base
<222> LOCATION: (32865)..(32865)
<223> OTHER INFORMATION: a, c, t, g, unknown or other
<220> FEATURE:
<221> NAME/KEY: modified_base
<222> LOCATION: (32922)..(32922)
<223> OTHER INFORMATION: a, c, t, g, unknown or other
<220> FEATURE:
<221> NAME/KEY: modified_base
<222> LOCATION: (32988)..(32988)
<223> OTHER INFORMATION: a, c, t, g, unknown or other
<220> FEATURE:
<221> NAME/KEY: modified_base
<222> LOCATION: (32991)..(32991)
<223> OTHER INFORMATION: a, c, t, g, unknown or other
<220> FEATURE:
<221> NAME/KEY: modified_base
<222> LOCATION: (33295)..(33295)
<223> OTHER INFORMATION: a, c, t, g, unknown or other
<220> FEATURE:
<221> NAME/KEY: modified_base
<222> LOCATION: (33364)..(33364)
<223> OTHER INFORMATION: a, c, t, g, unknown or other
<220> FEATURE:
<221> NAME/KEY: modified_base
<222> LOCATION: (35517)..(35517)
<223> OTHER INFORMATION: a, c, t, g, unknown or other
<220> FEATURE:
<221> NAME/KEY: modified_base
<222> LOCATION: (35526)..(35526)
<223> OTHER INFORMATION: a, c, t, g, unknown or other
<220> FEATURE:
<221> NAME/KEY: modified_base
<222> LOCATION: (35718)..(35718)
<223> OTHER INFORMATION: a, c, t, g, unknown or other
<220> FEATURE:
<221> NAME/KEY: modified_base
<222> LOCATION: (36058)..(36058)
<223> OTHER INFORMATION: a, c, t, g, unknown or other
<220> FEATURE:
<221> NAME/KEY: modified_base
<222> LOCATION: (36064)..(36064)
<223> OTHER INFORMATION: a, c, t, g, unknown or other
<220> FEATURE:
<221> NAME/KEY: modified_base
<222> LOCATION: (36607)..(36607)
<223> OTHER INFORMATION: a, c, t, g, unknown or other
```

```
<220> FEATURE:
<221> NAME/KEY: modified_base
<222> LOCATION: (36622)..(36622)
<223> OTHER INFORMATION: a, c, t, g, unknown or other
<220> FEATURE:
<221> NAME/KEY: modified_base
<222> LOCATION: (36667)..(36667)
<223> OTHER INFORMATION: a, c, t, g, unknown or other
<220> FEATURE:
<221> NAME/KEY: modified_base
<222> LOCATION: (36679)..(36679)
<223> OTHER INFORMATION: a, c, t, g, unknown or other
<220> FEATURE:
<221> NAME/KEY: modified_base
<222> LOCATION: (36985)..(36985)
<223> OTHER INFORMATION: a, c, t, g, unknown or other
<220> FEATURE:
<221> NAME/KEY: modified_base
<222> LOCATION: (37006)..(37006)
<223> OTHER INFORMATION: a, c, t, g, unknown or other
<220> FEATURE:
<221> NAME/KEY: modified_base
<222> LOCATION: (37249)..(37249)
<223> OTHER INFORMATION: a, c, t, g, unknown or other
<220> FEATURE:
<221> NAME/KEY: modified_base
<222> LOCATION: (37267)..(37267)
<223> OTHER INFORMATION: a, c, t, g, unknown or other
<220> FEATURE:
<221> NAME/KEY: modified_base
<222> LOCATION: (37306)..(37306)
<223> OTHER INFORMATION: a, c, t, g, unknown or other
<220> FEATURE:
<221> NAME/KEY: modified_base
<222> LOCATION: (37351)..(37351)
<223> OTHER INFORMATION: a, c, t, g, unknown or other
<220> FEATURE:
<221> NAME/KEY: modified_base
<222> LOCATION: (37429)..(37429)
<223> OTHER INFORMATION: a, c, t, g, unknown or other
<220> FEATURE:
<221> NAME/KEY: modified_base
<222> LOCATION: (37432)..(37432)
<223> OTHER INFORMATION: a, c, t, g, unknown or other
<220> FEATURE:
<221> NAME/KEY: modified_base
<222> LOCATION: (37504)..(37504)
<223> OTHER INFORMATION: a, c, t, g, unknown or other
<220> FEATURE:
<221> NAME/KEY: modified_base
<222> LOCATION: (37507)..(37507)
<223> OTHER INFORMATION: a, c, t, g, unknown or other
<220> FEATURE:
<221> NAME/KEY: modified_base
<222> LOCATION: (37510)..(37510)
<223> OTHER INFORMATION: a, c, t, g, unknown or other
<220> FEATURE:
<221> NAME/KEY: modified_base
<222> LOCATION: (37550)..(37550)
<223> OTHER INFORMATION: a, c, t, g, unknown or other
<220> FEATURE:
<221> NAME/KEY: modified_base
<222> LOCATION: (37579)..(37579)
<223> OTHER INFORMATION: a, c, t, g, unknown or other
<220> FEATURE:
<221> NAME/KEY: modified_base
<222> LOCATION: (37630)..(37631)
<223> OTHER INFORMATION: a, c, t, g, unknown or other
<220> FEATURE:
<221> NAME/KEY: modified_base
<222> LOCATION: (37642)..(37646)
<223> OTHER INFORMATION: a, c, t, g, unknown or other
<220> FEATURE:
<221> NAME/KEY: modified_base
<222> LOCATION: (37841)..(37841)
<223> OTHER INFORMATION: a, c, t, g, unknown or other
<220> FEATURE:
<221> NAME/KEY: modified_base
<222> LOCATION: (37856)..(37856)
```

-continued

```
<223> OTHER INFORMATION: a, c, t, g, unknown or other
<220> FEATURE:
<221> NAME/KEY: modified_base
<222> LOCATION: (37859)..(37859)
<223> OTHER INFORMATION: a, c, t, g, unknown or other
<220> FEATURE:
<221> NAME/KEY: modified_base
<222> LOCATION: (37970)..(37970)
<223> OTHER INFORMATION: a, c, t, g, unknown or other
<220> FEATURE:
<221> NAME/KEY: modified_base
<222> LOCATION: (38051)..(38051)
<223> OTHER INFORMATION: a, c, t, g, unknown or other
<220> FEATURE:
<221> NAME/KEY: modified_base
<222> LOCATION: (38198)..(38198)
<223> OTHER INFORMATION: a, c, t, g, unknown or other
<220> FEATURE:
<221> NAME/KEY: modified_base
<222> LOCATION: (38216)..(38216)
<223> OTHER INFORMATION: a, c, t, g, unknown or other
<220> FEATURE:
<221> NAME/KEY: modified_base
<222> LOCATION: (38243)..(38243)
<223> OTHER INFORMATION: a, c, t, g, unknown or other
<220> FEATURE:
<221> NAME/KEY: modified_base
<222> LOCATION: (38306)..(38306)
<223> OTHER INFORMATION: a, c, t, g, unknown or other
<220> FEATURE:
<221> NAME/KEY: modified_base
<222> LOCATION: (38367)..(38367)
<223> OTHER INFORMATION: a, c, t, g, unknown or other
<220> FEATURE:
<221> NAME/KEY: modified_base
<222> LOCATION: (38498)..(38498)
<223> OTHER INFORMATION: a, c, t, g, unknown or other
<220> FEATURE:
<221> NAME/KEY: modified_base
<222> LOCATION: (38624)..(38624)
<223> OTHER INFORMATION: a, c, t, g, unknown or other
<220> FEATURE:
<221> NAME/KEY: modified_base
<222> LOCATION: (38921)..(38921)
<223> OTHER INFORMATION: a, c, t, g, unknown or other
<220> FEATURE:
<221> NAME/KEY: modified_base
<222> LOCATION: (38933)..(38933)
<223> OTHER INFORMATION: a, c, t, g, unknown or other
<220> FEATURE:
<221> NAME/KEY: modified_base
<222> LOCATION: (38960)..(38960)
<223> OTHER INFORMATION: a, c, t, g, unknown or other
<220> FEATURE:
<221> NAME/KEY: modified_base
<222> LOCATION: (39092)..(39092)
<223> OTHER INFORMATION: a, c, t, g, unknown or other
<220> FEATURE:
<221> NAME/KEY: modified_base
<222> LOCATION: (39113)..(39113)
<223> OTHER INFORMATION: a, c, t, g, unknown or other
<220> FEATURE:
<221> NAME/KEY: modified_base
<222> LOCATION: (39149)..(39149)
<223> OTHER INFORMATION: a, c, t, g, unknown or other
<220> FEATURE:
<221> NAME/KEY: modified_base
<222> LOCATION: (39151)..(39151)
<223> OTHER INFORMATION: a, c, t, g, unknown or other
<220> FEATURE:
<221> NAME/KEY: modified_base
<222> LOCATION: (39227)..(39227)
<223> OTHER INFORMATION: a, c, t, g, unknown or other
<220> FEATURE:
<221> NAME/KEY: modified_base
<222> LOCATION: (39240)..(39240)
<223> OTHER INFORMATION: a, c, t, g, unknown or other
<220> FEATURE:
<221> NAME/KEY: modified_base
```

```
<222> LOCATION: (39324)..(39324)
<223> OTHER INFORMATION: a, c, t, g, unknown or other
<220> FEATURE:
<221> NAME/KEY: modified_base
<222> LOCATION: (39347)..(39347)
<223> OTHER INFORMATION: a, c, t, g, unknown or other
<220> FEATURE:
<221> NAME/KEY: modified_base
<222> LOCATION: (39545)..(39545)
<223> OTHER INFORMATION: a, c, t, g, unknown or other
<220> FEATURE:
<221> NAME/KEY: modified_base
<222> LOCATION: (39575)..(39575)
<223> OTHER INFORMATION: a, c, t, g, unknown or other
<220> FEATURE:
<221> NAME/KEY: modified_base
<222> LOCATION: (39665)..(39665)
<223> OTHER INFORMATION: a, c, t, g, unknown or other
<220> FEATURE:
<221> NAME/KEY: modified_base
<222> LOCATION: (39707)..(39707)
<223> OTHER INFORMATION: a, c, t, g, unknown or other
<220> FEATURE:
<221> NAME/KEY: modified_base
<222> LOCATION: (39731)..(39731)
<223> OTHER INFORMATION: a, c, t, g, unknown or other
<220> FEATURE:
<221> NAME/KEY: modified_base
<222> LOCATION: (39782)..(39782)
<223> OTHER INFORMATION: a, c, t, g, unknown or other
<220> FEATURE:
<221> NAME/KEY: modified_base
<222> LOCATION: (39820)..(39820)
<223> OTHER INFORMATION: a, c, t, g, unknown or other
<220> FEATURE:
<221> NAME/KEY: modified_base
<222> LOCATION: (39976)..(39976)
<223> OTHER INFORMATION: a, c, t, g, unknown or other
<220> FEATURE:
<221> NAME/KEY: modified_base
<222> LOCATION: (44407)..(44407)
<223> OTHER INFORMATION: a, c, t, g, unknown or other
<220> FEATURE:
<221> NAME/KEY: modified_base
<222> LOCATION: (46542)..(46542)
<223> OTHER INFORMATION: a, c, t, g, unknown or other
<220> FEATURE:
<221> NAME/KEY: modified_base
<222> LOCATION: (49791)..(49791)
<223> OTHER INFORMATION: a, c, t, g, unknown or other
<220> FEATURE:
<221> NAME/KEY: modified_base
<222> LOCATION: (54345)..(54345)
<223> OTHER INFORMATION: a, c, t, g, unknown or other
<220> FEATURE:
<221> NAME/KEY: modified_base
<222> LOCATION: (58249)..(58249)
<223> OTHER INFORMATION: a, c, t, g, unknown or other
<220> FEATURE:
<221> NAME/KEY: modified_base
<222> LOCATION: (59537)..(59537)
<223> OTHER INFORMATION: a, c, t, g, unknown or other
<220> FEATURE:
<221> NAME/KEY: modified_base
<222> LOCATION: (60478)..(60478)
<223> OTHER INFORMATION: a, c, t, g, unknown or other
<220> FEATURE:
<221> NAME/KEY: modified_base
<222> LOCATION: (60929)..(60929)
<223> OTHER INFORMATION: a, c, t, g, unknown or other
<220> FEATURE:
<221> NAME/KEY: modified_base
<222> LOCATION: (60934)..(60934)
<223> OTHER INFORMATION: a, c, t, g, unknown or other
<220> FEATURE:
<221> NAME/KEY: modified_base
<222> LOCATION: (60939)..(60940)
<223> OTHER INFORMATION: a, c, t, g, unknown or other
<220> FEATURE:
```

```
<221> NAME/KEY: modified_base
<222> LOCATION: (60949)..(60949)
<223> OTHER INFORMATION: a, c, t, g, unknown or other
<220> FEATURE:
<221> NAME/KEY: modified_base
<222> LOCATION: (60961)..(60962)
<223> OTHER INFORMATION: a, c, t, g, unknown or other
<220> FEATURE:
<221> NAME/KEY: modified_base
<222> LOCATION: (60968)..(60968)
<223> OTHER INFORMATION: a, c, t, g, unknown or other
<220> FEATURE:
<221> NAME/KEY: modified_base
<222> LOCATION: (60970)..(60970)
<223> OTHER INFORMATION: a, c, t, g, unknown or other
<220> FEATURE:
<221> NAME/KEY: modified_base
<222> LOCATION: (60979)..(60979)
<223> OTHER INFORMATION: a, c, t, g, unknown or other
<220> FEATURE:
<221> NAME/KEY: modified_base
<222> LOCATION: (60982)..(60982)
<223> OTHER INFORMATION: a, c, t, g, unknown or other
<220> FEATURE:
<221> NAME/KEY: modified_base
<222> LOCATION: (60988)..(60988)
<223> OTHER INFORMATION: a, c, t, g, unknown or other
<220> FEATURE:
<221> NAME/KEY: modified_base
<222> LOCATION: (61180)..(61180)
<223> OTHER INFORMATION: a, c, t, g, unknown or other
<220> FEATURE:
<221> NAME/KEY: modified_base
<222> LOCATION: (61195)..(61195)
<223> OTHER INFORMATION: a, c, t, g, unknown or other
<220> FEATURE:
<221> NAME/KEY: modified_base
<222> LOCATION: (61315)..(61315)
<223> OTHER INFORMATION: a, c, t, g, unknown or other
<220> FEATURE:
<221> NAME/KEY: modified_base
<222> LOCATION: (61397)..(61397)
<223> OTHER INFORMATION: a, c, t, g, unknown or other
<220> FEATURE:
<221> NAME/KEY: modified_base
<222> LOCATION: (61399)..(61399)
<223> OTHER INFORMATION: a, c, t, g, unknown or other
<220> FEATURE:
<221> NAME/KEY: modified_base
<222> LOCATION: (61427)..(61427)
<223> OTHER INFORMATION: a, c, t, g, unknown or other
<220> FEATURE:
<221> NAME/KEY: modified_base
<222> LOCATION: (61532)..(61532)
<223> OTHER INFORMATION: a, c, t, g, unknown or other
<220> FEATURE:
<221> NAME/KEY: modified_base
<222> LOCATION: (61623)..(61623)
<223> OTHER INFORMATION: a, c, t, g, unknown or other
<220> FEATURE:
<221> NAME/KEY: modified_base
<222> LOCATION: (61864)..(61864)
<223> OTHER INFORMATION: a, c, t, g, unknown or other
<220> FEATURE:
<221> NAME/KEY: modified_base
<222> LOCATION: (61957)..(61957)
<223> OTHER INFORMATION: a, c, t, g, unknown or other
<220> FEATURE:
<221> NAME/KEY: modified_base
<222> LOCATION: (62071)..(62071)
<223> OTHER INFORMATION: a, c, t, g, unknown or other
<220> FEATURE:
<221> NAME/KEY: modified_base
<222> LOCATION: (63256)..(63256)
<223> OTHER INFORMATION: a, c, t, g, unknown or other
<220> FEATURE:
<221> NAME/KEY: modified_base
<222> LOCATION: (63258)..(63259)
<223> OTHER INFORMATION: a, c, t, g, unknown or other
```

-continued

```
<220> FEATURE:
<221> NAME/KEY: modified_base
<222> LOCATION: (64474)..(64474)
<223> OTHER INFORMATION: a, c, t, g, unknown or other
<220> FEATURE:
<221> NAME/KEY: modified_base
<222> LOCATION: (64477)..(64477)
<223> OTHER INFORMATION: a, c, t, g, unknown or other
<220> FEATURE:
<221> NAME/KEY: modified_base
<222> LOCATION: (64493)..(64493)
<223> OTHER INFORMATION: a, c, t, g, unknown or other
<220> FEATURE:
<221> NAME/KEY: modified_base
<222> LOCATION: (64537)..(64538)
<223> OTHER INFORMATION: a, c, t, g, unknown or other
<220> FEATURE:
<221> NAME/KEY: modified_base
<222> LOCATION: (64541)..(64542)
<223> OTHER INFORMATION: a, c, t, g, unknown or other
<220> FEATURE:
<221> NAME/KEY: modified_base
<222> LOCATION: (64544)..(64544)
<223> OTHER INFORMATION: a, c, t, g, unknown or other
<220> FEATURE:
<221> NAME/KEY: modified_base
<222> LOCATION: (64551)..(64552)
<223> OTHER INFORMATION: a, c, t, g, unknown or other
<220> FEATURE:
<221> NAME/KEY: modified_base
<222> LOCATION: (64561)..(64561)
<223> OTHER INFORMATION: a, c, t, g, unknown or other
<220> FEATURE:
<221> NAME/KEY: modified_base
<222> LOCATION: (64632)..(64632)
<223> OTHER INFORMATION: a, c, t, g, unknown or other
<220> FEATURE:
<221> NAME/KEY: modified_base
<222> LOCATION: (64766)..(64766)
<223> OTHER INFORMATION: a, c, t, g, unknown or other
<220> FEATURE:
<221> NAME/KEY: modified_base
<222> LOCATION: (64845)..(64845)
<223> OTHER INFORMATION: a, c, t, g, unknown or other
<220> FEATURE:
<221> NAME/KEY: modified_base
<222> LOCATION: (65260)..(65260)
<223> OTHER INFORMATION: a, c, t, g, unknown or other
<220> FEATURE:
<221> NAME/KEY: modified_base
<222> LOCATION: (66845)..(66845)
<223> OTHER INFORMATION: a, c, t, g, unknown or other
<220> FEATURE:
<221> NAME/KEY: modified_base
<222> LOCATION: (66847)..(66847)
<223> OTHER INFORMATION: a, c, t, g, unknown or other
<220> FEATURE:
<221> NAME/KEY: modified_base
<222> LOCATION: (66855)..(66855)
<223> OTHER INFORMATION: a, c, t, g, unknown or other
<220> FEATURE:
<221> NAME/KEY: modified_base
<222> LOCATION: (66916)..(66916)
<223> OTHER INFORMATION: a, c, t, g, unknown or other
<220> FEATURE:
<221> NAME/KEY: modified_base
<222> LOCATION: (67185)..(67185)
<223> OTHER INFORMATION: a, c, t, g, unknown or other
<220> FEATURE:
<221> NAME/KEY: modified_base
<222> LOCATION: (67479)..(67479)
<223> OTHER INFORMATION: a, c, t, g, unknown or other
<220> FEATURE:
<221> NAME/KEY: modified_base
<222> LOCATION: (69105)..(69105)
<223> OTHER INFORMATION: a, c, t, g, unknown or other
<220> FEATURE:
<221> NAME/KEY: modified_base
<222> LOCATION: (69599)..(69599)
```

```
<223> OTHER INFORMATION: a, c, t, g, unknown or other
<220> FEATURE:
<221> NAME/KEY: modified_base
<222> LOCATION: (69653)..(69653)
<223> OTHER INFORMATION: a, c, t, g, unknown or other
<220> FEATURE:
<221> NAME/KEY: modified_base
<222> LOCATION: (70593)..(70593)
<223> OTHER INFORMATION: a, c, t, g, unknown or other
<220> FEATURE:
<221> NAME/KEY: modified_base
<222> LOCATION: (73334)..(73334)
<223> OTHER INFORMATION: a, c, t, g, unknown or other
<220> FEATURE:
<221> NAME/KEY: modified_base
<222> LOCATION: (78830)..(78830)
<223> OTHER INFORMATION: a, c, t, g, unknown or other
<220> FEATURE:
<221> NAME/KEY: modified_base
<222> LOCATION: (78897)..(78897)
<223> OTHER INFORMATION: a, c, t, g, unknown or other
<220> FEATURE:
<221> NAME/KEY: modified_base
<222> LOCATION: (78907)..(78907)
<223> OTHER INFORMATION: a, c, t, g, unknown or other
<220> FEATURE:
<221> NAME/KEY: modified_base
<222> LOCATION: (78925)..(78925)
<223> OTHER INFORMATION: a, c, t, g, unknown or other

<400> SEQUENCE: 12
cgatttgctt agtacattca ttacatttac tattcatcct tatttacctt taataaattt      60
gcttatcaaa agagcaatta attgggatag tgataacttc attagtaact acatgtttgc     120
ctgtcttttt aaagaattgg gcaaattttg aagtagctgg aattacaaag gtatcatccc     180
gatcattatt tgacatattg tanaaagtaa anttaccgtc tanntnaaac ctaatnnncc     240
antnaatatn ncgtantttg aaatctatac caaatcttaa ntgancatca atnaattcag     300
aaccaccgta ntcataagct ccggtgaaat tccaattaat ttctgcgaat tggaaagtta     360
caggatgttc gccatgttca tcttgtatgt agtaaccatc atgagctttc aatagatna     420 ctaaatcatg catgctacca gcctcaaaga ataataggg gagtctagac tcccctatta     480
atttattttg cttttagcca ntcttctant ggnggtaaat anttctcatg ngcccantta     540
atnattgttt ctacaacagg accntgtann tcaaggttnc ctgagatttc atgnggttca     600
tcaatagata gaacccacgt ntgtggcgca atgcgttcag ttgctttngt tagatacaca     660
tcaggcatta acgtaagatt caattgatcg ccgtcaaaat cagccgtatt gttcagtatc     720
agtcgttaat tgatacccgc accattacgt gcagctctag ctttcactag aagaccagac     780
tatatcttca cccttccttt cggagtgggg tgtctcccat ttcgagtcac ttgaccctac     840
atcctatttc taggaccggt gcacctgata ccgtgatagt cgttgaacct tctcctattc     900
ctaaatggaa tgttacggag cttggctgct gattgaccct acctaatctt tttcaaacct     960
tggctttgtc tttcgactcg cagtggtaga ttagtttaac aggatatccc agcaattaga    1020
gagaactcaa cccaacgatt actcattggg ggaactagat ttgattaact taataaggta    1080
tttatcaagc accccattct tttcaaagat tgctcttcga acagtattcg gatgcttaat    1140
accgacatct cttgcaaagt gtggaatact cggatacact ttggtagtgt tcaagatggt    1200
gtcagttact tcaattggag tacctttttcc attactaggt tttccaaatg aggcttcaat    1260 ttcttttga gtgtatttag ggaaatcttc aggattagcg gtatatgaga ataccaaacc    1320
atccatgatt tccttactac ctctaactag atggtaatag gctttattac gtttagtacc    1380
tagtgcaagt tccatttctg ctaagttatg aaacacatgt aatgtcttag tcttatagtc    1440
```

```
taaaacataa actgtcttgg tactatctcg atcagcaatc ttagtctcac cggtaataaa   1500
ttcaaatgtg aatctatttc tatacggctt agtcttatga tcacgtataa taacccaaac   1560
cgtatttta ttaactccta atgcccgagc aagttcattc atcgagtaat aagtagtctt    1620
ttcaccagtg gtaacgtcag ttgcaattac ccgtctattt tcttttctta atccattttt   1680
gtaagcatgc tcaatgtttt caccacgagt catccactcc aaattagatg gtaagttatt   1740
atgtttgttg ccgtctttat gattgacttc ataatctggt ccaggtgatg gaccatggaa   1800
agctaaacag attaatatat gaactccctt actcttagat gttttttcat cattttttgc   1860
accaatattg agatatgtcc caatcgatgt tttagtaagg aagaaattac atattctatt   1920
taaccgctta tgacgaattg ttcctaagtt actagcttca tatgctgagt atccaggaat   1980
atcccgccat tcaattttaa atgaagccgg atcaaagacg gacactactc cgttttgttc   2040
cattgttttt acccttattt agttattcaa ttgtccatta ggcgctttaa ggcataaaac   2100
tgacatgctg atagaattat cattaatgtc atcttttact ttagtaataa agaactgctg   2160
cgtagatcca cgttgaagcg ttggcaatat cttcagatag ttcgttaggc tatcccgcac   2220
cattacgtgc agctctagtt ctcactagat gttgagacta tatcttcacc tttggcttta   2280
tccagtaagg tgcttcccac ttcgatttaa gggattctat acccacccac ttgggcccta   2340
ctctactccc tctaccttac ggcatggttt cgatagtcgt tgaggattcc tcatactcct   2400
tttaattaag aaggttagag gctttcctgc tgattgactc tattcaatac ttttcgaact   2460
tttccgtatt agctttcgct atccgtttca gtgtattgac ctagcgagtt atcccagcat   2520
ttcaagaagt tttgtcgagt atcatttctg atacaaggaa accattatta agttgatcca   2580
ctacactaag attacttagg tggtatgtag cttctcttta cgcgctttgt atcggttata   2640
ttcgtcaatg gatttattaa ccatctcttg agttaattta gaaacgtatt cgaatagccg   2700
ttccttatct tcaactctac agatgacata tccattaaat aatctcagtt ctggtttctt   2760
caagatgtct tgcactgacc ccttgattaa tccagtccta agttgcaatt gtgttaagtt   2820
ctcatacctg ccaaaggtgt tagttttgaa gtctatgcaa taaacttcaa tagcgttctt   2880
ccgcttctgt ggatgataat ccccagttac ttcaaacacg tacttaccat tgtaaggttt   2940
agttagatgc gccatgacta catgcagccc tttaccatga cctagctcta agaactctgc   3000
aacttctttc atcgagatga agttatacac ctcacccgtg gttacatcag tgcatttaac   3060
agctaatgcg tgtttgtttg caccggttat aaatgcatgt tttacattac cactgcgagt   3120
ttcccactct aggttaaggt aatggttatg atgcttattg gtgtctttat ggttaacgtc   3180
caaggataca taattctcag gtaatccatg gaaagccata catacgaaac gatgcacgta   3240
tcgtattttg cgaacacctt catcattgtg gatattaacc gtcaggtaag tacccttaga   3300
tgttttgttc tcatgttgag aaatcaactc acctttaagg ttccttactt gaccatggtc   3360
actgacttca tagttactga aaccaggtat acttcgccat cttatttctt cattcatatt   3420
tcctcattag agattcttgg ttaccacacc cagaatctgt agcgctacga cttaataaat   3480
taatttcggt gaaaagtaca acccatccct ttataagggg ctgcttctgc aattagctct   3540
ttaaatagat ctgcaatgat ttggttatat tgaagtacat tctcatatac aaatgagaat   3600
gcttcacgag ttgtcatgtt aaacttngct tttagnttnt tngttagatg atactttaat   3660
aattgacaac ctacncccca nggnatatgt anttcatcat aatcatgcgg gtcactaata   3720
gaagtgatta ctgcacgtgc cgtagcgttg agacgagcac caaacatgtg acgccgagca   3780
```

```
agaccaggct tttgagcaat tcgtgatttt gcgtagatct cgtagaactg gccatatagt    3840
cttagtcctc gcatagtcct attctgagct ttaattggac taagtggtac agatgatgca    3900
tcaatactag cgaaggttaa ggtagcatca attgctgctt caattggttt atctaagtaa    3960
gtaccgatgt tggttgattc tgctacgaaa cagagtttag aaggaactgg taaatattta    4020
gggaataact tatctttatt ctgagcaacg aattgagcga attcggattt attattagan    4080
ataatatttg catctagtag gaattggaag atctcattga aattatcaat gaagtgattt    4140
aatcctcttt caaatcctcg atgcagtagc ctatctactt tnctgcgtgt ttctttagaa    4200
ccaatagatt cnacatcgta tcgataagaa gtatcagtta gatatgctaa gaaatcgaat    4260
tctttagtta ctagatatcc ggttagcata atgattaaac gtgggttaat tagnctacgt    4320
acntgttttg gtgtacgaac ccacattgat ggttcgatag gacggctaga agtattgaca    4380
actggagtat tacaaatatc acagattact ccgagtttat gtgcgtcttc gattgctcga    4440
caatcacagc ttacactact ttcaattgct tctgaatctt ggaaatgaga atagaaatgc    4500
ctatcaaatt cttctttctc atctgagtta ctcgtattgt aatcattggc ataaattcgt    4560
ttacccgtaa attgatcatg aacttcatta tgatcaacaa ctttggcata aagacccata    4620
ccaaactcct atttatcgat taacaaaaaa ggagatataa gcggccccg aaggagccgc    4680
tatatcagtt tttacaatgg accaccaacg gagcctggcc cgatcctagc gtcatctaca    4740
aagcttaacc tccgctcttc tctgtagcat accggcacta gtatcattta ccatccattg    4800
tagtttttga tcacacgtca cctttttgagt aactcctttc ggttaagtga tctatcatcc    4860
tcgtgtagtg ataggtcgac ctagactaag tccactagtc gattacttca cggaacctac    4920
tcctaaccgt tatcaccgaa gtgaaccagg gtcgcagtat tagaatcggg atgttactta    4980
tttaacatcc ctatctaccg aggtatttcc tattagtacc aggtacccgg tgcattatag    5040
gaaggagcgc cgtaagtttg acccatgctg ccagccatnc caacttgtgc actaccagaa    5100
acagccatgt tacccatacc ggtgtaacca gcgaagcgct gttgaccgaa gttggtaatt    5160
aggttttcca tggttacagt tacaccagcn gctgctgctg cggcatccat tgcggtgatg    5220
aatttcgggt taaaggttag acgacgagca cgaccagtat aggtaacgtt acctaggtac    5280
atcttgtcga agcctttact gttattcata cgacgcacaa tgtggtcatt acctacctga    5340
gtagcatacc aggtcttcca ctcttggtca ttaccttcag acatgttcat ggcacctaga    5400
acgtcgagat cacgacggtc gcttagttca ccatgctcat cagtgtagtg accgaggtct    5460
acttcatgat ggttgtcaaa gataatcgga ccagcttcag ctagattata gaactgacgg    5520
aaaatcagtgc cgtataggtt agttagagct tggaagatca gactaactgc acgagcttgg    5580
tttacgccac cagctgcatc taggacgact tgctcaatag ctgagttgtc tcccattgga    5640
tcgacatcga tctggaatgc agggttctgg ttaaccatct tgttcattag cattacgaag    5700
ttgctgtcgt ctgccatgaa tgcttcggtg cgagtttcaa tcgctttacc tagctctgag    5760
taataaccaa gtgcaccaat atcacgcatc ttactagtag cgatcttcgg cattagagta    5820
cgagcccatg cctgagatgc agttgcacga tacgcgttac caagcgcgaa cagccacatt    5880
tctagagtcc atgcttggat ccaggacgcc ttacgaacgt cagtaataac gatgtaagga    5940
gtgaactgcg gaggtagaac tgcaccaggt agagttacgc caaacatgcc ttgttgctgg    6000
ccagtggtcg gagtccaatg tagatctacg aatagactaa cttggtttag ctggctatcg    6060
gtatcataga actcgttctc aggtacgttg gttttcttac cacggctagt ggagatgacc    6120
aggtcagaac ggatcggatt accacagcta tctttaaccg gaataccatt gtagtctagn    6180
```

```
ttgcaggtaa gctgttcgtt ttctgctttg atgtgggtcg caatagagaa cggagtctca   6240
ttgttacgac gngcaatagc atcttcacag atnttaacng attcaactag taggttctta   6300
acagctagtt catctttgaa gtcgaagtca gcatacactg cacgtggacc ggcagatagt   6360
acttctagac cagggatgtt gtaacggttc cgtaggaact cgccgatctt gctccagtat   6420
tgagcagtga atacatcacg cggtagtacc ttctcttcaa tgatgtcatc agttagacca   6480
ttgttgattt tgtgggtacg gggacggatg cgagtaccag gtaggttatc gagtactaga   6540
gtacgaacga atgccttcat ggaaccattg atatctttag ctagtttaac aatgagtaga   6600
ccagccatac cnacttgttg ngcatcncga tcgaaacgat ggatatcgaa gtcatcaggt   6660
aggtcctgat ggcggattgc ttcttctttt actttagtga atacttgtag ggcatctgct   6720
gaacgagcat cagagccatc tagccgacca gagcgacgca ttagatggtt aatgccagta   6780
gtngacccag gngcgccagn nggacgttga gcttgacgnt gtgcagtggg ttgcggagcn   6840
ggagcngtag cttgagtttg aacggtgccg atttcgtttt cgttaacagc cattttaaat   6900 accttacga ttatggtttc ttgatcaaga agaacctaag tactnagtat actagattca   6960
atttagtaat ataaatctca aattttttc attacaacat agacgctata atctgctatc   7020
agcagatcgt aacgaacact atgttcacta catattatta caatctgagt attatttatt   7080
tttcatctta caatttccat atcttctttt ttgagtttat gggtataaag tttgaatcca   7140
gaaactaatt tacgtcagtc ctgtattaaa taataactat cagtattttt ataaaatgca   7200
gttatcattt acttcgcata tacttacgaa ctgttccaaa aagagaatga tacagtttgt   7260
atagtttact aactggatca actttattat tatcagttgt atcaaattta gcaataaatg   7320
gtgaatgtgc cgaagcagat gtttcattta ctttaactac actaccaaat cgatatgcga   7380 ctaataccctt tattaattcc tcatggagtt tagtagcagt tgctaatgga ttgggatcat   7440
taggatctat cttaatccta cgctcgacat tgaaaaagtt tactacaatt tctttgctag   7500
tcatgtatac agtaagatct ttgttattac ctaaatatag tggcggatct tcaacattat   7560
ttttagccat tgtatattcc tatttgtaat tactactgtt gttaccaaac tatgatatag   7620
atctcaatta attttaatc ggataataac catgtataat ttatttaaga atgctccgtc   7680
acgtaaattg gggcaggtgg ttgatcctaa catccattat atccgacgaa tctacgctga   7740
gcaaattagg gacgttaaaa gttattatag acgggcaccg aagtatgttg aatctaaaaa   7800
catattagca caaatgattc gacattttaa cgtagagtta ctaagtgatg atgctacttt   7860 tataagaac gtggacgatc gttcacgtgc tattattcgt tcatttggta ttacatcatc   7920
tttaaataaa ggtaaggttc atgtaggtgg tgttacactt ggtcctcaaa ctgaagaagt   7980
tctagtatcc acatcagaga gctttgatct aaaagatcta aataaacat ggtataaact   8040 ttccctgtt acgtatctgt atcatacacg tactgatact aatttaccta tcatgaacaa   8100
taccacacag ggtagaggct atggtgtaac tctagtaaat ataccaatgc ttcttgtgat   8160
gtaccgttac tggtatcgat ggcaagttga gaagaatcct gatgaagtag aagacactta   8220
taggtttata ggatcatttg tattgccaaa tatggttgac tcttatttag atatttcttt   8280
ctttaatagg ttagcaagga atgctttaga tattaaaaat ccaacattcc ctataccgca   8340 tccatttac atcactgata tgaatccacg tattgataaa ctatgtacaa ctatcaatag   8400
agaatccata ttaaaggtg tagacatgga aggtttatca tggataacac cagctatcgt   8460
acaatctaat ttgttcgata tgatgcggct cccacgagaa cctattaaca ggaataatga   8520
```

```
atgggcttat gtattggctc gcacacccctt cattaagtat cttgtagggc agcttttaaa    8580
gaatactggt tatgatcaat cttctgttaa cactgtatta attgatctta tagaagcatc    8640
taatgatcaa gcatttaagc aacaagcaaa tagtgagttt gtaaaagctc aacaggcaca    8700
agttgattgg atgatagatg cacttaaaag aaaagaaatg tgacataaac cccctcctaa    8760
attggagggg gttatatgcc gttttattag aaattacctt tcttcatttt agaaagtaat    8820
tttctacgtt cagctcggtt aattcctggg atagctggta atagcatttt attactaaac    8880
ttacctggct tgcggtcatg atttagtaat tgatcaacta cagcttggtc actgcttta    8940 actccattat ccatttcatc taatgggtcc ataatagctt tagcagtcaa tcttagatga    9000
gtaactagtt catcaaatga actatcggta ttaataagtt gtttatcaac accttcttta    9060
agagcttgtt taatagttac gtcttttacc aggatattat cacattccca aagagttgta    9120
tgatgggtat ttaacattaa ttcaagtgag acattattgt aatcgttgtc agcacttgag    9180
tgccaattga attcatcaat atagtcattt agactcatta actttggtgg ttcgttacta    9240
gaggtaatta aaccaattgg ttgaacatca tctagtgaac ttttatcact agtaattgca    9300
gttgtttcag tagtaacatc aacttctttt aattcgttgg tataagttac atatactaat    9360
tcttcactac cgtcatccaa aagaacatag gctgttgctt tggtggaatc atcaggtgct    9420
aatccatgga tcctaatacg attatcattt actaatttac tataatcatt ccagtgatta    9480
cacgaacttc attagtcttt tccattatca tctacctctt ttaattttatc tttaatatat    9540 ttcggataaa gctcgttttc ttcacgagtt aanccngntg gnncggttgg taatgtgata    9600
gtnccnctnt taattgcctt cttcatccga tctaagtcaa aattaaattc ggtatgattt    9660
ntcattatat tgaaccatat taagttagta attggcaatc agactatata aatcttaatt    9720 atttttagt atataagcct cccactaggg gaggctatat tcttaatag aagtcagaga    9780 tgagtcgatc gttattttta tcaataagga aaatacctag ggactctaag gttagataga    9840
atacacccat agtntttcca atgatagttc taacgtcagc aacacgcgta ataacttctg    9900
gaatacgacc agtttctact actgtactcg ggatatggaa atcaccaata ctggttttat    9960
tttcttcagt aacccatgct tgaatacgag cagctaattt cttatcttcg ataccatcaa    10020
tccattcttt gatcgcagtt ttattattaa gagtaactga gatctttaca tgtgaataag    10080
gtggatcacc agcgtcacca aatgatggag caaatacagt cttccacact aatcccttt    10140 tatgggttga gttatcttca gatttataag actcaggtcg tttagtttga ccacttgtca    10200
gatactcagc tttaccactt ctaacagact caataatttc tctttcgata tcaccaactt    10260
cttttagaat tgaagccaag tcgatttttct cttcagtctt tacagtttta atgatatctt    10320
ccatgagtgt tttagcacga ctattaatct tcttaggtac tttactatcc cttagtccna    10380
cnccnttnat ctccatncgn gantcattaa acatnacccc ttcttgggca tcctgtgatg    10440
caaagtaatg tttagaacga gtagttaagg ccagtactgc gaaataaat tcgttcttca    10500 ttgcaaatag acgaagctta tctttagata cacccatatt agcggattga atcgcnaaga    10560
tatgcataac tacttcagan actagaaaca ctagtgcnaa tactagtcgn ttagcttcat    10620
tgctaaaagt tactttacca aagaattcct caacccacca ttgtaatgta aacatagtgg    10680
agtcagtatc tgaaataaca gcagctcgtc tatacacagt tggaaaagca tgaatgcttg    10740
atggtacaca tttagtcaag aagaaagctt caatcaatag acgatattca ttaagagttt    10800
cagcgatatt tcgaccagtg gcataaactt ggttnantgt atctggatcn gantctttta    10860
gtttagcttt agatcgacct ttaacagtat caaagcaaat aaagctagcc aanagatcca    10920
```

```
tatcaccatc ataagttgaa tattcttctt cagtgatgat ttgttctttt gttccaacct   10980
ggcttaattt aattagaaag ctcttgatta attctttatt gtatttatat aagtgatata   11040
gatcacctac ntacataact gctgctcgtt cgactggtgt catcccagta gctagtttta   11100
aaatctgngc cgtgtantac ttattttgcc aatagtgttt agttgaataa agaaccatat   11160
caactacttc ttctggcgtt gggcaatgta gattaaaatt agttactgct ttttgaatta   11220
actccatatc agctacatta atantnttta ctaaattagc ttttgtgatt tctggagtat   11280
aataatgcct attacccata atgaattttt cattatttga gttagcataa gaggtaccag   11340
ttctacaggt agatgttaaa ctagagtgtg tggacttata ataaagaata gtggcagcag   11400
atacagtacc gcctgaatat gagttattgt taattttgaa gttttcttgn tcnccttatc   11460
gtacttgtgc aagttctgtt ttaatttgtg aattctcttt atcgccggcc tgtaggaaag   11520
cagctgcttc acgttcagcc tgcatctgnt cacctttaac acgcttacgg tttttcacac   11580
cttcngcaat atagatggag tgcgtngact gtctaacaga ctctggtaaa tatgcggtca   11640
ttgatggaga taataataga ttctgtttct taacacggtt aagaaaagcc ataaatgaaa   11700
ccgtctttaa ttccctatca ccaaacttat ttttatctag aatagttgct aatggattac   11760
gaagtgcata ttcgccattt tgacgtaatt gttctttaac aaattcttta cattcttcta   11820
aactaatatt taattcatct tttgtcatta attgaagata tttggcatta tcatcaagac   11880
atgcattaat gatatcaata tcacgatggt aatcattgac atcttttaaa aacggatttg   11940
gttgggcaaa tgcggtcatt tcacatatct ctcagtatac ttatttttta attatagtga   12000
atgatttctc tctntttaac taaaaaagaa aaggaaagaa tgggtacccct atacgggnac   12060 cctaaattga gaggtagcac atcaacttac attcacatta gatgatgtaa gnaagtaaaa   12120
ataanacaac ataaaaggag ccatnatggc tcctttatag ttattcatat gtcactgaag   12180
ttggtggtgc attattttgn cgcactgcca atagaatgcg atcatacatt ttattatcga   12240
catcatccca tactaatgtc anacgnttac catctacacg ttctaatgta ttcgcaacaa   12300
tccaaggnat nccaataaac atcacacttt cattattggc cattcgtaca cgaatntaat   12360
tgtattgtgt tggatcaact ggagctganc ctgctggtaa acttggatat acttgctgcc   12420
cngcagcagc tacatcaaaa cccattgcag atgctacaga cgcagtaaca ataccttcga   12480
ctgtaacgtt cttaaaatta gtacctagga tagcatatgg atagacctcg aatgagatcc   12540
tatcacctgc ttgaatgtct cgaatattaa cagccatggt aatacccctaa aatagttggt   12600 tacataggggt attactcatc tagtaatacn actacaccaa acagaccttt cgtatccatt   12660
ggnactgtaa tgantacatg tccatntgga tantttttctt taaagctatt gataaagtcg   12720
gtncaatatt caataacata tccttatgta gaataattct ctaactcaat atcttcntca   12780
ggatcatcaa atgagtcatg tccatacatc agcatatgga tntatatgtc attattaagc   12840
gtatccatat aacttaactt acgtgattct tcaaataaat caagtggtgt tggacaatct   12900
ggatatatca ttcgttttgt atattcacga agcaaatgtt gcgaatatac ttctgactct   12960
ttagatttaa atacgataaa tactcgtttt tccatatcgg ttcctagtag gaagcctatg   13020
tgaaccgata ggctttccta tttgcgtcaa ttgttaatat gtgtcactta atccacatca   13080
ttgtaacagt ccataccaaa gtcttcacct tctagaatat aaccctgatt atgttgatca   13140
actgctattg attggattct ttctacacca tatccattct gatagagatg tgctatttca   13200
gattgtagtt tgctagccaa tgttttacac acggtcgcaa accacatatt aagaatactc   13260
```

```
aatgcatatt tatcttgcat aatcacaggt gctaccgatg gaaagtattc ttgtaaataa   13320
tagtcaaccc ctataattgg ttgagtaggc tgttgcgcta gaaattcaat atatgaatta   13380
attgcctgat accataattg ttctatagac tggtgttcag tatatgggta agggtattgt   13440
aagacttatt gacaactaca tcagccattt tattaacaat gggccagata tcactgatgt   13500
taataactac gaaactcgtc attccttgtt gacctggagt tatgttatta gcatcattta   13560
tccgctgcat ttcttgttgt ctataaagaa gtggatgcat catgtttgag acctcataac   13620
taatttagtt accatcttat atttatctac ttctatacat ttaagactag taataagatt   13680
acctgcttga ataacttgtt tttggattat ctctaggaaa tcagttccaa ataaatccaa   13740 tacccttttcg ataatctcag cagatcttaa gtgccaattg atggtattag gatttccctg  13800
atgatcaaat accatcatac tcgtcggtct atccggttct atataggtat cgcttaagta   13860
atcttctaac cattgctcta aaaaggtagg ccaatctaat ctctgccagt ggttaaaata   13920
ttcacatatg ctgctagaag tctattgata caccacagta caaagtcagt cggttcatct   13980
acacctagct cttccgtaaa agaacgcggt ttcaaaatta gcaacaattg catattgact   14040 ccactctta ccagtgacta tagttaatag aacaactttg ttatctatta cactaatgaa    14100
cttatagtct attaaattct tcggtgttct atgtagtaat tggattccag ttgtatagaa   14160
caaattaatg aactcatccc aatctggacc atttcctagt tgtattgata tatccacaaa   14220
aggaataacc gtattatcct gttgtaattt agacatcatc ttaacaaccc attgagttaa   14280
taagacgatg actgtagctt catctttatt tgttaggtaa gtaaatttct ttatcaatgt   14340
gattaattgt gggaatacca cttcgattgg caatacatat accagacgtt gtacttcctc   14400
cgatgtacaa tccatctcgt gcttctgttt cataccacag ttccttagta tttgttggaa   14460
tgaggtgcat gatctgctca gcaccctcat cgagaagttc tattagttta tgcatgaaat   14520
gaatgtcttt agcatattca tagaacattt cttctttaac gaccatttgc ataagcttct   14580
gttctgccaa tgcaacaagc aaatgcattg cttcgatata actaatatct aaaaagtcca   14640
atacaaatct tagatagtta tcatctttaa taagtttact tttagtcgct cttagtaaaa   14700
aacgaggttc tngtgtgggt aatggtgacg tatagatctt ctggtttctc agtatcataa   14760
ataaccctat ttaactggat gttaccagct gatggtagaa ctacccggtt agaacaatta   14820
tacagataag ttgttaaatc aatatcacaa atatccctat aacccagcat ctgattaatt   14880
agttctatga catcattaga tgtncnaccn gatgcnctct cagacgctgc tgccaataca   14940
attgttaatg catattctgc accaatacta tttttatag atttccaaat atcagaatgt    15000
tgntcttgta caaaagatct tacttccatt ctgatacaca ttgatgtgtc tttatcatta   15060
gatatgttca ttataaaaac cttataancg ntataaagcc cnccntangg agggctttat   15120
ttagtataga ttattttcta aaatgtatcg ctcagcttgc gctcgctgat catcaggtan   15180
ataatcacca cgttgatatt caaatactaa tttctcaata ggataagttg cattcttatt   15240
cttgtataca gaaattacat agctatgata ctctagttca tacttaacat catgctcaat   15300
tctggttgaa aaataagcca tgttaataga actaactaga gggctaatat atttctcttc   15360
aaatagtaat aaattatcaa gtcctaaact tgcaaagaaa tcatggttaa ccttaggtat   15420
taggtaagat actttaatat tactatattg tttaacaatt acgccaataa gtaatgcagt   15480
taactgttct tgaatatatt ctactgcgat gttgtatgca tggttagtgg tgatgtggtc   15540
tttatttaaa gtatagctac cgccattggt aatagatggc tgagttttac gtctagattc   15600
gtagatacta taacctagtg tttgtaaatt aattttgtca aagccatgga agaaagtccg   15660
```

```
tagaaattca ctaaataaat agtttaatgg gttcagtagg ttaagtgata ccactgcatg   15720
atcatcacca ttatcaatcc catggacacg atcatattct gcgattcgat aatctttacc   15780
actgattaaa gttataactg aaccagcttt aactacatcc cattggatcc atgtaccgct   15840
atcgatatat tttgctactt gcttatagat atcgatag ataggttcta gataaggtag   15900
tttcattaga ttttctaccc aagcaacttt attactatct acgtcagtta cagcacaatt   15960
aaaaatagct gcggccatct taagattggt gtactggtct ttggctgttt tatatgaaac   16020
taaactctct actatatttt caaccattag atgtaaaaac tgttgagcca catctttact   16080
caatttcacc ccaatcgctt catcaattga agctgaagct gtaagctgac ctagtaaatc   16140
gtatattgct ttttcttggt ggcgcgtatc aagtacaatg agcttattcg acattatatt   16200
tctccaatta attttttgga atagcgatcc aaactgtgtt ctttaaccga tagaatatta   16260
caaacttacc tgcatttact ctaggtataa tttttaatat atcccaaaga tcagatgcgg   16320
cctcatgatt atcatgaaac cattggattt cttgaggggt gttatttatt ggattatatc   16380
cagtagtata catgaattca aaagagtcaa tagagtattt aaagaagtca tcaattaagc   16440
tgtcctctac tgatttaaat atatgctcta atgtaccata gtcatctgga tgtattccaa   16500
agctttggca cctaatcgct aaacgcgtat ttattaactc ttttggcgat cttggtacta   16560
acttggctat caccctcgtt acatctatta catacaggtc agccacttgg ggagtagtca   16620
cagtacaatc tctcgttaaa tgttcaggaa catgatatag atctaaaaat atttttagtc   16680
aaatctgttc gtggtaagcc gatgtatatt ataccttagt tgggtattat ctccatcgaa   16740
aaaacgcgta cagcgcatta taggacgttt ttatgaatcc aattactaag gctttacgtg   16800
atatttcttt taagatccca aaacagatat taaatactgt tttcntatct ancgaaatgt   16860
caggctgtgg tgcagctatc tcactagaaa ccaggatacg cgaagctgtt attgaaccac   16920
gtgttatgtt agatattgat ttagtcggtg gttcaaaagt attcattcca ctagattttc   16980
cagtgcaagc agaatatgtt gacccttata cagtggttta ttacattcca gacgaataca   17040
ctcagcaacg cccaattatc caatgttaca gtatccattt tggagtatta ggattccata   17100
ctgctggcta tgctatgcac tataatgaat caagtatggg tgcattaaca cgacgtgtac   17160
tagattcagc tagacagtta ccagtcgccc aaacagcata tatcaactta attaacccac   17220
acactgtcat ggtcaggtat atcaatatcc ctaactactc atcattcctt gcctgtcgcg   17280
taggtaatga tgangagcta aataccatac gacctacagc catacctgca ttttcaaaac   17340
tcattgagta tgctgttaag tcatacatct acaatgagtt atttgtatct atgggtgang   17400
cacagttatc aggtggtgct gagttaggtg tattccgtga taaggtttat gaatatgccg   17460
atgctgaaga actatatcag gaacaattaa tgcgttggat gaaaatatcc aggcagttca   17520
atgatcctga aggtaagcga catcatattc ggacaatcac agccgctcaa taaaaaaata   17580 aaaaaagac atattgccct cccattgcgg gagggcttat gccattaagg taatatctaa   17640
ataacacnat atttaaaaac atactggtat aanncatcat caattaacac tgttgagaat   17700 cttttgatg agatcaccag gtgcgatacc aatgcctgaa caataccgtc taaagttatt   17760
acacggttga catgctttct tttcaacgat atttaattca aagcaaatat tgccacgtga   17820
atctagaatg gatataaatg ctttgttacc tgttacgcga tatgtcttac cgaatacaac   17880
agttgtttta tatgcaaggc tattcatgat tattcccttta acatggatta ttatcatgtt   17940
tgtaatatag cctttaaatg tatttaaata tttattaaac cnnatagcga tgngctatat   18000
```

```
atgttttnaa tacctcatan gccttatcng ttgccatgga nctattgaca aaatcagaat    18060
gatcaatctt aataatctta ccgaatgaat cataatcgat agttgtaacn nctattcgat    18120
cactatcacg gatcaatagt ttattttatt taaaacaaaa atattccatt tctcgccatc    18180
ggctaaaata acatcctcat ctttaagatt aagacgaaca aactgtttta cataaatact    18240
taactgagca actgttgaca taatgatttc tcgatatctg ttaatgaact aatcatatct    18300
cggacattna tggtaataac attttttataa gttaaataag ttggatatga acccataaat    18360
gtaatagtcc cacagatatg attttatat ctaatatcaa nacanccgtc atatctccag    18420
ataaaatcaa atgatccttt agtgtggtgn tcaagtgnaa gaatagaacc actaactaat    18480
ttaggatatt gttcaaattc agacattaca taatctgcca gttccttaac ctcaggataa    18540
tcaatcaata atagcatata cgtaaatctc aatnagttaa tataacaccc catccagggt    18600
ggactctttc gaaaatggt aatgtattat ttcgtatact ntctgcatca atatttggaa    18660
tgtggatggt acaacagtgg gggttactgt caatcttgaa atagaaatta tcttttaaat    18720
cttcaacctt ggatgtttgn aatggatata aaataccatt cccccaaaca taccaacgnc    18780
tatacagctt atcgtttaac cgcttctcaa taaccgaatg cgatttgaaa cgaggaactc    18840
gcaaacgcat cccgttttact tcagcccatt tgtctacccg ntcatagcta ataattccat    18900
ccttaaccat tacaaagata aatccctcaa ctatgttggg gagacgaact acgtgtttca    18960
gaaccatagt aaacggagat aacgtcagat caagttcagc tgccatttgc tcgtcgagct    19020
ttttagcagt gttctttgcc atcggttatc tcctaatata cagattatta attatcgcta    19080
gttatttaat atctgcaaaa ttctgattta ctttacccat aaaaatacca tcggctctat    19140
cgtcataata aagcttccct gctttagcat tacatanaac tccataaatg tgaccattgt    19200
aaccatcaaa attaaataaa gatggattat gcggtacatg aatgaatccc attttatcgc    19260
acagaaactt agctacagca gccgatcggc taatacctgc ctcacagtgt acgaataggt    19320 gttganccctt accaagagct tcacagaang aaataatacg ttgtgcatgn cgatgatcaa    19380
atagatcata agaagaatca acataatcct caatgtcatc aacattgata cgtaaataat    19440
taagatgttt tgctgaataa agtgggactc tacctttctc cagtagacag atcatatttc    19500
taggggaata aaatgattca gccacatgca aaggaatata agtaactgta tttactggct    19560
tcatattaca cctcgttaca aaaaaataaa aggagccccg aagggctcca gtatangtta    19620
atcgaataca agaccactac tagttgcttg gtcatccaca tctagagtag actgacgctt    19680
acgcatatta gctttggctc gattcatcat ttcacgacgt tcttctaatc gnttacgaat    19740
atcttcaana gatagncnan tgatcacaaa atgcatttga tcgaaatcat atttctcggg    19800
atcagcataa ccagtggtac gagttaaaac agtgttaatg gatacttcgc gatcagggtc    19860
agtgtatagc gaagcaatag aaattgggtc cagaatagcc tgggcttctt gacgatcaaa    19920
acacacgtgt aattggacag tctgtacagg tacatcatgg tgtttatgga agtgtgccca    19980
gttagtgata tccattagat caagactttg gtgttcttga ttaaatagag ttactagtgc    20040
atntagtact tcnagaatgt tttggttcac cattgactgc ggtanaccctt caacattctc    20100 atgatagtta ataatcatcg gaacttact aacagaggaa acccttcaa angtcttaag    20160 gctaccactn ctattncgaa gactaatatc actgtcgtaa gatccaatga ccacacttac    20220
aactacttca ccttgttgtt gtagatgact nacaagngaa ggaccaatng ttgaaccaga    20280
agcaccaccc attgantana cnacnatgtt agnatccct gctgggaaat gatgggcaat    20340
ggcaggaata tgtgcagaga ttagttctgc ggctgcctta cgatctttac ccataccgat    20400
```

```
agcacgttta cgtgcngtct ggtcagctag cttagtatcc gcttcaataa tgatcgtatt   20460
atcgtcagta ttgtgtttgt gtttattntg tacactggta tcaatgtagc aaacatcctc   20520
atgataacca tggaatagtt caccaatacg gaaaccagca ccaccacaaa agtaaattcg   20580
agttttactt tagacatcat tacacctcat tgtgattaat ataattcata taccaacttg   20640
taaatggtat cagtgcttaa aagtaacgat ctcttcatga gttcgttctt gatgaacatt   20700
aattcattaa ccactttacc agtatcagat ttaaattcga ttaccatctt atctcgacac   20760
atgtatgttt gccaagtacc accagactta acacaatcaa taatcatgtt aagtacattc   20820
ttaacttcaa tcttactaac tttataacga taaacgttta gaagttcagt aagccatttc   20880
gtttttggga ttttggcatt tttacgttct tttgaaatat caaaaggaat tagtgcaatg   20940
atctcaccat ctttgttggt gaattcaaat accattcctt ttgagttagc taaggacga    21000 atgttntaat tnccttttanc actncatact tcttcagata acttaactaa cctatctagt   21060
tgaacatcag atgcatgaat gttatcttct ttaaatgctt tctttagttc atcatgagtt   21120
agtggagtac gtactagagt gtaatctttc tgttcagtca ttttttcattt ttncnatttt   21180 cnanttcaaa ttaaacggta ttggctttta tagccaatcc cttattacta aaagtaatag   21240
attctcgaac taaggatggt tatacccctt ctctaataat aaggaatatt atatgggacc   21300
ccccaaaggg tccccccaca taatatacta tttatataat ttcttttaga agaaaagaga   21360
taaataagag aaatacagtc tattaaagta atgaatttct caaaaattaa atagtacacc   21420
gcncnnnnnt tncgncggan ggtcctgccg gacnanngtc cggatgtgcg nnantagngg   21480 gttttttcaaa aatacntgca tcgcggttga attgagnggt tgattataac gtnngatctt   21540
aatngtaaat agaacttcnt caacatctgn atgncatcct tcnaaactaa aatatacttc   21600
agtccgatca ataaactgat acatttctac agctggttca gctggatctt taaaggccan   21660
cttattagcg aaataatcag tatnggctag aattaattct tttacattan ttgcattctt   21720
cttatcaaca aggaattcaa actcttcaag gttatctgtt ttgaaaatac cttgatanga   21780
tgacgactng attagtttnat cactgatatc atcaacatga acncctggca taaattcaat   21840
gactggtaga ataagcttgt tacctcctac gccntnagcn atatgaatnc caancacatt   21900
accatcacta atgtattcgt cattaccgca aataacggca ccagccgcta gatataaatt   21960
atcaacatat ttcagattat cggcaataat gcgagatagt acatattctc gcaccatggc   22020
atcatctgga cttgactgcg gtttaaaagt atagtgggtg ttatgactac tcatggtcgc   22080
acatgtaaca aaaactgaaa tatctactgg attaaatacc caatgaacgg agatatcctc   22140
taatttatgt ggatgatgta aaccatctag cttagatagg gcttggagtt gttcttccca   22200
ggtgatgtta aattgagtca tttttctaac ctcttcattt attaaaaata atacacttat   22260
tttactttag cagttgatac ttcacataca ttaactaatt gttcaaataa cggttcatta   22320
tctggatcat taactaattt gatgtattaa taataatacc agaatacagc atatcagctg   22380
catctcgatc acttgttttta attctggtta caccttccca cttccatcca tagtaaatta   22440
aatcaaatga tgaaccaatg ttaaaggttg attgaataaa tttgcatgta ccattttctt   22500
ttaaccaatc aggcctatat ggttcatttt tataaaattc atgcatgagt actttaaaat   22560
cagttttaat gttttcatga ataatgcaat caatagaatt aagagcttca tcaagagctg   22620
atttagactc aataatgatt tctaatacat tggcagattt tagtgtaatc atacctagtt   22680
catctgagtg tgctcttccg atttgaaata cattgagctt accaattggt aaggtggctt   22740
```

-continued

```
ttaatggcag attagtatag tgagatacat cgcttttata actgtcttca tatgactcaa   22800
ttaaattaag ccatgctctt tcaatacgtg tattctcaaa atgntgttct tcttctagta   22860
gtctagaaat tagatgatta atgtattgaa cattatggcc agtaccngta attnaattat   22920
atttcgtatt accggtaatt ccccatttat tattttcttt atttatccaa ccgtagatta   22980
cactgttttt aggatattta tttttaaaat tatcgtatat ttcttttaga tgtggattag   23040
gggtaaaact aaaagtagtt gattcagtca ttatagatac ctatttgaat attgtttatt   23100
attgcaaatt agtaatatag atcttaaact tttttaactc agcataaagc ctcccctagg   23160
ggaggcnata tgttcattta tctatttcag cgtttggatc ataccaaggt aataaactta   23220
gtagtgccgg ttgttgtttc ttcatatcct ctaagattgt tgcttcactt gcaccttcta   23280
acatagtggt gaaagtaatc atgttcttag agttatatat cggacgtaga ccattaccaa   23340
agaatttnac ntgttgaacc attattttga aatcagggtt atcgactaca tctgggatat   23400
agatancagg tggcgcactg aaataacgtt taattaactc aatagcccaa tacgttggta   23460
aatcaccaaa ctgtgatttc actgtagcta ggtttaattg gaatgcttta ggttcttcag   23520
gcggcggttc caccggatca attggatcag tgggttcttc agggccagta ggttcagtag   23580
gctcttcagg atcctctgga tcgccttctg ttggcttttc ttcagatgtg ccaccatcag   23640
ggtcacntga accatcatca tcttcaacgg gctcctcagg cgtttctata ggctccttcg   23700
gatcttcctg attctccgat agatcgggct cttctgattc cccatctcca tttgcttcag   23760
tagaagacgt gtcttctgat tcttcatctg ttgtcgagtc agttgnggct gtgttttctg   23820
aatcggcagt ggtatttcat tttcacttga ttcagtagaa acaatttcag taggagtggt   23880
ttcaagttca ttgacactat cctctgcatt agttacttca ttagggattt cactaatttc   23940
tgataatgtt actggtgcac ttactgcgcg agcttttcgt ttagccatgg ttgtaccttá   24000 gatagaatag tattatggta agtgactaat tcaggatcag ttaaattgat actttgaata   24060
gtcatattca gaattacata ggagtccatt gttctccggg tatatccagt taattccatc   24120
ttgttatatt tctgtacatg atctggaacc caatcaccaa agataacacc cagtttatga   24180
aaacgataca ccaatctgga taatgcacgt tgggtttcag ttgggaatat atcgggaaca   24240
ttttcgggaa cagtacattt atcactaaat ggagtaataa taggaccacg atgaatggtg   24300
tagctaagct taaagataac agcaccaagt tcgtcattaa tacgcctaag tatacgataa   24360
ccataatcgg tacgctcaag tttatataca ttactaggat cagcatctgc taaccttcta   24420
gcatgtcgtc tagtgcacgt ttgataccac ggttatagat gagttcacgt tctatgtaat   24480
ctctctcaaa agcggcctga gggctttctt tctcaaattc cttagttact gaccaagaaa   24540
ttgtttcacc agttaattca tcagttaaaa catacagata tgtcatagag tcaacgtatg   24600
aatactggat agagtancgt gataaatcac atggcttagc atttaatcgt tcttctttta   24660
aatagaaaaa catatcttgt aaatgattat aagtttggca gccaccacca agatgatcaa   24720
tatcaataga cgtatctggc ttgactggag ctttgcagca actcattaca cacctctaca   24780
attatatttg agttattgta ctacagatga taaagagaaa atacatcata agccctctcc   24840
ttatggagag ggnattatat ttacatagtg ttaaaacacg cattaaattt agataatgag   24900
cagccagtat aaattaatga ttgctctagt tgtatgatga catcgccatt actatcaaaa   24960
tcagcagcaa taaagtagaa ttcagttatc ttaaaagtag atggcagcat ttctaaataa   25020
ttaaatattg cttgattatc gatgtcatga ggatttaaat ccatatgtta cctatacatn   25080
gatagttatg gaccaaatat taacaggnct gcataagaca attgtgatta aatctccatg   25140
```

```
agttctctga taatggttga aacacataac tttgattaac tttaattttt tagtttcttt   25200
attttgaatt tctttgataa gtgattcaat aagatcagta gtaataagtg aatgaccatc   25260
aataaatggt tttatactta ctagcgaatc tttgttaaat agaattgcat catcatattc   25320
acatgtagat gcggtcttgt atatggatgc aactttatta actttgtcat nagtgactat   25380
agaaaaatta aattcantct tagttttact naacgatgtt tcaaataatt tatatttatc   25440
aataatagtt ttattatcaa taaatgattt cattccaata tttaaatcta tgtccagggt   25500
ataagantta tgtattaatc caactgatag ttgagtttca ttaccactat tgttaaactt   25560
aatattatta actgaacata tctgattatt aataaacgat aataatagtt tagaaatagt   25620
tttaataaca ttaacttcat aatcattatt agtacaagca agtgcagttg tcatgtatcg   25680
actaacttga cnaacatcta gtttctgata gnnactanca ctatctancc atgggtcaat   25740
anttaaaaaa atccttagac tagctagaat atcngaagat gtttcagaat aaatgaaaaa   25800
cacattatta ttaagatcat cttttagcca accactagtt ctaagatttt ctagatcttt   25860
ttcattagat accgattgac ttaattgctg aattaaacta gggttagcta ggtttaataa   25920
actaatcatt ttataaacca ttttattatc ctctaattta tgtaattaca tggaataaat   25980
aacataagta cttttatgac ttatgatttg attctccagg aggttttccc aatggcaact   26040
attaaagaag tccttgatag aaattttaag gatgttcaat ttgatcgcga tttatgtaaa   26100
agaattattg actttactat cagttttatg aataggaatg ctgatcactc tgctttcttt   26160
ggtggtgtat tactaggtgt acaacaagtt aaattcttcg atacggatcg tgagatttgg   26220
tatgatgatg ttttacgaat tgatgaagcg ctgttagtcc aagattttaa gtcagttgaa   26280
ttcattgacc ctaaccatcg tgtaatgtca gatgtattca atcatcttcc tgcctatatt   26340
tgttctaggc ttttaaaaac aactaatgtt cctttgaata ttagacatga agcaatggtt   26400
agttgtttca tggtgttgca ttttaaatat ctaacatctt tacttgtacc acgctttaaa   26460
tatcctgcac gtaaagaagt agccgaagct gcattcgccg cactcaatta tcgatttgac   26520
attaagacaa ttgggtcatg ggagaaacta tttaggcaac gggctgaagg tatcattgca   26580
cctgattcta tttatgcacc tttcttaact ggtaaaacac aagaactgga ttattggtct   26640
ggtcgtgtgg tatctgatac tcaaacacgt ctacgtgaat taatcaacaa gtactatgat   26700
gtttatatca gaacactgca atcaggtggt aaattagtta tttcatcgga tatggctgtt   26760
aattctgatg gtgagcagat tctacgcgat aagtctactg ggtatcgctc atatcttact   26820
tatatccatc aagttgcgca acaagaacaa aatttcatta gacctgagtt agtcggtatt   26880
attgaaaaga taatgcccac aatgccacca gaaatgttca tggcgacact tagacacctt   26940
tcccgtaaca tcggtcaacc tagggcacaa aagcttgaga actcgtaga tgagtgctta    27000 ttgtatgctt tcgattatat gcaatcactc cgtacaatgg ttgctagaaa taatgatcta   27060
caaacattgc ttgtaaaaat acgagcaaag ataatggcat ctaaaacaga aaatgctcaa   27120
gttattttca tgcgtgaaga aggtgagaag ttagttaggg atgcgactaa ttctagggta   27180
cctgcatata tcgcagcaac taggactggg ttgatgttgt atttaattct acgtgctatg   27240
actaagaatt actatacaaa acaaaataaa cataatgccc tcccgcaatg ggagggctta   27300
tgctgttaag taacattagc tagattgatc attacataaa ttttttcagag catcgtaaat   27360 agccacataa gtaaaatagt taaactatct ttaatttcct tacgtggggt gccactgaat   27420
ccaccccatg atacatttgt attactaacn catacagtgc taatagctgg ctcatgatag   27480
```

```
ccaccatcta ctttacgctt tgcataaacc ttagccgtaa tttctccacg taacttttg    27540 aagaaaacta gagcacccgg aacgactata cgtttattac caatcttcgt aataaattct    27600
ttacgattag taaagtgctc ttttaataaa tcattaataa ttttagttaa actatcaatt    27660
tcattcttca tcgacacgtt gttagttcct tacaaataaa cttgataacg tgatcactta    27720
caaatttcaa tggaccagaa caattagatt tctcaatagc ggtttcagtg tatgaaatta    27780
tttgatttcc acttaaggat aatgaatcaa ataattcata agagttatta ttttattctt    27840
aaaggatact gcatattgac tatttcacta ttgatgcaaa ataggttaat agctgggata    27900
gatacagagt tatctgaagt atggctattt tccgtaatat tccaattact gtatacagtg    27960
aaaatatttg cagctagtaa aaggttggca ttaaccgttt ctaaactaac atactccaca    28020
gaagtacctt tatgccaata tagttcaatt ggattaaccc aagtatacccc aatggtttta    28080 tagaaggcat gcattacata ttctcgccaa cgtgtgggtt tcttattatc agttaaaaca    28140
cacgtaatat tgcctgacgg ataaatgtgg tggatgctac atgcattaat ttcatctcta    28200
acattagttg tttcagtaat attagaatga tcctgtttga atagccattt taaatgacta    28260
ttagttgtgt catcaccttc cccatttgca atgtcatttt ctaaccactt ttcaaatgta    28320
gcttgtctat caggtgttgg cattccccaa taggtagcta aatgaaacga taatagtatc    28380
gaataatatc atcatcgtta agaatatttt atccagtttc cagtgatgtt gatactcgta    28440
tacttcgctt ggaatattat ttacttgata ccatgtatta attaatactt gaattgttaa    28500
ttgccgaata ctctcacttg ttagagtgta atattccctg ctatgcggct cttcaattgt    28560
cacttcttga tcagtataac caatgtattt aggtttacca tcgatgagtg caaaattaac    28620
attccatgat gtatcattac taaaagtgat attaataaaa ccttgttcaa agctaggctt    28680
cactacgaaa ctgacatcat ccttctgata tgtcatttgc gttagaatac caaaattaat    28740
tttagatgta aattctttat cgaagttatg tttataaagt aatcctagta aacaatcaat    28800
tttattaata gtgtggtttt ctaataataa atcagtattt gtaagttcat taattttcat    28860
tttaacctct ctaaaatta caatctagtt ttacttattg aataagcaaa catgtaatat    28920
atatcttaat tatttttagc atagtttta acaacataaa gcctcccga agggaggcga    28980 tatgctttag cttttttggtt agtaccgaca gtctgctcat tcttttcagt ttgagcatt    29040 cgccgaagtt gactaaccag accattgcca gccgcaacta catcgggaga aaagaatgca    29100
ttgatatcaa agttctgatc ttggttgcga gtcttcccag gtgggaccat cggatatact    29160
tttgccatta gcttaatcct acaccgtcgt aagttacccg attaccaact gcacgttcaa    29220
tctggtcttg aataccatta cgtgcacgta gtacgtcagc agataaacca ccccagtcta    29280
atttctggtt attggggttc ataccgcgaa tgtttagttt acggaacatt tgacgagcgt    29340
attcttgtac accttcagaa acatcagtca gtgcagagaa ctcaacgttt agatcaaggt    29400
tctgaccaat ctgtgatgca tctttacggt tttcccaagg accagtagtt aatgggaaca    29460
tgttggtgca aagataagcn ttaacgcaat cctggaaggt aggatcnggt tctacgaata    29520
gaacagtcat accgtagaag gtagcgtcgt atttctcaac cggtacaatg ccatctgata    29580
caatacgcgg tactttggta ttctcatctg caataccata gttgatccac cattgtaaga    29640
aacgttggat agcgcggttt tgtaattccc agcaaccaaa gtttgggtta gaccgggcac    29700
gggttacgtt agtagccgtt tggataactt caccagaacc accccagggt gcttcagcgt    29760
tatctacagt aagcgtacgt tgtaaaccat cgatggtacg agtatgcgtt tcaacgaaag    29820
ccttaagaca tgcaactaac cagttagtat tactagcata cttaaagaat cgtggagcat    29880
```

```
ctagtaggaa cggcactaag ttacgtgcca catatggcgt gttagtagcc aggttagcta    29940
agtcaggccg aaatacgtta gtaccagcct gagcaaggtt tacagtgtta cgggcaccac    30000
cagcaccata accagtctcg ggtgccatcg gatcattata gcgagccatt taactttcc    30060
tcattctgaa agccacccac tcattgctga gcaggtgggg tttcaatacg aacagtttcc    30120
agattgaagt tcaacgtggt ccgcgggtta ttagcctcaa cagttacgtt gcaagtccag    30180
ctggtgccgt tatttgcgtc aatcggagtg atctctgtac gcgggataat gttgacacga    30240
gtaccgaaca tatcacgtac tagatcgaga atatactcgt cacaacgctc aactaattgt    30300
tcaggtgtta gtgtagcatt accgctaaat tgagcgtgta ctttatggat cagtcggatt    30360
aatacacagc aaatattaac agtaatcggt gatagaagta cagatgtatc atctagcatt    30420
actgaacgta ggcacggata ataggagcta cgatggtcat atgactgact ccaagtagca    30480
ccattcgccc aagcttgtgc ccgtacacga tcatcaaaga atttaacatt tagatcttta    30540
acaaaagtaa cacggttatt aggacttaca tccatttcca tacctggaac tagattacca    30600
gttccagcac ctgcatagcg tgcccatgac atagctacgt ctaaaagctg cggtacatat    30660
ttacgatagg taccatccat tagtttgcca gattgcatta caatcatagc gcgacaaaca    30720
ccagttccgt atagagtgga ttctgggaaa gcttttaggc gagtgataat ctgttgaaca    30780
cgacttagct cagtagcttc atcaggtaga cgactatcag tttctacgaa tgtagtgaag    30840
aaatattgta gatcacgccg cgcacttagt acgcgcattg cccgatattt tgattccatc    30900
ggaaggccag tgtcataaag aacaccgaac tgatattctg caatgttatt atagcgatca    30960
tttaatttgc caaagttaat attttcaata tcaactaatt tggcatattc ttctagatca    31020
gttgtaccgt cagtaccacc actagcatag atgttaccat cttaccctaa cgtaatgccg    31080
ccatctagtg gaccgagtac ntgaataccc tggtaaggat caccatcaac agctaagaag    31140
gttaggaagt caatttcacc aggtgcagta gtatgcgcag cagcggctgg gttaactcgc    31200
atctcagtgt cataaatcat ctgacgaaca agatcaatgt tctcatgata gacgtagaac    31260
tgagagaacg gtgaataaag tggacttagg ccagagacta caccatcatc tgagtaagaa    31320
tcaactaata catcaccaac ataaaggtca gcgttataca tatcgctgta aacacctta    31380
tcaaatgtaa tgtttagata atcttgctgg tcagcagttt tgacaataac tggactagtg    31440
cctacttcag gcttctcaat taactgaata cggaattgac gagttttaaa cttcgccata    31500
gctgcttcat cgaactcttc gatatcagca gttgtagtac tccatacacg cataccgtta    31560
gaatcaccta atttaccaaa gaaggaaacc ggtgcttcaa ataacggata tactagtgat    31620
tgagatccat ctttatctga tactaaagta cctggtagta cacgttgtgt acctacttca    31680
gaggtattat cttcaataag aataaatacgt gcctttagac catcaacttt atcagcagtc    31740
gggactggtg cattaccaat gtcacgaaca ctgtttggat agttgaaacc actaagacga    31800
cgaatcgtaa gtgggatttc atcttccaca atttcaatag caacaattaa ccgagatgga    31860
ttagctgcat cttcaggacg tagacgttta acataaaacc attaccacgg ccaagaaggt    31920
taagtgctaa tagtgattgt gtattgaaaa acttactacg tggatcaagc gatgcttgac    31980
catagatgga tgcaaaacca tcatcagaat caccgacata agtggtttca gtcggtcctg    32040
tctcagtgaa gagacgtaat agcggacagt gttgtgcgaa cgtgatgtcc ggacggatca    32100
ggggccggcg gctacgatcc cggataccat taaacacaac cctagggaca gcgttgtaat    32160
atgccatctt tttgattctc ccaagttgga gctttgaact cgatgttatg agtgttaact    32220
```

```
aacagtcaat catagatatt aatcatagtt gaccatacta gttattttt actatccatt    32280
taaggagtag cggtaatgtt tttgctaccg tatgaaacta cagtttgtaa aactctatac    32340
aatcccaccg gcggtggaaa attatatcct aaacaatatg ttgatcaaat tgaaaatgcg    32400
atcaagaaag ccaatgtgta tctacccatt ccacctgttg atgcacgtaa tggtgaaacg    32460
ctagagcata gtggacagat tacccccagtt gatgattttg aggatattaa gaaatttact    32520
caaattgtca atatcggtga tcgtgataat cctaagctag tngttgatgc tcgtctatat    32580
aaaaagattg aacagcgtac tggtattcct aggattattc agcagaatga gtggcaattc    32640
caatatattc ggatggcact taatatcaaa ctattacgtg aaggcccgga cttcctccat    32700
cgcttaggtg atatcccagt taaagttttc tataattgga tctcaggcat cctaacacaa    32760
aaatacagcc taccacctga atcaacccaa gctatttggg taatctgtgc tgtttattac    32820
tttgctatgc aagatgatgn tctaacagaa ccagntcagg aacgngatcg gttaatacca    32880
attatttccc gtcttacata tattccagct ggttttattg cngatgttat tgatacatta    32940
ggtccacttc ataatgccgg tgatctagct tatgagattt caactaangg ncgttcgatc    33000
aggatgggta aactaaaatt cagtgatcta caattattag tatcaccgag ttggtttggt    33060
accgcttccc gtgaaaacgt aggtgtggca ctagaacaca tgccaactta catcacactg    33120
atctacatgg cattagctga tcgctcatac cgtaaaacag ttttaagtca gaaagttgaa    33180
atgatttcac gttctgatga tgcaagtcgt tttattaatc tagtgaatga agctgtaagt    33240
agccaattcg ttaagtaaat atagggtgta atcaatgaac gcatatctat tgcgncatgc    33300
gattgataac gtttggtgta acccagccca ggaccgacga tttgtttatg aactgaaaca    33360
gctnacccca cgctacggcg tgagggtaaa ctgggtggtt gattacaccc ggtataagct    33420
accagtccaa agtacacgtg attattggca tctttatcaa attggtaaaa tgattcctaa    33480
acacctgggc ttgcctaagg tttacaataa gtggatgagc ctaaatgagt tggctcaaaa    33540
ccatttaaat ttagcagacg tttatgtaaa tagtggtatt aattattcac gtaatgatac    33600
atacgtttta ataaccagtt cgcaaaatct tttaattgct gttaagatag atccattatt    33660
ccctgatctc gatgaaaatc aaccctatct tcatgtttat aacaatgctt actttcaatc    33720
aaatagatcg gatgtagctg gacatagatg gttagtttct gaatcgtatc gagttaaaac    33780
aatatctgaa ttaactcaat ttcagattaa gataatggat accatagcat ctaaaggtgg    33840
tgttcctaaa tactttgtaa atggtagata tgttaatgag atatctcctg ttacagcaac    33900
agtcggtgat gtttgtgatt tcattctaga tccatccatt aaaaggatgg tagatttga    33960
tctacgtaca ttacctgttt tcatgtcaga aatagatagt gaaagaaata tattttacac    34020
tacactgata agactgtgca aacaattgag ttctttgatg atgttgaagc atatatctat    34080
cagccattag gtaataatcg ttatactggt gttaattacc atcataacga gagccgttgg    34140
atgcggatgc ttcacacataa agattattct ataccaactg cacgaattga tcagtttaaa    34200
gcacttcatc cagaagatcc tcgacgtggt gctgatccta ctcgttggcc aagtcaaaac    34260
tggaaagcat tagataatct agtatttaga atctacatac atcattctgg ttatgatcgc    34320
ccattagttg ctgattcaca tcgtattcaa attctgtatc gtttaaaatc agaagatatc    34380
ataagggcta tgactggtgc agattctggt aatcctttat ggcgagctga aaatctagag    34440
caatcaccat attgctggtt catgtcagca ccatctagtt tcgtataccc attaacattc    34500
aatctaccctg aagaaacatc gcctagtaag gtagaagcgc agaatatggc tggtgatgtt    34560
tttggttatt atgaagcagc taatattcaa ggttataatc cagcttgggt ttataatgat    34620
```

```
gctggtctaa agaccgctga tttacgatac aactactggc tagatgcaac tgtatttgag   34680
tatgatgaga aaggtatctt attaggttat aattatcata cagcaggtcg caaatatttc   34740
cctaaagata gtcgttgtgc atatgttgaa tgcattaatg gtaaaggaag tgtagatcta   34800
catgaagcat atgggaatga tcccgtgcct ttacgtgatg gtgacaactg gcgagtttat   34860
gttagtcctg tttgggctgg cgtaccaact ggcgaatggc aagatataac agaccatcca   34920
gatcgaaaca actggggttt ttatgatgat accactgatg ataaacgttg ggtttggata   34980
gctaagtcaa atgagtggta tggcctagta agaaccgatg agtacttcta tctaaaagaa   35040
ttaaagttta ataaaactga tggtatcatt aaatggagta tacgtaatac tgaaactcat   35100
aatggtgtaa aagtcgataa attgatggag ataccatttg gtcagtatga tgtgtttgta   35160
aatggtcggc ctatcattga aggtcttgat tacacgcgtg aatggcctca aactgtatta   35220
tgtaatctgg aatatttaaa tgcagatcca aatgcagtta atacgattct tctacgtgga   35280
acaggtttcc caacaccaga tttaaaacca tacgaacctg gcgagattgg tttcattgag   35340
tatggcgtat tgtctaatga tggtatttat aaagtacatt caaataaaca atcacgcata   35400
atcattgatg gtcattatcg tgaccctgct gatcttgaat ccaagaaga tcaaggcact   35460 actgttatca ctgatgaacg caatggtgca ccattccaaa tacaaacacc acaggcncgc   35520
ttccngnatg tttataatga tgattaccaa gctaggatta aggatgatgc acgggataaa   35580
caagtcactg attttatgac tgaatatttc ccaatgaaac ctcaacctaa tccggacaag   35640
atcgattata gataccaggt gctttcagcg ttttcatgta agatcattca tgatatcgta   35700
aaagaatata tcaaaccncc atatcaaaat ggacggtata gtgacgatga tattgttaag   35760
cagctaaaag attacgagtg gttagcagct tatgacatta tcaataaagg ctacaacaaa   35820
aataaagttg tagtttatcc acattggtat actgaacctg tagaactaga tatttccaat   35880
gggaatattt aaatcgtatt ctatcgatat atctacgtga agtaccgcca ctatccttgt   35940
tcgttaagat taaaaggaat caaccatgac aacgtcatat gaaagtagcc agtaccaacc   36000
accacagcat aaaaaccatt tctggtttag aggtgatatt gtctcatatg ctggtganac   36060
tggnaaagca atccctgcta aaggagattt agtatttgac gcagcacaag gttggtttat   36120
tgttcgtgaa gttgatgaaa caactggggt atctatctta gatccatggt acatgcccca   36180
aaaaccaggc aatgaaaatg aacaaaacct actagttgct gtaggtccag gatatagctc   36240
agaatcttat cggttattcc tagatcagtc tgtaacacca tttaatattt gcccagaccg   36300
gcgattacat ttttatggat caatggtgca tggctataaa gttttcctag ttcagatat   36360 atcagaaata catggtaaag tgatttccct gttctatgat aatgctggta attatctagg   36420
gccaactata ccagttgaat cagtacccga tccattgact caacagaatg ttgttaaagc   36480
gttaatgaat ggtaggactg ctgagaaaat gcaaatggt gaacgtgtaa ctctagtagc   36540
ttatgatgac gtgggtggc ctgtttcgat tgctcaactc gttgtaatga atactgaagt   36600
tatagcncaa gaggatacct cnaagaaata tgtaggtggt atcactattg aatcaccatt   36660
catctcncca gctgatccna aagttattga gttcccatta aacgtaccag ttgaatcatt   36720
accgatgatg ggtgctgttc attaccgtga tggtaagaag catgtgatga atattgatgg   36780
tacggcaatg gcaatttatg gtttacgtaa ctatattgcc actgaggaag gacaagagtt   36840
taaattaact ctatccttacc aattagcaca agatgagtta tcatacttat cgactccttc   36900
ggctaaccgt cgtattcagg agacatatac agcgcgtacc acgcctgtac agggtgctta   36960
```

```
cagttgtcgt atgtttgttt atccngcttg ggttaatgag gcagtnggtt acagattaga    37020
attctggtta gccaatattg atcgtcaaca aatttggaat attacccat atgttgaatt     37080 aggtgcaaac tcagcaccct taacccacg tggttatggt actatccaaa cactaacata    37140
tgcggttaac ctaaaccaag ttgatggacg attcctacca gttcgatttg catctacttt    37200
ccaagtagca ctattgagcg ctggtaataa tcggaatgct aactgggana tctattcacg    37260
ccctgancaa ggtgaagcat atggtcgtga tcttaaagcc gatatngaat ttatcaatgg    37320
taatctttgg gatctccggt tagctaatgg ngcacagtca caagctgcct ggcttaagaa    37380
aatgtacttt gctgctgagc cattaactgg tccaatggaa gctactccnc cnacacctac    37440
gcatttccgg gtgcgtacag tgcataacga gtatgagtat acggtaagtc aatggaatac    37500
tgcnttncgn attaatgctc aagatatggc cgatggtgct ttactacaan tcacctggat    37560
tcgtcgtgag tatgatacng acctacagtt agccattacc gcattacctt gtttacaacg    37620
ttaaatatan ngcccctag gnnnnnccta gggggcttta taacgtcttt taacacatta    37680
tccatatgag actatacttt acaattgccg ttcaatacgg ctttattatg gcacattaaa    37740
ataagtacct taaagggcag tgtatggacg ttatacttt caatagtgat tgggataaat     37800
actacagcgc tagtgttgat cttactacta aaaataaatc ntttataaag ttagcnttna    37860
cttataaaaa gatgggtatt aaaaattaca aatttatact agctatattg gaccaaggtt    37920
taattggggt ggatccatat gaccctaatc ttagcgaaga aatgaagttn cgtattaaca    37980
tggaatgcaa atataatcct tggtattttt ttagggaagt ggcaagaatc cccctaact    38040 cgggtaataa nccaattcca ttccaagcta accgtggtaa tattgcttta ttctggtgtt    38100
atttcaatca cgtagatttt ggtttattac agcctcgtca gacaggtaag tccgtatcaa    38160
ctgacgtgct caatacaggc atgatgtata tctggggnga gaacactaag attaancta     38220 ttactaaaga taacaaacta cgnaatgcta acatcgagcg tctaaaagta atgcgtgatt    38280
tgttaccaga gtatatccac tatacngatc cattagatgc ggataactcc gaattgatga    38340
catgtattag attaggtaat aggtatntaa cagctgttgg tcgaaatgat gttaacgcag    38400
ctgataaatt aggtcgtggt cttactgtac caaatatgca cttttgacgaa cttgcctata    38460 ttaacttaat tggtgtttca ctacctgttg cacttgcntc aggttcagca gctcgtgatg    38520
aagctcgccg tgagaaccag ccttatggta acatctatac aactacagct ggtaacatca    38580
ctacccgtga tggtgaattt gcatatcact tcttaacagg tggntgccca tggtcagagg    38640
aattctttga tctaccagat cagaaaactc tacatcgtgt tgtagaaaaa ggcactactg    38700
gaaagaaacc tctagtttat ggtgcattta accaccgtca attaggacgt accgatgagt    38760
ggttatataa cacacttcgt gaatcaggtt cattcggtga aattgccgat agggacttct    38820
tcaatatctg gacagttggt ggtgaaggtt cacccttatc atcagatgag aaagataaac    38880
ttaaaaacaa tatgcgtgag ccaagctgga cagaaatcac ngatgatggt tanacacttc    38940
gttggtatat accaaaagan gaagtagcct cacggatgat gaagggtagg ttcgttatgg    39000
gtaccgaccc atctgaactt cttggtgaag ataatgacgc cactggcaca gttgtagttg    39060
acgtagaaac acatgaggtt atgtgtgttg gnagatacaa tgaatcatca gtnccatcaa    39120
tgggtaattt ctttgcaaca atgctattna natatcctaa tattctttgg ataccagaac    39180
gtaaatcaat aggtatatcg ttaattgacc atgttatctt gattctncat actaaaggan    39240
tagatccatt ccgcgtatc tttaacgaaa ttgtcaatga atcatcagaa agagaaaatg     39300
atttcagaga cattcaaact ccgntatcag caagacaacc atcgttntat gataggttta    39360
```

```
aacgttattt tggctatgca acgtcaggta ctggcgagta ttctcgtgat aatctattta   39420
aggtggcatt accatcagca atgcattatg gggtaaggac catctatgat aaaccactta   39480
gcacggagtt attagcactt actatccgta atggtagaat tgaccatgct aaggggaacc   39540
atgangactt agtggtatca ttattattag cccantggtt attaatacaa ggtaagaatt   39600
tatcttatta tggtatcaat gttcccatct taggtaaatc aaaattacgt gataaagaac   39660
caagncaact tgaaaatat catgaagaga aagaacagca aggtcgnaaa gaatttgaag    39720
agataattga ncagcttcgc ggtgaaaaga acccgatgat tgcagctaaa ttagaaatgc   39780
gnttgaaaca attgtctaaa cgtgttaata ttgatgatan cagtggtgta ggtattgatg   39840
ccatgttaaa tcaagctcgt gcagagcgta cacgtagagt gcgtattaac agatattcta   39900
gaaatagttg gtattaaaca aaaaaaataa taatacgtta ccctcttcgc aatgaagagg   39960
gtatttgaag ttaagnaact ctagcgaaca aaagattact ggagttagaa ttaatatgat   40020
agttagacga tccgtcaatc catttagcat cggaaatctt gtttacaagc tgaccattgc   40080
caatgtaacc taggaaagtt ttattatcat atacagcaat tttgattagc tcatttcgtc   40140
cgtagactag tggcttacca ttgaatgctg ttacttctaa accagacatg tatccataaa   40200
ttggatcagg tctggaactt gtttcaaaga ctttcattcg aagtctcatc tgcaagaaag   40260
cccatttggg gcaaaaaatg tcaagcttaa acttgacgac atatagccct cctggtgcga   40320
caggagggct aatcttttca gaacgtacgg tgttgttata atactgctag cgaaaatacc   40380
catgataggt aagtagctaa tccgcagttc tcttggatga tacctactga cagtgtagtt   40440
gcaaatgtgc tgtttggaac cccactggtt tagcggccag tgggaattcc ttttatgccg   40500
cttttctttt ctttactgga tatttcttat atttacaaac ccacgttctt acgctggtag   40560
gtatcttcct tcttattata ttcgtagttc tcgatgaggc acttgttgct gaactcgacc   40620
atcgaacaca tcttgtccat gatgacttca gatatttacc atgttcataa attcggcgta   40680
gttgtagccg gtattcatgt cgagatagtc ttgttcgacc atatcgtcat tcaggtactt   40740
gacgtaagcc tcggcgtgag cagtggctac cgacttggtg aagaagtaac gagcgtgctg   40800
acggttctgt tcgaactgac gcagattagt agtggcctga ccgccgaaac cattgacctc   40860
cattaccccg taaacagtac gatcatccag agtagtgatc tgtgcaatca ctacacgaga   40920
agcattttcc gaatggtcga tgaacgtcat actgtaaatc tcgatttctt tgaagtcttc   40980
cattagaatt tcctgttaaa aaatgaata gacaacccct accttcgggt aggggcttta    41040
tgccgtcaac cgacaataag gtcccgaatc gttacgatct aggtatcaga tgcaggttta   41100
gtcaaacgag ttacacgaat ataaaccatg tagtcactca gagatagaac ttttcactt    41160 atacatcttc cagcgtcatg attacgacat gataaggact atcagcattg tgacccatgc   41220
acgtctcgca tttgaagatc cgccacatgc catacgaagg cagctcgcgg tttttcacat   41280
aaacgtagtc gtgcgctgcc acgaggtatt tttgttgaat cgagaattca caagtgatgt   41340 aaccttttc acgatgaat tcttgagtca tctgatcaaa agtctgtttg agttcatcag      41400
taagagcgac ttgggttcg aacattgaaa tattccttt gatatattaa atagttttga     41460
ttatttcgga gttattgaat atttaggtta ccatctgctc tatatagact cggctgattt   41520
catttaagta agcgagtgcc aatagaatac cagcccaaat aacaattttt cgagtagtct   41580 gttttctat tacacctggg tgtgattcac gaatactacg gtgacaaaat acataaaaca    41640
gacacagact cattgtaaca aagataatgg taaaccatcc tagatagatc atttctctca   41700
```

```
cctattttta taaatagagt ttatagttta gtcaggcgga tgatttcttc taaagctgca    41760
tcaacttgat aatacggcca tgaatcaaca cgaggttcgt tatcaaagta tgtccaaagt    41820 tgaataccttt ggagtttatt gtagaataca ttgattctga ttccttcatg gccaacaaga   41880
ccttcaatgt aagctgcacc atgcacatac gtaacatgta gtgcgtactc gctatcttca    41940
ccagcgtatt gcataggtct ggagtagatg aaggaataag gattaaatgg atcagcctga    42000
gtgatatgtt cgaagaattc tttcaaacta gattttttca tattggacat tatattttcc    42060
tcatgattta ttaagtctat cttctaggag gtagacttaa tactattcga tgttatttta    42120
agacgcctgc cttgtaacct ttaacaacag ttctagcttc taatgcactg atttcgccaa    42180
tgtgtttacg cagtgcttta atagcgttga tggtaggttc attatccgcg atatgtcgcc    42240
agtttccctt acccttaatg agttcaacat cctggacata tagaccatct ttaactagat    42300
ccattgtttc taccaacttt tcgacttctt tagttagatg cgtatgaaga ctggcgaggg    42360
acatgtcagt catttgatgc acatcataga gaaatcccta ttatcagaag acgataaaat    42420
ttctttggtg agtttattta cagtgtcaat gtttgctgca attgaaacta gcagtgcagc    42480
atatttctct gcattataat tcattaatac gtattcctat ttaaaattgg atttagtgta    42540
atgcggtaat actgcgaata tctaattcat gtaaatcata tttctttagg aactcattca    42600
ccgcttgctg aatggtgtac ccactcggag attcccactg agtaccatta aaagcaataa    42660
tacgataacc taccattttt tattcctcta atcacaaaat aaatacccctc ccgaaggagg   42720 gtatttatat cgttaccaat tgattacagc gacaaactca ataccccgac acaattcttt   42780
atcacgatgg gcatgatgaa aagatttacc ttcaataccg caatacggat aaaacaattt   42840
tcggtgttcc gtgtcgccga accagaaggt ggtgttattg gaatcaacca caccatggat   42900
agccacatca cgaatgtact gaaatacatg aactgcctta tcagtgatca ctcgaagttc   42960 tacccgtgt tccttcatca tagccaggat gtcttccttg gtgtaatctg cttgttcagc    43020
attggtcatg atcttgtgag tcagagaacg cttttccttg tcaccgaaac agatacagac    43080
caattgcacc aactgacctt ctaccttgag accactggtc ggttttagta aacgaactc     43140 atcatatttg taatcattgg tgacaatcag tgccgactta ttgcgagtga caatgcctag    43200
gttatacgac ataattaatc ttcctcattt tagaatatgt tgaaccttgt ggatgtcttc    43260
caggctatga ccaagaccag tggctttgta agaatgttcc tgatcaacac gcttgtgata    43320
tgcaagcagt gcatctactg gatgttcagc gaagaagtat tcagtgttgt tgcagtccca    43380
agcgaactcc cattcaccat cacgaatctc tattttgtta gcactgaggt aagtgatatt    43440
gatggtattt acagtggcat taccaccaat gaggtagtac gatccttcat tgctacgaac    43500
atcgatcctg ccgccatcga tagtatcctg atagtagaaa ccacggtcga agaataactt    43560
cagcatcgaa gtgaagtagc tgttcaatac agcttgagca tctttctctt cgaccaccca    43620
ttttccatca acgatgttat tcaggtaatt acgatcatga ttgatcccga cattatccac    43680
gatgtcagcg tagttcttat ggaacttagc aatctcgtac aaacgttcca gagcagcaaa    43740
acggaaaggg ctggtgggat gcagagccag aatgatccga cctacgctcc acaaaccggt    43800
cccgttgacc tcgtaacttt cttcgaggta acctttgata ccacagttaa cttcaagttc    43860
atctgctggg aaaccggtgc ggagccgcct acggatagcc aatagtaccg attcggattc    43920
ttccggatcg aacaggtcta tgccgaaagt aatccagcta ccacgtactt tgtgctggta    43980
tgccaggcgt acagtatcac cgaatgggaga atgaaccag cgttcgtctt ccgatacgac    44040
caaatggcaa ccacattgcc acagggtact tagaggatcg ttagaggcga gaatgcgctt    44100
```

```
ggtgtcgttc atatccgacg aagtagcatc tggactgcca tgtaggtgtg tcagaataaa   44160
cagaagcgat gattctgtag tttgagcact caacattgcg cgagtgatgg ttgcattgat   44220
gatcatgaga tatcttcctt tttacagttt atgaatatat tgctaaataa aaaaatatta   44280
cgatgtagaa aataaaaggg agtccgaaga ctcccattat tgcgtgtaat ctatttgatg   44340
ataaccgctt tagaaagagt ttccatactt ccaataacta atttggattt ctcttcttca   44400
gggttcncca ttgcttcacg caggagttca ccaatagttt tgggttgaac atcatcactg   44460
atttcacgcg agcatgccga gtcgtcgtac atatcaaaca cattcagatc atcatcatcc   44520
aggggcgtgc tgtcattcca tgaatagctt gattcatccg aggtatcatc agactcacca   44580
tactgttcac tgaggtcacg gtccagttca gcctcataca tctcgctaat tgctttatcg   44640
tcttcttctt gcgccttacg acgagaagtc ttgtagaacg gaagcaggcg ttgcaggact   44700
ttatggaact tcttcttgct gatcaaccag ctaacagagt agcgagacag ctttacttca   44760
gctgctttga tagtcggatc ggagtacagc gccatgacta gcttgtccag tttgtgcaga   44820
tgatctttaa acgagtttgc ataagcagga tgttcccgaa gagtgaacat cacaaacgaa   44880
cgcatgtcag tgatatagta ctgactgtga tgtttgttga tttcgatgta taccggatct   44940
actgcgcggt tataatcgaa ttcctctgcc caggtaaggc tacgtacttt agtaggacga   45000
ggaccttctg cccaacgaac agtcggatgt ttctcacgga tgttccaacc atgattgcga   45060
tcatactcgg ttgactcttc tttgaaccag gtgaaattac cttcaccgcg cgatacaata   45120
ccacggcacc aactgacgtt gattgccttg ttacggcttt cagtaagatc acagggcatg   45180
tccagaatag cgacataact gttatgacca ttggccacaa cgccgagaac agtagcttcg   45240
aatgtctcgt agcgctgtcc aggatacaca cgttcattct catccaggta acgaagggag   45300
caggattcga agatagcacg agtaccggca gggaaatggg cacgaccgaa aggttgttcg   45360
gcctttcttt ctttacgacg gctgataacc cattccagtt tttctttggt cagacgggtt   45420
acgggttcac gatactgttt catggtaatt tccttttttac gattgattgg gttgagtaca   45480
tctcaatgca tcctttttcaa gacgcattga gatgggtgtct ccgaagagac ccatctatta   45540
ttcttgggtc agttccccaa gacgaccttc ggctttcatg cgacggattt ccgagatgga   45600
tttaccgtac attttggcca gttctttcac agtaccttca ggcacaggtt tgttcatgtc   45660
gcggaagttc tgcttagcga tattgtaacg ctgatgttga agagtcttca gttccgaacg   45720
taccagagcg ttaccggcac attgggagat gaatgtaacc atgaaggtct tcagcttgcc   45780
acggtagacg ttgacccaag cacaggactc atccacgtgg atgttcttgt actcggaaac   45840
cttggcgtat tccagcaggc cgacggcatc gggaccgttg tcctgataaa ccatcttgtt   45900
gaacaggccc agggcgatat cggaggaacg ctcaccttttt atgaaggcga tggcgtcttc   45960
gatgatcttg gtttccaggt ctttgtactt gaccgggtcg ttcttgatca acagtagcat   46020
ggcgtcgacc ttgacagtca aacccatgtc ggcaccgcgt cgatcgatca actcgttgtg   46080
ctgtttctgc gtgaacacgg gatctatgtt cttgaaagct ttcaggagac gctgttccat   46140
ttacttgtcc tctttgacgt tgaatgcata catggtacat ttcggcttag ccgggtgttg   46200
gcaccactct ttagatacct tgccctcagg tttagtgaga tcgtaataga actcaccacc   46260
tgcggcagcg atacccatca gtactgcaat gaatcccatt ccgatcttta ctttcatttg   46320
gcaatgatcc gttgtacgaa gtgttgaagg ttggctacca ggcgttcgaa ttcttcttcg   46380
gttacctggt cacgatgcga ttccagaagt acttctactt ccggcaggac gttcatggcg   46440
```

```
atatccaact ggatacggct gatgaactct tccgttgtga tatttcgatc acgacgaata    46500
cgacttacca gcttgcgatg ttgttcgctg ttgcggtagg tngagatctt atcgataaga    46560
atatcagaga tactgctttc gatctgttcg gctacagcct gaccgtcttc ctttacggta    46620
gctttgaccg cgaggatggc agcaacggct gttgcgccaa ctgccagtgc aataagacca    46680
agtgcgtttt ctttgatgaa gttcatattg attatccttt caaagttgca tcatcattga    46740
agatatcagg acccaccgag agacttccca gaagatccgg agcaatgtaa acagagttga    46800
gggtttcgta tacaccggta acagcatcta cgttaaccag gctagaactg cgcatgggta    46860
cccattcacc gttacggaag gcttcaccga ccagtacacg aacatcatct acgtcagtgc    46920
ggttcggcca tagatcctta ccttctacta tttttacatt acgagcatgg tagaccagtt    46980
taccattcat gcgagcaacg atattcggac ggcacatgtt gtcgattact ttaactgcta    47040
cggacttttc cattttatt tctctattta gttacgagca tttcttgacc attgggaccg    47100
atacgatgac cgaggataac agtttcatta gaaatagttt gctcttcaaa cttagcgttt    47160
acaaacagtc caccaaaagt caaaccaata accactagtg cgaatgcttt cattttaaa    47220 gtccctttt acattaattg aaggttaaat atcaagttag taatatactg tttaaatatg    47280
gtttgaataa gggagtagta gttattacat atcgtgcagg taggtctcat caatgatggc    47340
acgggctagc tcaatgagac tatcttcatc aacaacaatg ttaccatctt tccaggtagc    47400
gctatgggat aaccagttac ggtaatcctt acctcgtaca ggattgatgc atacctgacg    47460
agtagctgca tcacggtcac cacggaaacc catgatagca cgtgcacgac ggattgcttc    47520
tttctccaag tcttcgtcag atttaaaagt caggaaagtt gtcatagttt gattcctttt    47580
tactgattta ataggtttaa ttacactgtt gtgatatact ggttaaaatg gtttgaatgt    47640
attatttcat ttccacagac gacaaatagt catctacatgt cgagtgattt ctgcaacagc    47700
cctgagtcgc cggcggccag ttaatttaga gcagtgttta ttaactaatg tatcaacagt    47760
tttacgtaac ctaacacagc gttcttcatt aggtatatct tgttcgataa acaggctagt    47820
taatttatgg atttccatat ggattttctt acatacatcg ttagccgatt ttcttcattt    47880
aatttgttgt atgattcgac taacttaaca atagttgtag caacagtagt tgcggcaaca    47940
aaaatttgaa taccattgat aaaattttta ttaaacattt ttaaactcca actaatgtat    48000
taaaaaaata tgtctatatt gaaaataaag ccctccccga agggagggtg tatgtcgcca    48060
ataagtgtta ctaatttatt tagttagttt gaccatacgt tctttcaaag ttgtttacat    48120
cataacctga gtggtgtgtt gcagaaccac ctgaagtagt atctataatc ttaactacca    48180
cttcatcatt ttcaatgtaa accgacagtt tatctcgcat aaaatccacg tggtcatttc    48240
gataacgtag atatttcatt acagcttcgc cactgatttt actgttagcc attattattt    48300
cctcgattga ttccagttaa aattatcttt tgcattttta gtgaagaacc cgttacccca    48360
accaaatgag tatctaaagt ccttgattac accaacatcc gaatcgataa ccttatattc    48420
aatgacttta tcactattct ccagaatgac taagatcgcg ataagatctt taggatcacc    48480
tacagtcaat tcatgtcttt cagactcgtc tctgtggata acgatgtaca tggtacttta    48540
tcctctaatt atacccattt agttactggg agttcgaagg tttcacacaa gtcgagtact    48600
ttacgatgtt ccaagttatt ttctggatag aaggtaatgg gtgtagtcgg actaccccaa    48660
ttaacacgac atccagtttc tttatggatt tcgccaagta cagtatatgc acctgcccca    48720
tctgcataac ccatttgatt agggttaacg cagatttgag taaaacgctc cgtcaatact    48780
cgattaatag tgatggtcaa gagacgaacg aactcacgag tcttctcgat gtcgtctacc    48840
```

```
cagaattcca gaaggatcca tttcccatga gggttatcat gcccaccttg gaagaataca    48900
cagaaacctt cttttgcctt ataaaactcg tgattggtaa tgttacattc aaccatttgt    48960
ttcactgcat gccatacacg ctcggtgaca taatcaccat aaagttcgat gcagtgacca    49020
cggccaggga attgttcttt tttagaaaat ttaatttcga acatggtata gattcctttt    49080
tacattaatt gaaggttaaa tatcaagtta gtaatatact gtttaaaatg gtttgaatgt    49140
attatcggta ggggagggtt acccttttaa cttttttaata ctattggata agtacatgac    49200
actacggaaa attttgaatc ttgaaaagta ttcacgtact tcttttttag tcaatacaag    49260
tcttccatct ttgtttacat tatccaccaaa gacaatttcc tgagtattct tccataaaga    49320
tctataaaga taacagccat gtggtgcatc acaccaatca tagatcttaa gttcaaattc    49380
aactttgtcg acaatatcat catcaaataa aatagtattt cctttactat ttaattccat    49440
taactcattt gcacaattta ttgcaaactc aaccgctgcc caggttctac caccgctgaa    49500
catatcttta cttaatttat ttagatcgat agcattataa gttgttttct tagtgttttt    49560
catggactgc acccctcaat aataaataga ataatctgta tttaattcac ctttgtaata    49620
tactttaaat acatttgaat acatgacata aagccttccc ctggggaagg ctattattat    49680
gttttaatcc aatgggtata tgtacatagg tcagtttctt taataatggt tgatttccat    49740
ttatcccatt taatgatttc tttagggaaa taaacacaac tactattatc natttccatc    49800
ttgacagtag taatgtacat ttcgtctaaa atatcctttt caatgacttc tttataaagt    49860
tgagaaccgc caatgatcca tacatccttt ccagtttctt tattgaaatg agtggcataa    49920
acaatagctg cacttagatt agggagtaca cctaatttat tatcataggc tactggataa    49980
ttaccgttac gatataaact tgatgataca acaatgttat tacgattagg taacggttta    50040
ctacctaagg ataagaaagt attttttaccc atgataacac agcaaccagt tgtcatttct    50100
ttaaagaaag ctaaatcctc aggtatatgc caaggtaata gattattata tccaatgaca    50160
ccatttaggt catgggcaac gattaattta atagccatta attttcctta ggccagaatt    50220
tacaagatac ttcattatct ttaaattcaa tagcccaact acagcaagtg aaattagttt    50280
taaacttaaa tgtagacgct aataggtaat taatttgagc catttgtaat agcgttaatt    50340
caccatatac tttctcatca atcaatacac caggtctttt atgtttaata actaattcat    50400
tcaacttaat atcttgttca atatagaggt attccacttc gccttttttct agtataggca    50460 tgtcccaaag aatcagacta atctgttgtg tgaattcctc aatactagtt gtaatatcta    50520
gtccttcata acctatcaat agatttataa gtacttgtag actaatcaga ttaacaggta    50580
agtcttttaa atcgtcttct ttaatagttg ttctaaaata aacagtgcca tctaagtttt    50640
taactaataa tctatttaat agatgattga cttctgattt aatctgataa tccagtttga    50700
tcattagcta actccttgag tctagtcatg ccattactaa cttcaataat gtaactaaag    50760
tcaaaactat atttcatcat tttgaattct tctttaaagt tagcgatatt tccagacaga    50820
gcaatttgtt caaatcgact aaaatcagta atagtttcat cgaacattag ttctcttgcg    50880
gtaatatctg gatcatagtt aggatgatca actacagtac cttcgtggtt taaagtacct    50940
tgaaaattca aagtcttttt aacatggtct acagttattt tccaactagt tgcaatatac    51000
cgagctttaa ctaaattagg agcatacctg taaatacacc attgtaatgg agtgccaaca    51060
gtttgcgtat catgcgtggc ttttataact ttaataaaat tctcaagttg atcaaatgta    51120
acattcctag ttacaccatc attagtggtt atattaagag atggtcgaag accagtacca    51180
```

```
agatcattgg tgatgattat atcctcaact aaagcttcat ataactttag tccttctttt    51240
ctggatccaa catcattacc cattgtttag cttcctcttt tgttaccagt tgataaagtt    51300
tattaaattc acgttgacgc attaatttgt aatctagtat acgcccatta tttttacgaa    51360
ttaaaataat aaaatcaccc ggacagacaa ttttatcttt atctgggcct acacgtaaaa    51420
taccatgact agattcagtt agattacata atgggcaaat cgcattacta agagtagact    51480
ctttagtagg tatagcataa ccaacaatag caccttggtt gatattattg ataacgccat    51540
caccaggtat atcaccgttc ttttttccatt cgattgcttc aattggatcg gtgtatttcg    51600
gtagataaaa agacattctt aattaactcc gataaataat agtagtatag taaaaagcac    51660
ttaggtatat ttctatttta agctatattg ttgataaaat aaaacctaag ggtacatagt    51720
gggttattat ttaaagctct taaatagcat ggtagaacga tattggacta tatagctgta    51780
acccttaagg cactaaggct acagaggttt ttaagataaa gatatccaat gtaccataat    51840
atgcttttac aatagatcaa ctaaattcat ttaaaatggg tcgtaaaaat acttagttga    51900
tctaaagata tgttgaatac ttttttcacat gaacttacga ctcacaattg gaaattaaca    51960
atgttaaaaa ctatcattaa actagacggt actgaagaag catactcacc tgctaagatt    52020
aatggttggg gtgaatgggc agcccaacat cttggcgata aggtggattg gagtagtgtt    52080
gtgatggatg ctgttcaagc tcttggtgat aaaacttcat cacaagaact acaattacaa    52140
cttattgaag aatgtttaaa tcgtaagaca tggtcttatt atctaatggc tggtagacta    52200
tatgcgattt atcttcgtaa gaagttctat ggtctaaatg gcatcccaac tgttaaagcg    52260
cttcaaacca ggatgcgtaa agatggtatc attgttaaat tagattatag tagtaaagaa    52320
tacgctcaga ttgaaaagat cattgatcac gatcttgacc tactttgtcc gcattttttca    52380
cttcatcaca ttcgtggaaa gtatgctcta cgtaatcgta aaactggtca agaatatgag    52440
actgcccagt ttgtatatat gcgaatggca atggctctag ctgaaaaaga gccagctgaa    52500
actcgcatga ctcatgtgga gaattactat aaactacttt ctaataaaat tcttagtgcg    52560
ccaacaccta actacgttaa cctaggtact aagcttcgtg gttttgcatc atgttgccta    52620
tttgcttctg gtgataatgg tgtatcactg gcaatgggcg attatattgc taacatcatg    52680
acccaatcat cagcaggcat aggtgttaac ttaatgacta ggtcaattgg tgatcctatc    52740
cgtaatggcc taatcattca ccaaggtaag aaaccataca tcgatgtaat tggtaaagca    52800
gtaagggcta acctacaaaa tggtcgaggt ggtgctgtta cgtgttacta cagtgctttc    52860
gatcctgaag cagatatgat tactcagcta cgtaatccac gttctactga ggataggaag    52920
aaccgtgatc ttcactatgc attcctaagt aataagttct ttgctaagaa agcagctcag    52980
aaagatggta tgatctttgt attcaatcca tttactgctc cagatctaca tgatgctttc    53040
tatagtggtg atattgataa gtttattaag ctttatgaaa aatatgaagc ggatcctaaa    53100
tttgagaaaa cttatgtaaa tgctcgggat cttctcaaat caatgctagt tgaagcatat    53160
gagactggaa ccatctattc agctcaaatt gatgaactca atcatcatac accatttaaa    53220
gaacctattt acagttctaa cctatgcctt gaaatcgcag aacccactaa gccttactat    53280
cgaatggaag atctttattc tagtgaggat cacgggcgcg gtgagattgc tacttgttca    53340
ctggctgcta ttgcagtgga taacgttcct gataagcaaa cttatgaaat ggcggcttac    53400
tacgcactta agatgattga ctattgtatc cttaatgcag agtatgcttt cccacacctt    53460
gcactaaccg ctaagaatcg aatgagtgct ggtgttggta tcatgggtct agccacacat    53520
atggcacgtg ctggccttaa atatagcagc gatgctggta aagctgaaat ccacttcatt    53580
```

```
gctgaacggc atatgtactt ccttatcaag gcgtcactta agatttctaa agaacgcggg   53640
aatgcgcctt ggattcataa gactaaatgg ccagagggat ggactccacg taagacttat   53700
aataagtcag tggatactat cattgaaggt ggctttgaag aactttatcc atgggatgag   53760
ctagagaaag aaattaagga gaatggtggt attgcacact ccgtactagc tgcatacatg   53820
cctggtgagg catcatctaa agcactaggg tcaactaatg gtccatatcc ggtacgtcgt   53880
ctaattctga ataagactga taatggcgca cgtgtgttat gggctgctcc atatggagat   53940
gatgattcct atgtgtatga atcagcttat gatatcccca ctaaagatct tattgactgc   54000
tatgccatta ttcaaaagtg gactgatcaa acaatcagtg cagacctcta tcgacgcatt   54060
gtaggttcgg aaaagatctc ttctaatgaa atgctaagta atcacttcta catggtgaaa   54120
cgtggaatga aaacccggta ttatgtaaat ctagaaacag cggcaggact tgacattaaa   54180
tcacttgaac gtgctgttga ggtaactaat actgaagttg ggtgtgcagg tggttcgtgc   54240
actctttaag tgtatacacc ctcccttaat tgggagggtg ttattcccaa tttatactaa   54300
cctctattat ttattgtaag aaatattttt aaattgtaaa ggaantaaca tgtctactaa   54360
atctcaacta ccaaagaaaa tcttcaatgt tgctaagagt gattatcatc taccggaaat   54420
tattcttgga gatgatccag gtctactaga ttcaatccac actcattatc ctaaaatgtg   54480
ggagctatat aagcgtctaa agatgcttga ttgggatgag ctagaatttg acttttccac   54540
ttgtctagta gaatttgaaa cgtgtgataa atcaacttat gacatgatga ttaagacact   54600
ggcctggcaa tgggaagctg actctgtagc cagtcgttcc attgttaata ttctatcacc   54660
tgtcatgaca gattcacgag tatgggcggg atatgtacgt attaatgata tgaagacgt   54720 acatgcttta acttattctg aaattgtacg taatagcttt aaagatccta agttattct   54780 agacgaaatt cttagggtag aagaagcaca agaacgaatg gttgcagtag cccgcactat   54840
gggtgaagca catgacgcag ttcatgcgta tgctcttaat caggtaccca atgatcaaga   54900
actttacaat aaagtattca tgttcttcat cgctctatat ttcctagaac gtatccagtt   54960
catggcatcc tttgcagtaa cctttgctat tggtcgtact ggtgcattcc agcaaattgc   55020
aaccgctgtt aagaaaattg cccaagacga attcgaaatc catgcacaat atggacaaga   55080
agttattcgt gcactactgg caactgaacg cggtaaactc gcttacagtc aatgtaaaga   55140
taaaatcatt gaactactat gggaaattgt aaagactgaa gttacctgga ttaattatct   55200
attctctgaa ggtcgtgaac taactggtgt taatgcgact aaacttatta actgggtact   55260
tttcaatgct aatgccgcag caacattcct aagtattgaa aatgatgttg tagaacagta   55320
tcaagtggag tttaaagaat cagctggatt tgattttgtt tggccagaga agaacccact   55380
tctttatatg gaagactacc tagatatttc atcaacccaa gcatctcctc aggaagaaga   55440
gaagcctgat tacatggtca acgttgtaaa tgatgttggt gaagaagaag aatttgaggt   55500
tgacttctta tgattaagat tatcgcattc gtagttttaa tgtggtccac tgtcctattt   55560
gcagcaactg aagtaaaatc aactacagat ggtattattg cacattcaga atgtcagcta   55620
gttgctaaag atagtagtgt tgtcggcact actgttggag gtgcggttgg agccaccgca   55680
ggcgctgtat taggtcgagc aatctttggt aaatctggag gttgggtagg tggtttaatc   55740
ggtggtgccg caggcggcgc agtcggtaat aatgttagtg ctactgaaac atttcaatgt   55800
aaactgattg ttaatacaga tggcaagcag tacatggttc aaacagttac caatgaaaaa   55860
ccaaaggttg gtgataaagt cactgttgtt gaaatgaatg atggtacacg agatataatg   55920
```

```
tagacataat gaccctccct taattgggag ggtttatgct aacaattcta tagcactctt    55980
attaacagtc atcaacgaga gagtagacat gaataaaatg ctaaacttcc taaaccgtac    56040
gctatatagc ggtactgaaa aagtatcttc aaaagctaca ccaagtctag aacactttaa    56100
aacaaatgtt gaacaagtag ataaaaagat tctacaaccc tttagtacta aatttaaaac    56160
cattctaaaa gaatgttaca gtaatgagga gtgggttgaa gaacaatcat ttattgaaga    56220
acctattgat cttggttcag ctgcacgcgg tcttaccgag cgcggtatta tgcgtggtga    56280
ttggggacgc ttagcgcatt ccactattaa agaagcagaa ggtatgatgc gtacttatag    56340
tggtcgtcta aatgaagata tggaggcatc tgaaattaat gaagtaattc aagatatgcc    56400
ttataacttc acagctggct cagctaatac tagccgttta gaagaagatg actctatttt    56460
tgttgaagca gatacaactg tagttgaacc tctgtctaag cagactctgc aaaagtagc     56520
agagcttact aatcaattag tggaagtcta taaccgaatt actgaagaat ttacagaaac    56580
tggtattgct aaagttgaac aagttgaaca gccagcagtt cttgtagcac ttggtgagat    56640
cattagtagt tttaataaac taattgattt atcttgcggt gctctaccag tggaagaaac    56700
tgttattgta gaggaggatc cgttacctgc cattgttact ggtccaacta ctgaacccat    56760
tgatggtgaa attctaccgg ttgatgctat taataattct gcggcattag aagaattcat    56820
tgaagaagta ttaagtacta atccagaatt cattaaatat caagtatga atgatagtaa     56880
tattgattca tatctaactg gggatgactg gattatactg aaattcaaag atggttctta    56940
ttatttatac aatgcccaaa gtgccggtga acgaatata gaaatcatga aagatatggc      57000
cgaaactggt agtggtctta atggttttat aaatcgggtt attcgtggcg ggtatgtaga    57060
gaagtccatc attaatactc ccggttttat acaagtctca aatgaaggtc ttatcgattc    57120
aatcaaaaaa gttcttggca tttctaatcg aggtgatcag aaacgtatct ggcgttcatc    57180
gtccagtgca agaggatttc tggaacaact agaatctaca tttggcaatc cacaatggct    57240
taataagcag gtattcgtta ctggcgatat caatagtaat ggtatagcta acgtactgag    57300
tattaatggt aaagtcagta tcgaggatgc cattcgtgca gtagaaccat tcttcaaact    57360
cgaagaaaag tctaatcgcg aaatggagtc ttacaggcag aagactaaac ctgcattgga    57420
tctactcatt aagaatgcac ataacctaga cgctaacgta tacaaagaag caaaggctat    57480
cgtagacaag gcacgtgctg gattcaagac tagtgttaaa tggcctgccg gtactattac    57540
aggtaagggt acctataatt caccctcgcac cgtggtcgcg aaatatccat ctactgatag    57600
taaactcaaa gctcttactg aagaagaagc agctaaggcc atgaacttaa ttatatcggc    57660
attggaacgt cagataactc ttagcttcaa gttccctgat ttaccagatc cactggaagg    57720
actaatctac gatatgttgg ataacccctag tccaatagct ggtatcgatt actatgattg    57780
gaatgatttg ttattcgcat gctttggccc tgggattgat gatgatgtga tggaagttaa    57840
taaaatgcgg caataccact cattcattga tatcatggag gccgccgcaa atgggtaga    57900
tcggtctata aaaggtaggt tagcaatggg taatgaaaac taccagtaat gtatctaata    57960
ttatgtagaa ataatccctc ccccttgttt ctacattagt cataatagat cggagccagt    58020
cccccttcca actggctccc agagagtaaa actctttgct gggcattaat gacgatatat    58080
cgcctccctt cggggaggct ttatattttg ttttacgta tgtatattaa aatatgtata    58140
aacaacatag agtaattata aaatgatcaa aaatgaactt ttaccagggc taatctatgc    58200
ccaaaaagaa tttgataaaa ttgcagctaa tgtaaaagac tatgataant ataaaagacg    58260
cgaagctggt agggcaagtg ccgtttttaag aagtctagtg agcaatattg taaatcagaa    58320
```

```
taaaccatcc tcacttgaac atgaaggcaa agttagtact actaatacta atgaatattt    58380
agaagaagtt aataattact tctttaacat taataatatt aaattaattt ctcctaaact    58440
cataaaagag aaattaacaa ttgatctaat gaatatttat gttaaatgga atatgattgg    58500
agtggctggc cgaaatgatg ttccaattat tgaacacaga attaatgatt ggtgcgaagt    58560
gaccgatgtc tacattaatg gtaataagat aacttcttta caatggccac gttgaattta    58620
aaataagttg taataaaata cctagcatta catgttatgt attgaagcac aatgcccgaa    58680
tggtgaaatt ggtaaacaca gaagacttaa aatcttccgg ctacggtctt gtcggttcga    58740
atccgacttc gggcaccaat ttaaatacgg agtgtagcgc agttggtagc gcgcctgctt    58800
tgggagcagg atgtcgggag ttcgagtctc cccactccga ccattttaat aataggtaaa    58860
taggatggat aataaatgga tatcatggga acatcaaatt ataggaacag ctctttacgc    58920
tattcttagt gaccctgaat taactaatat tcaattagct caaggcttac actatctaac    58980
agaagcaaag tcttctgtat tacatgtttg taataaccat attacattca ctgtaaccta    59040
tccacatggc acatttagaa ccaatgtaat tagagagtgc cctgctagtg atacaaatac    59100
attcaaatgg tcaggtgtat tagtccgtca aaaagatgga acattcttac cagaataaat    59160
aaaaagggcc tatagctcag ttggttagag caggcgactc ataatcgctt ggtcgcaggt    59220
tcaagtcctg ctgggcccac catatactag cctcccactt gggggaggtt ttatactgtc    59280
tcattgagga aaacatgaat acagtaataa tgttggtatt atctatcaaa gttggattat    59340
ttggtttcat ttcgactaat gaaagtaata tcctatttga aaatagggaa cagtgtattt    59400
ctcatctgga tattctggaa cataaataca agtctcttga agttattcga aatgagaata    59460
ctctaaagat aaccgaaaga gataaccatt ctatttatat tttaaatgt ctctaggaaa    59520 atacatggaa catcaanaac aaaaagaact attgagacaa ccattacaaa cactttataa    59580
tcttactttt agtccccgtt tacgtaatgg agcgaaggct cccgattgga ttcacctgac    59640
cgatgaagta accctattcc caaacggatt agatattaca atcaacgctg ttacacgttg    59700
catcaaatgg gaacttatcg gcgaggatgt aagtaacatt acttatgttg aagctatgtt    59760
ctttaataaa ggtcttaaag cagttaaagc ctatctcaaa catacggagt aaatatggat    59820
catctaaccc caacgcagag cgctgtatat ttcacattta ttagccctga gtttataaag    59880
ctaactcttg ttgaatcttt tgtagcgatc cacaagaaac atccagaagt aaagcattgc    59940
gttaagaaaa agattagtgc taatgaaacg cagtttatct ttatcttcaa agatgggact    60000
gataatttaa tcattacacg taaaactgaa ccttgccctg aactggatag cccagtaggc    60060
gatagtatta agttgtccgg cgaagaactt aaaaatattc ttgctaagta cgatcgtccc    60120
aaggatggta actatttcaa gcactggact gatcgcccgt aataaaatat tactggttat    60180
gtaatactat gtaggaagtc atgtccatac gtttgcgctc atagttcagt tggttagaat    60240
acccgcctgt cacgcgggtg gtcagggggtt cgagtcccct tgggcgcgcc atttaattcc    60300
gtgatagctc agtcggtaga gcaagtgact gttaatcact gggtccctgg ttcgagtcca    60360
ggtcacggag ccatattcta agagtagct tcggctactc ttttatgttg ccatgggtta    60420
tcttatgaat taaaatgatt tacttgagag cacactcatg tttgaattac tattatcncc    60480
agatataggc gaagagttac ccttggttgg atttaatgaa attattaaat taggtgatct    60540
acctgtagcg ttagctggta caatgtcata tgtggatgga aatacactgt atgttggatc    60600
tggtcatcat actgaaggac aaacagctgc aactgtgttc agacgtttta ccatatcgcc    60660
```

```
atttgccgat ataggtgcaa ctgcttctgg aacattctta ccagggtat ctttaggatt    60720
tgggacatta cataagaata actttattgt ttatggcggt attactgat ggaactcggc    60780
tggtaatggt ggtacgggaa catctaactt tatacaacat tttgatatag ctacaggcaa   60840
tagggttgag cgatatagtg gtcccgtacc actttgggc acagcctccg catcagatgg    60900
taatgatctt attctatgcg ttaacccant tggngtaann gcaatgcgnt taaaaccatc   60960
nngtaagncn tggcttagng gncaaganta ttcaggtggt gctcgttcag gtaacagtt    61020
attcttttat aatggttact tttaccattt tggtggttgg gataatacaa agaacatacc   61080
taatcttgaa gtttatcgat ataatgcaac taccttaata tgggagcaaa caccttggat   61140
gattatacct gctgataaag gaacaatctg gcaaggtaan ggttatgtag atgngacta    61200
ttttaattac cttaacgctg ttgatgtcgg cggtgtaact aaaatgtttg cacaacgttt   61260
taatattagg cgccggaaat gggctgaacc atttgaacta ggtatcggat tcctnaatat   61320
ttcatctata gctaaaggtc cggataatag catgatcatt gtaggtggat ctaaaatgcc   61380
agttggtggt ggagcanana tgttgaaaag ccaattgtta tcaggtntct atcaggtaaa   61440
actagcacca ttaatcattg attaaaataa taatatttat aactatttag ataattatac   61500
tggcacgatg atattatgta agagtactat antaaagtat tcttaaatct atccactaaa   61560
cacactcggt ggtagaactt attatagagt gtgtctaaat gccaggggtt tgccaccct    61620
ggntatattc attgttacta ttataaattc atttatagat gagaaaggt tttatcacct    61680
tttcaaaatc ggcatttaat tccagttaaa aaaactgaat ctatgctaca ttgtaataaa   61740
ggagtctatt atgactaact ctaatccgtt tgtaagaact attgtaaagt accaagatat   61800
cctagatgct ttaattcaaa aaacgaatga gaactgggtt aattatcgat ctaattctat   61860
tggncatatt gttattcgtg aatacaggac tgttggatta tttgtaggtc ggcaatgtgg   61920
tagtacaact gcattgattg agtttgctaa tcgtcancct ggcgaatgtc tagctgtatt   61980
tgtagaagat aaaattaaac aggctgtact ggctaagttc cagaatgcta agataatat    62040
tgtttcttgt ttaattacac accaactccg naatatatt catcaacctg aagaatcatc   62100
tattcaaaaa gatattaaag aagaattaat atcgtctgta aaatatattc ttgttgacaa   62160
tgcctcattt aatctgaacc tacgcggtat cactgataaa gaatttaacc agtgggttgc   62220
agatactttt ggtacagagg taatggtggt tcgttttagt tagaattagt aactttgata   62280
gtttctaata agattaacta cacgttattt acataatgtc ataacaagaa ataaataata   62340
ctcagattgt aataatatgt agttattaca tatctatatt aggttgtcag taactcatct   62400
ctaatataaa atcgccataa ttcttccgtg atagctcagt cggtagagca agtgactgtt   62460
acgatttcat tggtaagtac ccgagtggca gcagggagcg gactgttaat ccgttggcga   62520
aagcccaccg taggttcgaa tcctacctta ccagccaaat tctaaagagt agccagctgg   62580
ctactttat cttgttctat agatcgaact agctatctat ttttaaacc ctaggttcga    62640
tatgaaagaa aaaaataatt aatggttatc gggctctgta tttacctgaa catcggcagg   62700
caaaagctaa ccccaaaatg tttggatggg tatacgaaca ccgtgtagtc ggtgaagata   62760
caatcggaag atctctttac gatgacgaag aggttcatca tttggatgag aacaaactca   62820
ataaccatcc cgataatctt ttgatcctcc ctcaatcaca gcatctaaaa ctacatgcat   62880
ggatgaaacg actgggcatt gatccaaaga actatcctac aaaactttgt ggtgcttgtg   62940
gtagggtaat gaatcataaa ttgattaaat tctgtaaccc tgagtgttct gccaaaggtc   63000
gacgtaaggt tgatcgacca tctaaagaac aactcgtcct tgacgttaca ttgttatctc   63060
```

```
ttgtgaaaat aggagaaaag tatggggtat cggataatgc aattcgtaaa tggtgtcggt    63120
catacaaaat caatattcca gctaggttta ttagggtcag cactaatggg ggtattagca    63180
ccttggcccc cacacaataa aaatatactc gatgtagatt aatatacaaa aacataatca    63240
ctgggtccct ggttcnannc caggtcacgg agccaattca tagttttaga tttagttata    63300
tttcactact atgtaaacta taaaggcagc taatgctgcc tttatgtcgt cttgtaaaag    63360
tacccagtag ttgaatctta tagctgaata caaatagggt aaagacatgt cacttaaagc    63420
attgcaagat atagttagta gtgttcctac aaatgaacaa aggaacgat tagttaaagt     63480 tcggaaaacg atggaagagc taatgagtc tattaagaat cagattcgta ataaacgacc     63540
tagtcaagct cttctcgaca aaacgataaa ctggggtacc aagtatggct aagacattag    63600
ttcgtgcaaa gctgattact gaagctggtc aatggatgtc gtctgactgg gaatgtggtt    63660
tccgtgcatg tcgattcgtg aaacttggta atgatcatgt aaacataaaa gactttgagg    63720
ctatgatcac ggcattcgaa gttggtgaca tgttagtgat ttggccaaat gggcttagaa    63780
cttcgtatag tgtggataat ttcaataagt acttttccca tatcaaagat gaataccatg    63840
agactgatct ccgtccactc ttttacccca agtagttgag cttatgataa ctatattcgt    63900
gtataaatac attacattcg ttatacccctt taattgattg aaatcaagct acataaaagt    63960
gatgaatact ttaacccaat gatgtataaa ttaaaaagta tgcacactaa aaatacagat    64020
ggtgtttatt tgatattttt accaacgcct actatcgatg atcaaattaa caccatgcaa    64080
gggtatatta tcaataaatc cggtaatctc attaggacta ctgtacagtc atggcgattt    64140
gagaaaattg aattcaaaga cttagccaaa catgatagac gttggttatt tattgaatat    64200
tacattaatg ttaaacaaac gaaaaataat ataatcaaag agcaacaaga tgaattaact    64260
aaatttattt attatagtac tctaagttaa aacaaataaa aaaataaata taagagctag    64320
cccctaatgg gctagcttta tgttatctta ctctgctaca tcttttacat caggtttatt    64380
attccaacgt actgctctcg caataccata cgtaagaata agagcaccca cggtgccaat    64440
agtggtgcta ataataatgc caagagtttt tggntcnata ttcatattta gtntcctatt    64500
tacaattaat agaaaatatt acttttagta atatcannt nntnatatac nntttaaata     64560
ngtttgaata taactttatt tattataata aattaaaata atactttcat atacactata    64620
tgtagaagat tncgccgcta tagctcagct aggtagagca acgcacttgt aatgcgtagg    64680
tcctccgttc gattcggagt ggcggcacca aatttactga ggtttaaact attcttaaat    64740
atattagtta ggatgggatt gaacgngaaa gactcagtaa atcatattgc ccctccatat    64800 ggagggggctt atgtttgtca ttaatcagga aaatataaaa tgagncatct attatttatc    64860
atccaagaat acattactaa taaatttgag ataacacgaa ttgatatgaa gccaggtaat    64920
agaatgttac gtgtatgttt atacggtcaa cataagggaa aaggtttcgt ccgtatagat    64980
ttatggtcag ttggttatcg cattacaaag aaataatact ccagattatt taatatgtat    65040
taatcaaagg agtttataat gagtaatgaa actaactatc taggttatga atggaaaaca    65100 gataaataactca cttcaaatct taatagagtg gttgatttat atacacttga attaacatgg    65160
ttaaaagaag attttaatga tactcttttt ataaagtctt ataaagtgct agagggtcta    65220
ttagaggaac cgtctagggc aatccatgat gatacagtan ccattcaaga tcaattagat    65280
gaattaaata ctgtttttaa attagtatt ggaaaagata ataacgtaga gttatcaatt     65340
aataatgatt caattattgt gatcggtgct acagatgcaa ctaaagaaaa gttagaagca    65400
```

```
gaggtgcgtg agtttgcata tagaaaatca ttaattgatg aacgttatcc agatattgta    65460
acggattaaa atacttacag ctatctagta tgtaactagg cggattgcca tttgtaaatt    65520
atctatttaa tcgaactgag gaaatactaa tgaaacaatt ctttcaacta cttctaagcc    65580
tacttttcaa actaccggtt ctatcatatt ttgctgagaa gaaacgatta gagaaagaga    65640
aaaaggaaga agaaaagcgt cagcaagaac aacgtcaaaa agaactactt gatgaacaac    65700
gtcgcgaaca agaagatcat tatcgaaaaa ccgcttacga tcgcctagca aaacttattc    65760
atactcggtg gtatgatgag tttaatgcat acgaaaagaa actagttgat cttgctgtat    65820
cgagtggtaa agcagttagt gttaagtatg gtaaagttac taagatgcag caccctcatc    65880
aatttaaact acttaatgat tggctggatg atattccagt agaagattat tctaagtgaa    65940
gaggagatat acaatggtct tcacactcga agatttcgtt ggggactggc gacagacagc    66000
cggctacaac ctggaccaag tccttgaaca gggaggtgtg tccagtttgt ttcagaatct    66060
cggggtgtcc gtaactccga tccaaaggat tgtcctgagc ggtgaaaatg ggctgaagat    66120
cgacatccat gtcatcatcc cgtatgaagg tctgagcggc gaccaaatgg gccagatcga    66180
aaaaattttt aaggtggtgt accctgtgga tgatcatcac tttaaggtga tcctgcacta    66240
tggcacactg gtaatcgacg gggttacgcc gaacatgatc gactatttcg gacggccgta    66300
tgaaggcatc gccgtgttcg acggcaaaaa gatcactgta acagggaccc tgtggaacgg    66360
caacaaaatt atcgacgagc gcctgatcaa ccccgacggc tccctgctgt tccgagtaac    66420
catcaacgga gtgaccggct ggcggctgtg cgaacgcatt ctggcgtaag tttaaataaa    66480
agaaaataaa gacgaagttt ttcttttacat ggagaggggt ttatgccgta attatacact    66540
tactttgata agatttttaa tatcagtaaa atgggtatat gttgcctttt tatctttgtg    66600
aaccagtaag caacaggtac cttcatttac tgtattggtt tgttttaatg ggatatttaa    66660
agcatattca aacagatcat ccatccagtt aaataccatg aacttattga taaggacatg    66720
atcgaaatca attaatccaa taaacgaatc gatctcagat tgataatact ctacaaccat    66780
tttagaccat tctttgttta tcgcctcaat gacattagga ttatttattt tattaaataa    66840
ctcantncgt tcctnagtag gtaaactgag gtaataatta atattactcc taacgatatc    66900
tggattagtg atatcnattt tttctggtaa gttatattta ctatctacat aattcttagt    66960
ttctggtgtc attctccagc aaccataatc agcagtagta cttgatggat ctattttagt    67020
ctccactact ttagaaaata catctacata taaattaaca gattcgtata catcaggtct    67080
gattggatta agtttaaac ttttaataag accctaact ggccgagtac caattagaca    67140
atgcaattca agcttaacat tttcctcttt agccatctta aatanatcag caaaactgag    67200
cttttctgcc atttagaata tacctttat taattggaca aatagattag atacacatag    67260
caatagaata aaccataaac ctagtctttg taatttatct atacgcttag cttttttgttt    67320 cctctttaat ctaactaata atgtattttt aaatatcattc attaaattat ctcagatttt    67380
tagacggtgt ataaaccctc agtattacat gttgttatga tattgtaaag acgatgccaa    67440
tagcgatcat acgtattttt acgtttgtag ctattggtnc ggatgactag attggcgacc    67500
cagtgattct gatcaatggt ctcatgtaga tgcccgaaat aagcccccag ttcaatttcg    67560
aatgggatct tacactcacg ccccttacac attgcttcac gcaataaacg cattgcagaa    67620
ttctctgcat tggtatcttt aaataaaaga ctaatgtatc cagggctacc accagtttct    67680
tcatcaacat ggcctgaaca gcaataaata gttgcaacat tgataaattg attaaaccat    67740
ttaattaatg gcctacatgc ttcatcaata agatcttcat attcaggttt atacattact    67800
```

```
ttaacagtat catctgcacg ttgtttcaca tgatgaaaat attgctccca atttacatta    67860
gtgtaatata gcatatccat attagaatta ctcatacaaa tcaaccccat atgttattgg    67920
catattcgcg gtcattgaaa atgcgggtaa gatccatccg cttttgaatg cgcgctagta    67980 tccatttag ttgtttagtt gatagttctt gattttgctt gtactcacct gtagcatgga     68040
tgtaataatc aaatttacga cttacagtag tagtatgtgc acatgcaata gcaaatgctt    68100
caagtgcagt tagtttggtt gatccattat cattacaatt agggataaac tcaagtacac    68160
tattaactgc atctacacca ctacccaaat gagcccaatc tttcttggtg atgttgatac    68220
ccatgtcttt aagaataact gtatatatgt caccattctc catagtgaac atcatagaag    68280
tattaccatt aaacaacctg cgttctatga ctggcaagat atttacttca actttaaacc    68340
aatcagctaa atcaacacct gcggtaaggg cattcaatag atcataaaca ttatctatag    68400
ttccagcaaa agccatagtt ttaacacgtt taccttgcca agtaactgtc ggatgaaaaa    68460
ttatcttgtg gcaatcattg taatatacat ctacaccttc agctttagca gttagatcaa    68520
tataaccgtt atctaatact ggaagtcgcc caatgctatc agttgcatta ttccgctcaa    68580
ttaataggca gtctgcaatc atgactttac catcatttac gatatatgtc attttcactc    68640
cttataataa aataaatagg cttaagcgaa ataaagccct ccccgaaggg agggcattat    68700
caataggtgg gatctcggcg gcaccttcat ttgcggacgg gaacgctgaa gggagatagt    68760
ccgggagatc ccgatttggg tattctttac atatggtatt actgcaagta tttgttcccc    68820
gcagtataat caccattgat ccaattttg attacaacac tgatcccttc attttcttta    68880
acggtaaccc ccaactcaag atcgattgat tgataagcta cagccgccag tgttaaccga    68940
agataaacgg atccatcttt ttcgatatcg taggatacta cgaacccgtc ttgtagattt    69000
gtagctggaa tgtattagca tgttgtggat ggagacgatc catattgtac tcgacgacat    69060
ctagtagata ttgccgagca tcagcagcat tatcaaatcc gagancgcac agaccgatcg    69120
gatagcgagc ttgcgtgcat gtaactttca tagatactac acgatgttgt ttgcacatta    69180
tattttcctc ttagatgtca aaaccctccc gatcagggga gggtatctca ttggtacttc    69240
ttcagcaaaa ctgaaactaa gataaaagag caatcgtaaa ggaactacat agaatagtgt    69300 atttcttttta ctatttttac acaacctctt tagatgggggg ttctttatga atccagtcta    69360
aagttgttgg taaactatta tctgatctga aggtacacac cgtccggaac cgagagtgat    69420
caactacaga taattgcccg ttaatcgcag cctcatattg cctacacaac ttcacacacc    69480
ttttctctag atcagttggt tcgtaacctt cttctcttgg ttcagtgtat ggtccatccc    69540
aaaagaatat taatctaaga tcaatcccag atttatactc cgcttggtat gaatattgnt    69600
gaacatcaaa atcatctaat tcttcaacta gatgtgatgt tattgttcta ggntgttcat    69660
gagttaattc actgtatata tgtttatttc tagggttttg taaatcaact acgataagtt    69720
gactagtcat tttaactttt atccagatgt ctattacgag tgcgttccac tgctgtaggt    69780
tcgacagtgg ctcgcggtag ataagtaatc tccgggaaag tcttattaag agcatcttca    69840
attagctctt tagcaatctc tgcatcgatg taatggttta gaataatacc acgatgatac    69900
aggaagaagc tgtattcatc ataaccatgg cgaagactta ctttaccacg atacccacca    69960
taggttagag tatcttcgtt aattcattcc gataaatatc aagttggata ttattttgaa    70020
gatgcatttg aatgaagtca ttactatcac cgccgaatag ggttggtcgt ttccgaccag    70080
taacaacatc ttggatggaa tccattagtc ggttaatgtc tgtttctaat cgttggatat    70140
```

-continued

```
cacattgaga attcattgct tcatggaaac gagttacaac tgcattgaat tcttcttcag   70200
tccaaccact ggtacgtttt cataatcaac aatgataata ccgaaccagg cataaccgtt   70260
agaatgttta ctttaacaca tagatgaggt acattatcag cacctgactg atggttaaca   70320
gtgtaattat tattacggct gattactagt ttgataaaag gtagactaat gattgacgcc   70380
atggaaatat tcctttgta ttttttaaat taaagtagga gttattattg agtttcaact   70440
caatacatca ataactccag tatgttttca aaattaaata catgtattta cagttacatt   70500
gtaaccagtt agttttgcca acaatacaaa ttagcgaacc tgttcgattt tttcagaaac   70560
aatgaaaata tgtgcaatac gatcctcatc aanataccga tatcgaaatg aggtataact   70620
agatgacaca tccgtatcgt ttaaataggt gatattaaaa tcatctactt ccctaccatt   70680
agcagccgca acggtattta gaatgttgag tagactcatt ttacagattc cttttagta    70740 tattaatatt tcaatagact attgataaaa gcattagggt cataacggtt atttgaaaaa   70800
gccgccatta catcacaccc tggctgatct ttaaatctga tatcttcagg aatatcgaag   70860
tcagggaaca ttagtttaat atactcccta acttcttgat ctcgtagata tggaatctcc   70920
accatgtaat caacgcgacc tttccttaga agtgctttat caatattctc aggatggttt   70980
gtagttagaa tggtcatagt ctcatctagt ggaacaatgc catctagccc atttaataga   71040
gctgacaaag ttaatccgct agctggttgt tcatacgtga ttccattctt catgcatttc   71100
tttaatttcc accatcggcg aattgtggta ataatggat cttttcatc ggcccatttg     71160 aaacacccag ttcagccata gcataagcac ttatcccaaa accttgatca tcgctatttt   71220
catcaaagat atagatggtg tcattaaccc aactacagag tatccttcat agtcatcttt   71280
aagatcaacc catgcagacg gatatttttc aattaaatca ataaagaat atttcctctc    71340 taattccttt atctctttat ctagttttac aggatcattt aaaacacgat ctttaactgc   71400
cggggtatca tcgaaatctt caattagaag aatattacct ttaggtagtg tagtaaatgc   71460
ccgcctaaga ctatcattgg tcatagaggc taatgacagt gcactaacat ttttattaaa   71520
atgtgaggca atcgctttac tgattgaggt ttaccagtac caggaggacc tgttagaaca   71580
caagtgaatt tatagggtag tccacgatca tcgtaccatt tccgatcaga atagaattct   71640
tcaatcttat taaggaattc ttcttgatc tctttacgca aaatcaccgt gttgatatcg     71700 cgttagtaa cttcaatctc attgccccaa cggttaccat cccaatgtga aatagtcaga    71760 ccccttcat ttgggcgcca atggtaagca tctactaaat caataattag tttactactc    71820
ctagataatc cacggatagt aatatccatt tgatctcgac tggcattttg actatcccgg   71880
cgtgctttta caaaccagaa taacctacct ttaaacagaa agaaatgtaa gccaaaacca   71940
acaccaattt tctgtttagt tgcactataa ctttgctcat caacattagt tgaaaaacgt   72000
cgattaaatc cagctaatgg ctgcttaata taccattcca tgaaacaatc aaagttcttc   72060
tcgttcagcc cattacccat gttggtaata tgtagactaa ctgtaaactg atttaatgcg   72120
aacctagcta gtttacttgg taagcctctt agagtggtcc agaataaacc accaattgcc   72180
attccgatag ctccacccat aaccatattc ttctgagaga tatcgatgaa catggcgtaa   72240
tattgcaata aggtttctat aatcatacta gcatccctct ggatagctta ggaaatattg    72300
tccacagatc atgtattcac gttctagaaa tctagagtat gactttcaaa tatttcacct   72360
acatctttac catagatttc cgtatacccca ttttgaata cggccattac ataaacatca    72420
gacatagtca tgccgtagtt ataaatttga ttgtctctgt attttggatg aaataggtca   72480
tataaaaaac gagtcattga actattggca acagttgtca cccctttctg ctttaaggca   72540
```

```
taacgtactt gtttaaccac atagttaact ttagagcgct cgccaaatac cgtcagttta   72600
tctacattgc aattacgata tcccataaca ccaggattag ctatcacggt gtgttttgga   72660
acacgtacat caaagataat gccattaggg gatagaataa tcttttcatg gttaaataga   72720
acatgaaata aatgtcgttc tggtttagtg attttgatac ttaacccaat caccccacta   72780
atctttcttt ctagatcttc tagtgactgc atcaccatgt gatattgatt gaagaaagca   72840
ttgttcttat attgatctaa ttcaaagtat ttccaacttc cacgaaatga atagcatggc   72900
tttggtataa cctttagtta atcgacactt gagtttgtca aaccagcttt caagataact   72960
ctcgactgta aaccaagtgg gttattatat aagtttattg gaatatgata agctaaatct   73020
gtacatagtt cgacgatgca tttatattcc tgccaaataa agaaaaataa agggctccga   73080
agagcccttt atgtattaga ttttacaga ccaactttgc tcgaattcct gatataggaa    73140
attgtctgac gcattatccc aattttctcg atcagttaca ccataataat ggaattctag   73200
ttcagtaggt ccaccaacaa aaccattctt agcatagcta taaacttgcc attggttagc   73260
ttaatcagtg tatccacata gaaactatta cggttccata tttcattgtg gatgtactta   73320
aataccacac tgtngatata cttaaattgc gcacttggtt ttccgagtac actccaatag   73380
aatttacgga tacctatttc ggtcttgaaa ttaaactctc cgttgcgaat gttgttagaa   73440
acaatacgtg ccagtttatt aacccgattt cttcaccgat tagatagatc ccggaaacac   73500
tacatccatc tcctattgat ccattattaa ctagtggatc aacaccatat tcatcagtga   73560
aaatggtttt gataacctct ttaccttctc gacgcactaa catattcagg tgaccatctt   73620
cgatatatga catatggcta ggctgaatat attcacttgt atcgacgata acatcattcg   73680
ccattacatt aaactgtaga tggtttacca gatcactaat accttaaaa cgaatggctt     73740 ggttcgctgt atttagatcg acatacacca cgacatcaat aatgccttgt tttagtgatt   73800
tgtcatcttt gtcagtagtt gtatcaattt tacgtaattt tgatatagtt cactaaaaca   73860
agatatgatg tcatcatgta gtttaattac atcagatcca tttcgttcaa gcgctttaag   73920
cgatacgtta aaccaatacg aattttatta gaacgacgtg ccatggttat atcacctatg   73980
ttaaattaat gaattattta ttcaattacc gtactacatc tgtgattaga ataagttcac   74040
catcactatt gataacacta tagcttttac aatttcgatg cgcttactaa taatcttatt   74100
ctctagatct acttttacga tattaacacg aattacctta ttcgattgat catgcatttc   74160
tttaaaatgc attcgatatt ttaccaatga cagcttttaa ttttcaatgc tgtcaatgga   74220
tgaatattta aaactatatg cttctgccag ggttttgcat tacccacaac cgtagttagg   74280
gtaccccaat aatcataaac atacaacgca gtatcactat tgggattatc gataatttca   74340
attataaatc cacttgtatc actcctatta gtttattgat agtacacttg taatatagat   74400
cttaaataaa ttatgatcta accattaaa atagataaag cctctatatg ccaatggtgt     74460
attagttctt ctttactaat aatattattg aagtagttta accgatgtga taccattaat   74520
ttagaatgca tatcgacttc actacttacc ttaatcaccc cagtctctaa taattgcaga   74580
gatccaacat acgcaaataa agttggtttt aaataccagt gttccctata ttgttttga    74640 tcaggtacat ttcctataat gtagtcagta gaattacttc ggtatgcgta aatagttgat   74700
ttagaaccaa gtaaattaag atcgatatca taactcccgc ttttagctgc aatacattca   74760
ataactgatg gggccacaca tatacggttg gttacactgt cttcgccatc agctctatta   74820
cttggaatat atggccttaa taaacataat ccccaaggta tactgtcgat atgtgataca   74880
```

```
taattaacct atttaattaa aacagataac gctctgttac tgaacgatat tgtgacatga    74940
tgtttaatgg atcaacatcc actggtgctt tagtgacagt taagcgagca cctttttaaaa   75000 atcaccaata tctaatttcc ttacagtaac atcatggata gtgttttcg taatccactc     75060 agtatcaatg ctattgtgag gatattattc ttaatccatt tgtcagagtc cctaaatgga    75120
atggtataaa catacacaac cattttaaaa tatcactttt atcgatatta tttgacaata    75180
gattgtaata tccctatcaa cagtagcata tctatcacta tcaaataact tttcgatagc    75240
gctaccaata cctaaataag atgcatcttt ttcagatgac gttgcatata ggtattggtt    75300
agactcaata ccatcccaca taacaagttc accagatctt ttaaatcctg gcattaattc    75360
atcttgttta taaagagaac catggtaagt aattctggtt tattcataat aaaatccact    75420
atgctttata agagttatgg ttatcaatta acttcaaggt agtagtgtgg cagtattgaa    75480
gtgattggtt actgcttcga tcagcatttg ctcgatgttg attttgtagt attctggttc    75540
ttcgttcaat tcccaataat agtcgcacgt aatagtgcag gtgctatgaa tctaactacc    75600
ttaccatgtg tgtcaaactc tacatgaaca ttgcatattg ttcagtagta tgattttata    75660
gaaatgaatt accagcgtaa ctgcgacctc tatttcacca tgaatactgg agtaggtttc    75720
ctggtggaat actttacctt taaggcgtgt attctcttca atgatattac caattctttc    75780
aatttgtctt atctagttgc atttgtaggt tcctattaat aaatgtatac gatggatatc    75840
ttttacgatt tccggtgctt atccatatct agttttatat cagtatatat cttgaatcta    75900
ttagataggc tatccatatc tacgtgcaat gcccgaatat gcatatcagt atcttttggt    75960
ttaccttcag actcccatac ggcctttgcg atatcaaatg ctacattgtt caaatagtat    76020
tcgacttcat gttcatcaag caaaagagca tcatggaaac caatacgtga tagaatggcg    76080
taatcacgct gattaacatc tctccaatct ttacgcacta agtaacttttt accaattcca    76140 tcttttttac aacttttact aataatttct ataatgaact tatcatgcca tttataatcc    76200
ataatcatta ctcctttatt taatcagctt cattactaga ggaacagata gacttatgcc    76260
attagccatt ttagctagaa tatgatagac atcgtctgct tcttgattat tgtacaaggt    76320
atagaaatgg catcaccata gtaaggactg tagttaatac ggtcgccata cacaccactc    76380
acaaaactat aatctaatcc atccgtggta gtcataataa ctacaacatg atcatcccca    76440
actataccgg attctaaatc ctcacatagt tctagttttg ttgcacacct cgttgacaga    76500
tccatacttc acggtattga tgatgaggat atggattaca tgctacatca tttttcactaa   76560 cgaagtacat agtcccccag ttgtaagact ggaattgggt tgttgtttgt gggcttccca    76620
tacctcttcc atacaaaggt atgttgttaa cccatagacc atcgttatta agactatcaa    76680
cgatccatca cggacacgta ctacacgag tgttttttgcc atttttaatt atcctaaata    76740
cataaaggaa tcacttagta aacaccattg acaatagcat cgcggaaacg agaccattcc    76800
gtttgaccaa ctacgaatac tcgttcttta ggacgccata gatgatcacc gcagtcaaga    76860
cccaagtaaa gcatattggt tttccatgat tgcgatgaac acgtagttta gctgatacac    76920
tgaactcaca cattacttca tttacatcaa gatgtgtagt gtatcactat catacctgac    76980
atactgatac caattgattt acgaactcgg attagatcct cagtcatcac ccgccaagtt    77040
accagatgct cgtaatactc atctggtgtc atgttgtttt tataattcag tgcacctgga    77100
gtcattgaca tcagttagtg aactggaagt catgtaatac atccaatcac tattatgacg    77160
gagttcttta agcttctctg tattacgata ttagtagttg ctttagtcat ctacgtaccc    77220
tcatcagata cataagtacg ttcaggctga acacatattt gatgttatta attacagctg    77280
```

```
tgatataaac ctgatattct tttgaaatag attccatcag ttcaatagat acggaattga    77340
actctgaata agttatttac tttcttagtt catcaattct accgaccgta attacaccaa    77400
catctctgaa actgataact ggatagtgtt tccaatataa caattcagtt taccaagatg    77460
aattacttga attgtttcat cgcaccattg tttcttttct attgtagtat tcaacacgac    77520
gttcgatgaa gacgcgagta ccagaaacag aggtgtacgc attcagtcat aaccatactt    77580
atggtacgtt atttggatct tggcgccatt ttggatgaat gctttcattt gtattttcct    77640
tttacgaaat agaagccctc ccgaaggagg gcaattacca ttattaaatt acgagtctat    77700
tacttctttt aattttcacc aggggtagct agataatcta cattatattt aatagcaatt    77760
acaccacaag ttcttttttca tagctgttct acctgatcgc atatttatca atagctccat    77820
cttctacatc ctcgtataat ggatattgac tataatatta tcaggtgtaa gtacagacag    77880
tttcaatccc atctttacca atgactgggt gatatgtctg tttaagacct ttacaatgat    77940
agtgataggt atgcgctgtg tttaggtggt catgtaaaga tacctcataa accgttgggt    78000
agtccgtctt taagacagtt agttgattaa catctttcaa tgattatctg caatattctt    78060
agccaataac agtagatcat tggtgatatg ttttaatgag aacttaagcc tctccctttg    78120
tttatatcgg aaccttatta tcacagtaac tccatccggt tatttttata attcagtaca    78180
gtgattggtg tattcggtac aaagacggct agttcgtcat cgaatacaat gtaaaccatc    78240
actttataat tattaaccga ttcttggaat tgttgtgtga ttacattata gtcttttgtg    78300
cgatggctaa gaaacagctc actattagct cggcagaaac tatgtcgcgc tttttatcag    78360
cactcataac agcgatacca cggataatga atttattatc taaggtatat tttctttgag    78420
acatcgcata gtcgactaca tcaacatcgc cgccaaatag cacggcattt tcaccgtatc    78480
cacaaataag agccatttat aattacctgt ttaaaaatta tattcaataa attgagagtg    78540
aatagttcac tacattccca tgtacgactt gctaatttat atttacctttt aacaggtaag    78600 tcaaataacg taatgctttt ctactgaacc agcctcatga ttaaccaata gaacattcct    78660
agccttcaga atatttgaac aatttacaag ttcataatca tctcgcttag gtgtcaatag    78720
ctacattagt gcctggtttc tagcatacca gagcacctca tgaccctctg gattaataat    78780
agagatatag ctgacgttca gcgggtaacc acaagttacg tggatcatan tctccattaa    78840
catcaaagaa tttaaatatc atagagttgg aaccggtttt gatggatcag caattantgc    78900
agattcntct acataaacca ttgcnaagtt ttcaccttct ttacgaatac cagtagaagg    78960
tgttttcgat ggatcataac gataattggc actgctgtcc agctgttaaa taagttgggc    79020
cagttaatgc attgggtttt ggatgaggaa tatcaatttt agtaatacaa tattgaccag    79080
tacgaaactc acgcattata ttaacctctt aatgaataac tgttcagaa ggacgacatt     79140 tcatagtttt aaaaatgtca gtaggataga tattaccagc ttgtccgaaa ggtttatcgg    79200
ctagaagaaa ctgcggacaa actgtttgta gataaccact atcagtgggt aggaatcctt    79260
caatatcact gatgagaatt tgccagatgg gcaattggtt ataatagtca tccatattgt    79320
agtatgcgtg gagtttacca ccgaacccat atacaaactg atgagtatca attagacgaa    79380
taccaaattt aggttgtcgt cccatcctt                                      79409
```

<210> SEQ ID NO 13
<211> LENGTH: 22
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 13
caggttcatc atgccgtttg tg                                              22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tatttgccca tggacgcaca c                                               21

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atatagaaaa tcattaattg atgaacg                                         27

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Ile Glu Asn His
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Arg Lys Ser Leu Ile Asp Glu Arg
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ile Leu Ala
1

<210> SEQ ID NO 19
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 19
ctttgtttat cgcctcaatg acatta                                              26

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Gln Lys Asp Gly
1               5
```